United States Patent 
Flynn et al.

(10) Patent No.: US 7,666,895 B2
(45) Date of Patent: Feb. 23, 2010

(54) ANTI-INFLAMMATORY MEDICAMENTS

(75) Inventors: Daniel L. Flynn, Lawrence, KS (US);
Peter A. Petillo, Arlington, MA (US)

(73) Assignee: Deciphera Pharmaceuticals, LLC, Lawrence, KS (US)

( * ) Notice: Subject to any disclaimer, the term of this patent is extended or adjusted under 35 U.S.C. 154(b) by 349 days.

(21) Appl. No.: 11/450,850

(22) Filed: Jun. 9, 2006

(65) Prior Publication Data

US 2008/0299639 A1    Dec. 4, 2008

(51) Int. Cl.
*A61K 31/415* (2006.01)
*A61K 31/41* (2006.01)
*C12N 9/96* (2006.01)

(52) U.S. Cl. .................. 514/406; 514/359; 514/403; 435/188

(58) Field of Classification Search .............. 435/188; 514/359, 403, 406
See application file for complete search history.

(56) References Cited

U.S. PATENT DOCUMENTS

| 3,818,024 | A | 6/1974 | Krenzer |
| 4,093,624 | A | 6/1978 | Revankar et al. |
| 4,296,237 | A | 10/1981 | Cragoe, Jr. |
| 4,432,992 | A | 2/1984 | Cragoe, Jr. et al. |
| 5,103,014 | A | 4/1992 | Musser et al. |
| 5,494,925 | A | 2/1996 | Court et al. |
| 6,020,357 | A | 2/2000 | Pinto et al. |
| 6,235,786 | B1 | 5/2001 | Dai et al. |
| 6,294,573 | B1 | 9/2001 | Curtin et al. |
| 6,319,921 | B1 | 11/2001 | Cirillo et al. |
| 6,645,990 | B2 | 11/2003 | Askew et al. |
| 7,144,911 | B2 * | 12/2006 | Flynn et al. .................. 514/406 |
| 7,202,257 | B2 | 4/2007 | Flynn et al. |
| 7,342,037 | B2 | 3/2008 | Flynn et al. |
| 7,531,566 | B2 | 5/2009 | Flynn et al. |
| 2001/0008898 | A1 | 7/2001 | Tomiyama et al. |
| 2003/0181411 | A1 | 9/2003 | Bosch et al. |
| 2003/0186221 | A1 | 10/2003 | Lockhart et al. |
| 2004/0171075 | A1 | 9/2004 | Flynn et al. |
| 2007/0078121 | A1 | 4/2007 | Flynn et al. |
| 2007/0191336 | A1 | 8/2007 | Flynn et al. |
| 2008/0045531 | A1 | 2/2008 | Flynn et al. |
| 2008/0045706 | A1 | 2/2008 | Flynn et al. |
| 2008/0113967 | A1 | 5/2008 | Flynn et al. |
| 2008/0132506 | A1 | 6/2008 | Flynn et al. |
| 2008/0187978 | A1 | 8/2008 | Flynn et al. |
| 2008/0220497 | A1 | 9/2008 | Flynn et al. |
| 2008/0248487 | A1 | 10/2008 | Flynn et al. |
| 2008/0248548 | A1 | 10/2008 | Flynn et al. |
| 2009/0069310 | A1 | 3/2009 | Flynn et al. |
| 2009/0075986 | A1 | 3/2009 | Flynn et al. |
| 2009/0105230 | A1 | 4/2009 | Flynn et al. |
| 2009/0137021 | A1 | 5/2009 | Flynn et al. |

FOREIGN PATENT DOCUMENTS

| DE | 1115350 | | 5/1968 |
| DE | 2156343 | | 5/1972 |
| DE | 2341064 | | 3/1974 |
| DE | 3406329 | A1 | 8/1985 |
| DE | 4302702 | A1 | 4/1994 |
| DE | 4337847 | A1 | 5/1995 |
| DE | 4343831 | A1 | 6/1995 |
| DE | 4414840 | A1 | 11/1995 |
| EP | 0021228 | A1 | 6/1980 |
| EP | 0021228 | B1 | 6/1980 |
| EP | 0025232 | A1 | 9/1980 |
| EP | 0025232 | B1 | 9/1980 |
| EP | 0031796 | A2 | 7/1981 |
| EP | 0031796 | B1 | 7/1981 |
| EP | 0692483 | | 1/1996 |
| EP | 0739884 | A2 | 4/1996 |
| EP | 0739884 | B1 | 4/1996 |
| EP | 0956855 | A1 | 4/1996 |
| EP | 0956855 | B1 | 4/1996 |
| EP | 0927555 | A1 | 12/1996 |
| EP | 0867435 | A1 | 3/1998 |
| EP | 0867435 | B1 | 3/1998 |
| EP | 1281399 | A2 | 7/2002 |
| FR | 2337554 | | 8/1977 |
| FR | 2396549 | | 2/1979 |
| GB | 971307 | | 3/1961 |
| GB | 1115350 | | 5/1968 |

(Continued)

OTHER PUBLICATIONS

Investigation of the relationship between the Inhibitory activity of glycolic acid oxidase (GAO) and its chemical structure: electron-topological approach; Y. Guzel; Journal of Molecular Structure 366 (1996) 131-137.
Protein kinase inhibitors: emerging pharmacophores 1997-2000; Jacques Dumas; Exp. Opin. Ther. Patent (2001) 11(3): pp. 405-429.
Inhibition of p38 MAP kinase by utilizing a novel allosteric binding site: Pargellis, Tong. Churchill, Cirillo, Gilmore, Graham, Grob, Hickey, Moss, Pav and John Regan; Nature Structural Biology; vol. 9, No. 4, Apr. 2002; p. 268-272.
Structural Mechanism for STI-571 Inhibition of Abelson Tyrosina Kinase; Schindler, Bornmann, Pellicana, Miller, Clarkson, Kurlyan; Science Magazine; Sep. 15, 2000; vol. 289; pp. 1938-1942.
Synthesis of Novel Uracil-5-Sulphonamide Derivatives of Possible Biological Activity; Nofal, Gadalla, Fathalla and Kamel; Egypt J. Chem. 33; No. 4, pp. 375-380 (1990).
The Stereochemistry of Oxidation at Sulfur Oxidation of 2-Thiablcyclo[2.2.1]Heptane; Johnson, Diefenbach, Keiser and Sharp; vol. 25, p. 5649 to 5633; Pergamon Press 1969.

(Continued)

*Primary Examiner*—Kamal A Saeed
*Assistant Examiner*—Samantha L Shterengarts
(74) *Attorney, Agent, or Firm*—Wilmer Cutler Pickering Hale and Dorr LLP

(57) ABSTRACT

Novel compounds and methods of using those compounds for the treatment of inflammatory conditions are provided. In a preferred embodiment, modulation of the activation state of p38 kinase protein comprises the step of contacting the kinase protein with the novel compounds.

8 Claims, 8 Drawing Sheets

FOREIGN PATENT DOCUMENTS

| | | |
|---|---|---|
| GB | 1127875 | 3/1987 |
| GB | 2220206 | 1/1990 |
| JP | 59-15247 | 1/1984 |
| JP | 59177557 | 10/1984 |
| JP | 0-221476 | 8/1997 |
| JP | 10-7804 | 1/1998 |
| JP | 11-209350 | 8/1999 |
| JP | 2000-275886 | 10/2000 |
| JP | 2001-2687 | 1/2001 |
| WO | WO9119708 | 12/1991 |
| WO | WO9208693 | 5/1992 |
| WO | WO9404095 | 10/1994 |
| WO | WO9505954 | 6/1995 |
| WO | WO9534540 | 12/1995 |
| WO | WO9616046 A2 | 5/1996 |
| WO | WO9616046 A3 | 5/1996 |
| WO | WO9619477 | 6/1996 |
| WO | WO9734900 | 9/1997 |
| WO | WO9822103 | 6/1998 |
| WO | WO-98/52558 | 11/1998 |
| WO | WO9915164 | 4/1999 |
| WO | WO-99/23091 | 5/1999 |
| WO | WO9923093 | 5/1999 |
| WO | WO-99/32106 | 7/1999 |
| WO | WO-99/32110 | 7/1999 |
| WO | WO-99/32111 | 7/1999 |
| WO | WO-99/32455 | 7/1999 |
| WO | WO9959959 | 11/1999 |
| WO | WO0002851 | 1/2000 |
| WO | WO0006550 | 1/2000 |
| WO | WOOO7980 | 2/2000 |
| WO | WO0018738 | 4/2000 |
| WO | WO0021927 | 4/2000 |
| WO | WO-00/43384 | 7/2000 |
| WO | WO0041698 | 7/2000 |
| WO | WO0043384 | 7/2000 |
| WO | WO-00/55139 | 9/2000 |
| WO | WO0059506 | 10/2000 |
| WO | WO0112621 | 2/2001 |
| WO | WO0114372 A2 | 3/2001 |
| WO | WO0114372 A3 | 3/2001 |
| WO | WO0174771 | 10/2001 |
| WO | WO0196298 | 12/2001 |
| WO | WO0214291 | 2/2002 |
| WO | WO0214311 | 2/2002 |
| WO | WO0228835 | 4/2002 |
| WO | WO0234727 A2 | 5/2002 |
| WO | WO0234727 A3 | 5/2002 |
| WO | WO0240458 | 5/2002 |
| WO | WO 02060869 | 8/2002 |
| WO | WO 02060876 | 8/2002 |
| WO | WO-02/070662 | 9/2002 |
| WO | WO-03/005999 | 1/2003 |
| WO | WO 03000189 | 1/2003 |
| WO | WO 03053368 | 7/2003 |
| WO | WO 03059373 | 7/2003 |
| WO | WO-03/068223 | 8/2003 |
| WO | WO 03072577 | 9/2003 |
| WO | WO-03/084539 | 10/2003 |
| WO | WO-2004/056783 | 7/2004 |
| WO | WO-2004/060306 | 7/2004 |
| WO | WO-2004/061084 | 7/2004 |
| WO | WO-2004/113352 | 12/2004 |
| WO | WO-2005/110994 | 11/2005 |
| WO | WO-2006/014290 | 2/2006 |
| WO | WO-2006/071940 | 7/2006 |
| WO | WO-2006/081034 | 8/2006 |
| WO | WO-2007/008917 | 1/2007 |

OTHER PUBLICATIONS

TPAP: Tetra-n-propylammonium Perruthenate, A Mild and Convenient Oxidant for Alcohols; Griffith and Ley; Aldrichimica Acta, vol. 23, No. 1, 1990; pp. 13-19.

Aminolysis and Polymerlzation of 3-(p-Toluenesulfonaxy) Hydantoin; Zvillchovsky and Zucker, Israel Journal of Chemistry; vol. 7, 1969, p. 547-554.

Palladium-catalyzed amination of arly halides and sulfonates; Yang and Buchwald: Journal of Organometallic Chemistry 576 (1999) pp. 125-146.

General, Efficient, and Inexpensive Catalyst System for the Coupling of Aryl Iodides and Thiois; Kwong and Buchwald; Organic Letters 2002; vol. 4, No. 20, pp. 3517-3520.

Novel Solution Phase Strategy for the Synthesis of Chemical Libraries Containing Small Organic Molecules; Cheng, Comer, Williams, Myers, and Boger, J. Am. Chem. Soc. 1996, 118, pp. 2567-2573.

A Useful 12-I-5 Triacetoxyperiodlane (the Des-Martin Periodland) for the Selective Oxidation of Primary of Secondary Alcohols and a Variety of Related 12-I-5 Species; Dess and Martin; J. Am. Chem. Soc. 1991, 113, pp. 7277-7287.

Proton-Transfer Chemistry of Urazoles and Related Imides, Amides, and Diacyl Hydrazides; Bausch, David, Dobrowolski, Guadalupe-Fasano, Gostowski, Setmarten, Prasad, Vaughn and Wang; J. Org. Chem. 1991, 56, pp. 5643-5651.

A General Synthesis of 4-Substituted 1,1-Dioxo-1,2,5-thiadiazolidin-3-ones Derived from a-Amino Acids; Muller and DuBois; J. Org. Chem. 1989, 54, pp. 4471-4473.

The Reaction of S-Methiodide Derivatives of Activated Thioureas with Hydroxylic Compounds. A Novel Synthesis of Mercaptans; Klayman, Shine, and Bower. J. Org. Chem., vol. 37, No. 10, 1972; pp. 1532-1537.

Efficient Solid-Phase Synthesis of Sulfahydantions; Tremblay, Voyer, Boujabi and Dewynter; J. Comb. Chem. 2002, 4, pp. 429-435.

Identification of Novel Inhibitors of BCR-ABL Tyrosine Kinase via Virtual Screening; Peng, Huang, Qi, Xie, Xu, Wang and Yang; Bioorganic & Medicinal Chemistry Letters 13 (2003) 3693-3699.

Implications of Protein Flexibility for Drug Discovery; Simon J. Teague; astrazeneca.com; Reviews.

The Conformational Plasticity of Protein Kinases; Huse and Kurlyan; Cell, vol. 109, pp. 275-282; May 3, 2002.

Discovery of a Novel Family of CDK Inhibitors with the Program Lidaeus: Structural Basis for Ligand-Induced Disordering of the Activation Loop; Wu, McNae, Kontopkils, McClue, McInnes, Stewart, Wang, Zheleva, Marriage, Lane, Taylor, Fischer, and Walkinshaw; Structure, vol. 11, pp. 399-410; Apr. 2003.

Molecular Recognition with Convergent Functional Groups. 6. Synthetic and Structural Studies with a Model Receptor for Nucielc Acid Components; Askew, Ballester, Buhr, Jeong, Jones, Parris, Williams and Rebek, Jr.; J. Am. Chem. Soc. 1989, 111, pp. 1082-1090.

Pyrazole Urea-Based Inhibitors of p38 MAP Kinase: From Lead Compound to Clinical Candidate; Regan, Breitfelder, Cirillo, Gilmore, Graham, Hickey, Klaus, Madwed, Moriak, Mass, Pargellis, Pav, Proto, Swinamer, Tong, and Torcellini; J. Med. Chem. 2002, 45, pp. 2994-3008.

The Sequence of the Human Genome; J. Craig Venter, et al; Science Magazine; Feb. 16, 2001; vol. 291; pp. 1304-1351 (including Erratum/post date Jun. 8, 2001), 1 pg.

Initial sequencing and analysis of the human genome; Nature/vol. 409; Feb. 15, 2001; pp. 860-921.

Copper-Catalyzed Coupling of Aryl Iodides with Aliphatic Alcohols; Walter, Nordmann, Job, and Buchwald; Organic Letters 2002; vol. 4, No. 6, pp. 973-976.

First Non-ATP Competitive Glycogen Synthase Kinase 3 (GSK-3) Inhibitors; Thladizolidinones (TDZD) as Potential Drugs for the Treatment of Alzheimer's Disease; Martinez, Alonso, Castro, Perez, and Moreno; J. Med. Chem. 2002, 45, pp. 1292-1299.

On the preparation of 1-aryl-2heteroaryl- and 2-aryl-1-heteroaryl-pyrroles as useful building blocks for biologically Interesting heterocycles; Almerico, Montalbano, Diana, Barraja, Lauia, Cirrinclone and Daltolo; Dipartimento Farmacochimico, Tossicologico a Biologico, Palermo, Italy; pp. 129-142.

Qsar and Molecular Modelling for a Series of Isomeric X-Sulfanilamido-1-phenylpyrazoles; Koch, Seydel, Gasco, Tironl, Fruttero; Quant. Struct. Act. Relat. 12, pp. 373-382 (1993).

Disposition of 1-[3-Aminomethyl) phenyl]-N-3-fluoro-2'-methyisulfonyl)-[1,1'-biphenyl]-4-yl:-3-(trifluomethyl)-1H-pyrazole-5-carboxamide (DPC 423) by Novel Metabolic Pathways. Characterization of Unusual Metabolites by Liquid Cgrinatigraogt/Mass Spectrometry and NMR; Mutilb, Shockcor, Chen, Espina, Pinto, Orwat, Prakash, and Gan; Chem. Res. Toxicol. 2002, 15, pp. 48-62.

P450-Mediated Metabolism of 1-[3-(Aminomethyl)phenyl]-N-3-fluoro-2'-(methyisulfonyl)-[1,1'-biphenyl]-4-yll-3(trifluoromethyl)-1H-pyrazole-5-carboxamide (DPC 423) and Its Analogues to Aldoximes. Characterization of Glutathione Conjugates of Postulated Intermediates Derived from Aloximes; Mutlib, Chen, Espina, Shockcor, Prakash, and Gan; Chem. Res. Toxlcol. 2002, 15. pp. 63-75.

Synthesis and Characterization of Conjugated Mono- and Dithlol Oligomers and Characterization of Their Self-Assembled Monolayers; Boer, Mang, Perepichka, Zheng, Frank, Chabal, and Bao; Langmuir 2003, 19, pp. 4272-4284; 2003 American Chemical Society.

An evaluation of the effect of light stabilisers on the exterior durability of polyester powder coatings for the architectural market; Johnson, Parducci and Nascovilli; Surface Coatings International 1999 (3); pp. 134-141.

Synthesis and Spectral-Luminescence Properties of Hetarylethylene Derivatives of 2,5-Diphenyloxazole and 2,5-Diphenyl-1,3,4-Oxadizole; Krasovitskif, Egorova, Afanasladl, Lysova, Polyakov and Tsukerman; 1982 Plenum Publishing Corporation; pp. 461-465.

The Difluoromethylensulfonic Acid Group as a Monoanionic Phosphate Surrogate for Obtaining PTP1B Inhibitors; Leung, Grzyb, Lee, Meyer, Hurn, Jia, Liu, and Taylor; Bioorganic & Medicinal Chemistry 10 (2002) pp. 2309-2323.

Abnormal Diels-Alder Reaction of 5-Alkoxythiazoles with Highly Reactive Dienophiles; 4-Phenyl-3$H$-1,2,4-triazole-3,5(4$H$)-dione, Diethyi Azodicarboxylate, and Diethyl Oxomalonate; Shi, Ibata, Suga, and Matsumoto; Bul.. Chem. Soc. Jpn., 65, pp. 3315-3321 (1992).

Telomere Shortening and Growth Inhibition of Human Cancer Cells by Novel Synthetic Telomerase Inhibitors MST-312, MST-295, and MST-199; Seimiya, Oh-hara, Suzuki, Naasani, Shimazaki, Tsuchiya, and Tsuruo; Molecular Cancer Therapeutics; vol. 1, Jul. 2002, pp. 657-665.

The Synthesis of some Substituted Biphenyl-4-carboxylic Acids, 4-Biphenytylacetic Acids, and 4-Aminobiphenyls; Byron, Gray, and Wilson; J. Chem. Soc. (1966); pp. 840-845.

Synthesis of a Sulfahydantoin Library; Albericlo, Bryman, Garcia, Michelotti, Nicolas, and Tice; J. Comb. Chem. 2001, 3, pp. 290-300.

Novel Chromophoric Heterocycles Based on Maleimide and Naphlhoquinone; Katritzky, Fan, Li, and Bayyuk; J. Heterocyclic Chem., 26, (1989) pp. 885-892.

Nitrofuryl Heterocyclics 1;Closier and Islip; Journal of Medicinal Chemistry, 1970, vol. 13, No. 4; pp. 638-640.

Discovery of Novel Mesangial Cell Proliferation Inhibitors Using a Three-Dimensional Database Searching Method; Kurogi, Miyata, Okamura, Hashimoto, Tsutsumi, Nasu, and Moriyasu; J. Med. Chem. 2001, 44, pp. 2304-2307.

Nitrofuryl Heterocyclics 3; Islip and Johnson; Journal of Medicinal Chemistry, 1973, vol. 16, No. 11; pp. 1308-1310.

Inhibitors of Glycolic Acid Oxidase. 4-Substituted 3-Hydroxy-1$H$-pyrrole-2,5-dione Derivatives; Rooney, Randall, Streeter, Ziegler, Cragoe, Schwam, Michelson, Williams, Eichler, Duggan; Ulm. and Noll; J. Med. Chem. 1983, 26, pp. 700-714.

Organic Phosphorus Compounds. 2. Synthesis and Coronary Vasodilator Activity of (Benzothizolylbenzyl) phosphonate Derivatives; Yoshino, Kohno, Morita, and Tsukamoto: J. Med. Chem. 1989, 32, pp. 1528-1532.

Additions and Corrections; Journal Of Medicinal Chemistry; 1989, vol. 32, No. 12, pp. 2583.

Inhibitors of Acyl-CoA: Cholesterol o-Acyltransferase, 17. Structure-Activity Relationships of Several Series of Compounds Derived from n-Chlorosulfonyl Isocyanate; Picard, O'Brien, Silskovic, Anderson, Bousley, Hamelehie, Krause, and Stanfield; J. Med. Chem. 1996, 39, pp. 1243-1252.

Convergent Functional Groups: Synthetic and Structural Studies; Rebek, Jr., Marshall, Wolak, Parris, Kiforan, Askew, Nerneth, and Islam; J. Am. Chem. Soc. 1985, 107, pp. 7476-7481.

Laser-Jet Delayed Trapping: Electron-Transfer Trapping of the Photoenol from 2-Methylbenzophenone; Wilson, Hannemann, Heineman, and Kirchoff; J. Am. Chem. Soc. 1987, 109, pp. 4743-4745.

Molecular Recognition in the Solid Waste State: Controlled Assembly of Hydrogen-Bonded Molecular Sheets; Garcia-Tellado, Geib, Goswami, and Hamilton; J. Am. Chem. Soc. 1991, 113, pp. 9265-9269.

Theoretical Study of a Molecular Resonant, Tunneling Diode; Seminario, Zacarias, and Tour; J. Am. Chem. Soc. 2000, 122, pp. 3015-3020.

A New Synthesis of Purines; Yoneda, Matsumoto, and Higuchi; J.C.8, Chem. Comm., 1974; p. 551.

Alkyl- and Arylthiation of Uracll and Indole; Kentaro Anzai; 3. Heterocyclic Chem., 16, (1979) p. 567-569.

Synthesis of 8-Substituted 5-Deazaflavins; Link, van der Plas, and Muller; J. Heterocyclic Chem., 22, (1985) pp. 841-848.

Irrevarsible Enzyme Inhibitors. 188. Inhibition of Mammalian Thymidine Phsphorylase; Baker and Kelly; Journal of Medicinal Chemistry, 1971, vol. 14, No. 9; pp. 612-616.

Correlation Analysis of Baker's Studies on Erizyrne Inhibition. 2. Chyotrypsin, Trypsin, Thymidine Phosphorylase, Uridine Phosphorylase, Thymidylate Syntheiase, Cytosine Nucleoside Desminase, Dihodrofolate reductase, Malate Dehydrogenase, Glutamate Dehydrogenase, Lactate Dehydrogenase, and Glyceraldehyde-phosphate Dehydrogenase: Yoshimoto and Hansch; Journal of Medicinal Chemistry, 1976, vol. 19, No. 1: pp. 71-98.

Synthesis and Pharmacological Evaluation of New Pyrazolidine-3,5-diones as AT, Angiotensin II Receptor Antagonista; Bourdonnec, Meulon, Yous, Goossens, Houssin, and Henichart; J. Med. Chem. 2000, 43, pp. 2685-2697.

Convergent Functional Groups. 2. Structure and Selectivity in Olefin Eposidation with Peracids; Rebek, Jr.; Marshall, McManis, and Wolak/ J. Org. Chem. 1986, 61, pp. 1649-1653.

A Convenient Synthesis of Perfluoroallkyiated and Fluorinated-Aryl Nitrogen Bases by Electrochemically Induced $S^{RH}$ 1 Substitution; Medebielle, Oturan, Pinson, and Saveant; J. Org. Chem. 1996, 61, pp. 1331-1340.

Coenzyme Models, Part 45. $_1$ Synthesis of Atropisomeric Flavins and their Novel Redox-induced Racemisation; Shinkal, Nakao, Kuwahara, Miyamoto, Yamaguchi, and Manabe; J. Chem. Soc. Perkin Trans. (1988).

Inhibition of Nucleoside Transport by Protein Kinase Inhibitors; Huang, Wang, Cogut, Mitchell, and Graves; The Journal of Pharmacology and Experimental Therapeutics; vol. 304, No. 2; pp. 753-760.

Relative Reactivities of the Chlorine Atoms of 2,2', 4-Trichloro-4', 5-Dipyrimidinyl in its Reaction with Piperidine; Mikhaleva, Naumenko, and Mamaev; 1979 Plenum Publishing Corporation; pp. 671-676.

Solid phase synthesis of benzamidine and butylamine-derived hydantoin libraries; Kim, Koh, Lee, and Ro; Molecular Diversity 3; 1998, pp. 129-132.

Synthesis of sequentially controlled isorneric, wholly aromatic polyketones composed of 2-Trifluoromethylbiphenylene and 2.2'-dimethoxybiphenylene units; Yonezawa, Nakamura, and Maeyama; Reactive & Functional Polymere 52 (2002) pp. 19-30.

Solubility of Polytherm in the System $HNO_3^- $-$H^2$ -O-$(C^4 H^9 $-O)PO$(C^4 H^8)^2$; Translated from Dokiady Akademii Nauk SSSR, vol. 160, No. 4, pp. 841-844, Feb. 1968, Original Article submitted Aub. 31, 1964; pp. 135-138.

Condensation Reaction of Ethyl (4-Uracil)-Acetate with Ethyl Orthoformate; Nantaka-Namirski, and Wojciechowski; ACTA Polon. Pharm. XXVII, No. 5, 1971; pp. 455-463.

Inhibition of endogenous oxalate production: biochemical consideration of the roles of glycoliate oxidase and lactale dehydrogenase; Bals, Rofe, and Conyers; Clinical Science (1989) 76, pp. 303-309.

1-(4 Substituted-thiazol-2-yl)hydantoins as Anti-inflammatory and CNS-Active Agents; Satsangi, Zaidi, and Misar; Pharmazie 38 (1983) H.5; pp. 341-342.

Addition of 4-Ethoxyimidazoles to Dimethyl Acetylenedicarboxytate and Transformation of the Adducts to Pyrimidian-5-yl Acetates[1)]; Furyua, Omura and Furukawa; Chem. Pharm. Bull. 36(5) (1998) pp. 1669-1675.

New Anti-mycobacterial Hydantoins; Zaidi, Satsangi, Mohd, Agarwal, and Tiwari; Pharmazie 35, H. 12 (1980) pp. 755-768.

Molecular arrangement and electrical conduction of self-assembled monolayers made from terphenyl thiols; Ishida, Mizutani, Azehara, Miyake, Aya, Sasaki, and Tokumoto; Surface Science 514 (2002) pp. 187-193.

Depropargylation under palladium-copper catalysis: synthesis of diaryl sulfides; Kundu and Nandi; Tetrahedron 57 (2001); 2001 Elsevier Science Ltd., pp. 5885-5895.

A New Convenient Synthesis of 5-Aryi Uractis Using SRN1 Aromatic Nucleophilic Substitution; Medeblene, Oturan, Pinson and Saveant; Tetrahedron Letters, vol. 34, No. 21, pp. 3409-3412.

o-Bromophenylzinc Compound: A Readily Available and Efficient Synthetic Equivalent of o-Phenylene 1-Anion 2-Cation; Okano, Amano, and Takagl; Tetrahedron Letters 39 (1998) pp. 3001-3004.

Synthesis of thiol substituted oligoanilines for molecualr device candidates; Flatt and Tour; Tetrahedron Letter 44 (2003) pp. 6699-6702.

Consecutive cross-coupling of o-phenylenedizinc compound with acyl and/or aryl handes in the presence of Pd(0)-tris(2,4,6-trimethoxyphenyl)phosphine; Saiga, Hossain, and Takagl; Tetrahedron letters 41 (2000) pp. 4629-4632.

Synthesis of 2,5'-Bipyrimidines from Substituted 5-Cyanopyrimidines; 1988 Plenum Publishing Corporation; pp. 303-307.

Antimicrobial activities of 2-arylthio-$N$-alkylmaieimides; Igarashi and Watanabe; Journal of Industrial Microbiology, 9 (1992), pp. 91-96.

Syntheals of New Uracil-5-Sulfonamide Derivatives and Immuno-Stimulatory Effect of a Chemically Modified Hemolymph of Biomphalaria alexandrina on Schistosome mansoni Infected Mice; Fathalia, Halba, and Maghraby; Arch Pharm Res vol. 26, No.5, pp. 358-366 (2003).

Synthesis of New Pyrazolo[1,5-a]pyrimidine Derivative Using 5-Aminouracil and Ketene Dithloacetal; O. A. Fathalia; Arch Pharm Res vol. 22, No. 6, (1999); pp. 571-574.

Synthesis of Some New Uracil—5—Sulphonamide-p-Phenyl Derivatives and Their Effect on Biomphaiaria alexandina Snails Nucleoproteins; Fathalia, Gad, and Maghraby; Bun. N.R.C. Egypt, 25, No. 4 (2000) pp. 341-363.

Characterization of pp60$^{D-NC}$ Tyrosino Kinase Activities Using a Continuous Assay: Autoactivation of the Enzyme Is an Intermolecular Autophosphorylation Process; Baker, Kassel, Weigl, Huang, Luther, and Knight; Biochemistry 1995, 34, 14843-14851.

c-Abul Has High Intrinsic Tyrosine Kinase Activity That is Stimulated by Mutation of the Src Hoology 3 Domain and by Autophosphorylation at Two Distinct Regulatory Tyrosines; Brasher and Van Etten; The Journal of Biological Chemistry; vol. 276, No. 45, Issue of Nov. 10, pp. 35831-35837, 2000.

A New Practical One-Pot Access to Sulfonimidates; Leca, Fensterbank, Lacote and Maiacria; Organic Letters, 2002, vol. 4, No. 23; pp. 4093-4095.

Kern et al., "Synthesis of Macromolecules II. Synthesis of New Diol Ollgourethans," Makromoleculare Chemie, vol. 16, pp. 89-107 (1966).

O'Dell, J., et al., "Treatment of Rheumatoid Arthritis with Methotrexale Alone, Sulfasalazine and Hydroxychioroquina, or a Combination of All Three Medications," New Engl. J. Med., vol. 334(20), pp. 1287-1291 (May 1996) at p. 1287, col. 1, lines 6-9.

U.S. Appl. No. 11/721,026, filed Nov. 2, 2008, Flynn et al.

U.S. Appl. No. 12/268,997, filed Nov. 11, 2008, Flynn et al.

"NHIBI LBC Computational Biophysics Scetion", CHARMM Documentation Index, http://www.lobos.nih.qov/Charmm/chmdoc.html, printed Mar. 4, 2005 (1 page).

"Trilateral Project WM4 -Comparative Studies in New Technologies: Report on Comparative Study on Protein 3-Dimensional Structure Related Claims - ANNEX 3: Comments of the USPTO", Vienna, Austria, Nov. 4-8, pp. 58-79 (2002).

Benvenuti, et al., "Crystallization of Soluble Proteins in Vapor Diffusion for X-Ray Crystallography", Nature Protocols, 2(7):1633-1651 (2007).

Bosca, et al., "Circular Dichroism Analysis of Ligand-Induced Conformational Changes in Protein Kinase C", Biochem J., 290:827-832 (1993).

Boyer, "Small Molecule Inhibitors of KDR (VEGFR-2) Kinase: An Overview of Structure Activity Relationships", Current Topics in Medicinal Chemisty, 2:973-1000 (2002).

Brady, et al., "Fast Prediction and Visualization of Protein Binding Pockets with PASS". Journal of Computer-Aided Molecular Design, 14:383-401(2000).

Bullock, et al., "Prospects for Kinase Activity Modulators in the Treatment of Diabetes and Diabetic Complications", Current Topics in Medicinal Chemistry, 2:915-938 (2002).

Cardillo, et al., "Sulle 1,2-difenil-3.5-dichetopirazolidine", Gazz. Chim., Ital., 9:973-985 (1966) - Italian Language.

Chen, et al., "Biochemical Evidence for the Autophosphorylation and Transphosphorylation of Transforming Growth Factor β Receptor Kinases", Proc. Natl. Acad. Sci. USA, 92:1565-1569 (1995).

Chu, et al., "Using Affinity Capillary Electrophoresis to Determine Binding Stoichiometries of Protein-Ligand Interactions", Biochemistry, 33:10616-10621 (1994).

Cockerill, et al., "Small Molecule Inhibitors of the Class 1 Receptor Tyrosine Kinase Family", Current Topics in Medicinal Chemistry, 2:1001-1010 (2002).

Colton, et al., "Affinity Capillary Electrophoresis: A Physical-Organic Tool for Studying Interactions in Biomolecular Recognition", Electrophoresis, 19:367-382 (1998).

Cross, et al., "Inhibition of Glycogen Synthase Kinase-3 by Insulin Mediated by Protein Kinase B", Nature, 378:785-789 (1995).

Cudney, "Preface: Protein Crystallization and Dumb Luck", The Rigaku Journal, 16(1):1-7 (1999).

Dajani, et al., "Crystal Structur of Glycogen Synthase Kinas 3β: Structural Basis for Phosphate-Primed Substrate Specificity and Autoinhibition", Cell, 105:721-732 (2001).

Dajani, et al., "Structural Basis for Recruitment of Glycogen Synthase Kinase 3β to the Axin-APC Scaffold Comples", EMBO, 22(3):494-501 (2003).

Davis, et al., "Iterative Size-Exclusion Chromatography Coupled with Liquid Chromatographic Mass Spectrometry to Enrich and Identify Tight-Binding Ligands from Complex Mixtures", Tetrahedron, 55:11653-11667 (1999).

Deng, et al., "Expression, Characterization, and Crystallization of the Pyrophosphate-Dependent Phosphofructo-1-Kinase of Borrelia Burgdorferi", Archives of Biochemistry and Biophysics, 371(2):326-331 (1999).

Dumas, "Preface", Current Topics in Medicinal Chemistry (2002) (1 page).

Dumas, et al., "Discovery of a New Class of p38 Kinase Inhibitors", Bioorganic & Medicinal Chemistry Letters, 10:2047-2050 (2000).

Ewing, "Critical Evaluation of Search Algorithms for Automated Molecular Docking and Database Screening", Journal of Computational Chemistry, 18(9):1175-1189 (1997).

Farooqui, et al., "Interactions Between Neural Membrane Glycerophospholipid and Sphingolipid Mediators: A Recipe for Neural Cell Survival or Suicide", Journal of Neuroscience Research, 85:1834-1850 (2007).

Frame, et al., "A Common Phosphate Binding Site Explains the Unique Substrate Specificity of GSK3 and Its Inactivation by Phosphorylation", Molecular Cell, 7:1321-1327 (2001).

Greene, et al., "Chapter 7: Protection for the Amino Group", in Protective Groups in Organic Synthesis, Third Edition, pp. 494-653 (1999).

Haar, et al., "Structure of GSK3β Reveals a Primed Phosphorylation Mechanism", Nature Structural Biology, 8(7):593-596 (2001).

Haesslein, et al., "Recent Advances in Cyclin-Dependent Kinase Inhibition. Purine-Based Derivatives as Anti-Cancer Agents. Roles and Perspectives for the Future", Current Topics in Medicinal Chemistry, 2:1037-1050 (2002).

Heegaard, et al., "Affinity Capillary Electrophoresis: Important Application Areas and Some Recent Developments", Journal of Chromatography B, 715:29-54 (1998).

Honda, et al., "Determination of the Association Constant of Monovalent Mode Protein-Sugar Interaction by Capillary Zone Electrophoresis", Journal of Chromatography, 597:377-382 (1992).

Hu, et al., "Capillary Electrophoresis for the Analysis of Biopolymers", Anal., Chem., 74:2833-2850 (2002).

Hubbard, "Crystal Structure of the Activated Insulin Receptor Tyrosine Kinase in Complex with Peptide Substrate and ATP Analog", EMBO, 16(18):5573-5581 (1997).

Hubbard, et al., "Crystal Structure of the Tyrosine Kinase Domain of the Human Insulin Receptor", Nature, 374:746-754 (1994).

Hughes, et al., "Modulation of the Glycogen Synthase Kinase-3 Family by Tyrosine Phosphorylation", EMBO, 12(2):803-808 (1993).

Huse, et al., "Crystal Structure of the Cytoplasmic Domain of the Type TGFβ Receptor in Complex with FKBP12", Cell, 96:425-436 (1999).

Huse, et al., "The TGFβ Receptor Activation Process: An Inhibitor- to Substrate-Binding Switch", Molecular Cell, 8:671-682 (2001).

International Human Genome Sequencing Consortium, "Initial Sequencing and Analysis of the Human Genome", Nature, 409:860-921 (2001).

Jackson, et al., "N-Terminal Mutations Activate the Leukemogenic Potential of the Myristoylated form of c-abl", EMBO, 8(2):449-456 (1989).

Jackson, et al., "Pyridinylimidazole Based p38 MAP Kinase Inhibitors", Current Topics in Medicinal Chemistry, 2:1011-1020 (2002).

Jiang, et al., "Soft Docking": Matching of Molecular Surface Cubes, J. Mol. Biol., 219:79-102 (1991).

Johnson, "Circular Dichroism Spectroscopy and The Vacuum Ultraviolet Region", Ann. Rev. Phys. Chem., 29:93-114 (1978).

Johnson, "Protein Secondary Structure and Circular Dichroism: A Practical Guide", Proteins: Structure, Function, and Genetics, 7:205-214 (1990).

Kleywegt, et al., "Detection, Delineation, Measurement and Display of Cavities in Macromolecular Structures", Acta Cryst, D50:178-185 (1994).

Kuhn, et al., "The Genesis of High-Throughput Structure-Based Drug Discovery using Protein Crystallography", Analytical Techniques, Current Opinion in Chemical Biology, 6:704-710 (2002).

Kumar, et al., "P38 Map Kinases: Key Signalling Molecules as Therapeutic Targets for Inflammatory Diseases", Nature Reviews Drug Discovery, 2:717-726 (2003).

Kundrot, "Which Strategy for a Protein Crystallization Project", CMLS, Cell. Mol. Life Sci., 61:525-536 (2004).

Laskowski, "Surfnet: A Program for Visualizing Molecular Surfaces, Cavities, and Intermolecular Interactions", Journal of Molecular Graphics, 13:323-330 (1995).

Lesort, et al., "Insulin Transiently Increases Tau Phosphorylation: Involvement of Glycogen Synthase Kinase-3β and Fyn Tyrosine Kinase", Journal of Neurochemistry, 72(2):576-584 (1999).

Li, et al., "Targeting Serine/Threonine Protein Kinase B/Akt and Cell-cycle Checkpoint Kinases for Treating Cancer, Current Topics in Medicinal Chemistry, 2:939-971 (2002).

Lipinski , et al., "Experimental and Computational Approaches to Estimate Solubility and Permeability in Drug Discovery and Development Settings", Advanced Drug Delivery Reviews, 23:3-25 (1997).

Mallakpour, et al., "Uncatalyzed Polymerization of Bistriazolinediones with Electron-Rich Aromatic Compounds via Electrophilic Aromatic Substitution", Journal of Polymer Science: Part A: Polymer Chemistry, 27:217-235 (1989).

March's Advanced Organic Chemistry: Reactions, Mechanisms, and Structure, Fifth Edition, Smith and March Editors, Wiley-Interscience Publication (2001) (4 pages).

Mattsson, et al., "Six X-Linked Agammaglobulinemia-Causing Missense Mutations in the Src Homology 2 Domain of Bruton's Tyrosine Kinase: Phosphotyrosine-Binding and Circular Dichroism Analysis", Journal of Immunology, pp. 4170-4177 (2000).

Mcpherson, "Current Approaches to Macromolecular Crystallization", Eur. J. Biochem, 189:1-23 (1990).

Morris, et al., "Automated Docking of Flexible Ligands to Macromolecules", AutoDock Website, www.scripps.edu/mb/olson/doc/autodock/, printed Mar. 3, 2005 (3 pages).

Morris, et al., "Automated Docking Using a Lamarckian Genetic Algorithm and an Empirical Binding Free Energy Function", Journal of Computational Chemistry, 19(14):1639-1662 (1998).

Murayama, et al., "JNK (c-Jun $NH_2$ Terminal Kinase) and p38 During Ischemia Reperfusion Injury in the Small Intestine" Transplantation, 81(9):1325-1330 (2006).

Nagar, et al., "Crystal Structures of the Kinase Domain of c-Abl in Complex with the Small Molecule Inhibitors PD173955 and Imatinib (STI-571)", Cancer Research, 62:4236-4243 (2002).

Nagar, et al., "Structural Basis for the Autoinhibition of c-Abl Tyrosine Kinase", Cell, 112:859- 871 (2003).

O'Neill, "Targeting Signal Transduction as a Strategy to Treat Inflammatory Diseases", Nature Review Drug Discovery, Published Online 9 Jun. 2006, www.nature.com/reviews/drugdisc (15 pages).

Okishio, et al., "Differential Ligand Recognition by the Src and Phosphatidylinositol 3-Kinase Src Homology 3 Domains: Circular Dichroism and Ultraviolet Resonance Raman Studies", Biochemistry, 42:208-216 (2003).

Okishio, et al., "Identification of Tyrosine Residues Involved in Ligand Recognition by the Phosphatidylinositol 3-Kinase Src Homology 3 Domain: Circular Dichroism and UV Resonance Raman Studies", Biochemistry, 40:15797-15804 (2001).

Okishio, et al., "Role of the Conserved Acidic Residue Asp21 in the Structure of Phosphatidylinositol 3-Kinase Src Homolgy 3 Domain: Circular Dichroism and Nuclear Magnetic Resonance Studies", Biochemistry 40:119-129 (2001).

Parang, et al., "Mechanism-based Design of a Protein Kinase Inhibitor", Nature Structural Biology, 8(1):37-41 (2001).

Pearlman, et al., "Assisted Model Building with Energy Refinement", Amber Home Page, amber.scripts.edu (9 pages).

Raimbault, et al., "Effects of pH and KCl on the Conformations of Creatine Kinase from Rabbit Muscle", Eur. J. Biochem., 234:570-578 (1995).

Reed, et al., "Circular Dichroic Evidence for an Ordered Sequence Ligand/Binding Site Interactions in the Catalytic Reaction of the cAMP-Dependent Protein Kinase", Biochemistry, 24:2967-2973 (1985).

Regan, et al., "Structure-Activity Relationships of the p38α MAP Kinase Inhibitor 1-(5-tertButyl-2-p-tolyl-2H-pyrazol-3-yl)-344-(2-morpholin-4-yl-ethoxy)naph-thalen-1-yl]urea (BIRB 796)", J. Med. Chem., 46:4676-4686 (2003).

Roux, et al., "ERK and p38 MAPK-Activated Protein Kinases: A Family of Protein Kinases with Diverse Biological Functions", Microbiology and Molecular Biology Reviews, 68(2):320-344 (2004).

Shah, et al., "Circular Dichroic Studies of Protein Kinase C and its Interactions with Calcium and Lipid Vesicles", Biochimica et Biophysica Acta, 1119:19-26(1992).

Shiozaki, et al., "Impaired Differentiation of Endocrine and Exocrine Cells of the Pancreas in Transgenic Mouse Expressing the Truncated Type II Activin Receptor", Biochimica et Biophysica Acta, 1450:1-11 (1999).

Stout, et al., "High-Throughput Structural Biology in Drug Discovery: Protein Kinases", Current Pharmaceutical Design, 10:1069-1082 (2004).

Sugden, et al., ""Stress-Responsive" Mitogen-Activated Protein Kinases (c-Jun N-Terminal Kinases and p38 Mitogen-Activated Protein Kinases) in the Myocardium", Circulation Research - Journal of the American Heart Association, 83:345-352 (1998).

Tanis, et al., "Two Distinct Phosphorylation Pathways Have Additive Effects on Abl Family Kinase Activation", Molecular and Cellular Biology, 23(11):3884-3896 (2003).

Tominaga, et al., "General model for Estimation of the Inhibition of Protein Kinases Using Monte Carlo Simulations", J. Med. Chem., 47:2534-2549 (2004).

Waetzig, et al., "Review Article: Mitogen-Activated Protein Kinases in Chronic Intestinal Inflammation - Targeting Ancient Pathways to Treat Modern Diseases", Aliment Pharmacol Ther, 18:17-32 (2003).

Wan, et al., "Mechanism of Activation of the RAF-ERK Signaling Pathway by Oncogenic Mutations of B-RAF", Cell, 116:855-867 (2004).

Welker, et al., "Glucocorticoid-Induced Modulation of Cytokine Secretion from Normal and Leukemic Human Myelomonocytic Cells", Int. Arch. Allergy Immunol, 109:110-115 (1996).

Wilson, et al Structural Basis for the Specificity of Pyridinylimidazole Inhibitors of p38 Map Kinase", Chemistry & Biology, 4(6):423-431 (1997).

Wrana, et al., "Mechanism of Activation of the TGF-β Receptor", Nature, 370:341-347 (1994).

Yang, et al., "Molecular Mechanism for the Regulation of Protein Kinase B/Akt by Hydrophobic Motif Phosphorylation", Molecular Cell, 9:1227-1240 (2002).

Zinner, et al., "Zur Weiteren Kenntnis Bicyclischer 3.5-Dioxopyrazolidine", Die Pharmazie, 25(5):309-312 (1970)—German Language.

* cited by examiner

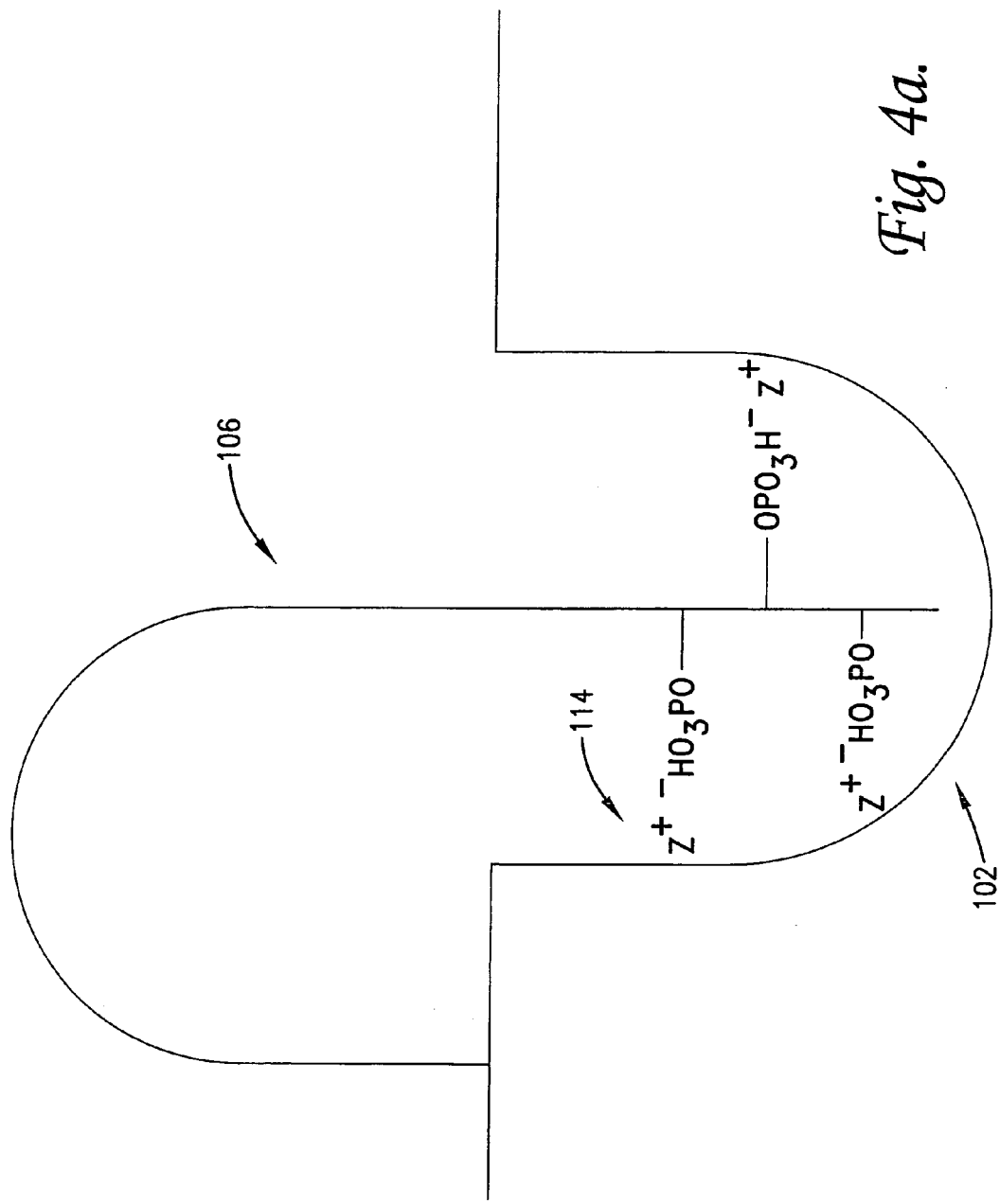

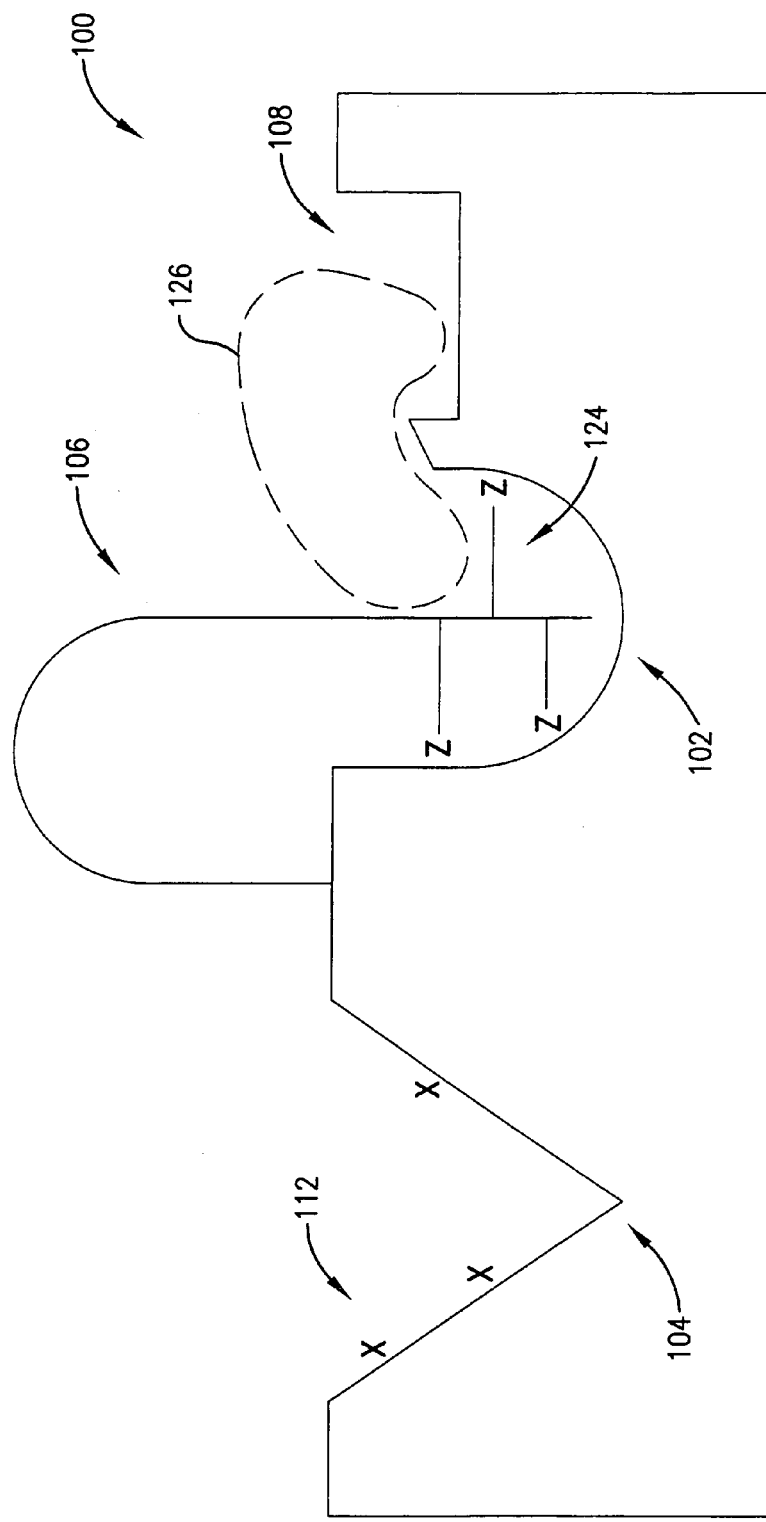

SEQUENCE LISTING

```
<160> NUMBER OF SEQ ID NOS: 6

<210> SEQ ID NO 1
<211> LENGTH: 360
<212> TYPE: PRT
<213> ORGANISM: Homo sapiens

<400> SEQUENCE: 1

Met Ser Gln Glu Arg Pro Thr Phe Tyr Arg Gln Glu Leu Asn Lys Thr
1               5                   10                  15

Ile Trp Glu Val Pro Glu Arg Tyr Gln Asn Leu Ser Pro Val Gly Ser
            20                  25                  30

Gly Ala Tyr Gly Ser Val Cys Ala Ala Phe Asp Thr Lys Thr Gly Leu
        35                  40                  45

Arg Val Ala Val Lys Lys Leu Ser Arg Pro Phe Gln Ser Ile Ile His
    50                  55                  60

Ala Lys Arg Thr Tyr Arg Glu Leu Arg Leu Leu Lys His Met Lys His
65                  70                  75                  80

Glu Asn Val Ile Gly Leu Leu Asp Val Phe Thr Pro Ala Arg Ser Leu
                85                  90                  95

Glu Glu Phe Asn Asp Val Tyr Leu Val Thr His Leu Met Gly Ala Asp
            100                 105                 110

Leu Asn Asn Ile Val Lys Cys Gln Lys Leu Thr Asp Asp His Val Gln
        115                 120                 125

Phe Leu Ile Tyr Gln Ile Leu Arg Gly Leu Lys Tyr Ile His Ser Ala
    130                 135                 140

Asp Ile Ile His Arg Asp Leu Lys Pro Ser Asn Leu Ala Val Asn Glu
145                 150                 155                 160

Asp Cys Glu Leu Lys Ile Leu Asp Phe Gly Leu Ala Arg His Thr Asp
                165                 170                 175

Asp Glu Met Thr Gly Tyr Val Ala Thr Arg Trp Tyr Arg Ala Pro Glu
            180                 185                 190
```

```
Ile Met Leu Asn Trp Met His Tyr Asn Gln Thr Val Asp Ile Trp Ser
        195                 200                 205

Val Gly Cys Ile Met Ala Glu Leu Leu Thr Gly Arg Thr Leu Phe Pro
    210                 215                 220

Gly Thr Asp His Ile Asp Gln Leu Lys Leu Ile Leu Arg Leu Val Gly
225                 230                 235                 240

Thr Pro Gly Ala Glu Leu Leu Lys Lys Ile Ser Ser Glu Ser Ala Arg
                245                 250                 255

Asn Tyr Ile Gln Ser Leu Thr Gln Met Pro Lys Met Asn Phe Ala Asn
                260                 265                 270

Val Phe Ile Gly Ala Asn Pro Leu Ala Val Asp Leu Leu Glu Lys Met
            275                 280                 285

Leu Val Leu Asp Ser Asp Lys Arg Ile Thr Ala Ala Gln Ala Leu Ala
        290                 295                 300

His Ala Tyr Phe Ala Gln Tyr His Asp Pro Asp Asp Glu Pro Val Ala
305                 310                 315                 320

Asp Pro Tyr Asp Gln Ser Phe Glu Ser Arg Asp Leu Leu Ile Asp Glu
                325                 330                 335

Trp Lys Ser Leu Thr Tyr Asp Glu Val Ile Ser Phe Val Pro Pro Pro
            340                 345                 350

Leu Asp Gln Glu Glu Met Glu Ser
        355                 360

<210> SEQ ID NO 2
<211> LENGTH: 17
<212> TYPE: PRT
<213> ORGANISM: Homo sapiens
<220> FEATURE:
<221> NAME/KEY: MISC_FEATURE
<222> LOCATION: (2)..(16)
<223> OTHER INFORMATION: X is any amino acid

<400> SEQUENCE: 2

Ile Ile Xaa Xaa Lys Arg Xaa Xaa Arg Glu Xaa Xaa Leu Leu Xaa Xaa
1               5                   10                  15
Met

<210> SEQ ID NO 3
<211> LENGTH: 6
<212> TYPE: PRT
<213> ORGANISM: Homo sapiens

<400> SEQUENCE: 3

Asp Ile Ile His Arg Asp
1               5

<210> SEQ ID NO 4
<211> LENGTH: 10
<212> TYPE: PRT
<213> ORGANISM: Homo sapiens

<400> SEQUENCE: 4

Asp Phe Gly Leu Ala Arg His Thr Asp Asp
1               5                   10

<210> SEQ ID NO 5
<211> LENGTH: 12
<212> TYPE: PRT
<213> ORGANISM: Homo sapiens

<400> SEQUENCE: 5
```

```
Glu Met Thr Gly Tyr Val Ala Thr Arg Trp Tyr Arg
1               5                   10
```

<210> SEQ ID NO 6
<211> LENGTH: 4
<212> TYPE: PRT
<213> ORGANISM: Homo sapiens

<400> SEQUENCE: 6

```
Trp Met His Tyr
1
```

ANTI-INFLAMMATORY MEDICAMENTS

RELATED APPLICATIONS

This application claims the benefit of U.S. patent application Ser. No. 10/746,460 filed Dec. 24, 2003, provisional applications entitled Process For MODULATING PROTEIN FUNCTION, Ser. No. 60/437,487 filed Dec. 31, 2002, ANTI-CANCER MEDICAMENTS, Ser. No. 60/437,403 filed Dec. 31, 2002, ANTI-INFLAMMATORY MEDICAMENTS, Ser. No. 60/437,415 filed Dec. 31, 2002, ANTI-INFLAMMATORY MEDICAMENTS, Ser. No. 60/437,304 filed Dec. 31, 2002, and MEDICAMENTS FOR THE TREATMENT OF NEURODEGENERATIVE DISORDERS OR DIABETES, Ser. No. 60/463,804 filed Apr. 18, 2003. Each of these applications is incorporated by reference herein.

BACKGROUND OF THE INVENTION

1. Sequence Listing

The following application contains a sequence listing in computer readable format (CRF), submitted as a text file entitled "34477.ST25," created on Jul. 26, 2006, as 4.17 KB. The content of the CRF is hereby incorporated by reference.

2. Field of the Invention

The present invention relates to novel compounds and methods of using those compounds to treat anti-inflammatory diseases.

3. Description of the Prior Art

Basic research has recently provided the life sciences community with an unprecedented volume of information on the human genetic code and the proteins that are produced by it. In 2001, the complete sequence of the human genome was reported (Lander, E. S. et al. Initial sequencing and analysis of the human genome. *Nature* (2001) 409:860; Venter, J. C. et al. The sequence of the human genome. *Science* (2001) 291: 1304). Increasingly, the global research community is now classifying the 50,000+ proteins that are encoded by this genetic sequence, and more importantly, it is attempting to identify those proteins that are causative of major, under-treated human diseases.

Despite the wealth of information that the human genome and its proteins are providing, particularly in the area of conformational control of protein function, the methodology and strategy by which the pharmaceutical industry sets about to develop small molecule therapeutics has not significantly advanced beyond using native protein active sites for binding to small molecule therapeutic agents. These native active sites are normally used by proteins to perform essential cellular functions by binding to and processing natural substrates or transducing signals from natural ligands. Because these native pockets are used broadly by many other proteins within protein families, drugs which interact with them are often plagued by lack of selectivity and, as a consequence, insufficient therapeutic windows to achieve maximum efficacy. Side effects and toxicities are revealed in such small molecules, either during preclinical discovery, clinical trials, or later in the marketplace. Side effects and toxicities continue to be a major reason for the high attrition rate seen within the drug development process. For the kinase protein family of proteins, interactions at these native active sites have been recently reviewed: see J. Dumas, Protein Kinase Inhibitors: Emerging Pharmacophores 1997-2001, *Expert Opinion on Therapeutic Patents* (2001) 11:405-429; J. Dumas, Editor, New challenges in Protein Kinase Inhibition, in *Current Topics in Medicinal Chemistry* (2002) 2: issue 9.

It is known that proteins are flexible, and this flexibility has been reported and utilized with the discovery of the small molecules which bind to alternative, flexible active sites with proteins. For review of this topic, see Teague, *Nature Reviews/Drug Discovery*, Vol. 2, pp. 527-541 (2003). See also, Wu et al., *Structure*, Vol. 11, pp. 399-410 (2003). However these reports focus on small molecules which bind only to proteins at the protein natural active sites. Peng et al., *Bio. Organic and Medicinal Chemistry Ltrs.*, Vol. 13, pp. 3693-3699 (2003), and Schindler, et al., *Science*, Vol. 289, p. 1938 (2000) describe inhibitors of abl kinase. These inhibitors are identified in WO Publication No. 2002/034727. This class of inhibitors binds to the ATP active site while also binding in a mode that induces movement of the kinase catalytic loop. Pargellis et al., *Nature Structural Biology*, Vol. 9, p. 268 (2002) reported inhibitors p38 alpha-kinase also disclosed in WO Publication No. 00/43384 and Regan et al., *J. Medicinal Chemistry*, Vol. 45, pp. 2994-3008 (2002). This class of inhibitors also interacts with the kinase at the ATP active site involving a concomitant movement of the kinase activation loop.

More recently, it has been disclosed that kinases utilize activation loops and kinase domain regulatory pockets to control their state of catalytic activity. This has been recently reviewed (see, e.g., M. Huse and J. Kuriyan, *Cell* (2002) 109:275).

SUMMARY OF THE INVENTION

The present invention is broadly concerned with new compounds for use in treating anti-inflammatory conditions and methods of treating such conditions. In more detail, the inventive compounds have the formula

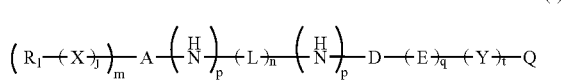

(I)

wherein:

$R^1$ is selected from the group consisting of aryls (preferably $C_6$-$C_{18}$, and more preferably $C_6$-$C_{12}$) and heteroaryls;

each X and Y is individually selected from the group consisting of —O—, —S—, —$NR_6$—, —$NR_6SO_2$—, —$NR_6CO$—, alkynyls (preferably $C_1$-$C_{18}$, and more preferably $C_1$-$C_{12}$), alkenyls (preferably $C_1$-$C_{18}$, and more preferably $C_1$-$C_{12}$), alkylenes (preferably $C_1$-$C_{18}$, and more preferably $C_1$-$C_{12}$), —O(CH$_2$)$_h$—, and —NR$_6$(CH$_2$)$_h$—, where each h is individually selected from the group consisting of 1, 2, 3, or 4, and where for each of alkylenes (preferably $C_1$-$C_{18}$, and more preferably $C_1$-$C_{12}$), —O(CH$_2$)$_h$—, and —NR$_6$(CH$_2$)$_h$—, one of the methylene groups present therein may be optionally double-bonded to a side-chain oxo group except that where —O(CH$_2$)$_h$— the introduction of the side-chain oxo group does not form an ester moiety;

A is selected from the group consisting of aromatic (preferably $C_6$-$C_{18}$, and more preferably $C_6$-$C_{12}$), monocycloheterocyclic, and bicycloheterocyclic rings;

D is phenyl or a five- or six-membered heterocyclic ring selected from the group consisting of pyrazolyl, pyrrolyl, imidazolyl, oxazolyl, thiazolyl, furyl, pyridyl, and pyrimidyl;

E is selected from the group consisting of phenyl, pyridinyl, and pyrimidinyl;
L is selected from the group consisting of —C(O)— and —S(O)$_2$—;
j is 0 or 1;
m is 0 or 1;
n is 0 or 1;
p is 0 or 1;
q is 0 or 1;
t is 0 or 1;
Q is selected from the group consisting of
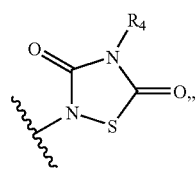
Q-1
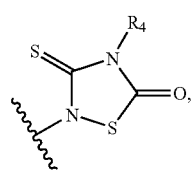
Q-2
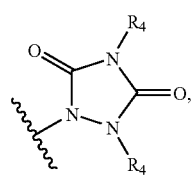
Q-3
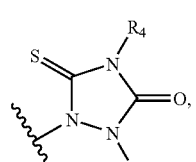
Q-4
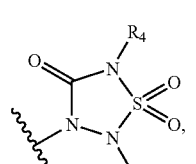
Q-4
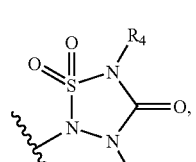
Q-6
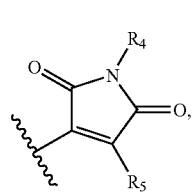
Q-7
-continued
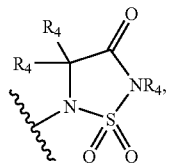
Q-8
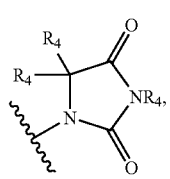
Q-9
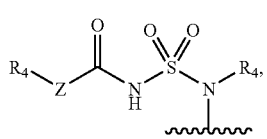
Q-10
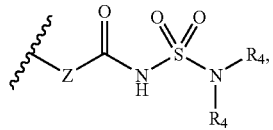
Q-11
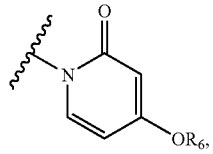
Q-12
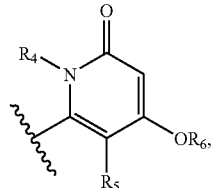
Q-13
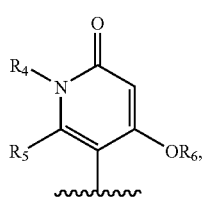
Q-14
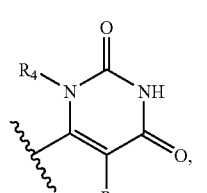
Q-15
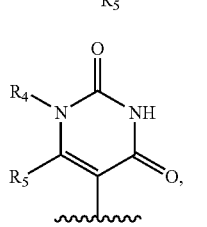
Q-16

-continued
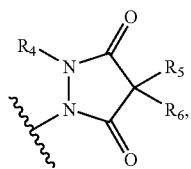 Q-17
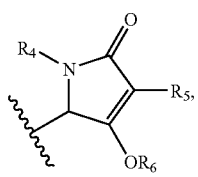 Q-18
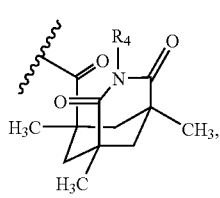 Q-19
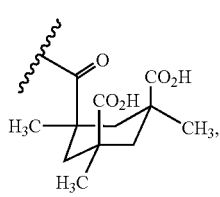 Q-20
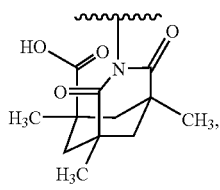 Q-21
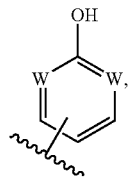 Q-22
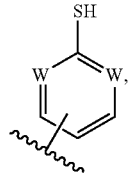 Q-23
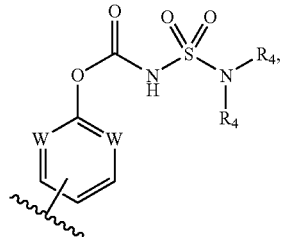 Q-24
-continued
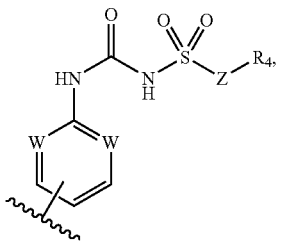 Q-25
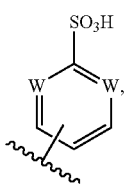 Q-26
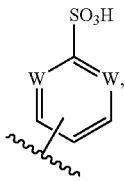 Q-27
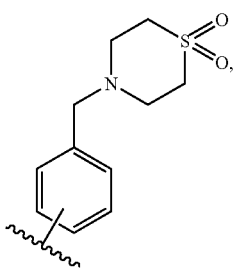 Q-28
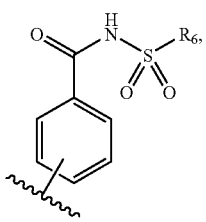 Q-29
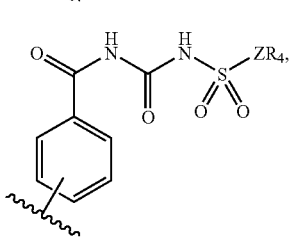 Q-30
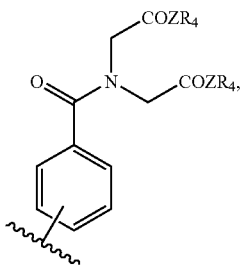 Q-31
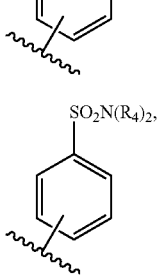

-continued

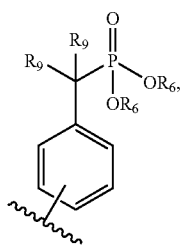
Q-32

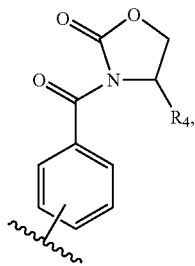
Q-33

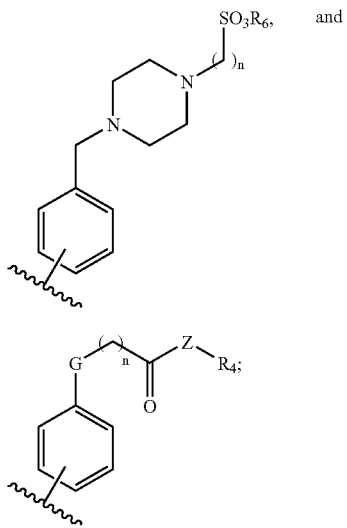
A-34 and Q-35 each $R_4$ group is individually selected from the group consisting of —H, alkyls (preferably $C_1$-$C_{18}$, and more preferably $C_1$-$C_{12}$), aminoalkyls (preferably $C_1$-$C_{18}$, and more preferably $C_1$-$C_{12}$), alkoxyalkyls (preferably $C_1$-$C_{18}$, and more preferably $C_1$-$C_{12}$), aryls (preferably $C_6$-$C_{18}$, and more preferably $C_6$-$C_{12}$), aralkyls (preferably $C_6$-$C_{18}$, and more preferably $C_6$-$C_{12}$ and preferably $C_1$-$C_{18}$, and more preferably $C_1$-$C_{12}$), heterocyclyls, and heterocyclylalkyls except when the $R_4$ substituent places a heteroatom on an alpha-carbon directly attached to a ring nitrogen on Q;

when two $R_4$ groups are bonded with the same atom, the two $R_4$ groups optionally form an alicyclic or heterocyclic 4-7 membered ring;

each $R_5$ is individually selected from the group consisting of —H, alkyls (preferably $C_1$-$C_{18}$, and more preferably $C_1$-$C_{12}$), aryls (preferably $C_6$-$C_{18}$, and more preferably $C_6$-$C_{12}$), heterocyclyls, alkylaminos (preferably $C_1$-$C_{18}$, and more preferably $C_1$-$C_{12}$), arylaminos (preferably $C_6$-$C_{18}$, and more preferably $C_6$-$C_{12}$), cycloalkylaminos (preferably $C_1$-$C_{18}$, and more preferably $C_1$-$C_{12}$), heterocyclylaminos, hydroxys, alkoxys (preferably $C_1$-$C_{18}$, and more preferably $C_1$-$C_{12}$), aryloxys (preferably $C_6$-$C_{18}$, and more preferably $C_6$-$C_{12}$), alkylthios (preferably $C_1$-$C_{18}$, and more preferably $C_1$-$C_{12}$), arylthios (preferably $C_6$-$C_{18}$, and more preferably $C_6$-$C_{12}$), cyanos, halogens, perfluoroalkyls (preferably $C_1$-$C_{18}$, and more preferably $C_1$-$C_{12}$), alkylcarbonyls (preferably $C_1$-$C_{18}$, and more preferably $C_1$-$C_{12}$), and nitros;

each $R_6$ is individually selected from the group consisting of —H, alkyls (preferably $C_1$-$C_{18}$, and more preferably $C_1$-$C_{12}$), allyls, and β-trimethylsilylethyl;

each $R_8$ is individually selected from the group consisting of alkyls (preferably $C_1$-$C_{18}$, and more preferably $C_1$-$C_{12}$), aralkyls (preferably $C_6$-$C_{18}$, and more preferably $C_6$-$C_{12}$) preferably $C_1$-$C_{18}$, and more preferably $C_1$-$C_{12}$), heterocyclyls, and heterocyclylalkyls (preferably $C_1$-$C_{18}$, and more preferably $C_1$-$C_{12}$);

each $R_9$ group is individually selected from the group consisting of —H, —F, and alkyls (preferably $C_1$-$C_{18}$, and more preferably $C_1$-$C_{12}$), wherein when two $R_9$ groups are geminal alkyl groups, said geminal alkyl groups may be cyclized to form a 3-6 membered ring;

each Z is individually selected from the group consisting of —O— and —N($R_4$)—; and each ring of formula (I) optionally includes one or more of $R_7$, where $R_7$ is a noninterfering substituent individually selected from the group consisting of —H, alkyls (preferably $C_1$-$C_{18}$, and more preferably $C_1$-$C_{12}$), aryls (preferably $C_6$-$C_{18}$, and more preferably $C_6$-$C_{12}$), heterocyclyls, alkylaminos (preferably $C_1$-$C_{18}$, and more preferably $C_1$-$C_{12}$), arylaminos (preferably $C_6$-$C_{18}$, and more preferably $C_6$-$C_{12}$), cycloalkylaminos (preferably $C_1$-$C_{18}$, and more preferably $C_1$-$C_{12}$), heterocyclylaminos, hydroxys, alkoxys (preferably $C_1$-$C_{18}$, and more preferably $C_1$-$C_{12}$), aryloxys (preferably $C_6$-$C_{18}$, and more preferably $C_6$-$C_{12}$), alkylthios (preferably $C_1$-$C_{18}$, and more preferably $C_1$-$C_{12}$), arthylthios, cyanos, halogens, nitrilos, nitros, alkylsulfinyls (preferably $C_1$-$C_{18}$, and more preferably $C_1$-$C_{12}$), alkylsulfonyls (preferably $C_1$-$C_{18}$, and more preferably $C_1$-$C_{12}$), aminosulfonyls, and perfluoroalkyls (preferably $C_1$-$C_{18}$, and more preferably $C_1$-$C_{12}$).

In one preferred embodiment, the compound has the structure of formula (I) except that:

when Q is Q-3 or Q-4, then the compound of formula (I) is not

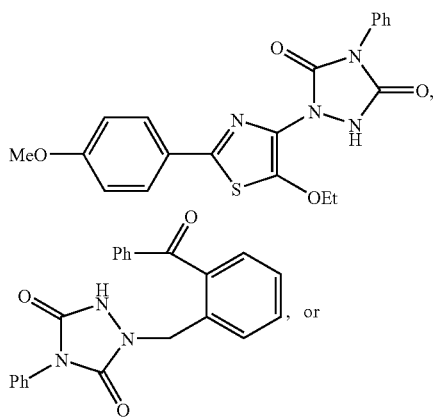

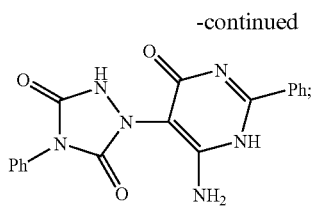

when Q is Q-7, q is 0, and R₅ and D are phenyl, then A is not phenyl, oxazolyl, pyridyl, pyrimidyl, pyrazolyl, or imidazolyl;

when Q is Q-7, R₅ is —OH, Y is —O—, —S—, or —CO—, m is 0, n is 0, p is 0, and A is phenyl, pyridyl, or thiazolyl, then D is not thienyl, thiazolyl, or phenyl;

when Q is Q-7, R₅ is —OH, m is 0, n is 0, p is 0, t is 0, and A is phenyl, pyridyl, or thiazolyl, then D is not thienyl, thiazolyl, or phenyl;

when Q is Q-7, then the compound of formula (I) is not

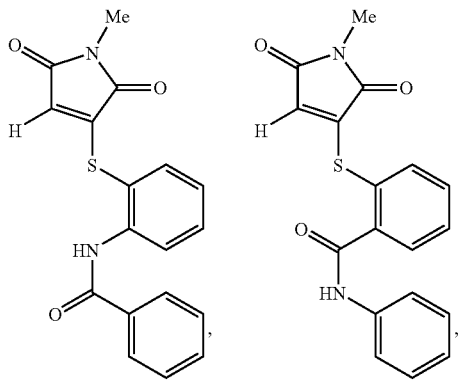

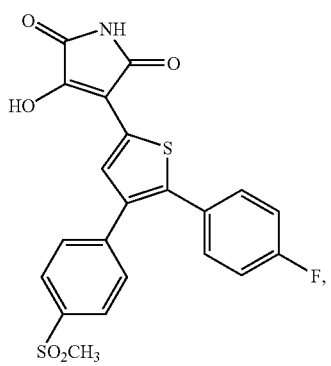

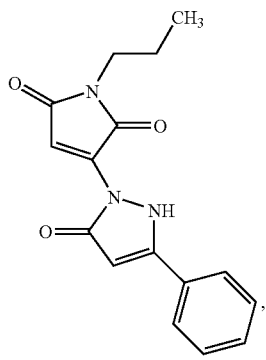

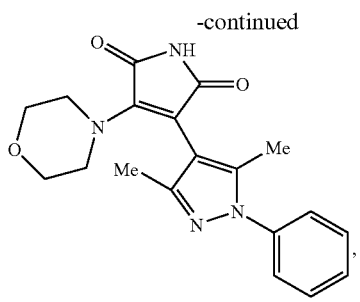

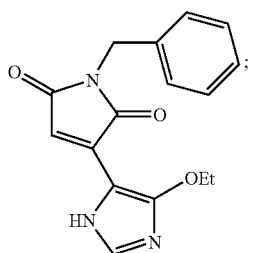

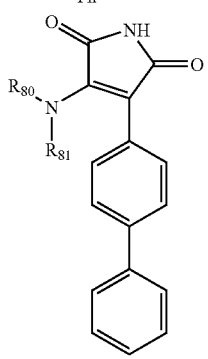

R80 is H, Me
R81 is substituted phenyl

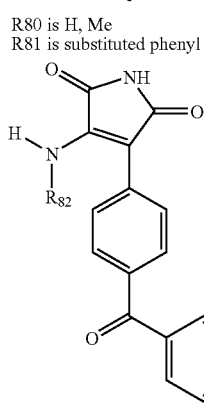

R82 is substituted phenyl when Q is Q-8, then Y is not —CH₂O—;
when Q is Q-8, the compound of formula (I) is not

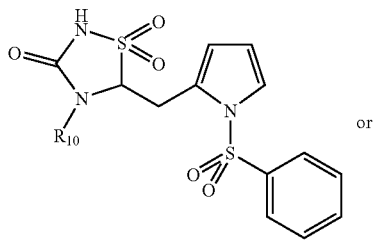

or

-continued

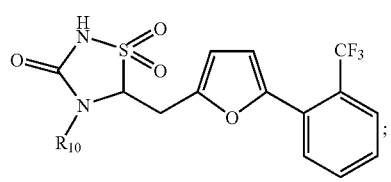

R$_{10}$=alkyl, aryl, arylalkoxyalkyl, or arylalkyls
when Q is Q-9, then the compound of formula (I) is not

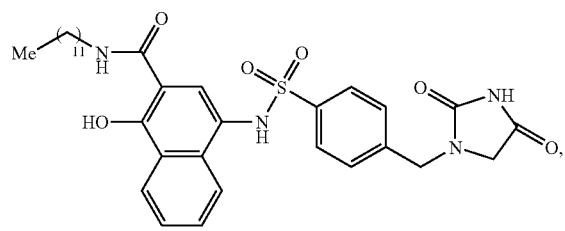

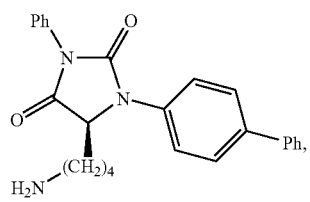

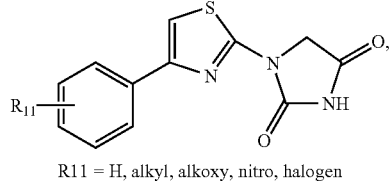

R11 = H, alkyl, alkoxy, nitro, halogen

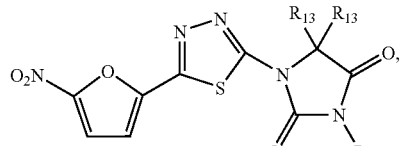

R12, R13 = H, alkyl

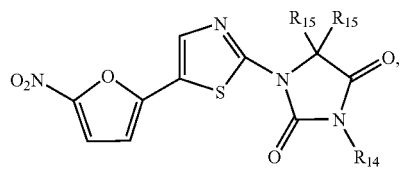

R14 = H, alkyl, allyl, propargyl
R15 = H, alkyl,

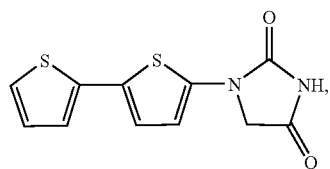

-continued

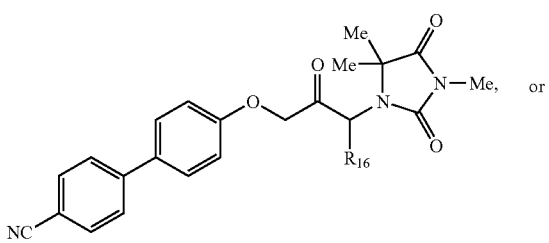

R16 = H, methyl

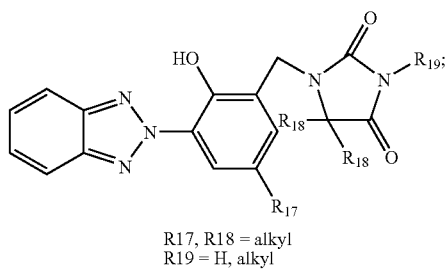

R17, R18 = alkyl
R19 = H, alkyl when Q is Q-10, t is 0, and E is phenyl, then any R$_7$ on E is not an o-alkoxy;
when Q is Q-10, then the compound of formula (I) is not

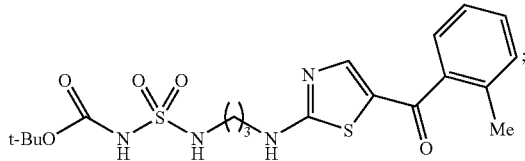

when Q is Q-11, t is 0, and E is phenyl, then any R$_7$ on E is not an o-alkoxy;
when Q is Q-11, then the compound of formula (I) is not

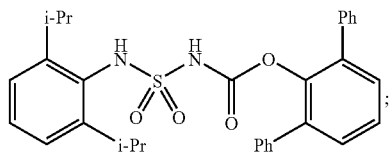

when Q is Q-15, then the compound of formula (I) is not

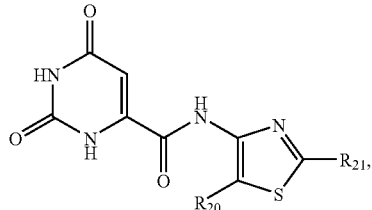

-continued

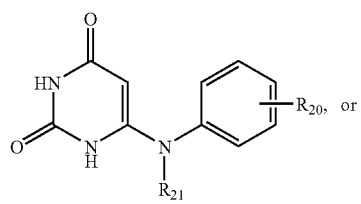

$R_{20}$ = substituted phenyl, $R_{21}$ = H, alkyl when Q is Q-16 and Y is —NH—, then

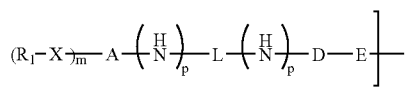

of formula (I) is not biphenyl;
when Q is Q-16 and Y is —S—, then

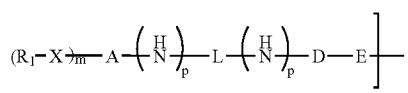

of formula (I) is not phenylsulfonylaminophenyl or phenylcarbonylaminophenyl;
when Q is Q-16 and Y is —SO$_2$NH—, then the compound of formula (I) is not

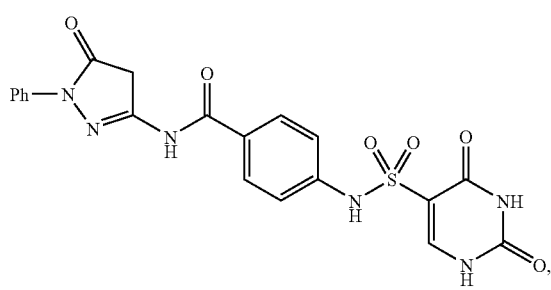

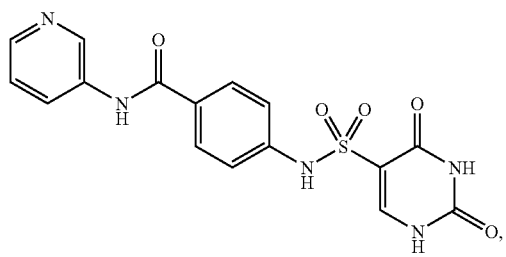

-continued

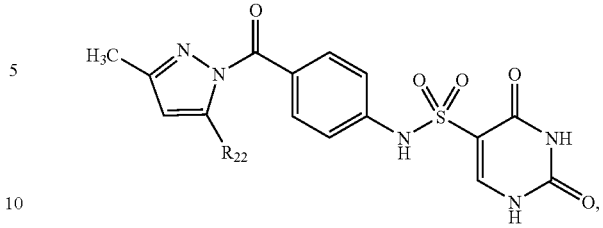

$R_{22}$ = Me, OH

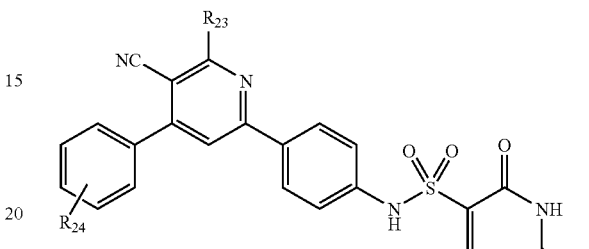

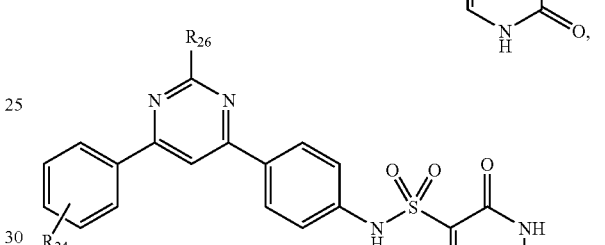

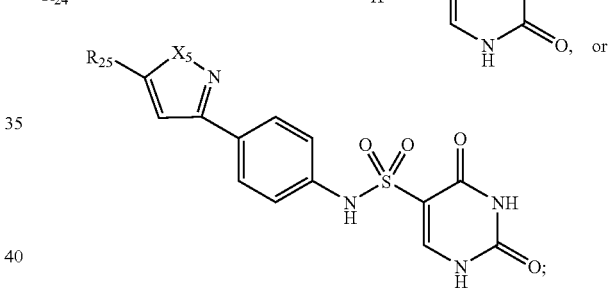

when Q is Q-16 and $R_{23}$ = OH, SH, NH2
$R_{24}$ = hydrogen or one or more methoxy, hydroxy, fluoro, chloro, nitro, dimethylamino, or furanyl
$R_{25}$ = substituted phenyl, furanyl
$R_{26}$ = OH or Cl
$X_5$ = O, NH;

Y is —CONH—, then

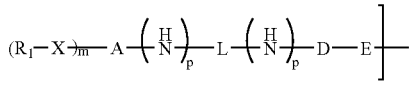

of formula (I) is not imidazophenyl;
when Q is Q-16 and Y is —CONH—, then the compound of formula (I) is not

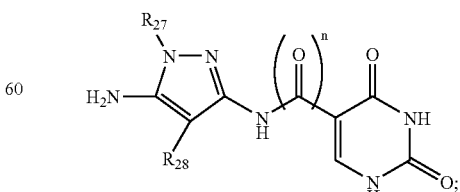

$R_{27}$ = substituted phenyl, pyridylcarbonyl
$R_{28}$ = CN, methoxycarbonyl
n = 0 or 1 when Q is Q-16 and t is 0, then

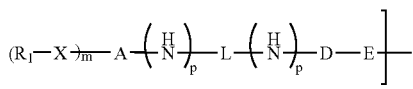

of formula (I) is not phenylcarbonylphenyl, pyrimidophenyl, phenylpyrimidyl, pyrimidyl, or N-pyrolyl;
when Q is Q-17, then the compound of formula (I) is not

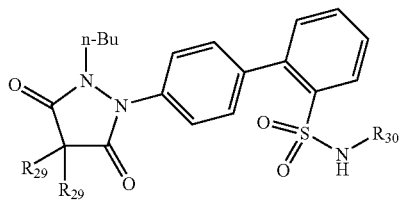

$R_{29}$ = alkyl
$R_{30}$ = H, t-Bu, benzoyl

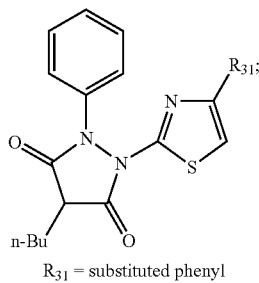

$R_{31}$ = substituted phenyl when Q is Q-21, then the compound of formula (I) is not

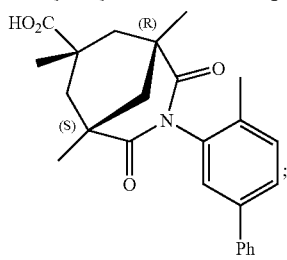

when Q is Q-22, then the compound of formula (I) is selected from the group consisting of

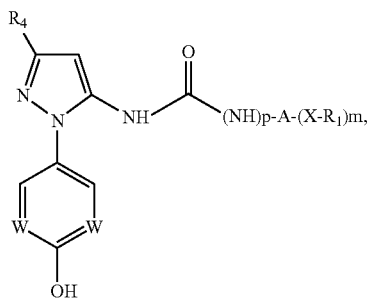

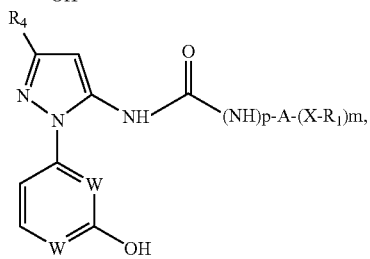

-continued

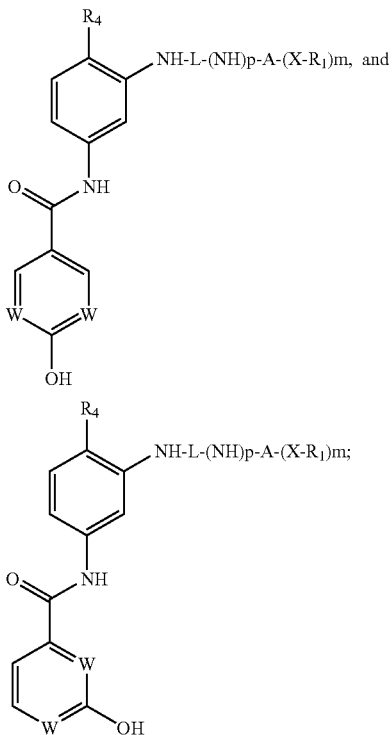

when Q is Q-22 and q is 0, then the compound of formula (I) is selected from the group consisting of

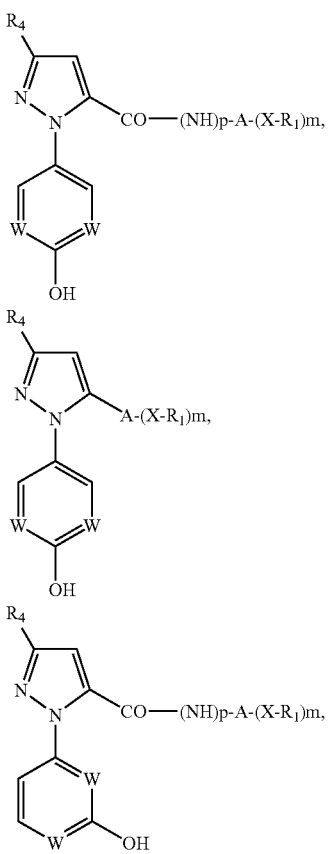

-continued
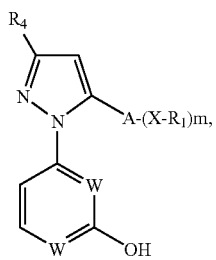
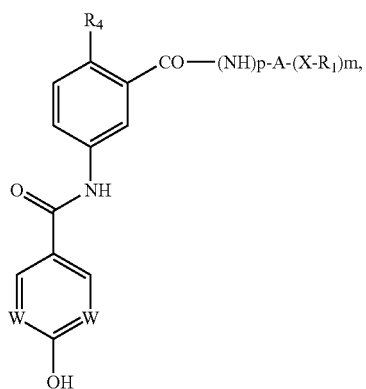
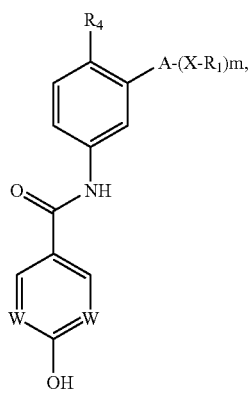
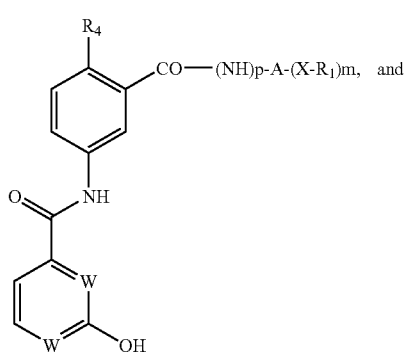 and
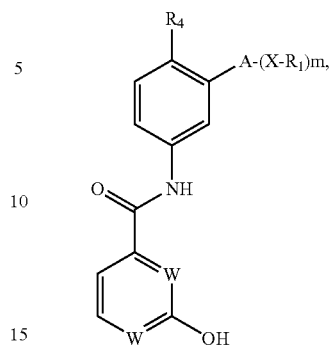
but excluding
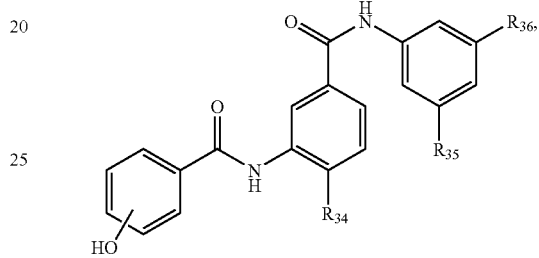
meta or para-
R34 = Me, Cl
R35 = —N(Me)2, morpholino
R36 = H, F
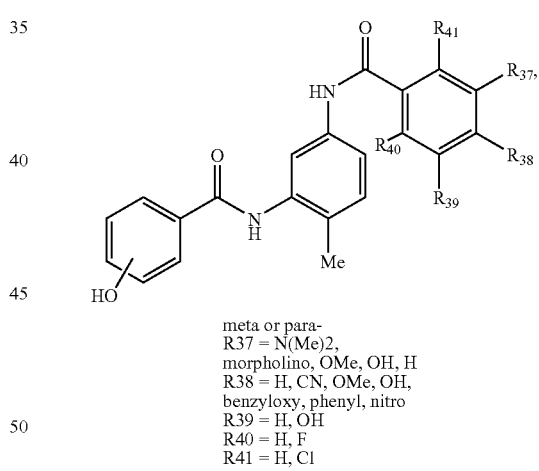
meta or para-
R37 = N(Me)2, morpholino, OMe, OH, H
R38 = H, CN, OMe, OH, benzyloxy, phenyl, nitro
R39 = H, OH
R40 = H, F
R41 = H, Cl
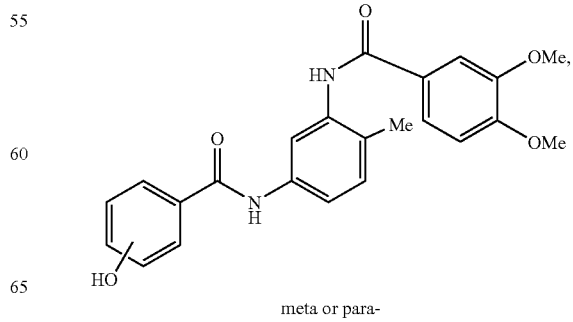
meta or para- -continued
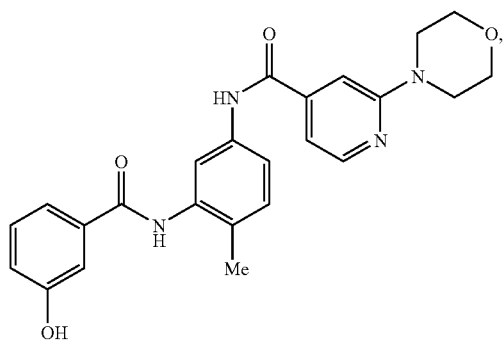
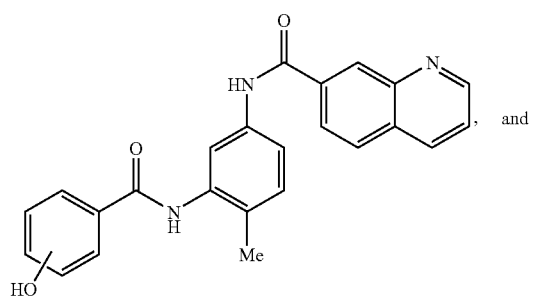
meta or para-
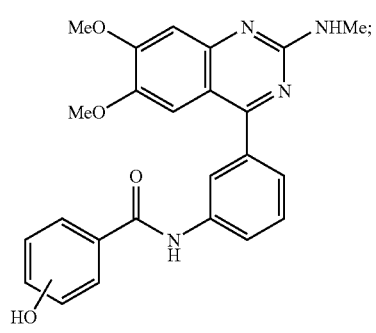
meta or para-
when Q is Q-23, then the compound of formula (I) is not
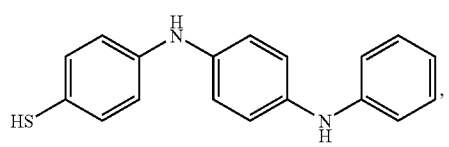
R₄₂ = H, Me
-continued
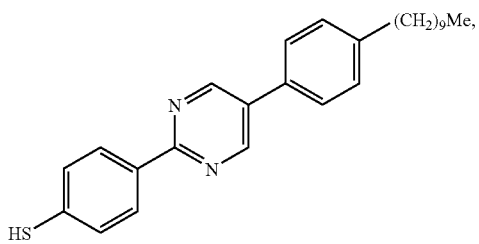
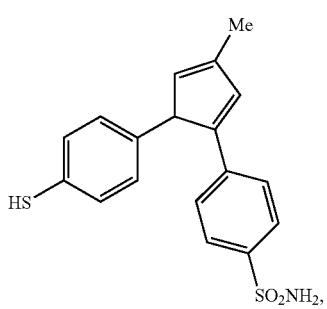
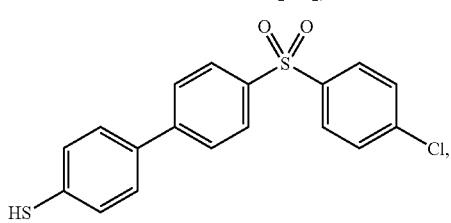
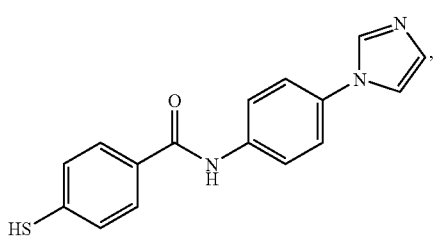
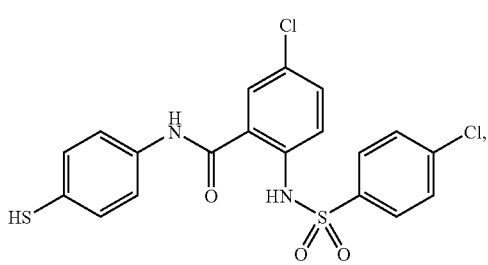
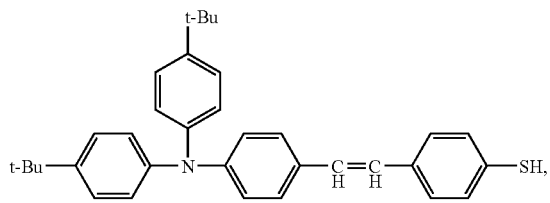
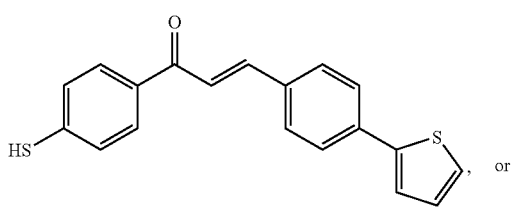, or

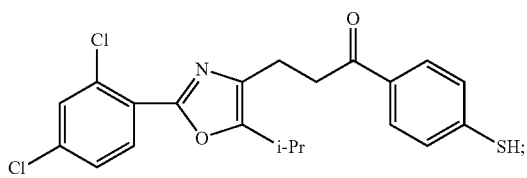
when Q is Q-24, Q-25, Q-26, or Q-31, then the compound of formula (I) is selected from the group consisting of
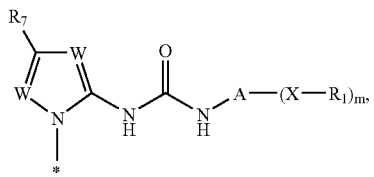
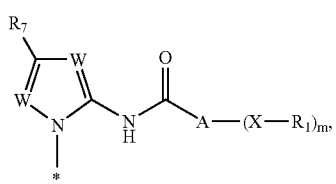
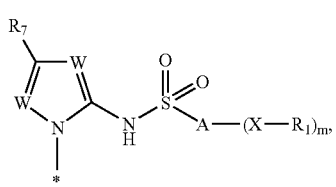
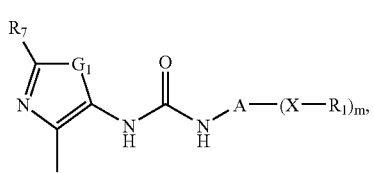
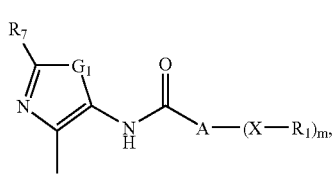
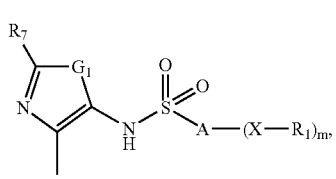
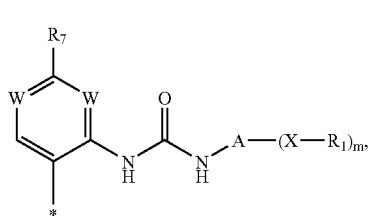
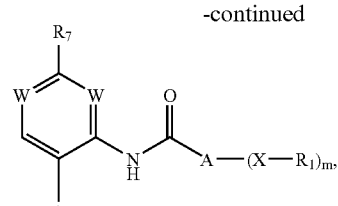
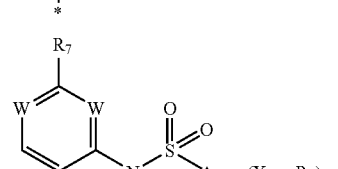
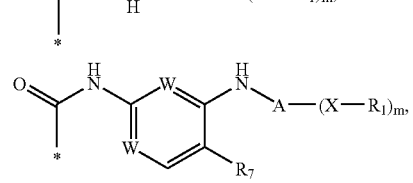
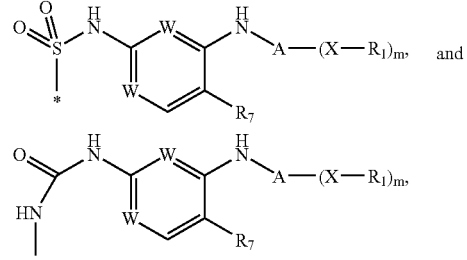
wherein each W is individually selected from the group consisting of —CH— and —N—;
each $G_1$ is individually selected from the group consisting of —O—, —S—, and —N($R_4$)—; and
* denotes the point of attachment to Q-24, Q-25, Q-26, or Q-31 as follows:
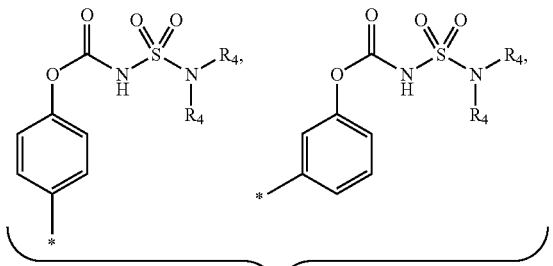
Q-24
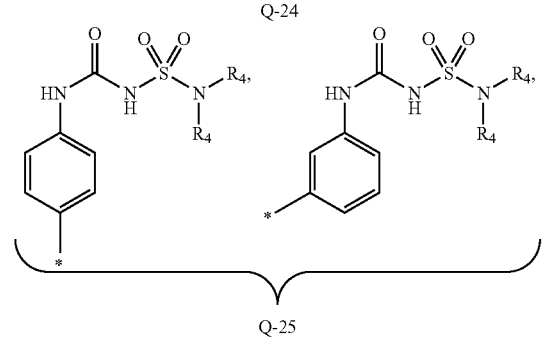
Q-25

-continued

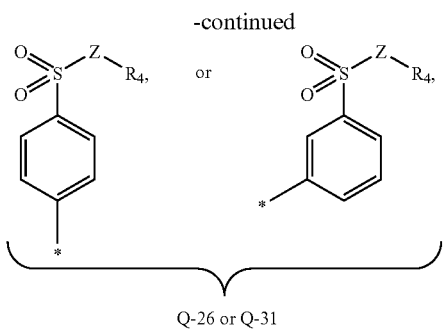

Q-26 or Q-31 wherein each Z is individually selected from the group consisting of —O— and —N(R₄)—;

when Q is Q-31, then the compound of formula (I) is not

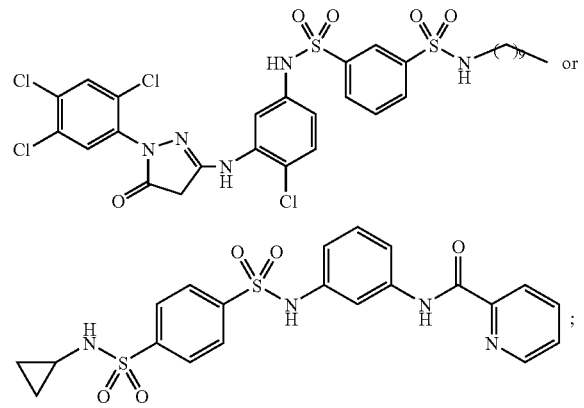

when Q is Q-28 or Q-29 and t is 0, then the compound of formula (I) is not

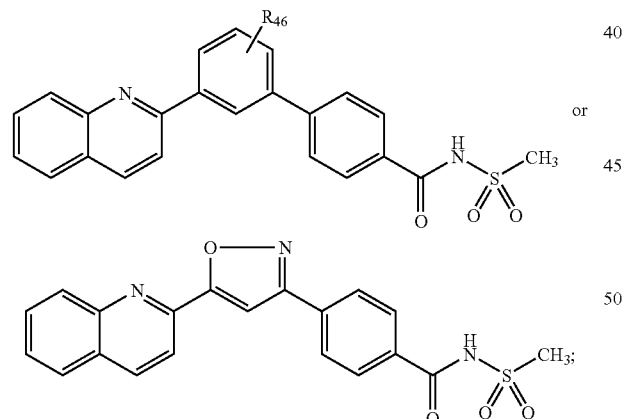

R₄₆ = hydrogen, hydroxyalkyl, alkoxyalkyloxy, hydroxy when Q is Q-28 or Q-29 and Y is an ether linkage, then the compound of formula (I) is not

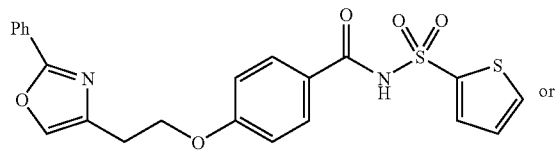

-continued

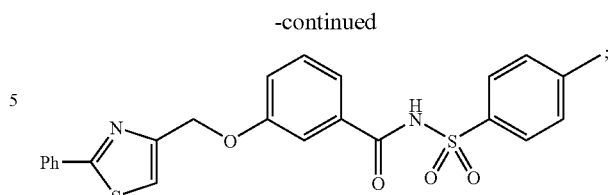

when Q is Q-28 or Q-29 and Y is —CONH—, then the compound of formula (I) is not

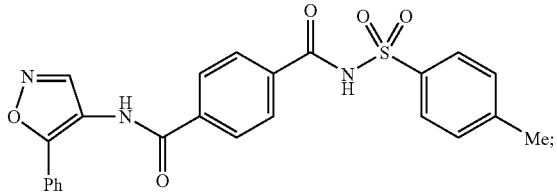

when Q is Q-32, then

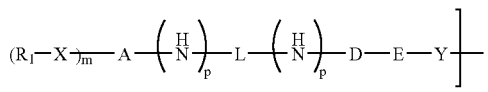

is not biphenyl, benzoxazolylphenyl, pyridylphenyl or bipyridyl;

when Q is Q-32, Y is —CONH—, q is 0, m is 0, and

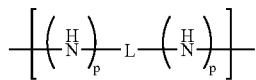

of formula (I) is —CONH—, then A is not phenyl;

when Q is Q-32, q is 0, m is 0, and

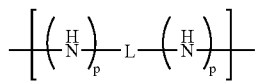

is —CONH—, then the compound of formula (I) is not

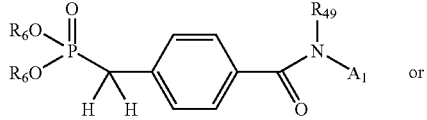

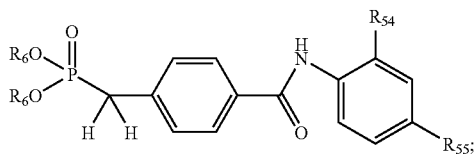

A₁ =

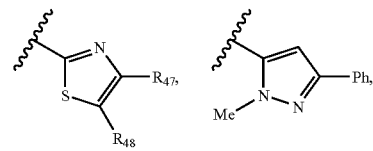

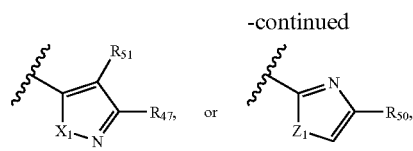

R47 = alkyl, substituted phenyl, thienyl, phenacetyl naphthyl
R48 = H, alkyl, Br, substituted phenyl, benzoyl, phenylsulfonyl
R49 = H, alkyl, phenyl
R50 = substituted phenyl
R54 = benzoyl, phenylalkylaminocarbonyl, substituted phenylaminocarbonyl H, Br
R55 = Cl, Br, SPh, benzoyl, phenylsulfonyl
R51 = H, phenylsulfonyl, phenyl, benzyl
R6 = Et, i-Pr
R53 = substituted phenyl, substituted benzyl
X1 = O, N-Ph, N-alkyl, N-carbamoyl
Z1 = N(R50), O when Q is Q-32, D is thiazolyl, q is 0, t is 0, p is 0, n is 0, and m is 0, then A is not phenyl or 2-pyridone;

when Q is Q-32, D is oxazolyl or isoxazolyl, q is 0, t is 0, p is 0, n is 0, and m is 0, then A is not phenyl;

when Q is Q-32, D is pyrimidyl q is 0, t is 0, p is 0, n is 0, and m is 0, then A is not phenyl;

when Q is Q-32 and Y is an ether linkage, then

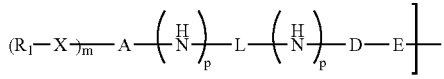

of formula (I) is not biphenyl or phenyloxazolyl;

when Q is Q-32 and Y is —CH=CH—, then

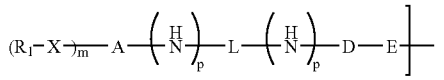

of formula (I) is not phenylaminophenyl;

when Q is Q-32, then the compound of formula (I) is not

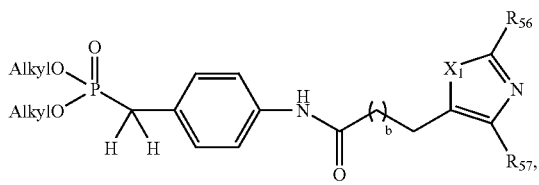

b = 0-1
X1 = O, S
R56 = H, CF3, Cl, imidazolyl, amino, morpholino, phenylthio, cycloalkyl, benzyl, phenyl, phenoxy, thienyl, substituted alkyl, pyridylthio, pyrimidyl, benzylamino, N-benimidazolyl, pyridylcarbonylamino, ureido,N-thiourea, substituted alkanoylamino, phenylsulfonyl, substituted benzoyl, phenylalkenoyl, furanoyl, thienoyl, pyridinoyl,
R57 = substituted phenyl, substituted biphenyl

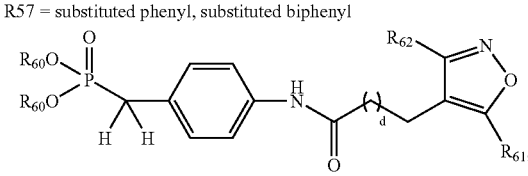

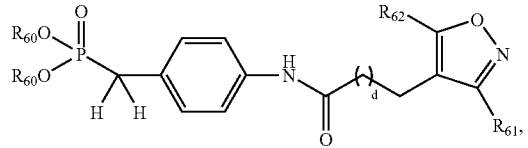

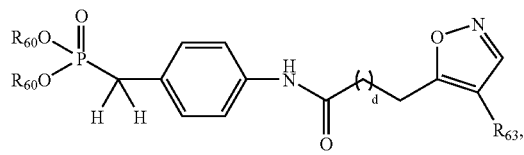

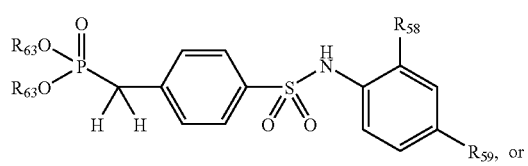

R58 = substituted alkylaminocarbonyl, phenylaminocarbonyl
R59 = H, Cl

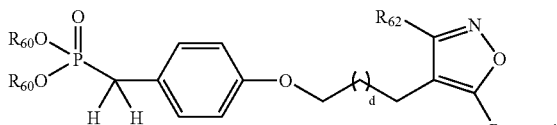

d = 0-2
R60 = H, alkyl
R61 = substituted phenyl, thienyl, Br
R62 = H, alkyl, phenyl
R63 = substituted phenyl when Q is Q-35 as shown

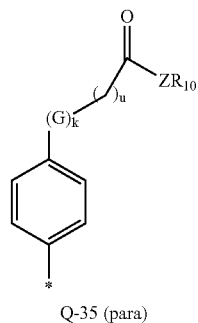

Q-35 (para)

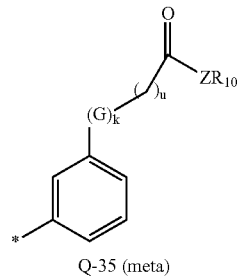

Q-35 (meta)

wherein G is selected from the group consisting of —O—, —S—, —NR4—, and —CH2—, k is 0 or 1, and u is 1, 2, 3, or 4, then

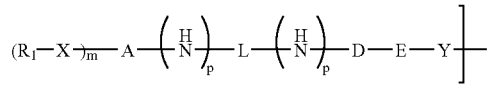

is selected from the group consisting of

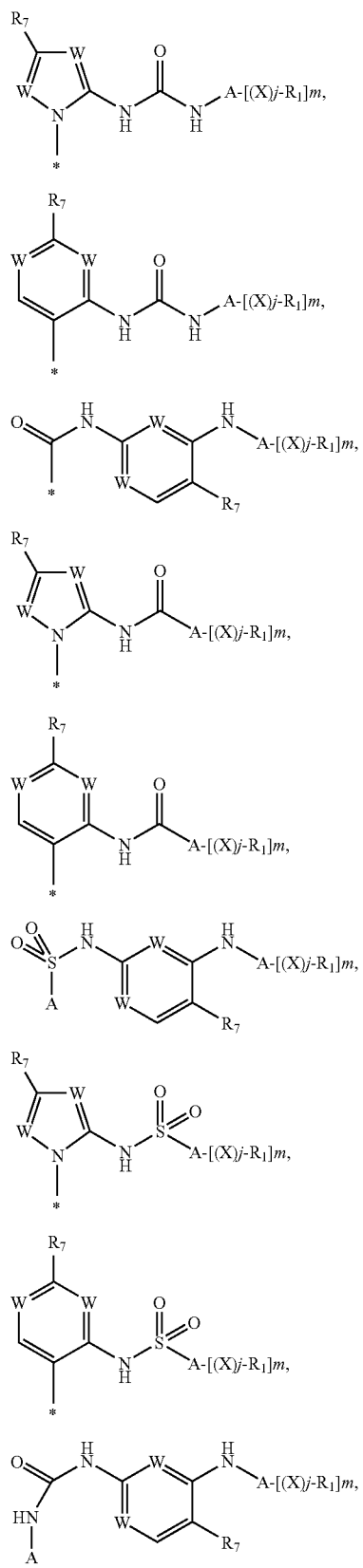
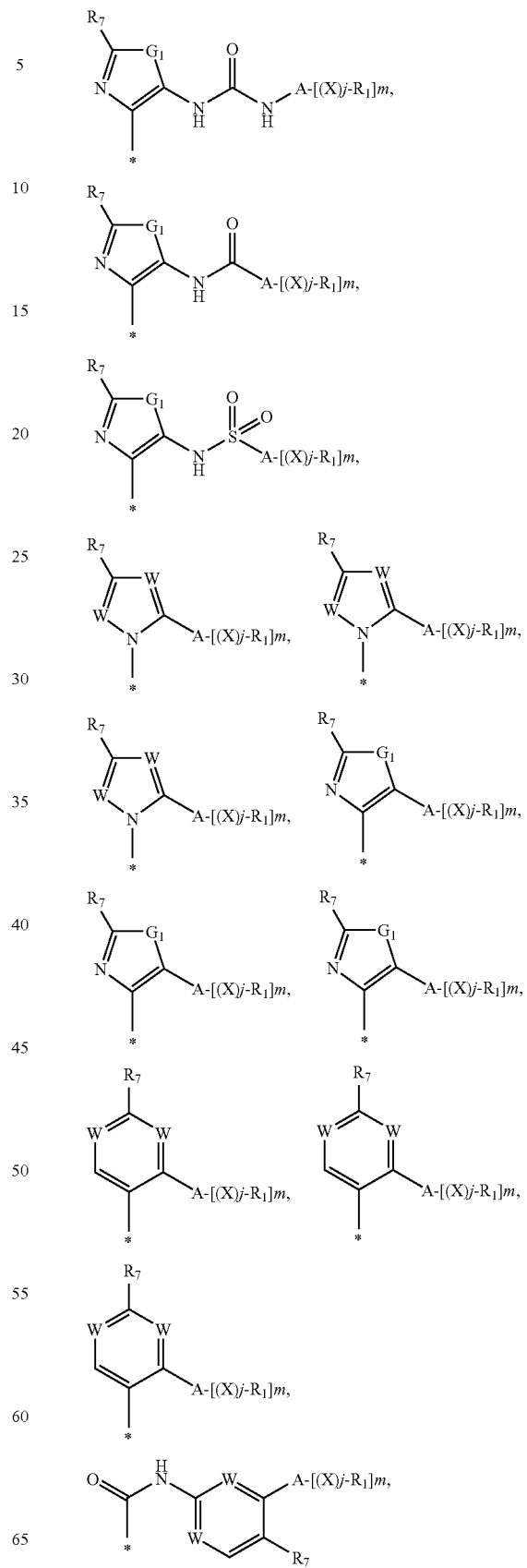

-continued
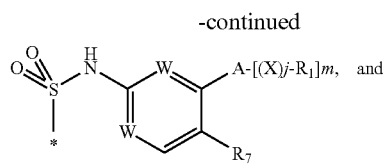
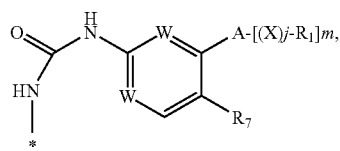
except that the compound of formula (I) is not
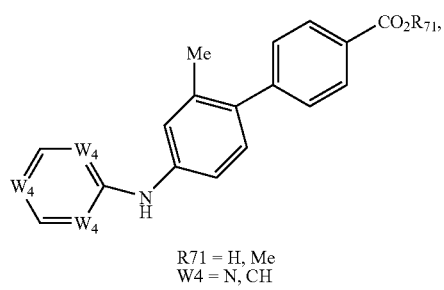
R71 = H, Me
W4 = N, CH
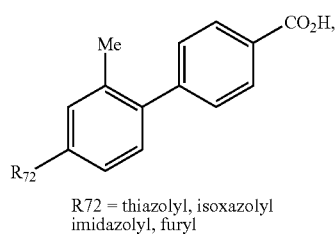
R72 = thiazolyl, isoxazolyl
imidazolyl, furyl
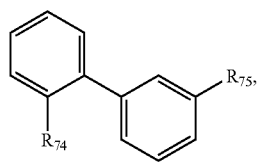
28.1 R73 = —OCH2CO2H
R74 = oxazolyl, imidazolyl
28.2 R73 = CO2Me
R74 = chlorophenyl
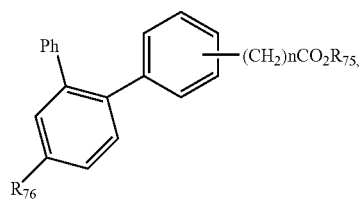
meta, para
R75 = H, Et
R76 = H, NH2, NO2
n = 0-1
-continued
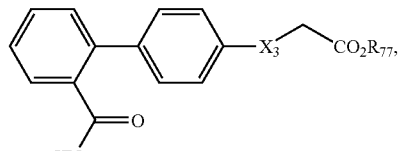
R77 = H, alkyl
X3 = O or CH2
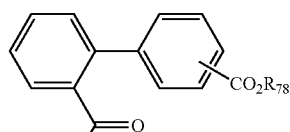
meta, para
R78 = H, alkyl
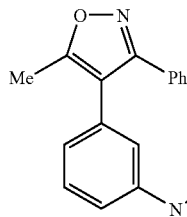
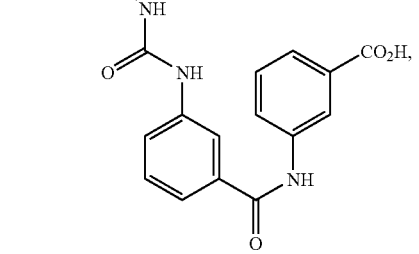
meta, para

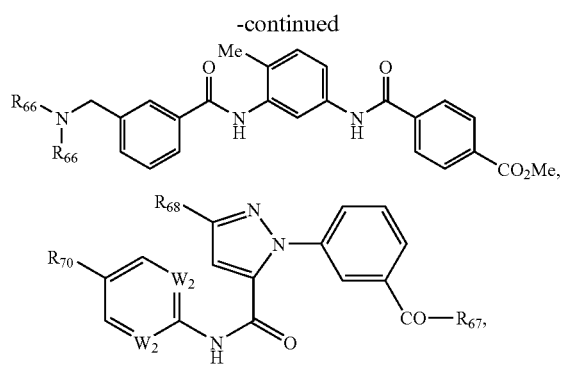
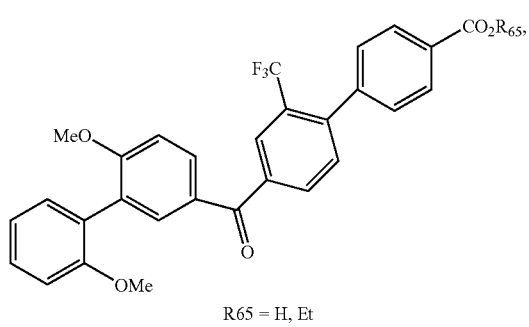
R67 = OH, NH2
R68 = CF₃, Me
R70 = 2-MeSO₂-phen-1-yl,
2-NH₂SO₂-phen-1-yl
morpholino, imidazolyl, N(Et)₂
W2 = CR₆₉ or N
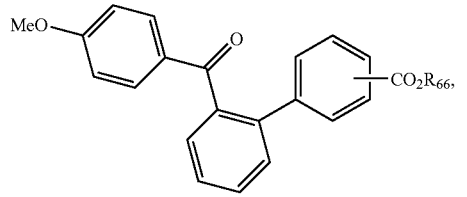
R65 = H, Et
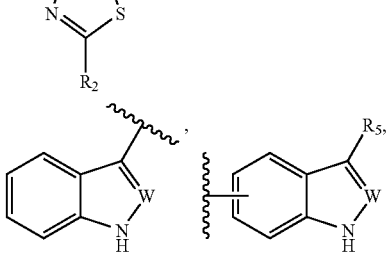
meta, para
R66 = alkyl
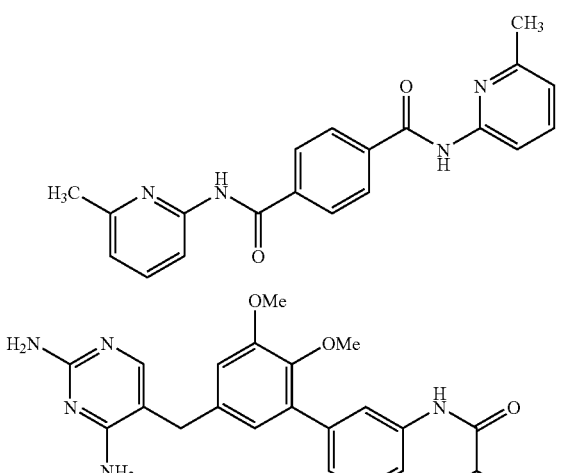
R79 = H, Me
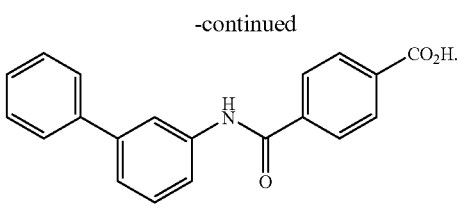
Even more preferably, $R_1$ as discussed above is selected from the group consisting of 6-5 fused heteroaryls, 6-5 fused heterocyclyls, 5-6 fused heteroaryls, and 5-6 fused heterocyclyls, and even more preferably, $R_1$ is selected from the group consisting of
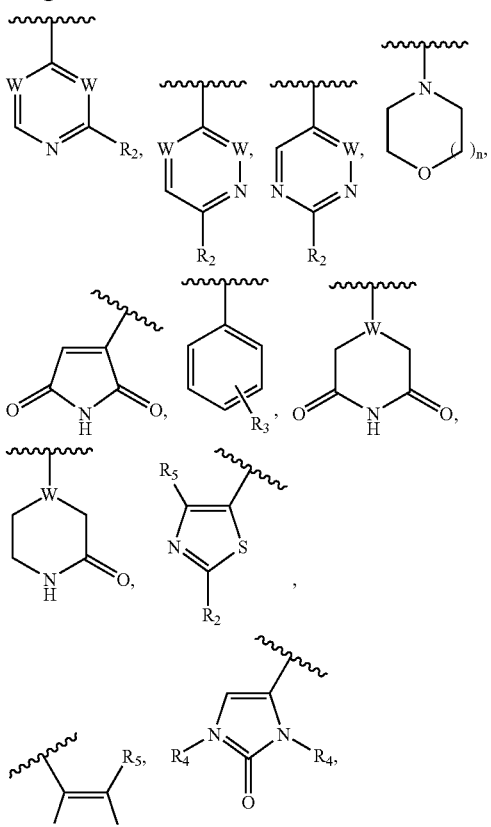
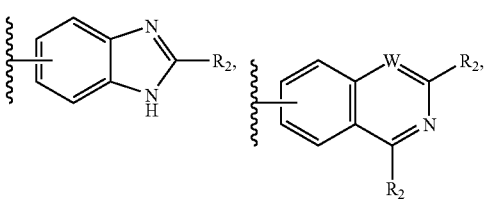

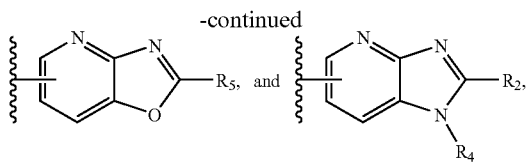
-continued each $R_2$ is individually selected from the group consisting of —H, alkyls (preferably $C_1$-$C_{18}$, and more preferably $C_1$-$C_{12}$), aminos, alkylaminos (preferably $C_1$-$C_{18}$, and more preferably $C_1$-$C_{12}$), arylaminos (preferably $C_6$-$C_{18}$, and more preferably $C_6$-$C_{12}$), cycloalkylaminos (preferably $C_1$-$C_{18}$, and more preferably $C_1$-$C_{12}$), heterocyclylaminos, halogens, alkoxys (preferably $C_1$-$C_{18}$, and more preferably $C_1$-$C_{12}$), and hydroxys;

each $R_3$ is individually selected from the group consisting of —H, alkyls (preferably $C_1$-$C_{18}$, and more preferably $C_1$-$C_{12}$), alkylaminos (preferably $C_1$-$C_{18}$, and more preferably $C_1$-$C_{12}$), arylaminos (preferably $C_6$-$C_{18}$, and more preferably $C_6$-$C_{12}$), cycloalkylaminos (preferably $C_1$-$C_{18}$, and more preferably $C_1$-$C_{12}$), heterocyclylaminos, alkoxys (preferably $C_1$-$C_{18}$, and more preferably $C_1$-$C_{12}$), hydroxys, cyanos, halogens, perfluoroalkyls (preferably $C_1$-$C_{18}$, and more preferably $C_1$-$C_{12}$), alkylsulfinyls (preferably $C_1$-$C_{18}$, and more preferably $C_1$-$C_{12}$), alkylsulfonyls (preferably $C_1$-$C_{18}$, and more preferably $C_1$-$C_{12}$), $R_4NHSO_2$—, and —$NHSO_2R_4$; and V is selected from the group consisting of O and $H_2$.

Finally, in another preferred embodiment, A as described above is selected from the group consisting of phenyl, naphthyl, pyridyl, pyrimidyl, thienyl, furyl, pyrrolyl, thiazolyl, oxazolyl, imidazolyl, indolyl, indazolyl, benzimidazolyl, benzotriazolyl, isoquinolyl, quinolyl, benzothiazolyl, benzofuranyl, benzothienyl, pyrazolylpyrimidinyl, imidazopyrimidinyl, purinyl, and

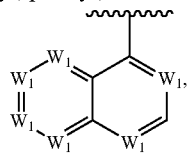

where each $W_1$ is individually selected from the group consisting of —CH— and —N—.

With respect to the method of using the novel compounds, the activation state of a kinase is determined by the interaction of switch control ligands and complemental switch control pockets. One conformation of the kinase may result from the switch control ligand's interaction with a particular switch control pocket while another conformation may result from the ligand's interaction with a different switch control pocket. Generally interaction of the ligand with one pocket, such as the "on" pocket, results in the kinase assuming an active conformation wherein the kinase is biologically active. Similarly, an inactive conformation (wherein the kinase is not biologically active) is assumed when the ligand interacts with another of the switch control pockets, such as the "off" pocket. The switch control pocket can be selected from the group consisting of simple, composite and combined switch control pockets. Interaction between the switch control ligand and the switch control pockets is dynamic and therefore, the ligand is not always interacting with a switch control pocket. In some instances, the ligand is not in a switch control pocket (such as occurs when the protein is changing from an active conformation to an inactive conformation). In other instances, such as when the ligand is interacting with the environment surrounding the protein in order to determine with which switch control pocket to interact, the ligand is not in a switch control pocket. Interaction of the ligand with particular switch control pockets is controlled in part by the charge status of the amino acid residues of the switch control ligand. When the ligand is in a neutral charge state, it interacts with one of the switch control pockets and when it is in a charged state, it interacts with the other of the switch control pockets. For example, the switch control ligand may have a plurality of OH groups and be in a neutral charge state. This neutral charge state results in a ligand that is more likely to interact with one of the switch control pockets through hydrogen boding between the OH groups and selected residues of the pocket, thereby resulting in whichever protein conformation results from that interaction. However, if the OH groups of the switch control ligand become charged through phosphorylation or some other means, the propensity of the ligand to interact with the other of the switch control pockets will increase and the ligand will interact with this other switch control pocket through complementary covalent binding between the negatively or positively charged residues of the pocket and ligand. This will result in the protein assuming the opposite conformation assumed when the ligand was in a neutral charge state and interacting with the other switch control pocket.

Of course, the conformation of the protein determines the activation state of the protein and can therefore play a role in protein-related diseases, processes, and conditions. For example, if a metabolic process requires a biologically active protein but the protein's switch control ligand remains in the switch control pocket (i.e. the "off" pocket) that results in a biologically inactive protein, that metabolic process cannot occur at a normal rate. Similarly, if a disease is exacerbated by a biologically active protein and the protein's switch control ligand remains in the switch control pocket (i.e. the "on" pocket) that results in the biologically active protein conformation, the disease condition will be worsened. Accordingly, as demonstrated by the present invention, selective modulation of the switch control pocket and switch control ligand by the selective administration of a molecule will play an important role in the treatment and control of protein-related diseases, processes, and conditions.

One aspect of the invention provides a method of modulating the activation state of a kinase, preferably p38 α-kinase and including both the consensus wild type sequence and disease polymorphs thereof. The activation state is generally selected from an upregulated or downregulated state. The method generally comprises the step of contacting the kinase with a molecule having the general formula (I). When such contact occurs, the molecule will bind to a particular switch control pocket and the switch control ligand will have a greater propensity to interact with the other of the switch control pockets (i.e., the unoccupied one) and a lesser propensity to interact with the occupied switch control pocket. As a result, the protein will have a greater propensity to assume either an active or inactive conformation (and consequently be upregulated or downregulated), depending upon which of the switch control pockets is occupied by the molecule. Thus, contacting the kinase with a molecule modulates that protein's activation state. The molecule can act as an antagonist or an agonist of either switch control pocket. The contact between the molecule and the kinase preferably occurs at a region of a switch control pocket of the kinase and more preferably in an interlobe oxyanion pocket of the kinase. In some instances, the contact between the molecule and the pocket also results in the alteration of the conformation of other adjacent sites and pockets, such as an ATP active site. Such an alteration can also effect regulation and modulation of the active state of the protein. Preferably, the region of the switch control pocket of the kinase comprises an amino acid residue sequence operable for binding to the Formula I molecule. Such binding can occur between the molecule and a specific region of the switch control pocket with preferred regions including the α-C helix, the α-D helix, the catalytic loop, the activation loop, and the C-terminal residues or C-lobe residues (all residues located downstream (toward the C-end) from the Activation loop), and combinations thereof. When the binding region is the α-C helix, one preferred binding sequence in this helix is the sequence IIXXKRXXREXXLLXXM, (SEQ ID NO. 2). When the binding region is the catalytic loop, one preferred binding sequence in this loop is DIIHRD (SEQ ID NO. 3). When the binding region is the activation loop, one preferred binding sequence in this loop is a sequence selected from the group consisting of DFGLARHTDD (SEQ ID NO.4), EMTGYVATRWYR (SEQ ID NO. 5), and combinations thereof. When the binding region is in the C-lobe residues, one preferred binding sequence is WMHY (SEQ ID NO. 6). When a biologically inactive protein conformation is desired, molecules which interact with the switch control pocket that normally results in a biologically active protein conformation (when interacting with the switch control ligand) will be selected. Similarly, when a biologically active protein conformation is desired, molecules which interact with the switch control pocket that normally results in a biologically inactive protein conformation (when interacting with the switch control ligand) will be selected. Thus, the propensity of the protein to assume a desired conformation will be modulated by administration of the molecule. In preferred forms, the molecule will be administered to an individual undergoing treatment for a condition selected from the group consisting of human inflammation, rheumatoid arthritis, rheumatoid spondylitis, ostero-arthritis, asthma, gouty arthritis, sepsis, septic shock, endotoxic shock, Gram-negative sepsis, toxic shock syndrome, adult respiratory distress syndrome, stroke, reperfusion injury, neural trauma, neural ischemia, psoriasis, restenosis, chronic pulmonary inflammatory disease, bone resorptive diseases, graft-versus-host reaction, Chron's disease, ulcerative colitis, inflammatory bowel disease, pyresis, and combinations thereof. In such forms, it will be desired to select molecules that interact with the switch control pocket that generally leads to a biologically active protein conformation so that the protein will have the propensity to assume the biologically inactive form and thereby alleviate the condition. It is contemplated that the molecules of the present invention will be administrable in any conventional form including oral, parenteral, inhalation, and subcutaneous. It is preferred for the administration to be in the oral form. Preferred molecules include the preferred compounds of formula (I), as discussed above.

Another aspect of the present invention provides a method of treating an inflammatory condition of an individual comprising the step of administering a molecule having the general formula (I) to the individual. Such conditions are often the result of an overproduction of the biologically active form of a protein, including kinases. The administering step generally includes the step of causing said molecule to contact a kinase involved with the inflammatory process, preferably p38 α-kinase. When the contact is between the molecule and a kinase, the contact preferably occurs in an interlobe oxyanion pocket of the kinase that includes an amino acid residue sequence operable for binding to the Formula I molecule. Preferred binding regions of the interlobe oxyanion pocket include the α-C helix region, the α-D helix region, the catalytic loop, the activation loop, the C-terminal residues, and combinations thereof. When the binding region is the α-C helix, one preferred binding sequence in this helix is the sequence IIXXKRXXREXXLLXXM, (SEQ ID NO. 2). When the binding region is the catalytic loop, one preferred binding sequence in this loop is DIIHRD (SEQ ID NO. 3). When the binding region is the activation loop, one preferred binding sequence in this loop is a sequence selected from the group consisting of DFGLARHTDD (SEQ ID NO.4), EMTGYVATRWYR (SEQ ID NO. 5), and combinations thereof. Such a method permits treatment of the condition by virtue of the modulation of the activation state of a kinase by contacting the kinase with a molecule that associates with the switch control pocket that normally leads to a biologically active form of the kinase when interacting with the switch control ligand. Because the ligand cannot easily interact with the switch control pocket associated with or occupied by the molecule, the ligand tends to interact with the switch control pocket leading to the biologically inactive form of the protein, with the attendant result of a decrease in the amount of biologically active protein. Preferably, the inflammatory condition is selected from the group consisting of human inflammation, rheumatoid arthritis, rheumatoid spondylitis, ostero-arthritis, asthma, gouty arthritis, sepsis, septic shock, endotoxic shock, Gram-negative sepsis, toxic shock syndrome, adult respiratory distress syndrome, stroke, reperfusion injury, neural trauma, neural ischemia, psoriasis, restenosis, chronic pulmonary inflammatory disease, bone resorptive diseases, graft-versus-host reaction, Chron's disease, ulcerative colitis, inflammatory bowel disease, pyresis, and combinations thereof. As with the other methods of the invention, the molecules may be administered in any conventional form, with any convention excipients or ingredients. However, it is preferred to administer the molecule in an oral dosage form. Preferred molecules are again selected from the group consisting of the preferred formula (I) compounds discussed above.

BRIEF DESCRIPTION OF THE DRAWINGS

FIG. 4a is an enlarged schematic view illustrating a representative binding between the phosphorylated residues of the switch control ligand, and complemental residues from the on switch control pocket;

FIG. 7 is a schematic view of the protein in a situation where a combined switch control pocket is formed with portions of the on switch control pocket, the switch control ligand sequence, and the active ATP site, and with a small molecule in binding relationship with the combined switch control pocket.

DETAILED DESCRIPTION OF THE PREFERRED EMBODIMENTS

Figure 1:
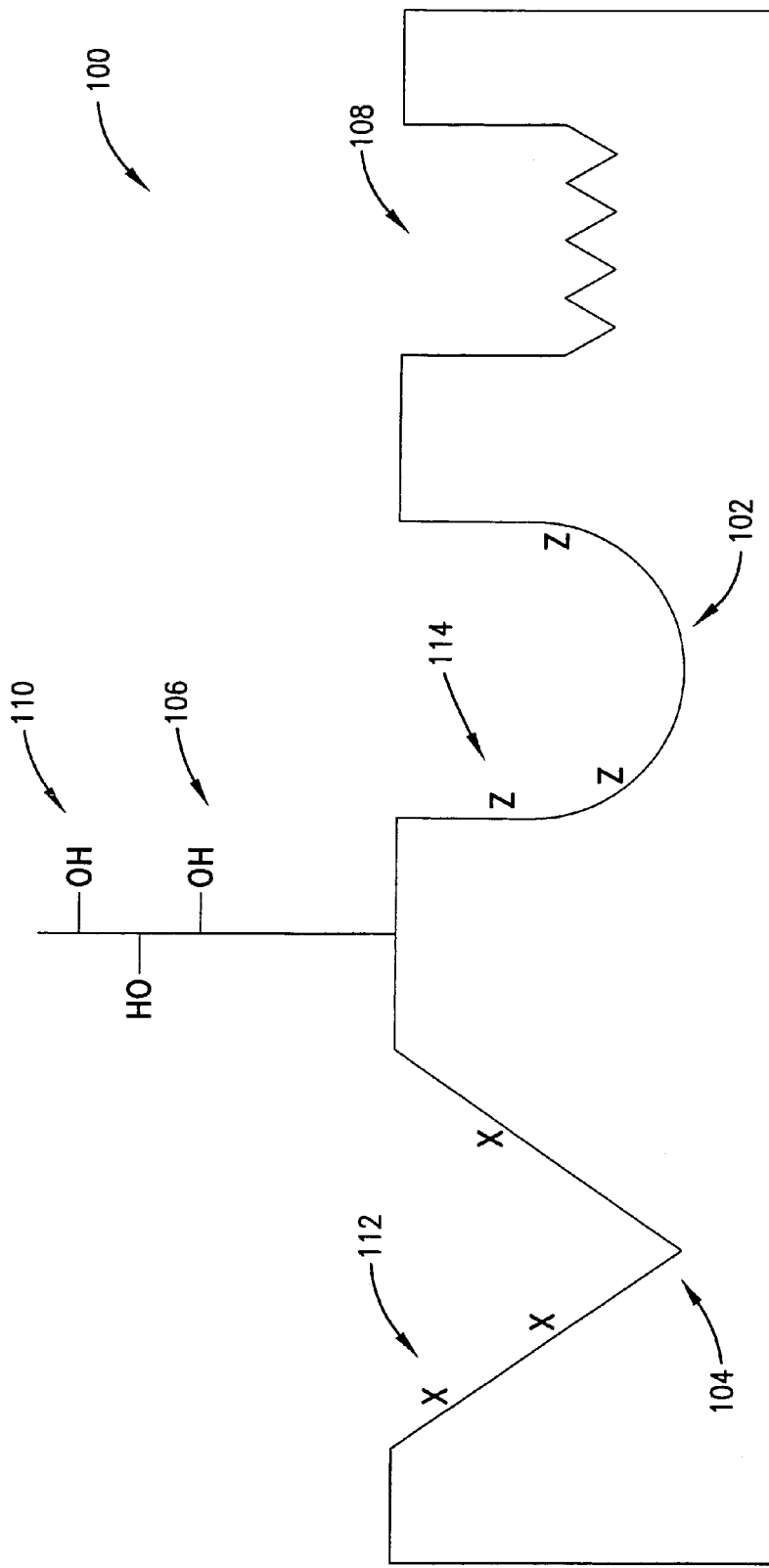
FIG. 1 is a schematic representation of a naturally occurring mammalian protein in accordance with the invention including "on" and "off" switch control pockets, a transiently modifiable switch control ligand, and an active ATP site.

The present invention provides a way of rationally developing new small molecule modulators which interact with naturally occurring proteins (e.g., mammalian, and especially human proteins) in order to modulate the activity of the proteins. Novel protein-small molecule adducts are also provided. The invention preferably makes use of naturally occurring proteins having a conformational property whereby the proteins change their conformations in vivo with a corresponding change in protein activity. For example, a given enzyme protein in one conformation may be biologically upregulated, while in another conformation, the same protein may be biologically downregulated. The invention preferably makes use of one mechanism of conformation change utilized by naturally occurring proteins, through the interaction of what are termed "switch control ligands" and "switch control pockets" within the protein.

As used herein, "switch control ligand" means a region or domain within a naturally occurring protein and having one or more amino acid residues therein which are transiently modified in vivo between individual states by biochemical modification, typically phosphorylation, sulfation, acylation or oxidation. Similarly, "switch control pocket" means a plurality of contiguous or non-contiguous amino acid residues within a naturally occurring protein and comprising residues capable of binding in vivo with transiently modified residues of a switch control ligand in one of the individual states thereof in order to induce or restrict the conformation of the protein and thereby modulate the biological activity of the protein, and/or which is capable of binding with a non-naturally occurring switch control modulator molecule to induce or restrict a protein conformation and thereby modulate the biological activity of the protein.

A protein-modulator adduct in accordance with the invention comprises a naturally occurring protein having a switch control pocket with a non-naturally occurring molecule bound to the protein at the region of said switch control pocket, said molecule serving to at least partially regulate the biological activity of said protein by inducing or restricting the conformation of the protein. Preferably, the protein also has a corresponding switch control ligand, the ligand interacting in vivo with the pocket to regulate the conformation and biological activity of the protein such that the protein will assume a first conformation and a first biological activity upon the ligand-pocket interaction, and will assume a second, different conformation and biological activity in the absence of the ligand-pocket interaction.

The nature of the switch control ligand/switch control pocket interaction may be understood from a consideration of schematic FIGS. 1-4. Specifically, in FIG. 1, a protein 100 is illustrated in schematic form to include an "on" switch control pocket 102, and "off" switch control pocket 104, and a switch control ligand 106. In addition, the schematically depicted protein also includes an ATP active site 108. In the exemplary protein of FIG. 1, the ligand 106 has three amino acid residues with side chain OH groups 110. The off pocket 104 contains corresponding X residues 112 and the on pocket 102 has Z residues 114. In the exemplary instance, the protein 100 will change its conformation depending upon the charge status of the OH groups 110 on ligand 106, i.e., when the OH groups are unmodified, a neutral charge is presented, but when these groups are phosphorylated a negative charge is presented.

Figure 2:
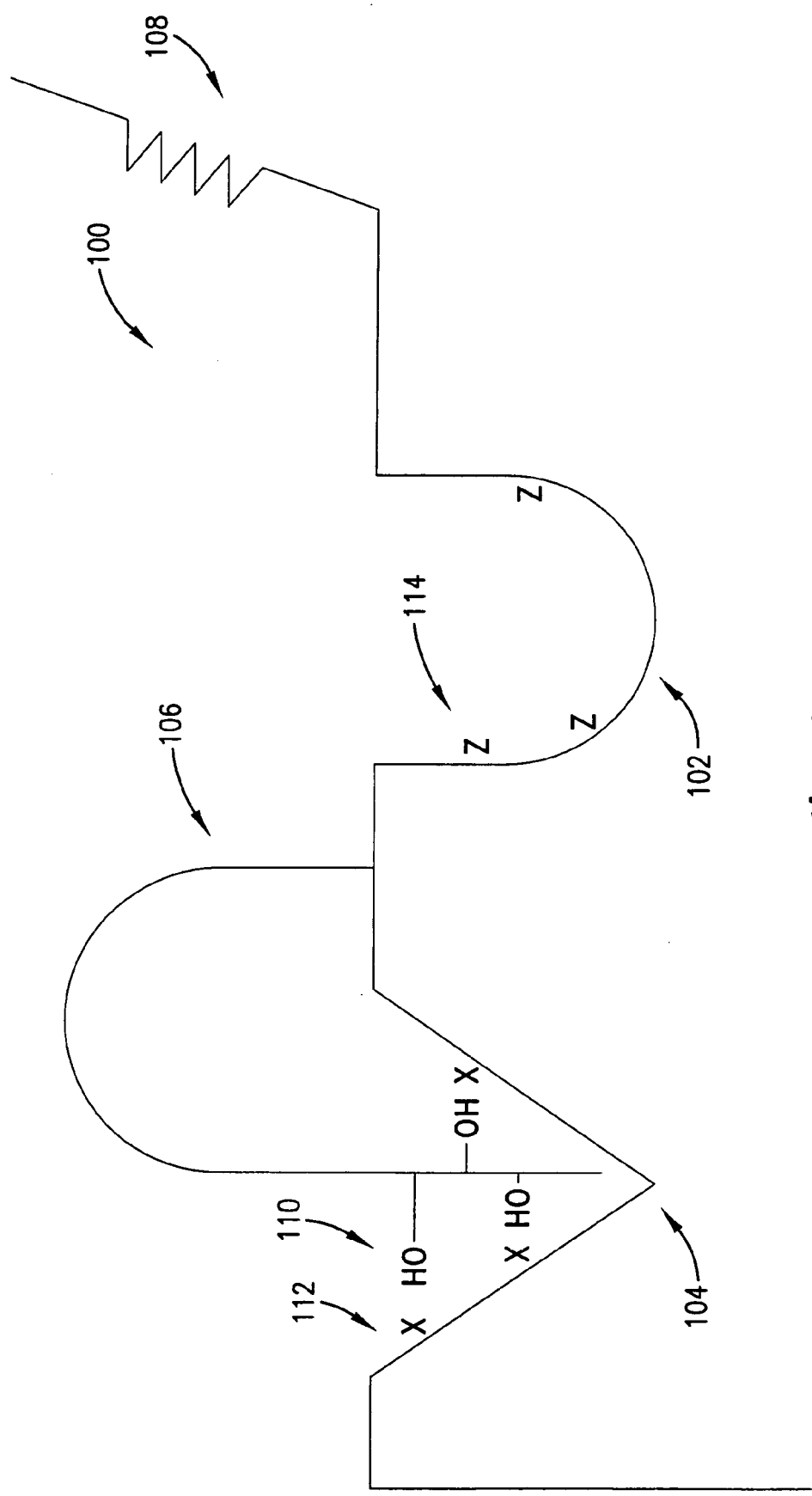
FIG. 2 is a schematic representation of the protein of FIG. 1, wherein the switch control ligand is illustrated in a binding relationship with the off switch control pocket, thereby causing the protein to assume a first biologically downregulated conformation.
Figure 3:
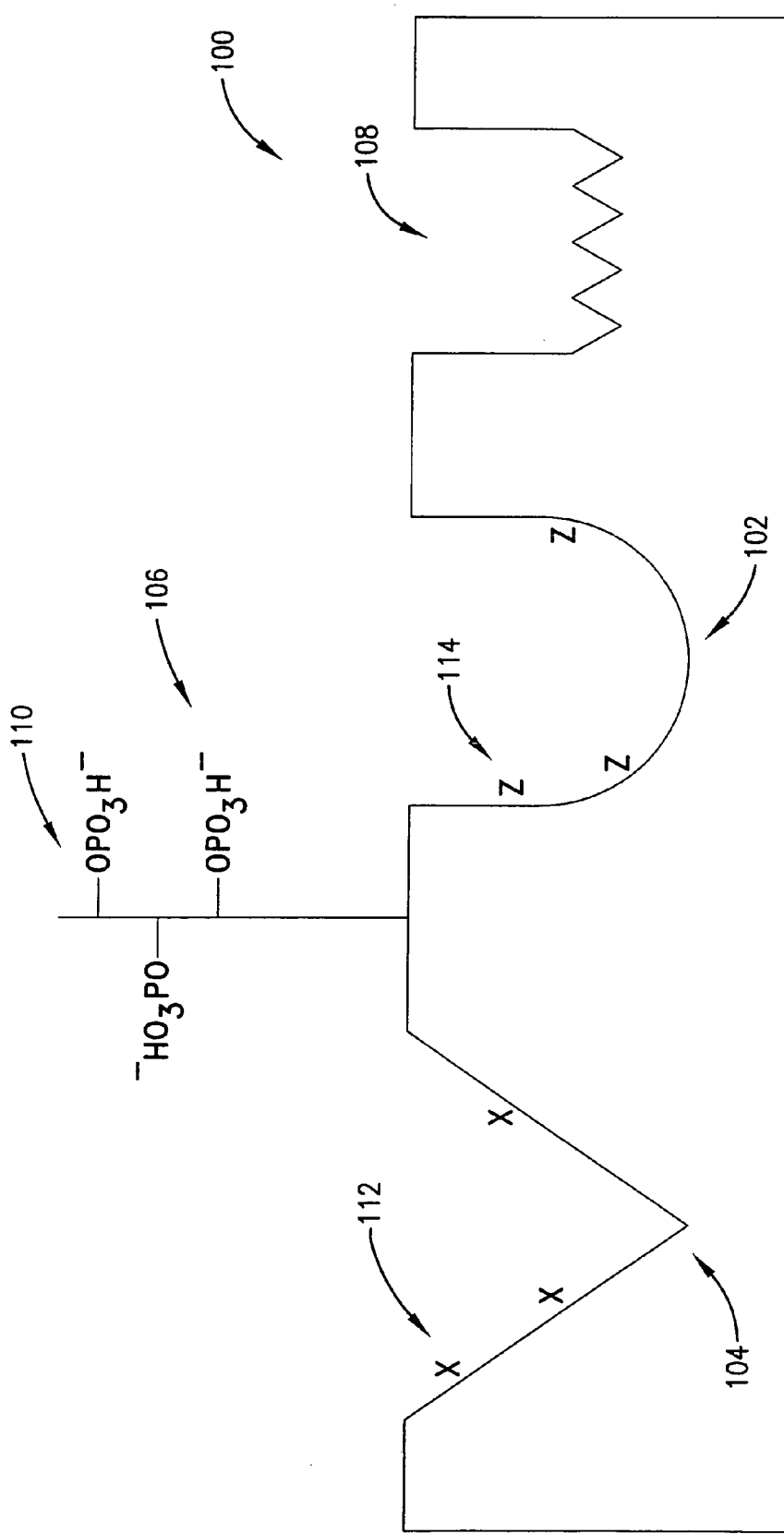
FIG. 3 is a view similar to that of FIG. 1, but illustrating the switch control ligand in its charged-modified condition wherein the OH groups of certain amino acid residues have been phosphorylated.
Figure 4:
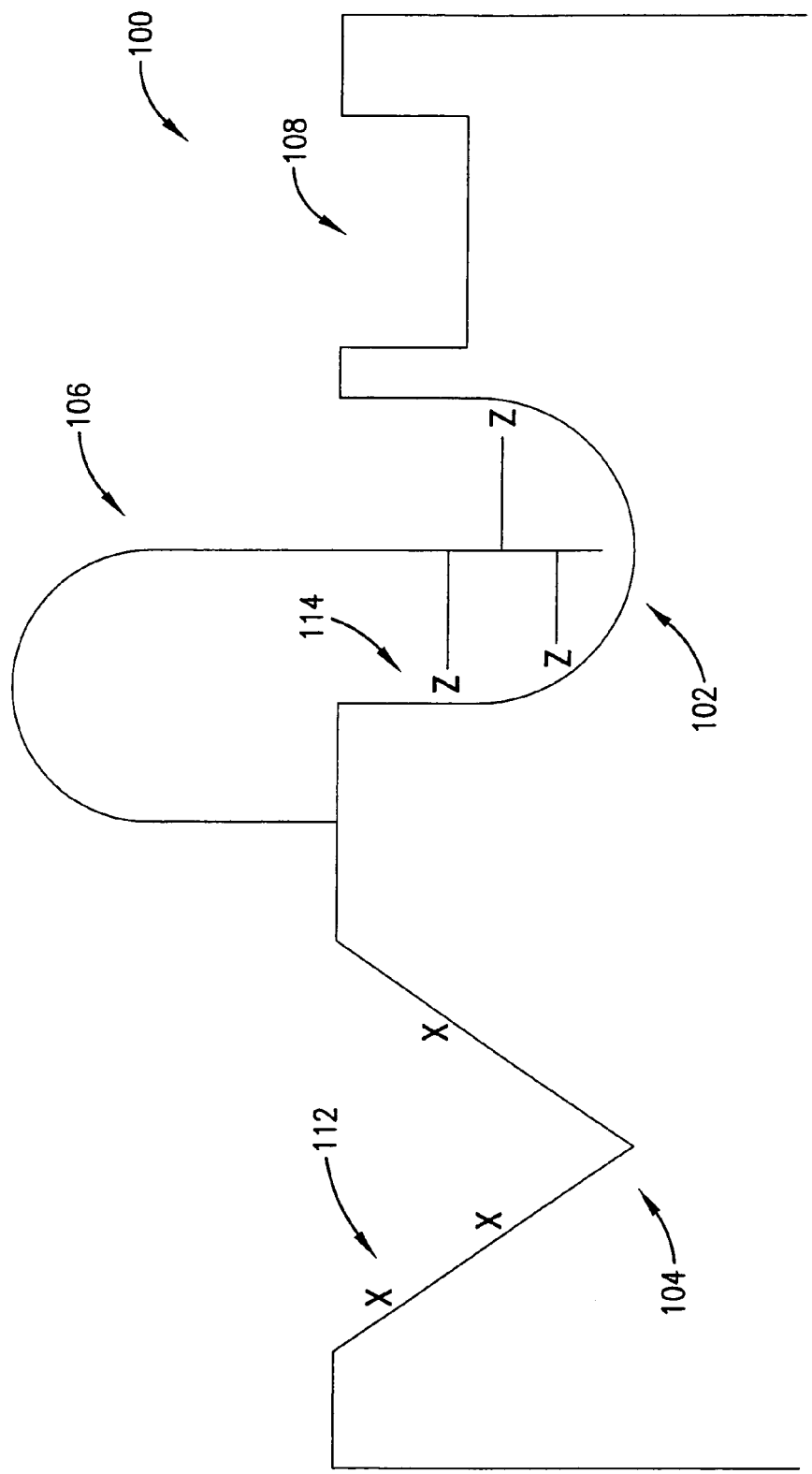
FIG. 4 is a view similar to that of FIG. 2, but depicting the protein wherein the switch control ligand is in a binding relationship with the on switch control pocket, thereby causing the protein to assume a second biologically-active conformation different than the first conformation of FIG. 2.
Figure 5:
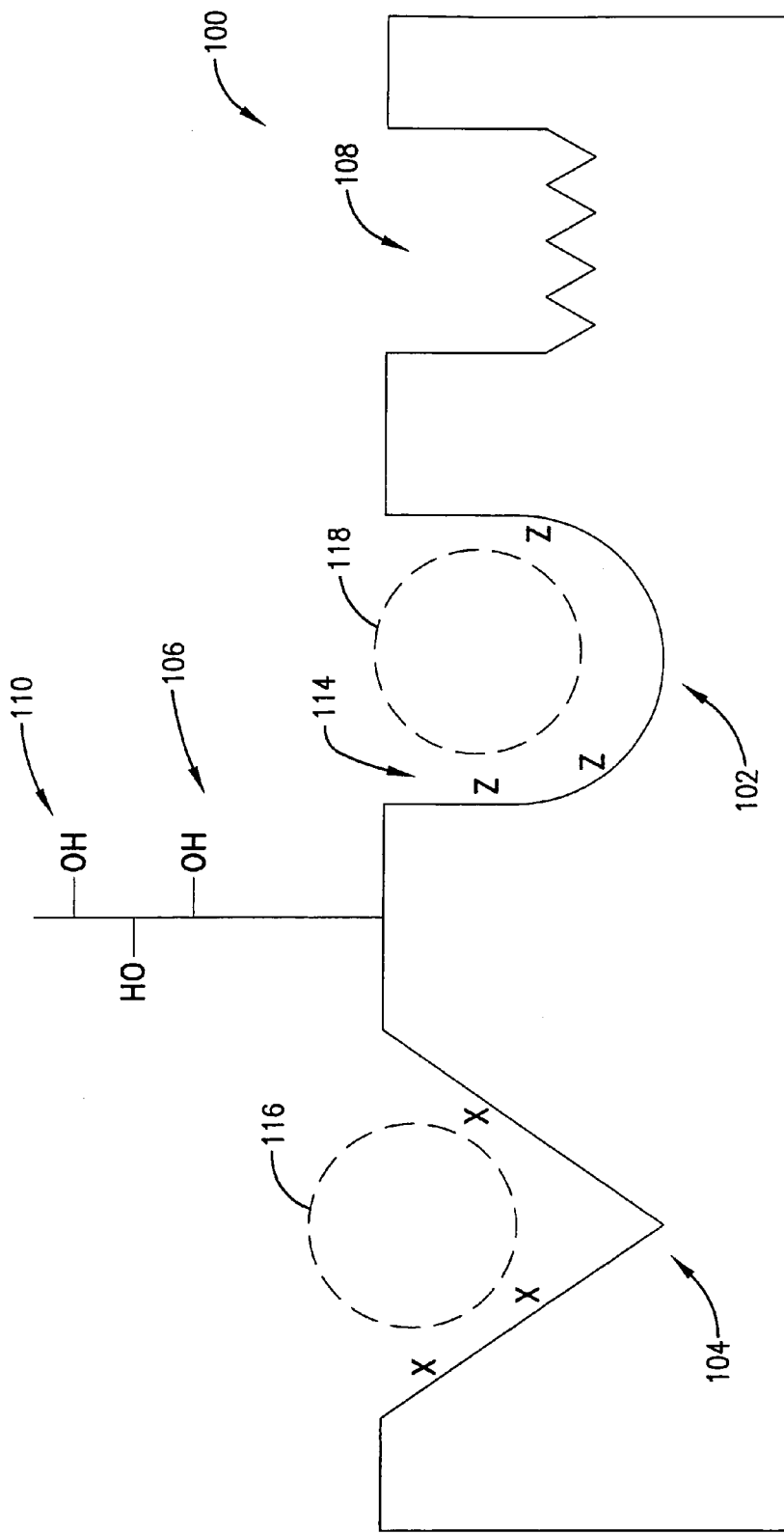
FIG. 5 is a view similar to that of FIG. 1, but illustrating in schematic form possible small molecule compounds in a binding relationship with the on and off switch control pockets.

The functionality of the pockets 102, 104 and ligand 106 can be understood from a consideration of FIGS. 2-4. In FIG. 2, the ligand 106 is shown operatively interacted with the off pocket 104 such that the OH groups 110 interact with the X residues 112 forming a part of the pocket 104. Such interaction is primarily by virtue of hydrogen bonding between the OH groups 110 and the residues 112. As seen, this ligand/pocket interaction causes the protein 100 to assume a conformation different from that seen in FIG. 1 and corresponding to the off or biologically downregulated conformation of the protein.

FIG. 3 illustrates the situation where the ligand 106 has shifted from the off pocket interaction conformation of FIG. 2 and the OH groups 110 have been phosphorylated, giving a negative charge to the ligand. In this condition, the ligand has a strong propensity to interact with on pocket 102, to thereby change the protein conformation to the on or biologically upregulated state (FIG. 4). FIG. 4a illustrates that the phosphorylated groups on the ligand 106 are attracted to positively charged residues 114 to achieve an ionic-like stabilizing bond. Note that in the on conformation of FIG. 4, the protein conformation is different than the off conformation of FIG. 2, and that the ATP active site is available and the protein is functional as a kinase enzyme.

Figure 6:
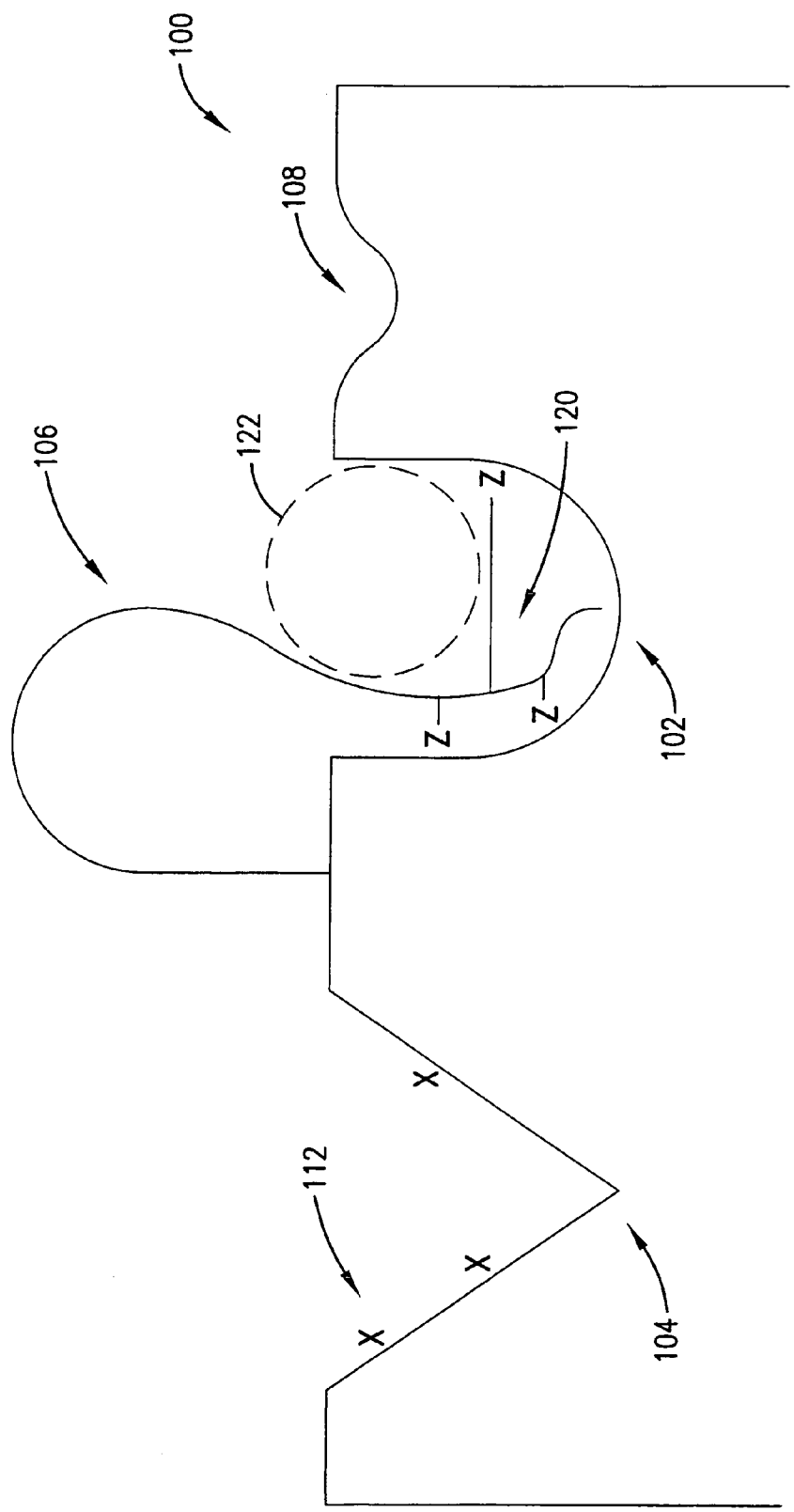
FIG. 6 is a schematic view of the protein in a situation where a composite switch control pocket is formed with portions of the switch control ligand and the on switch control pocket, and with a small molecule in binding relationship with the composite pocket.

FIGS. 1-4 illustrate a simple situation where the protein exhibits discrete pockets 102 and 104 and ligand 106. However, in many cases a more complex switch control pocket pattern is observed. FIG. 6 illustrates a situation where an appropriate pocket for small molecule interaction is formed from amino acid residues taken both from ligand 106 and, for example, from pocket 102. This is termed a "composite switch control pocket" made up of residues from both the ligand 106 and a pocket, and is referred to by the numeral 120. A small molecule 122 is illustrated which interacts with the pocket 120 for protein modulation purposes.

Another more complex switch pocket is depicted in FIG. 7 wherein the pocket includes residues from on pocket 102, and ATP site 108 to create what is termed a "combined switch control pocket." Such a combined pocket is referred to as numeral 124 and may also include residues from ligand 106. An appropriate small molecule 126 is illustrated with pocket 124 for protein modulation purposes.

It will thus be appreciated that while in the simple pocket situation of FIGS. 1-4, the small molecule will interact with the simple pocket 102 or 104, in the more complex situations of FIGS. 6 and 7 the interactive pockets are in the regions of the pockets 120 or 124. Thus, broadly the small molecules interact "at the region" of the respective switch control pocket.

Materials and Methods

General Synthesis of Compounds

In the synthetic schemes of this section, q is 0 or 1. When q=0, the substituent is replaced by a synthetically non-interfering group $R_7$.

Compounds of Formula I wherein Q is taken from Q-1 or Q-2 and Y is alkylene are prepared according to the synthetic route shown in Scheme 1.1. Reaction of isothiocyanate 1 with chlorine, followed by addition of isocyanate 2 affords 3-oxothiadiazolium salt 3. Quenching of the reaction with air affords compounds of Formula I-4. Alternatively, reaction of isothiocyanate 1 with isothiocyanate 5 under the reaction conditions gives rise to compounds of Formula I-7. See A. Martinez et al, *Journal of Medicinal Chemistry* (2002) 45: 1292.

Intermediates 1, 2 and 5 are commercially available or prepared according to Scheme 1.2. Reaction of amine 8 with phosgene or a phosgene equivalent affords isocyanate 2. Similarly, reaction of amine 8 with thiophosgene affords isothiocyanate 5. Amine 8 is prepared by palladium(0)-catalyzed amination of 9, wherein M is a group capable of oxidative insertion into palladium(0), according to methodology reported by S. Buchwald. See M. Wolter et al, *Organic Letters* (2002) 4:973; B. H. Yang and S. Buchwald, *Journal of Organometallic Chemistry* (1999) 576(1-2):125. In this reaction sequence, P is a suitable amine protecting group. Use of and removal of amine protecting groups is accomplished by methodology reported in the literature (Protective Groups in Organic Synthesis, Peter G. M. Wutts, Theodora Greene (Editors) 3rd edition (April 1999) Wiley, John & Sons, Incorporated; ISBN: 0471160199). Starting compounds 9 are commercially available or readily prepared by one of ordinary skill in the art: See March's Advanced Organic Chemistry: Reactions, Mechanisms, and Structure, Michael B. Smith & Jerry March (Editors) 5th edition (January 2001) Wiley John & Sons; ISBN: 0471585890.

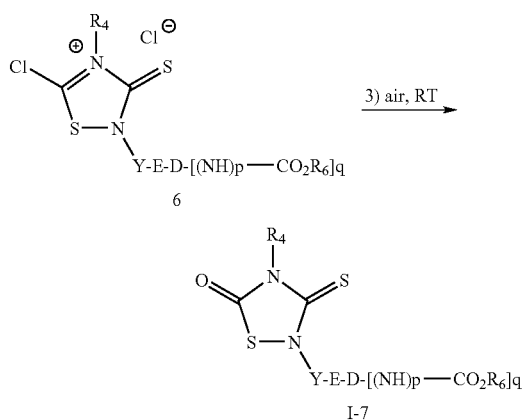

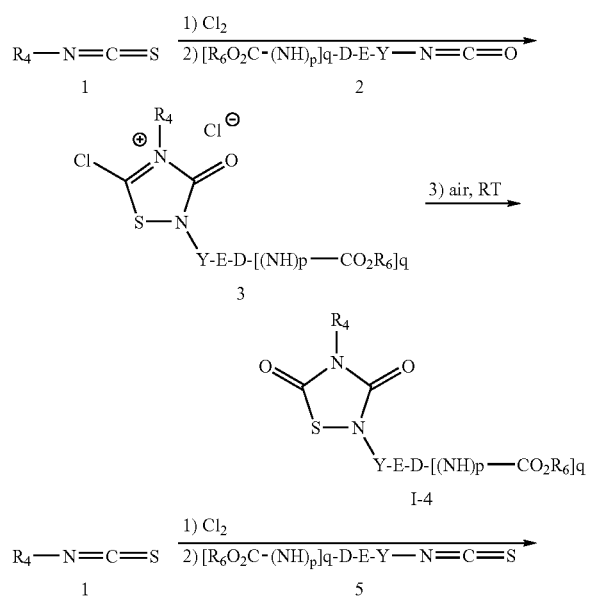

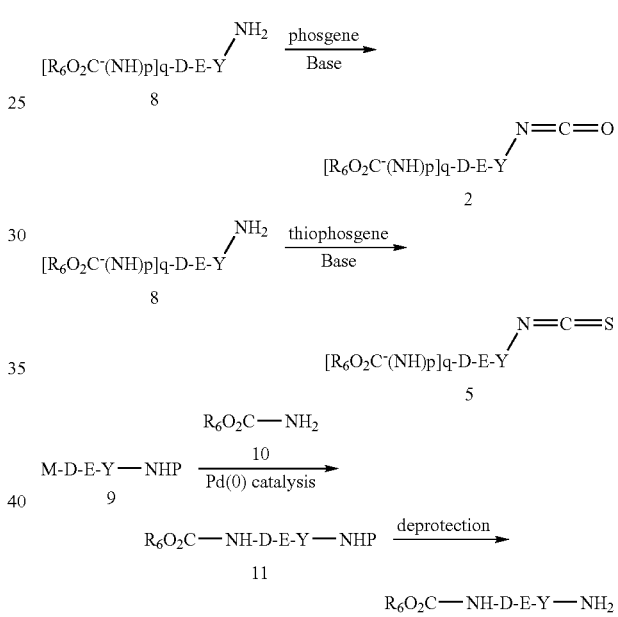

Compounds of Formula I wherein Q is taken from Q1 or Q-2 and Y is alkylene are also available via the synthetic route shown in Scheme 1.3. Reaction of amine 8 with isocyanate or isothiocyanate 2a yields the urea/thiourea 8a which can be cyclized by the addition of chlorocarbonyl sulfenyl chloride. See GB1115350 and U.S. Pat. No. 3,818,024, Revankar et. al U.S. Pat. No. 4,093,624, and Klayman et. al *JOC* 1972, 37(10), 1532 for further details. Where $R_4$ is a readily removable protecting group (e.g. R=3,4-d-methoxybenzyl amine), the action of mild, acidic deprotection conditions such as CAN or TFA will reveal the parent ring system of I-4 (X=O) and I-7 (X=S).

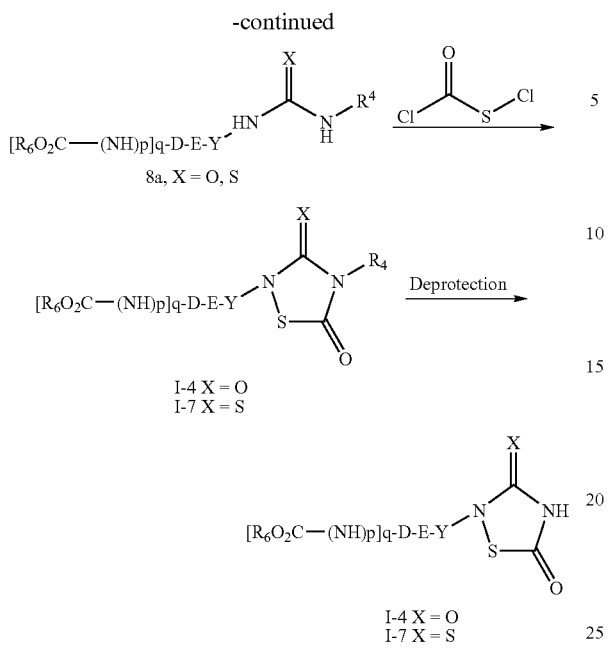

I-7 is also available as shown in Scheme 1.4. Condensation of isocyanate or isothiocyanate 2a with amine $R_5NH_2$ yields urea/thiourea 2b, which, when reacted with chlorocarbonyl sulfenyl chloride according to GB1115350 and U.S. Pat. No. 3,818,024 yields 2c. Where $R_4$ is a readily removable protecting group (e.g. R=3,4-d-methoxybenzyl amine), the action of mild, acidic deprotection conditions such as CAN or TFA will reveal the parent ring system of 2d. Reaction of 2d with NaH in DMF, and displacement wherein M is a suitable leaving group such as chloride, bromide or iodide yields I-4 (X=O) and I-7 (X=S).

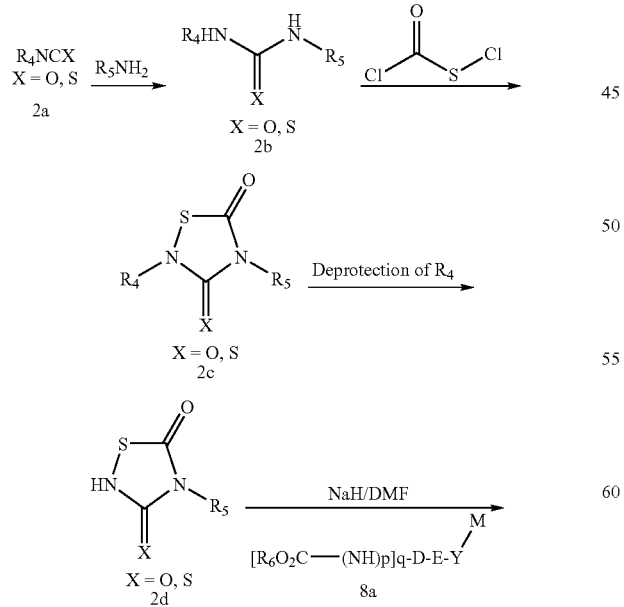

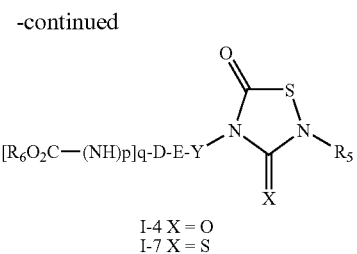

Compounds of Formula I wherein Q is taken from Q-1' or Q-2' and Y is alkylene are available via the synthetic route shown in Scheme 1.3. Condensation of isocyanate or isothiocyanate 2a with ammonia yields urea/thiourea 2e, which, when reacted with chlorocarbonyl sulfenyl chloride according to GB1115350 and U.S. Pat. No. 3,818,024 yields 2f. Reaction of 2f with NaH in DMF, and displacement wherein M is a suitable leaving group such as chloride, bromide or iodide yields I-4' (X=O) and I-7' (X=S).

Scheme 1.5

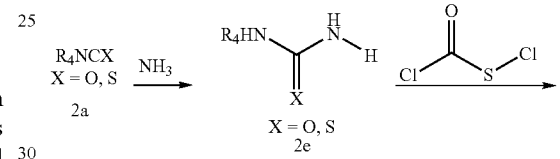

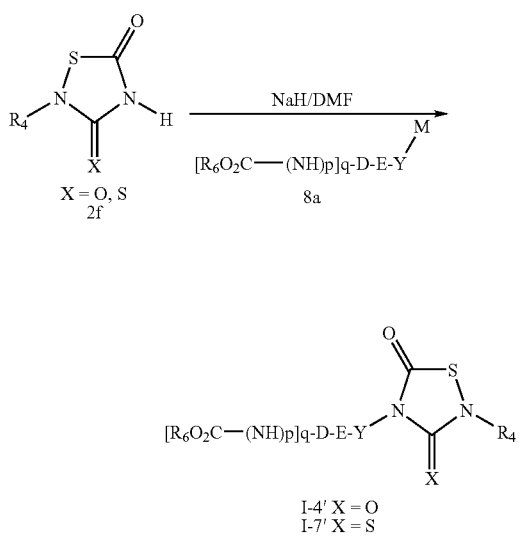

Compounds of Formula I wherein Q is taken from Q-3 or Q-4 and Y is alkylene, are prepared according to the synthetic route shown in Schemes 2.1 and 2.2, respectively. Reaction of 12, wherein M is a suitable leaving group, with the carbamate-protected hydrazine 13 affords intermediate 14. Reaction of 14 with an isocyanate gives rise to intermediate 15. Thermal cyclization of 15 affords 1,2,4-triazolidinedione of Formula I-16. By analogy, scheme 2.2 illustrates the preparation of 3-thio-5-oxo-1,2,4-triazolidines of Formula I-18 by reaction of intermediate 14 with an isothiocyanate and subsequent thermal cyclization.

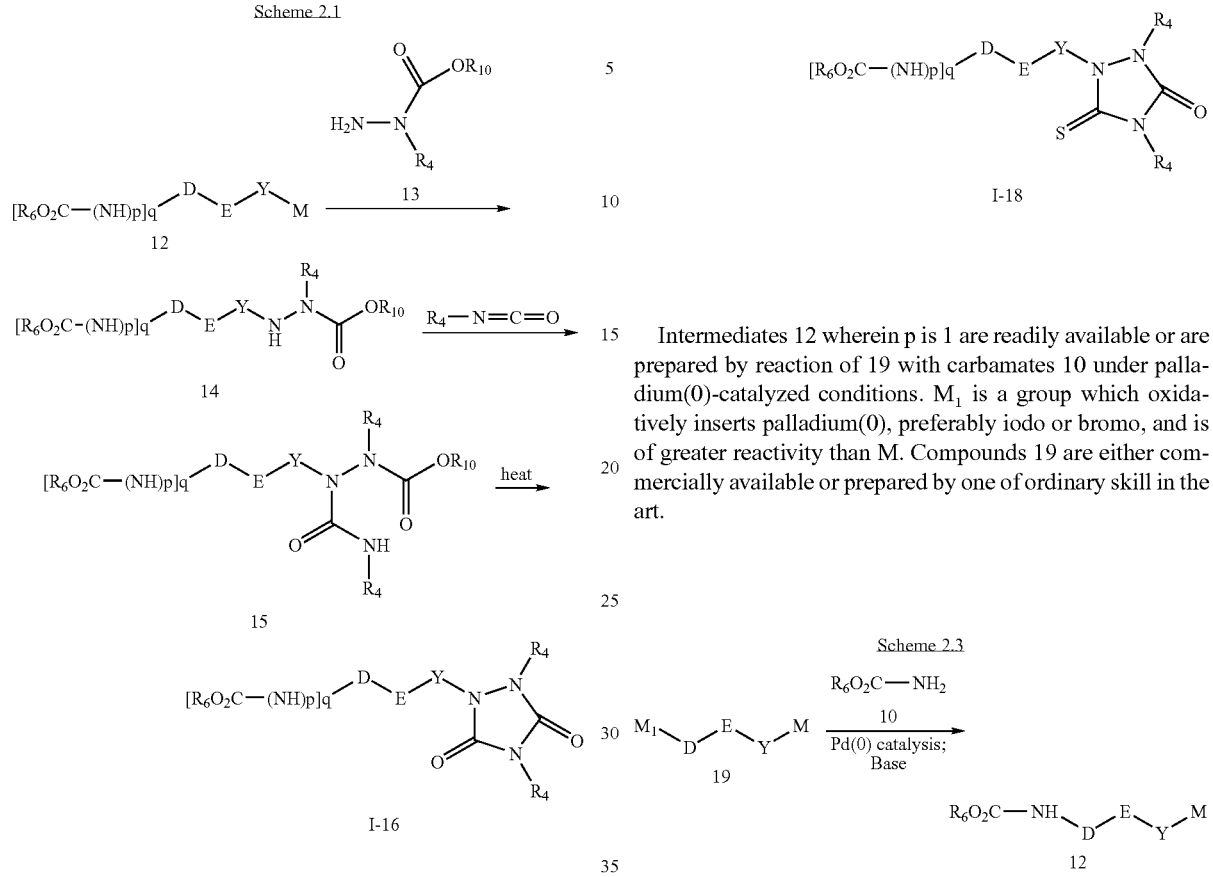

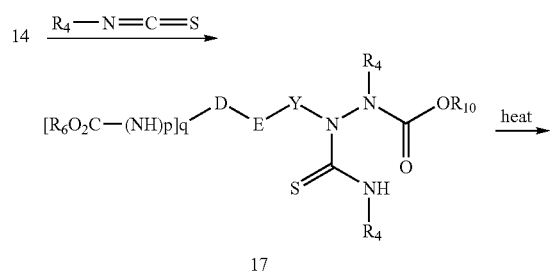

Intermediates 12 wherein p is 1 are readily available or are prepared by reaction of 19 with carbamates 10 under palladium(0)-catalyzed conditions. $M_1$ is a group which oxidatively inserts palladium(0), preferably iodo or bromo, and is of greater reactivity than M. Compounds 19 are either commercially available or prepared by one of ordinary skill in the art.

Compounds of Formula I wherein D is taken from Q-3 or Q-4 and Y is alkylene, are also prepared according to the synthetic route shown in Scheme 2.4. Oxidation of amine $R_4NH_2$ to the corresponding hydrazine, condensation with ethyl chloroformate subsequent heating yields 1,2,4-triazolidinedione 15a. After the action of NaH in DMF, displacement wherein M is a suitable leaving group such as chloride, bromide or iodide yields I-16 (X=O) and I-18 (X=S).

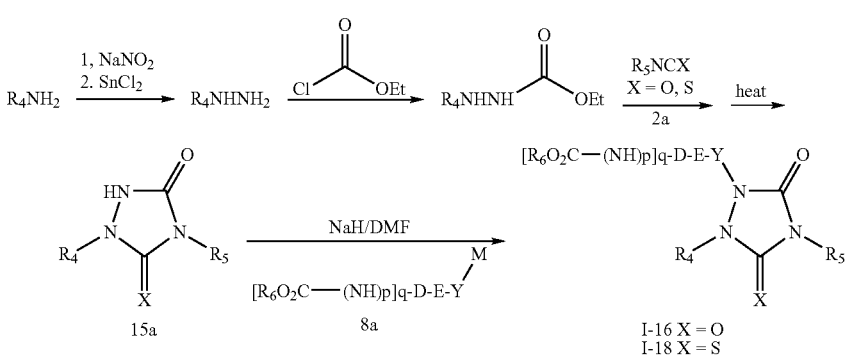

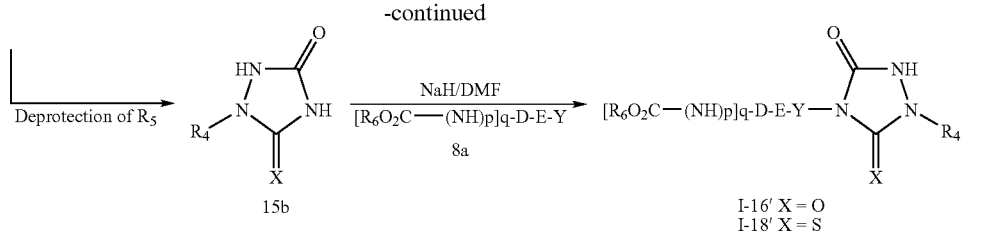

Compounds of Formula I wherein D is taken from D-3' or D-4' and Y is alkylene, are also prepared according to the synthetic route shown in Scheme 2.4. When $R_5$ is a readily removable protecting group (e.g. R=3,4-d-methoxybenzyl amine), the action of mild, acidic deprotection conditions such as CAN or TFA on 15a will reveal 1,2,4-triazolidinedione 15b. After deprotonation of 15b by NaH in DMF, displacement wherein M is a suitable leaving group such as chloride, bromide or iodide yields I-16' (X=O) and I-18' (X=S).

Compounds of Formula I wherein Q is taken from Q-5 or Q-6 and Y is alkylene are prepared according to the synthetic route shown in Scheme 3. Reaction of hydrazine 20 with chlorosulfonylisocyanate and base, such as triethylamine, gives rise to a mixture of intermediates 21A and 21B which are not isolated but undergo cyclization in situ to afford compounds of Formulae I-22A and I-22B. Compounds I-22A and I-22B are separated by chromatography or fractional crystallization. Optionally, compounds I-22A and I-22B can undergo Mitsunobu reaction with alcohols $R_4OH$ to give compounds of Formulae I-23A and I-23B. Compounds 20 are prepared by acid-catalyzed deprotection of t-butyl carbamates of structure 14, wherein $R_{10}$ is t-butyl.

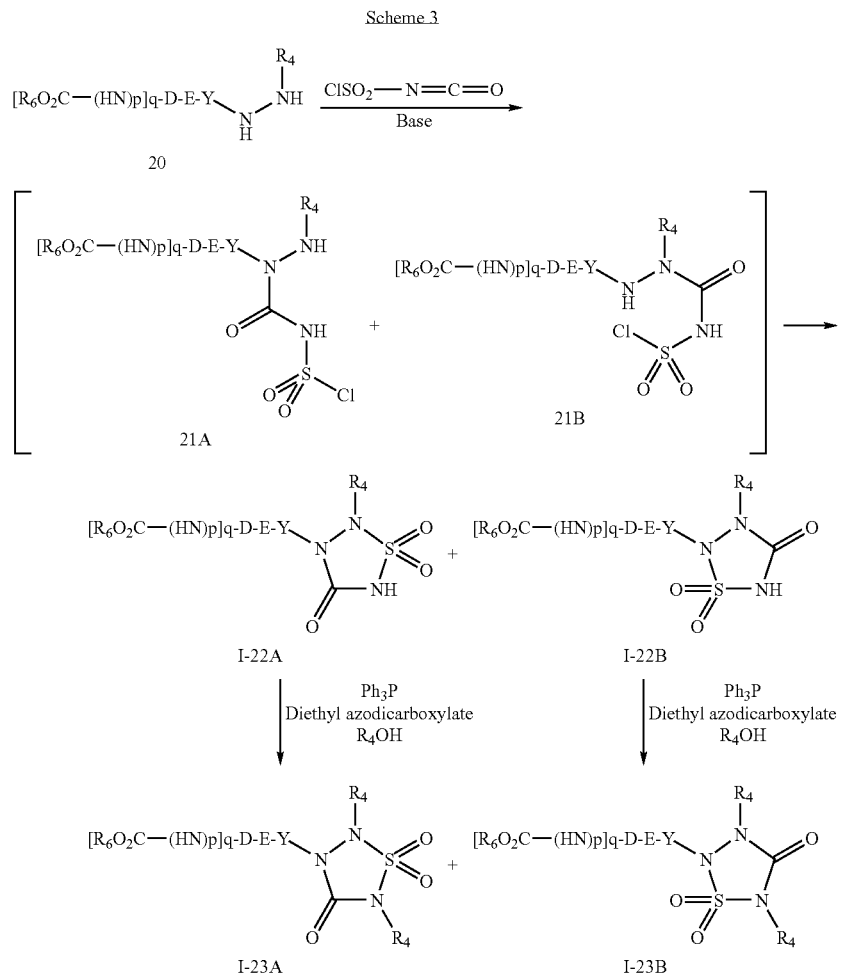

Compounds of Formula I wherein Q is Q-7 and Y is alkylene are prepared as shown in Scheme 4. Reaction of amine 8 with maleimide 24, wherein M is a suitable leaving group, affords compounds of Formula I-25. Reaction of compound 26, wherein M is a group which can oxidatively insert Pd(0), can participate in a Heck reaction with maleimide 27, affording compounds of Formula I-28. Maleimides 24 and 27 are commercially available or prepared by one of ordinary skill in the art.

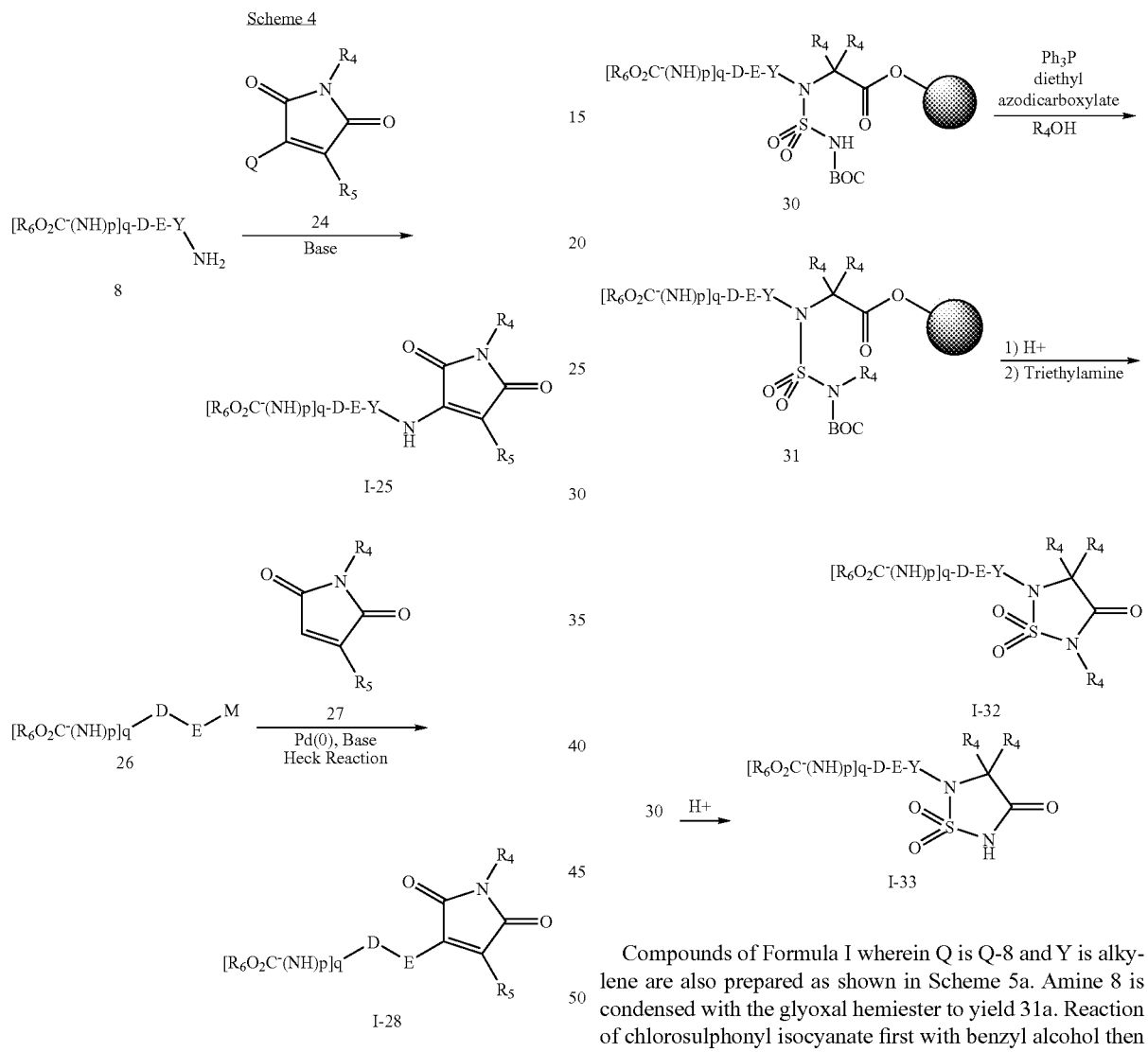

Compounds of Formula I wherein Q is Q-8 and Y is alkylene are prepared as shown in Scheme 5, according to methods reported by M. Tremblay et al, *Journal of Combinatorial Chemistry* (2002) 4:429. Reaction of polymer-bound activated ester 29 (polymer linkage is oxime activated-ester) with chlorosulfonylisocyante and t-butanol affords N-BOC sulfonylurea 30. Subjection of 30 to the Mitsunobu reaction with $R_4OH$ gives rise to 31. BOC-group removal with acid, preferably trifluoroacetic acid, and then treatment with base, preferably triethylamine, provides the desired sulfahydantoin I-32. Optionally, intermediate 30 is treated with acid, preferably trifluoroacetic acid, to afford the N-unsubstituted sulfahydantoin I-33.

Compounds of Formula I wherein Q is Q-8 and Y is alkylene are also prepared as shown in Scheme 5a. Amine 8 is condensed with the glyoxal hemiester to yield 31a. Reaction of chlorosulphonyl isocyanate first with benzyl alcohol then 31a yields 31b, which after heating yields I-32.

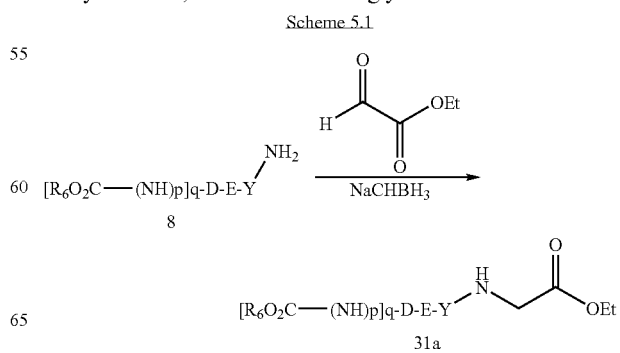

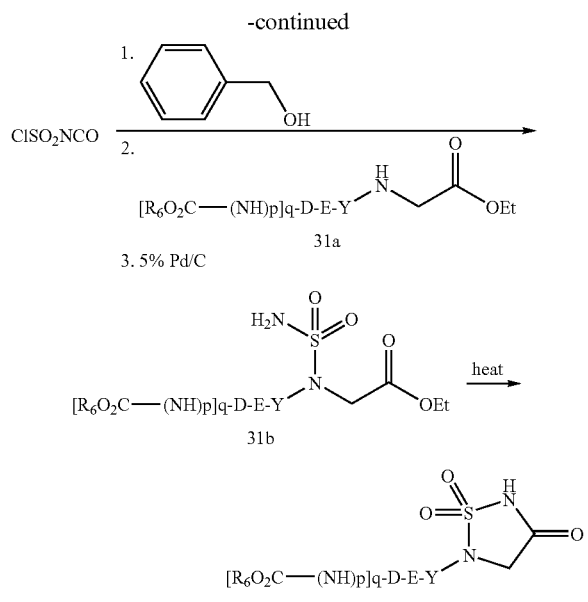

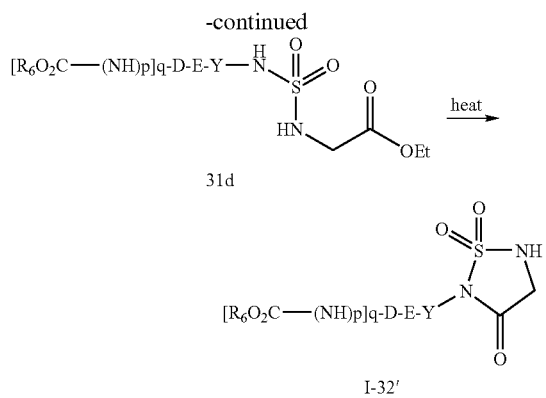

Compounds of Formula I wherein Q is taken from Q-8', are prepared according to the synthetic route shown in Scheme 5.2. Formation of 31c by the method of Muller and DuBois *JOC* 1989, 54, 4471 and its deprotonation with NaH/DMF or NaH/DMF and subsequently alkylation wherein M is a suitable leaving group such as chloride, bromide or iodide yields I-32'. Alternatively, I-32' is also available as shown in Scheme 5.3. Mitsunobu reaction of boc-sulfamide amino ethyl ester with alcohol 8b (made by methods analogous to that for amine 8) yields 31c, which after Boc removal with 2N HCl in dioxane is cyclized by the action of NaH on 31d results in I-32'.

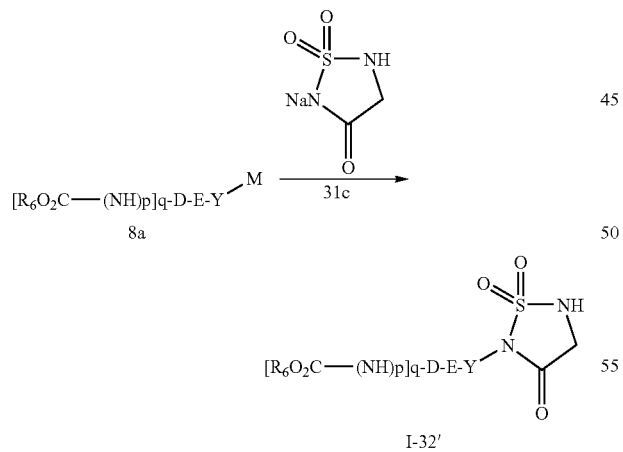

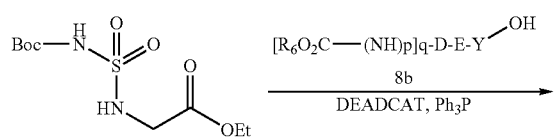

Compounds of Formula I wherein Q is Q-9 and Y is alkylene are prepared as shown in Scheme 6. Reaction of polymer-bound amino acid ester 34 with an isocyanate affords intermediate urea 35. Treatment of 35 with base, preferably pyridine or triethylamine, with optional heating, gives rise to compounds of Formula I-36.

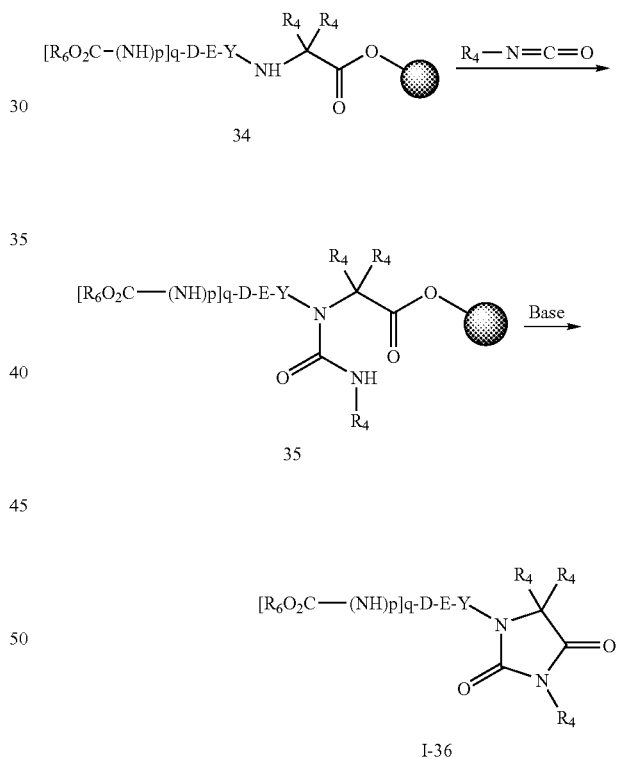

Compounds of Formula I wherein Q is Q-9 and Y is alkylene are also prepared as shown in Scheme 6.1. Reaction of aldehyde 8c under reductive amination conditions with the t-butyl ester of glycine yields 35a. Isocyanate 2a is condensed with p-nitrophenol (or the corresponding $R_4NH_2$ amine is condensed with p-nitrophenyl chloroformate) to yield the carbamic acid p-nitrophenyl ester, which when reacted with deprotonated 35a and yields the urea that when deprotected with acid yields 35b. Formula I-36 is directly available from 35b by the action of NaH and heat.

Scheme 6.1

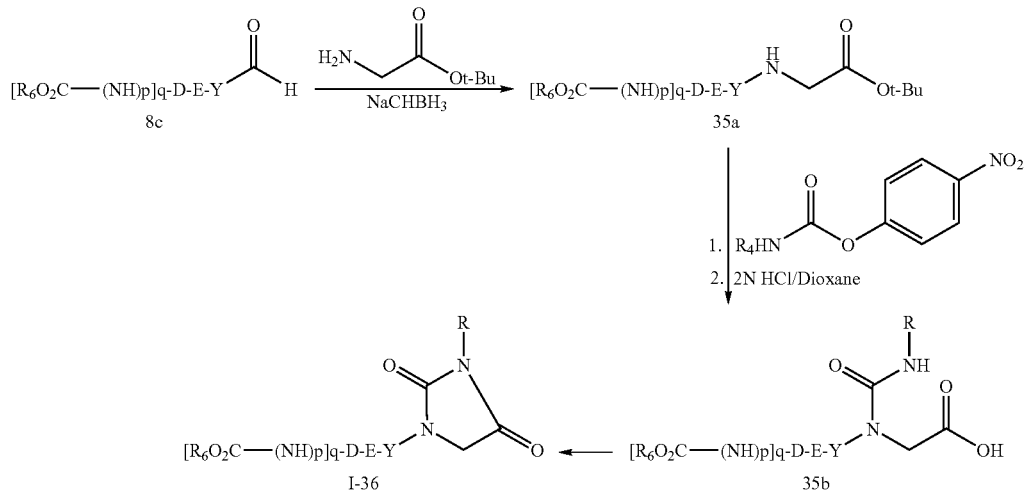

Compounds of Formula I wherein Q is taken from Q-9', are prepared according to the synthetic route shown in Scheme 6.2. Formation of 35c by the method described in JP10007804A2 and Zvilichovsky and Zucker, Israel Journal of Chemistry, 1969, 7(4), 547-54 and its deprotonation with NaH/DMF or NaH/DMF and its subsequent displacement of M, wherein M is a suitable leaving group such as chloride, bromide or iodide, yields I-36'.

Scheme 6.2

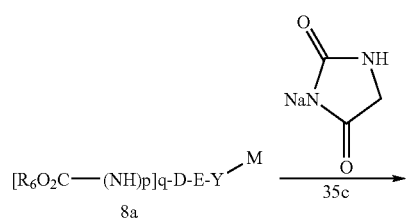

Compounds of Formula I wherein Q is Q-10 or Q-11, and Y is alkylene are prepared as shown in Schemes 7.1 and 7.2, respectively. Treatment of alcohol 37 (Z=O) or amine 37 (Z=NH) with chlorosulfonylisocyanate affords intermediate carbamate or urea of structure 38. Treatment of 38 with an amine of structure $HN(R_4)_2$ and base, preferably triethylamine or pyridine, gives sulfonylureas of Formula I-39. Reaction of chlorosulonylisocyanate with an alcohol (Z=O) or amine (Z=NR_4) 40 affords intermediate 41. Treatment of 41 with an amine 8 and base, preferably triethylamine or pyridine, gives sulfonylureas of Formula I-42.

Scheme 7.1

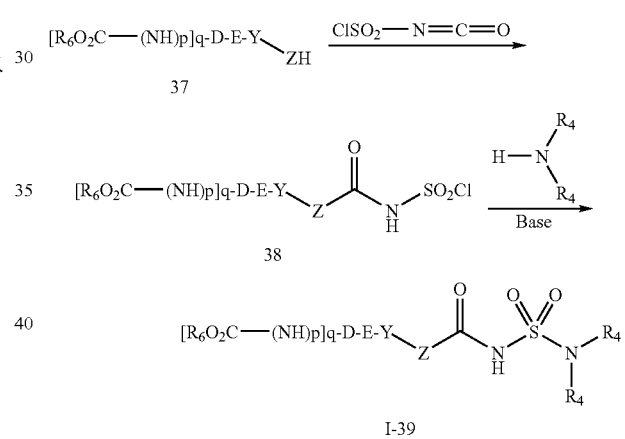

Scheme 7.2

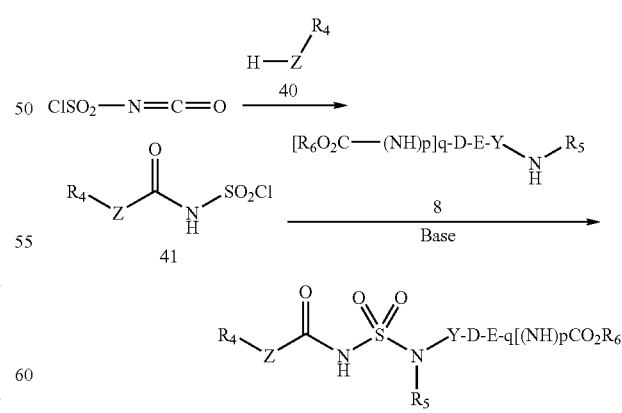

Compounds of Formula I wherein Q is taken from Q-12 are prepared according to the synthetic route shown in Scheme 8. Alkylation of pyridine 43, wherein TIPS is tri-isopropylsilyl, under standard conditions ($K_2CO_3$, DMF, $R_4$—I or Mitsunobu conditions employing $R_4$—OH) yields pyridine derivative 44 which is reacted with compound 12, wherein M is a suitable leaving group, to afford pyridones of formula I-45.

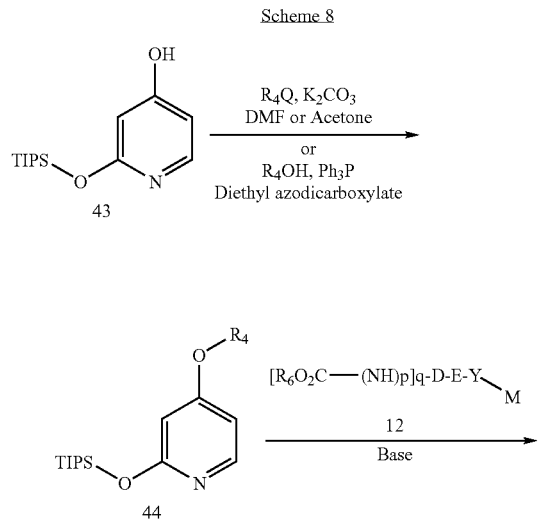

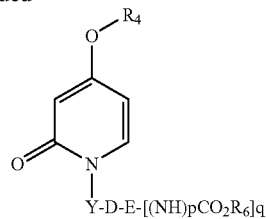

Compounds of Formula I wherein Q is taken from Q-13 are prepared according to the synthetic route shown in Scheme 9. Starting from readily available pyridine 46, alkylation under standard conditions ($K_2CO_3$, DMF, $R_4$—I or Mitsunobu conditions employing $R_4$—OH) yields pyridine derivative 47. N-alkylation with $K_2CO_3$, DMF, $R_4$—I affords pyridones of formula 48. Intermediate 48 is partitioned to undergo a Heck reaction, giving I-49; a Buchwald amination reaction, giving I-51; or a Buchwald Cu(I) catalyzed O-arylation reaction, to give I-52. The Heck reaction product I-49 may be optionally hydrogenated to afford the saturated compound I-50. Wherein the phenyl ether $R_4$ group is methyl, compounds of formula I-49, I-50, I-51, or I-52 are treated with boron tribromide or lithium chloride to afford compounds of Formula I-53, wherein $R_4$ is hydrogen.

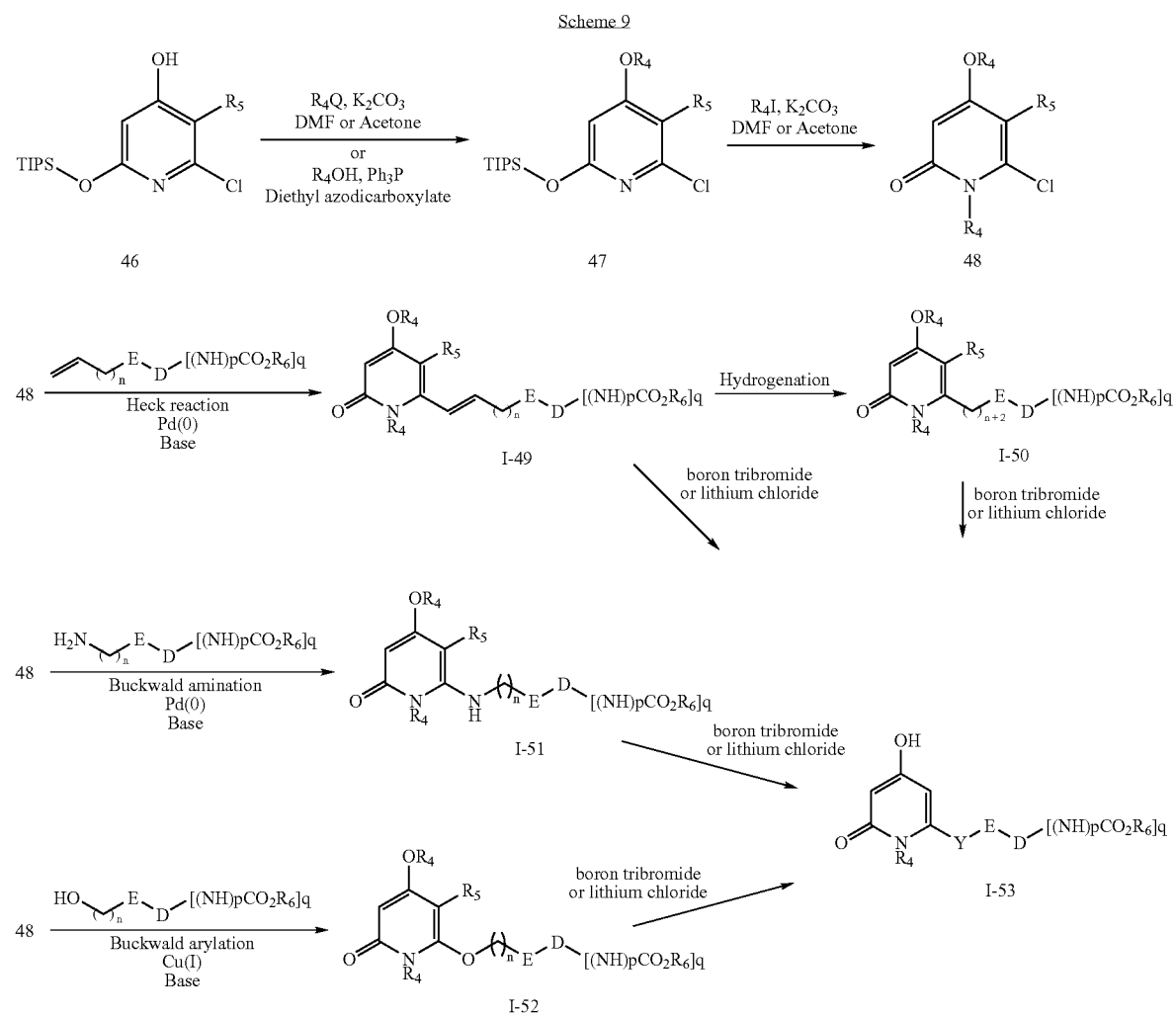

Compounds of Formula I wherein Q is taken from Q-14 are prepared according to the synthetic route shown in Scheme 10. Starting from readily available pyridine 54, alkylation under standard conditions ($K_2CO_3$, DMF, $R_4$—I or Mitsunobu conditions employing $R_4$—OH) yields pyridine derivative 55. N-alkylation with $K_2CO_3$, DMF, $R_4$—I affords pyridones of formula 56. Intermediate 56, wherein M is a suitable leaving group, preferably bromine or chlorine, is partitioned to undergo a Heck reaction, giving I-57; a Buchwald amination reaction, giving -I-59; or a Buchwald Cu(I) catalyzed O-arylation reaction, to give I-60. The Heck reaction product I-57 may be optionally hydrogenated to afford the saturated compound I-58. Wherein $R_4$ is methyl, compounds of formula I-57, I-58, I-59, or I-60 are treated with boron tribromide or lithium chloride to afford compounds of Formula I-61, wherein $R_4$ is hydrogen.

somers. Alternatively, reaction of 62 with dimethylamine affords the vinylogous carbamate 64. Formation of the dihydropyrimidinedione 66 proceeds by condensation with urea 65 with azeotropic removal of dimethylamine or methanol. Dihydropyrimidinedione 66 may optionally be further substituted by Mitsunobu reaction with alcohols $R_4OH$ to give rise to compounds 67.

Scheme 12 illustrates the further synthetic elaboration of intermediates 67. Removal of the silyl protecting group (TBS) is accomplished by treatment of 67 with flouride (tetra-n-butylammonium fluoride or cesium flouride) to give primary alcohols 68. Reaction of 68 with isocyanates 2 gives rise to compounds of Formula I-69. Alternatively, reaction of 68 with $[R_6O_2C(NH)p]q$-D-E-M, wherein M is a suitable leaving group, affords compounds of Formula I-70. Oxidation of 68 using the Dess-Martin periodinane (D. Dess, J. Martin, *J.*

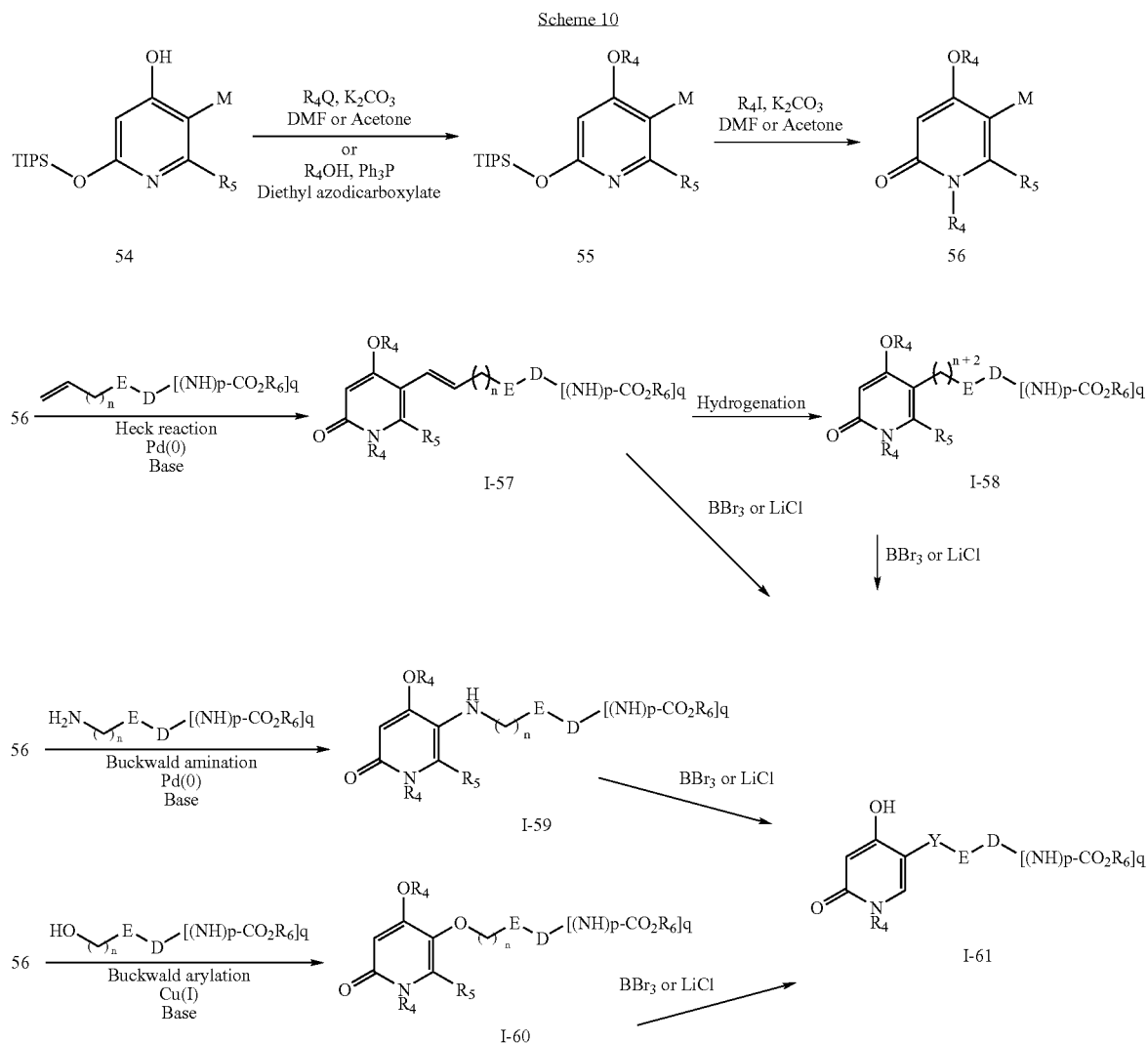

Scheme 10

Compounds of Formula I wherein Q is taken from Q-15 are prepared according to the synthetic routes shown in Schemes 11 and 12. Starting esters 62 are available from the corresponding secoacids via TBS-ether and ester formation under standard conditions. Reaction of protected secoester 62 with Meerwin's salt produces the vinyl ether 63 as a pair of regioi-

*Am. Chem. Soc.* (1991) 113:7277) or tetra-n-alkyl peruthenate (W. Griffith, S. Ley, *Aldrichimica Acta* (1990) 23:13) gives the aldehydes 71. Reductive amination of 71 with amines 8 gives rise to compounds of Formula I-72. Alternatively, aldehydes 71 may be reacted with ammonium acetate under reductive alkylation conditions to give rise to the primary amine 73. Reaction of 73 with isocyanates 2 affords compounds of Formula I-74.
Scheme 11
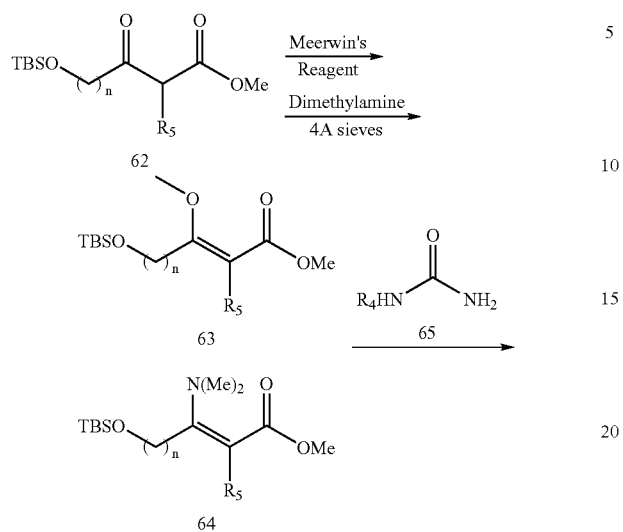
-continued
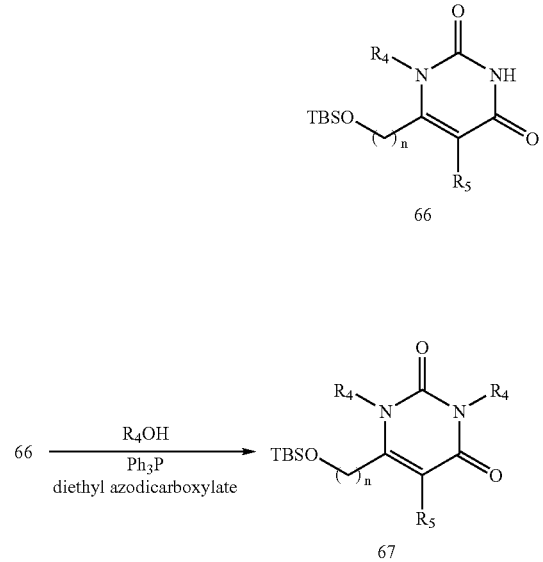

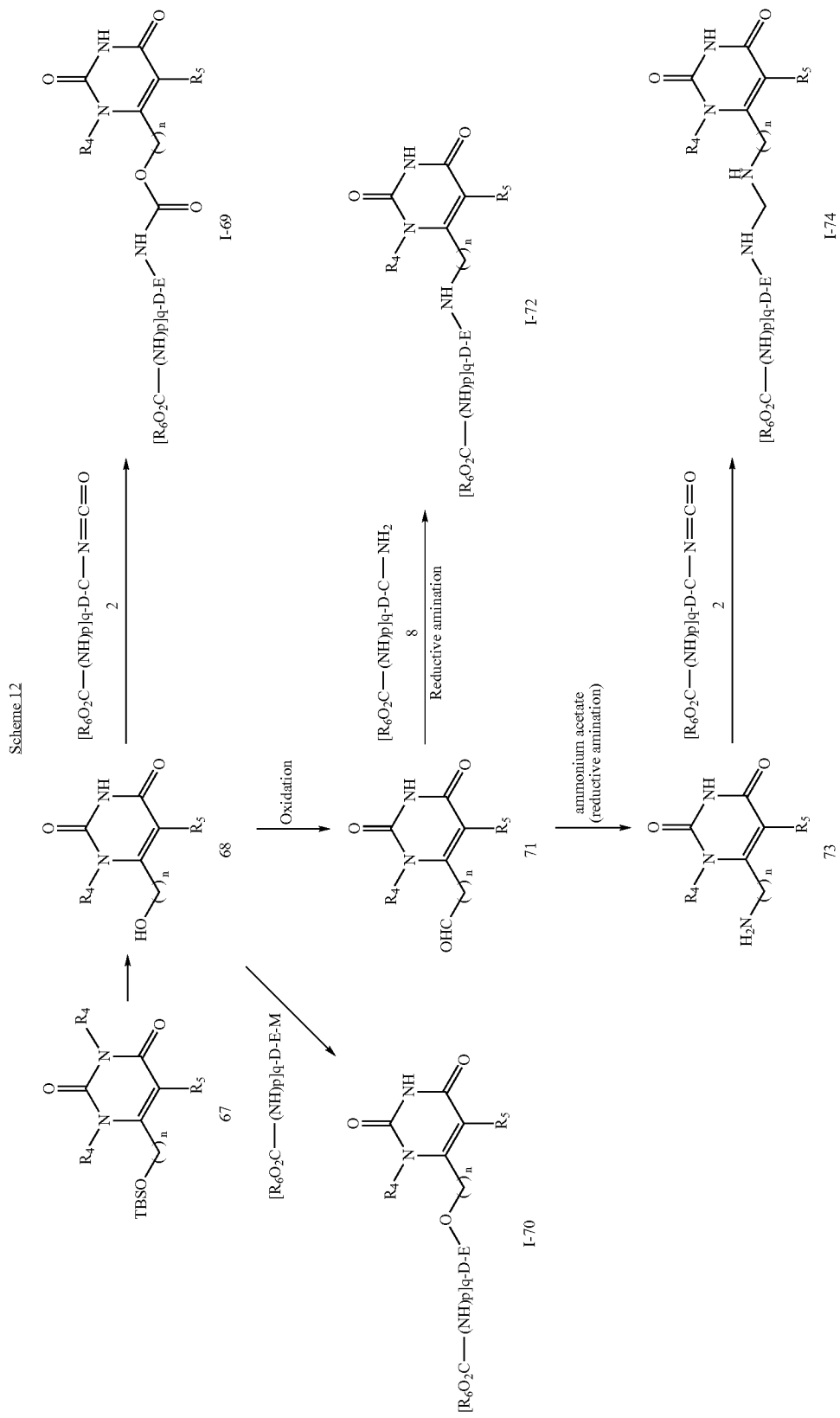

Compounds of Formula I wherein Q is taken from Q-16 are prepared according to the synthetic routes shown in Schemes 13 and 14. Starting esters 75 are available from the corresponding secoacids via TBS-ether and ester formation under standard conditions. Reaction of protected secoester 75 with Meerwin's salt produces the vinyl ether 76 as a pair of regioisomers. Alternatively, reaction of 75 with dimethylamine affords the vinylogous carbamate 77. Formation of the dihydropyrimidinedione 78 proceeds by condensation with urea 65 with azeotropic removal of dimethylamine or methanol. Dihydropyrimidinedione 78 may optionally be further substituted by Mitsunobu reaction with alcohols $R_4OH$ to give rise to compounds 79. Compounds of Formulae I-81, I-82, I-84, and I-86 are prepared as shown in Scheme 14 by analogy to the sequence previously described in Scheme 12.

Scheme 13

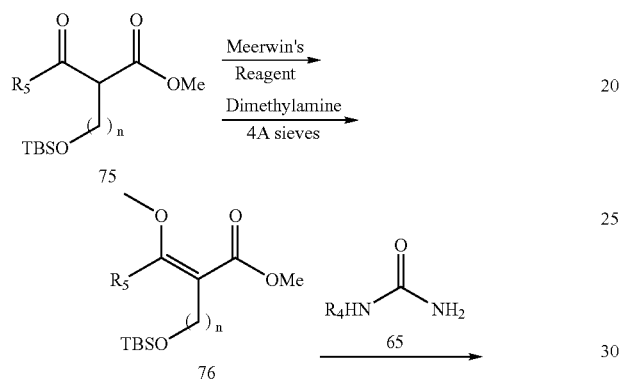

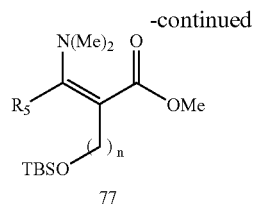

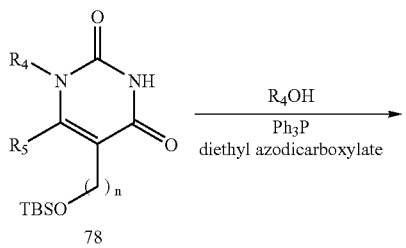

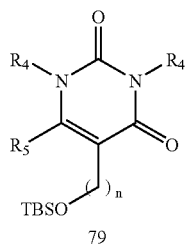

Scheme 14

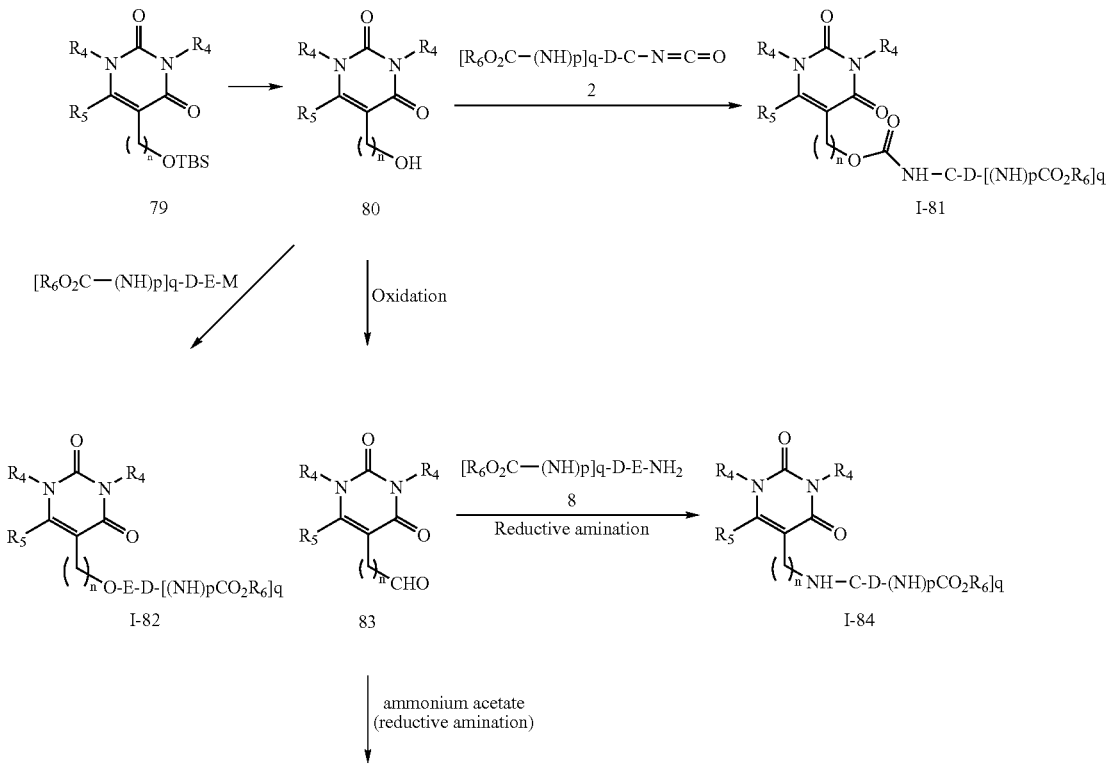

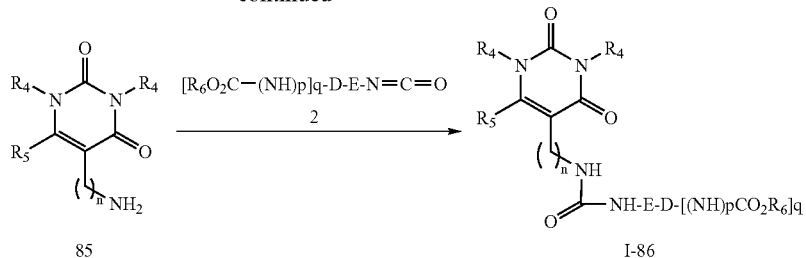

Alkyl acetoacetates 87 are commercially available and are directly converted into the esters 88 as shown in Scheme 15. Treatment of 87 with NaHMDS in THF, followed by quench with formaldehyde and TBSCl (n=1) or Q-(CH2)n-OTBS (n=2-4), gives rise to compounds 88.

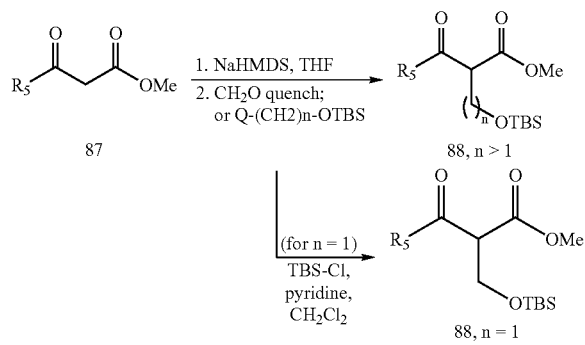

Compounds of Formula I wherein Q is taken from Q-17 are prepared according to the synthetic routes shown in Schemes 16.1 and 16.2, and starts with the BOC-protected hydrazine 13, which is converted to the 1,2-disubstituted hydrazine 89 by a reductive alkylation with a glyoxal derivative mediated by sodium cyanoborohydride and acidic workup. Condensation of 89 with diethyl malonate in benzene under reflux yields the heterocycle 90. Oxidation with $N_2O_4$ in benzene (see Cardillo, Merlini and Boeri *Gazz. Chim. Ital.*, (1966) 9:8) to the nitromalonohydrazide 91 and further treatment with $P_2O_5$ in benzene (see: Cardillo, G. et al, *Gazz. Chim. Ital.* (1966) 9:973-985) yields the tricarbonyl 92. Alternatively, treatment of 90 with Brederick's reagent (t-BuOCH(N (Me_2)_2, gives rise to 93, which is subjected to ozonolysis, with a DMS and methanol workup, to afford the protected tricarbonyl 92. Compound 92 is readily deprotected by the action of CsF in THF to yield the primary alcohol 94. Alcohol 94 is optionally converted into the primary amine 95 by a sequence involving tosylate formation, azide displacement, and hydrogenation.

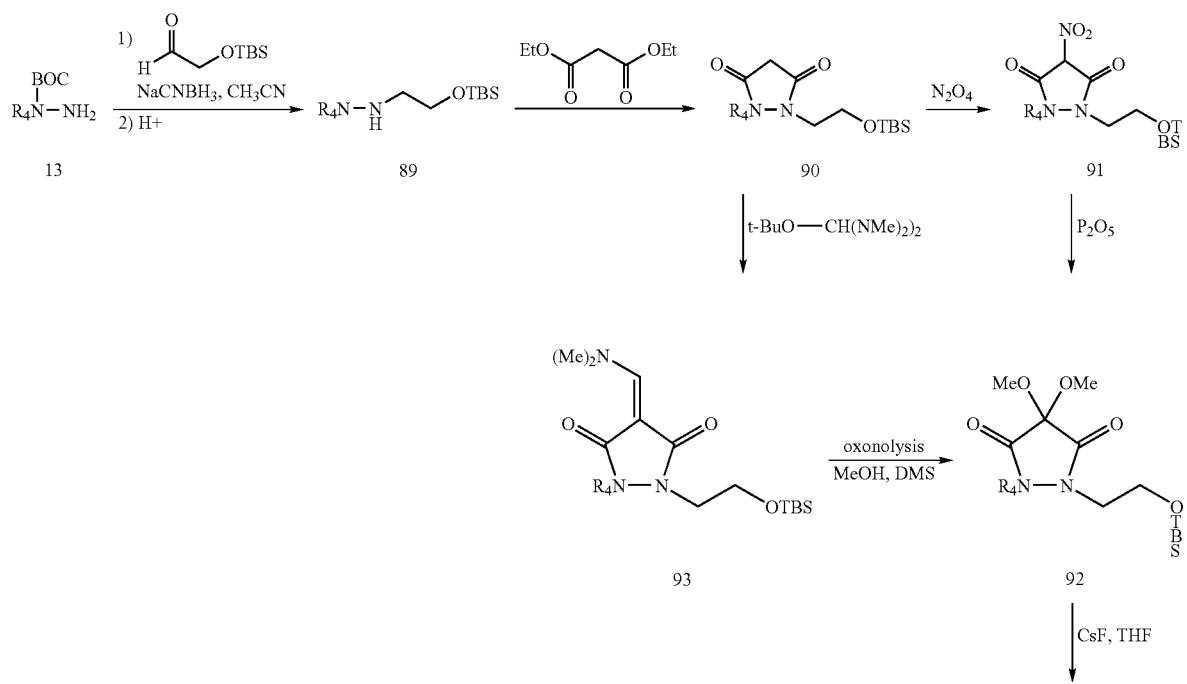

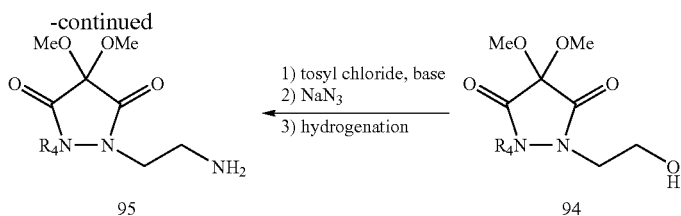

Reaction of 94 with (hetero)aryl halide 26, wherein M is iodo, bromo, or chloro, under copper(I) catalysis affords compounds I-96. Optional deprotection of the di-methyl ketal with aqueous acid gives rise to compounds of Formula I-98. By analogy, reaction of amine 95 with 26 under palladium(0) catalysis affords compounds of Formula I-97. Optional deprotection of the di-methyl ketal with aqueous acid gives rise to compounds of Formula I-99.

Scheme 16.2

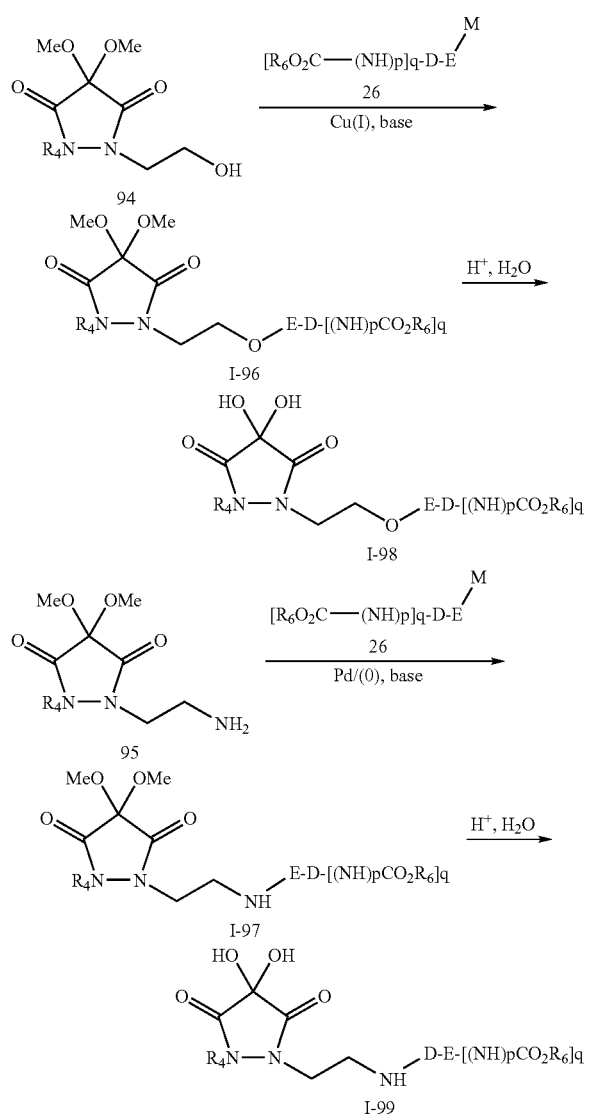

Compounds of Formula I wherein Q is taken from Q-17 are also prepared according to the synthetic route shown in Scheme 16.3. Deprotonation of 4,4-dimethyl-3,5-dioxo-pyrazolidine (95a, prepared according to the method described in Zinner and Boese, D. *Pharmazie* 1970, 25(5-6), 309-12 and Bausch, M. J. et. al *J. Org. Chem.* 1991, 56(19), 5643) with NaH/DMF or NaH/DMF and its subsequent displacement of M, wherein M is a suitable leaving group such as chloride, bromide or iodide yields I-99a.

Scheme 16.3

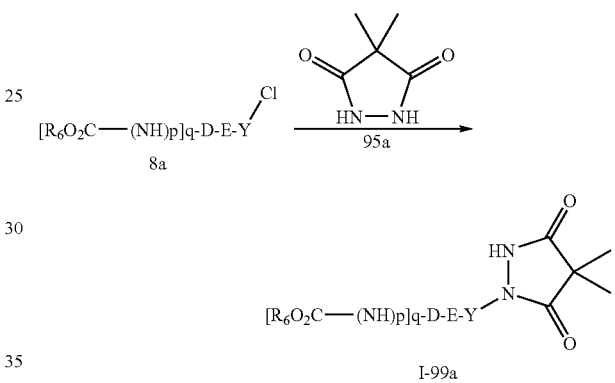

Compounds of Formula I wherein Q is taken from Q-18 are prepared as shown in Schemes 17.1 and 17.2. Aminoesters 100 are subjected to reductive alkylation conditions to give rise to intermediates 101. Condensation of amines 101 with carboxylic acids using an acid activating reagent such as dicyclohexylcarbodiimide (DCC)/hydroxybenzotriazole (HOBt) affords intermediate amides 102. Cyclization of amides 102 to tetramic acids 104 is mediated by Amberlyst A-26 hydroxide resin after trapping of the in situ generated alkoxide 103 and submitting 103 to an acetic acid-mediated resin-release.

Scheme 17.1

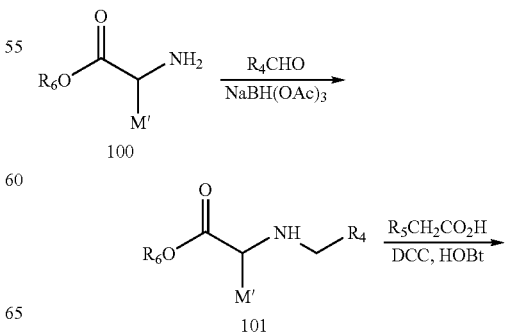

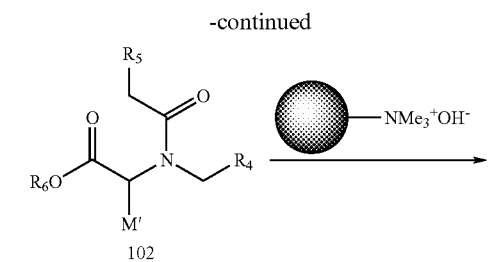

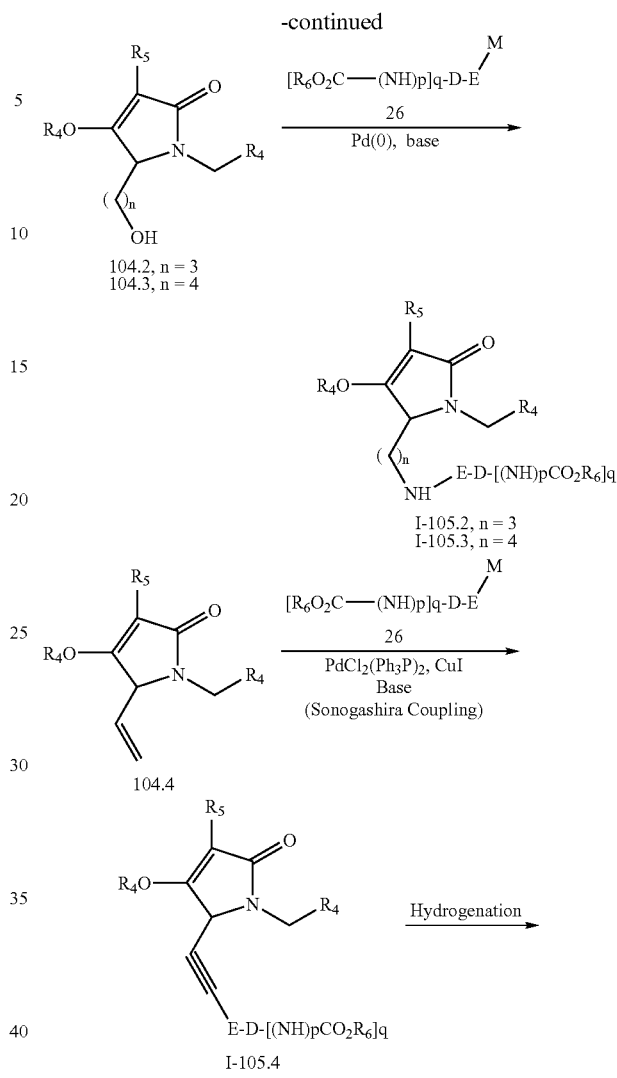

M' is t-BuOCH$_2$-, BOCNH(CH$_2$)$_3$-, BOCNH(CH$_2$)$_4$-, HC≡C—CH$_2$-
Y is HOCH$_2$-; H$_2$N—(CH$_2$)$_3$-; H$_2$N—(CH$_2$)$_4$-; HC≡C—CH$_2$-

Scheme 17.2 illustrates the synthetic sequences for converting intermediates 104 to compounds of Formula I. Reaction of alcohol 104.1 with aryl or heteroaryl halide 26 (Q=halogen) under copper(I) catalysis gives rise to compounds of Formula I-105.1. Reaction of amines 104.2 and 104.3 with 26 under Buchwald palladium(0) catalyzed amination conditions affords compounds of Formulae I-105.2 and I-105.3. Reaction of acetylene 104.4 with 26 under Sonogashira coupling conditions affords compounds of Formula I-105.4. Compounds I-105.4 may optionally be reduced to the corresponding saturated analogs I-105.5 by standard hydrogenation.

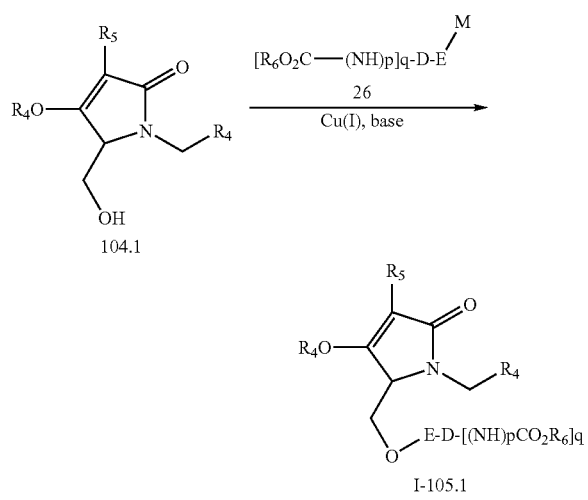

Compounds of Formula I wherein Q is taken from Q-19, Q-20, or Q-21 are prepared as illustrated in Scheme 18. Commercially available Kemp's acid 106 is converted to its anhydride 107 using a dehydrating reagent, preferably di-isopropylcarbodiimide (DIC) or 1-(3-dimethylaminopropyl)-3-ethylcarbodiimide (EDC). Reaction of 107 with amines R$_4$NH$_2$ affords the intermediate amides which are cyclized to the imides 108 by reaction with DIC or EDC. Alternatively, 107 is reacted with amines 8 to afford amides of Formula I-110. Amides I-110 may optionally be further reacted with DIC or EDC to give rise to compounds of Formula I-111. Acid 108 is further reacted with amines 8 to give compounds of Formula I-109.

Scheme 18

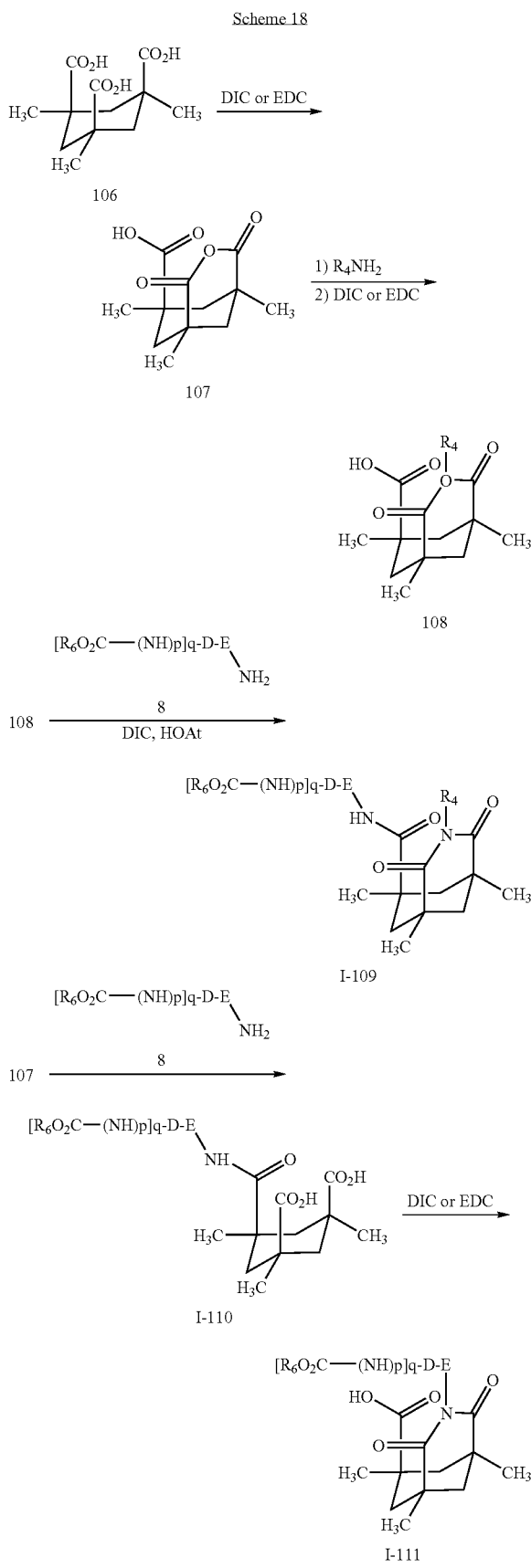

Compounds of Formula I wherein Q is taken from Q-22 or Q-23 are prepared as shown in Schemes 19.1 through 19.3. Preparation of intermediates 113 and 114 are prepared as shown in Scheme 19.1 from di-halo(hetero)aryls 112, wherein $M_2$ is a more robust leaving group than $M_1$. Reaction of 112 with amines 37 (Z=NH) either thermally in the presence of base or by palladium(0) catalysis in the presence of base and phosphine ligand affords compounds 113. Alternatively, reaction of 112 with alcohols 37 (X=O) either thermally in the presence of base or by copper(I) catalysis in the presence of base affords compounds 114.

Scheme 19.1

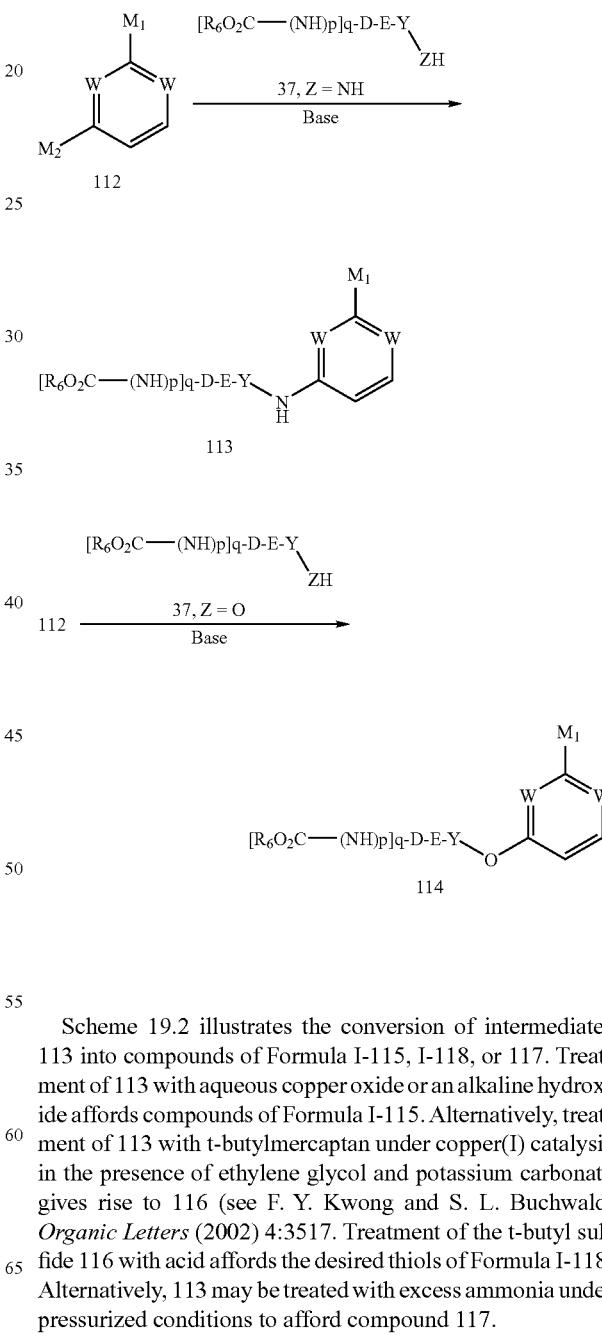

Scheme 19.2 illustrates the conversion of intermediates 113 into compounds of Formula I-115, I-118, or 117. Treatment of 113 with aqueous copper oxide or an alkaline hydroxide affords compounds of Formula I-115. Alternatively, treatment of 113 with t-butylmercaptan under copper(I) catalysis in the presence of ethylene glycol and potassium carbonate gives rise to 116 (see F. Y. Kwong and S. L. Buchwald, *Organic Letters* (2002) 4:3517. Treatment of the t-butyl sulfide 116 with acid affords the desired thiols of Formula I-118. Alternatively, 113 may be treated with excess ammonia under pressurized conditions to afford compound 117.

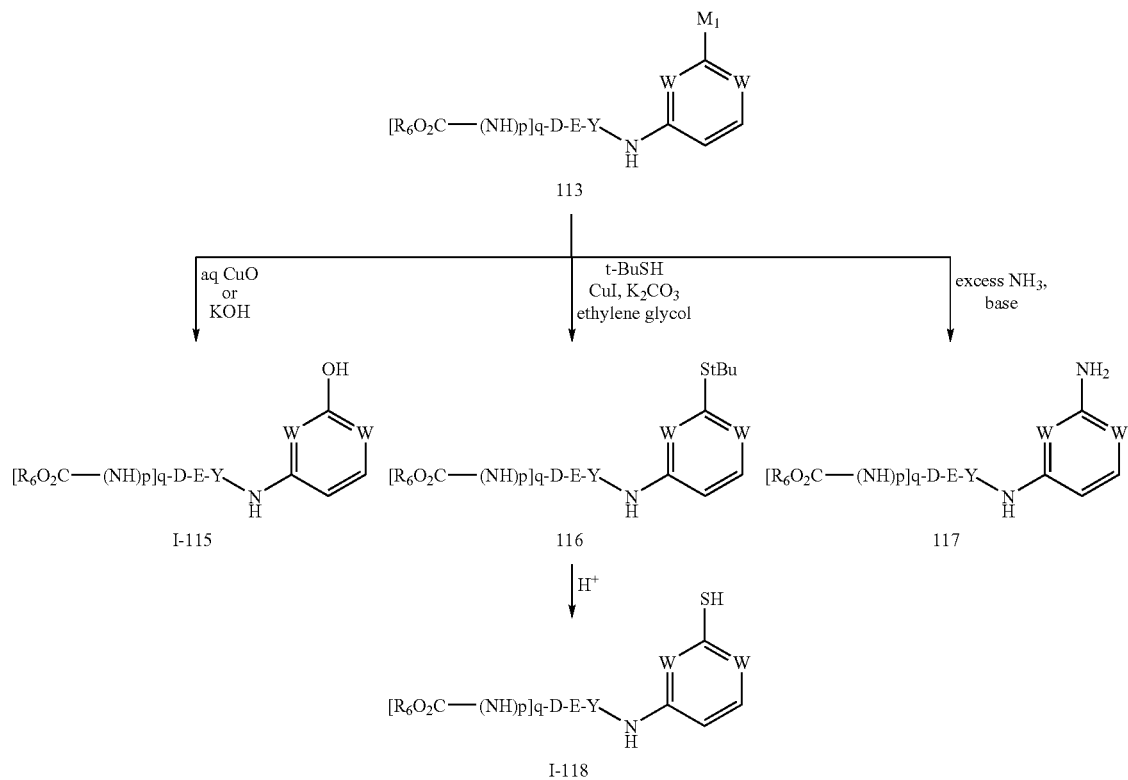
Scheme 19.3 illustrates the conversion of intermediate 114 into compounds of Formula I-119, I-122, and 121, by analogy to the sequence described in Scheme 19.2.
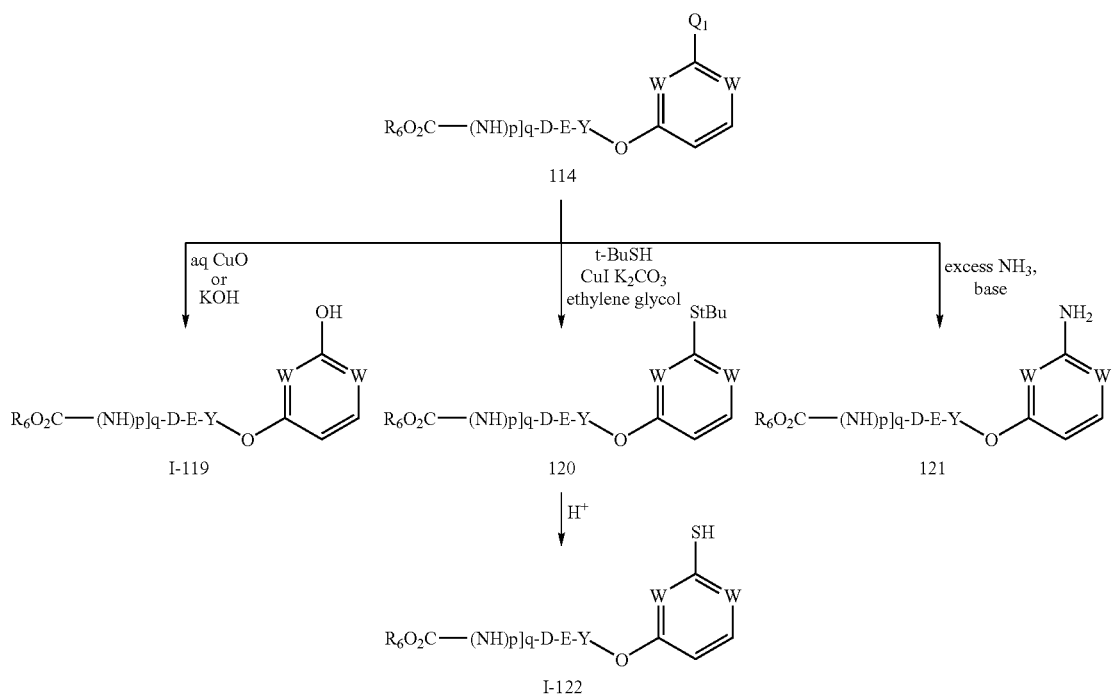

Compounds of Formula I wherein q is taken from Q-24, Q-25, or Q-26 are prepared as shown in Scheme 20. Reaction of compounds I-115 or I-119 with chlorosulfonylisocyanate, followed by in situ reaction with amines HN(R$_4$)$_2$ gives rise to compounds of Formulae I-123 or I-124. Reaction of compounds I-118 or I-122 with a peracid, preferably peracetic acid or trifluoroperacetic acid, affords compounds of Formula I-125 or I-126. Reaction of compounds 117 or 121 with chlorosulfonylisocyanate, followed by in situ reaction with amines HN(R$_4$)$_2$ or alcohols R$_4$OH, affords compounds of Formulae I-127, I-128, I-129, or I-130.

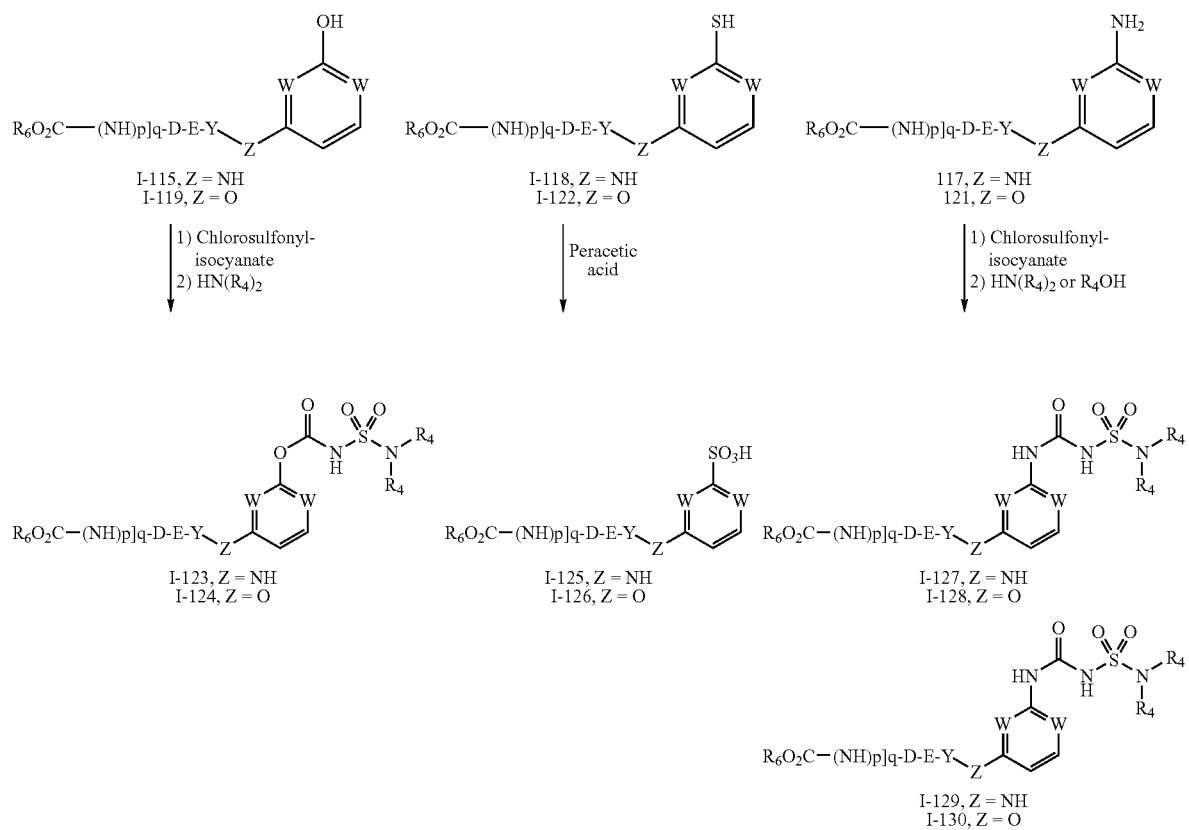

Compounds of Formula I wherein Q is taken from Q-27 are prepared as illustrated in Scheme 21. Reductive alkylation of thiomorpholine with aldehydes 131 affords benzylic amines 132, which are then subjected to peracid oxidation to give rise to the thiomorpholine sulfones 133 (see C. R. Johnson et al, *Tetrahedron* (1969) 25: 5649). Intermediates 133 are reacted with amines 8 (Z=NH$_2$) under Buchwald palladium-catalyzed amination conditions to give rise to compounds of Formula I-134. Alternatively, compounds 133 are reacted with alcohols 8 (Z=OH) under Buchwald copper(I) catalyzed conditions to afford compounds of Formula I-135. Alternatively, intermediates 133 are reacted with alkenes under palladium(0)-catalyzed Heck reaction conditions to give compounds of Formula I-136. Compounds I-136 are optionally reduced to the corresponding saturated analogs I-137 by standard hydrogenation conditions or by the action of diimide.

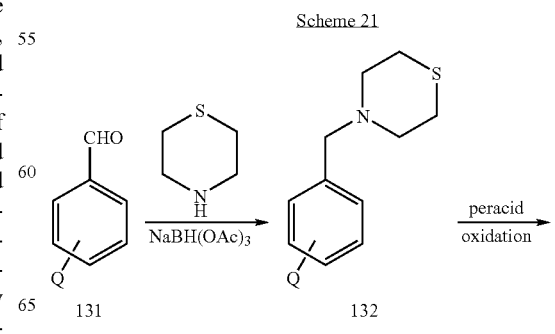

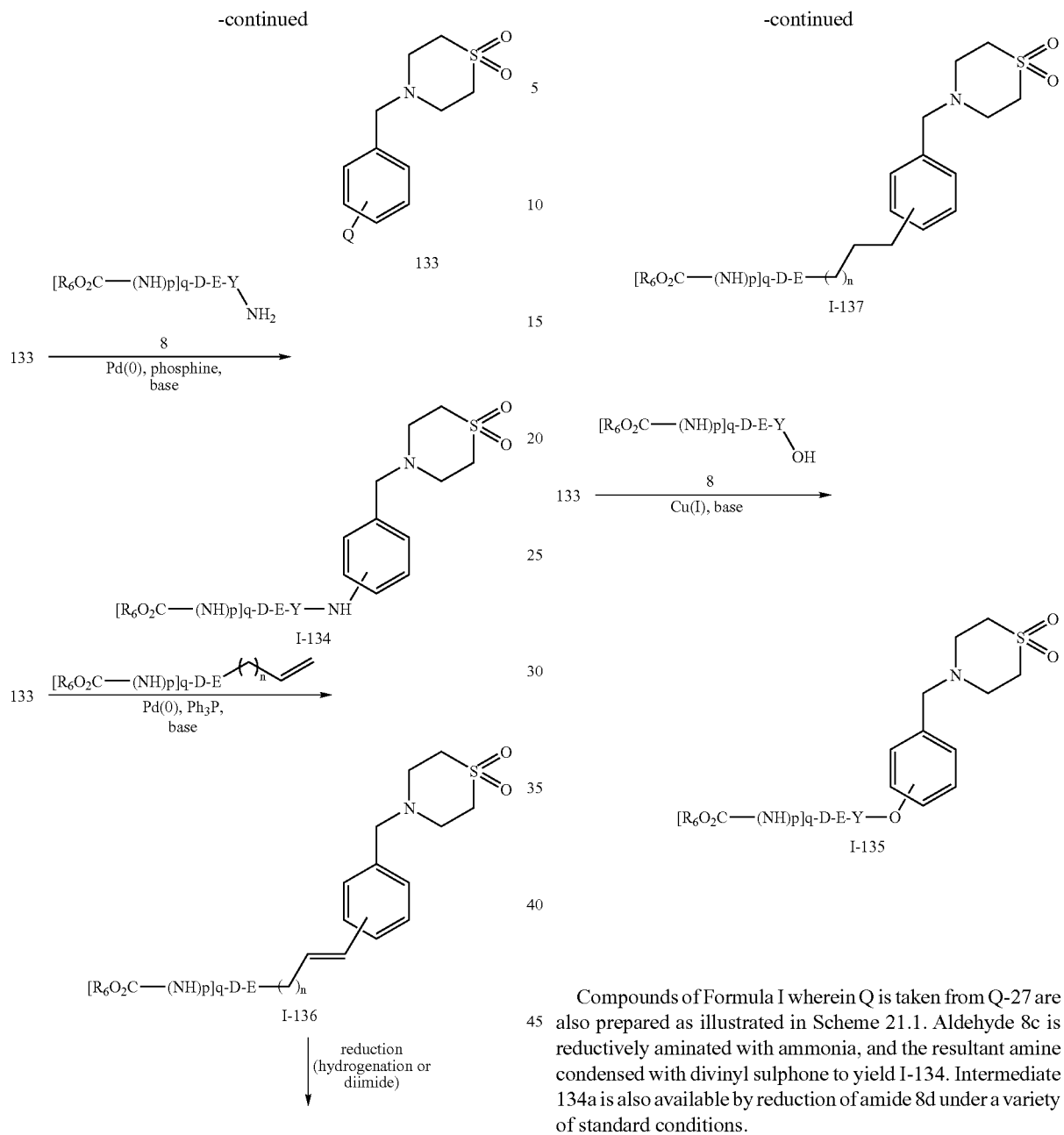
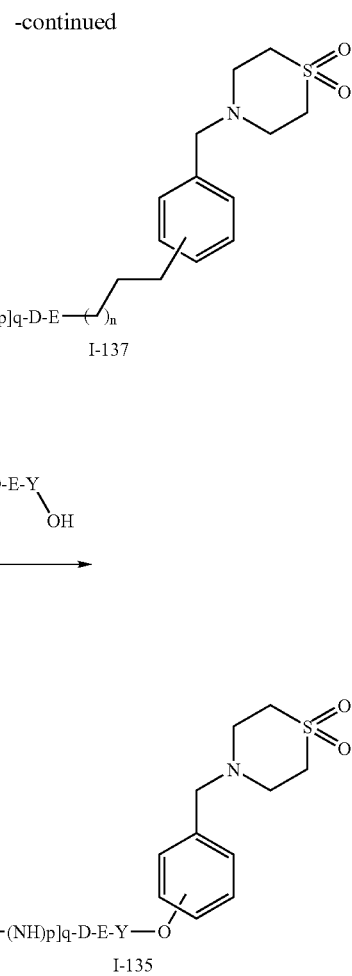
Compounds of Formula I wherein Q is taken from Q-27 are also prepared as illustrated in Scheme 21.1. Aldehyde 8c is reductively aminated with ammonia, and the resultant amine condensed with divinyl sulphone to yield I-134. Intermediate 134a is also available by reduction of amide 8d under a variety of standard conditions.
Scheme 21.1
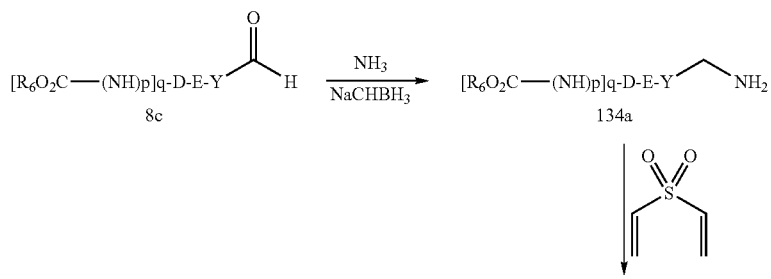

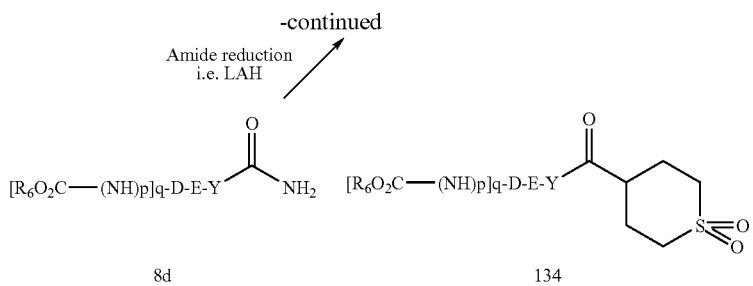

More generally, amines 134c are available via the reduction of amides 134b as shown in Scheme 21.2. The morpholine amide analogues 134d and morpholine analogues 134e are also available as shown in Scheme 21.2.

Scheme 21.2

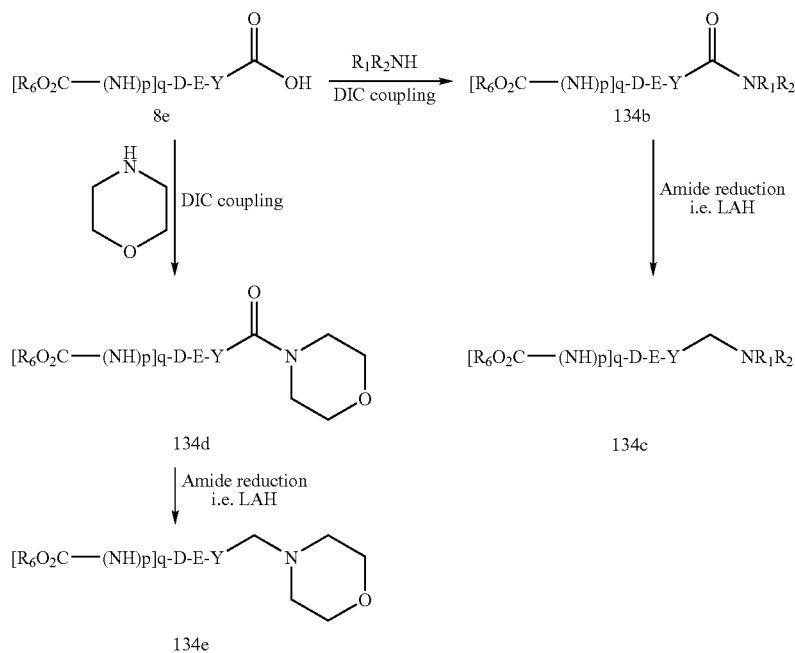

Compounds of Formula I wherein Q is taken from Q-28 or Q-29 are prepared according to the sequences illustrated in Scheme 22. Readily available amides 138 are reacted with chlorosulfonylisocyanate to give intermediates 140, which are reacted in situ with amines $HN(R_4)_2$ or alcohols $R_4OH$ to afford compounds of Formulae I-141 or I-142, respectively. Alternatively, amides 138 are reacted with sulfonylchlorides to give compounds of Formula I-139.

Scheme 22

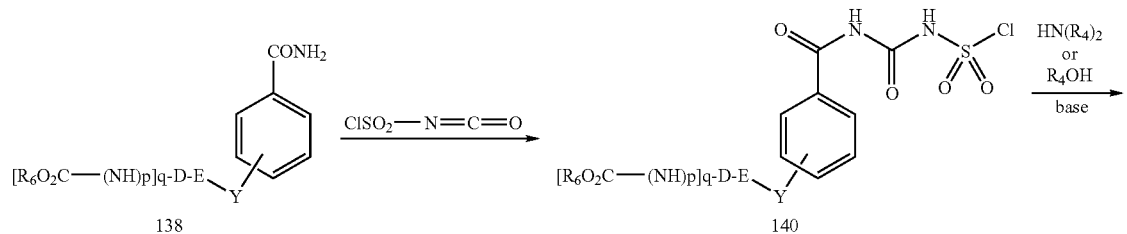

-continued

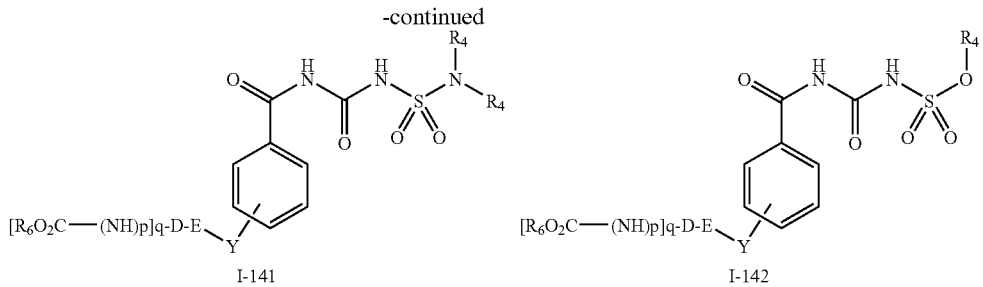

I-141    I-142

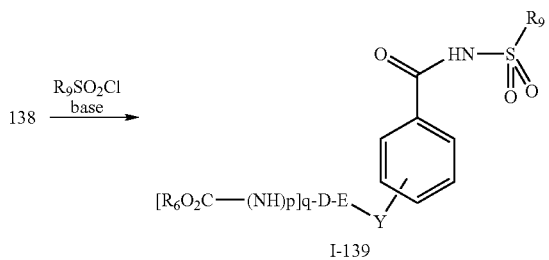

I-139

Compounds of Formula I wherein Q is taken from Q-30 are prepared as shown in Scheme 23. Readily available N-BOC anhydride 143 (see S. Chen et al, *J. Am. Chem. Soc.* (1996) 118:2567) is reacted with amines HN(R$_4$)$_2$ or alcohols R$_6$OH to afford acids 144 or 145, respectively. Intermediates 144 or 145 are further reacted with amines HN(R$_4$)$_2$ in the presence of an acid-activating reagent, preferably PyBOP and di-isopropylethylamine, to give diamides 146 or ester-amides 147. Intermediate 145 is converted to the diesters 148 by reaction with an alkyl iodide in the presence of base, preferably potassium carbonate. Intermediates 146-148 are treated with HCl/dioxane to give the secondary amines 149-151, which are then condensed with acids 152 in the presence of PyBOP and di-isopropylethylamine to give compounds of Formula I-153.

Scheme 23

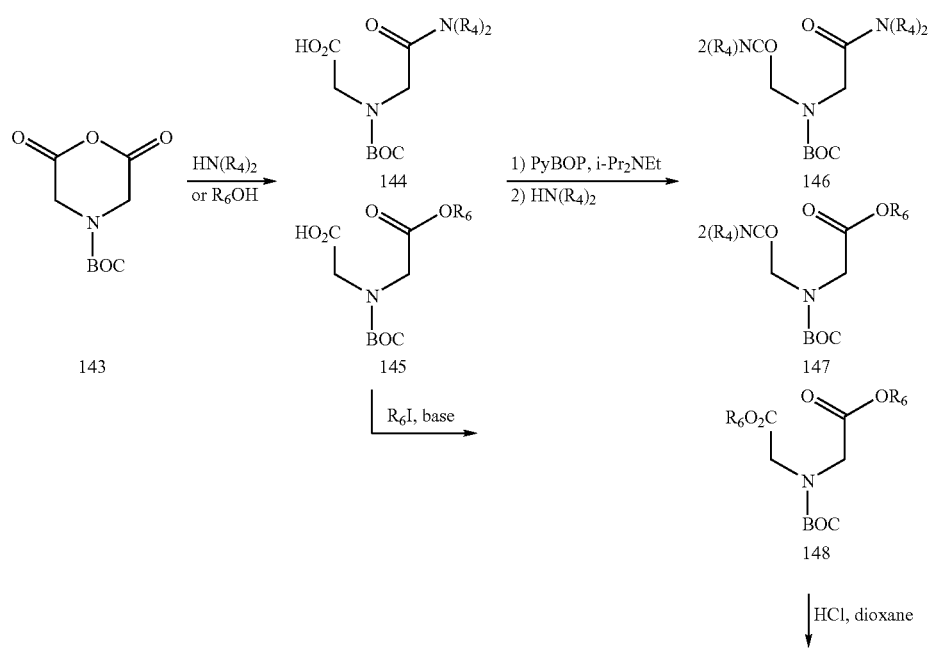

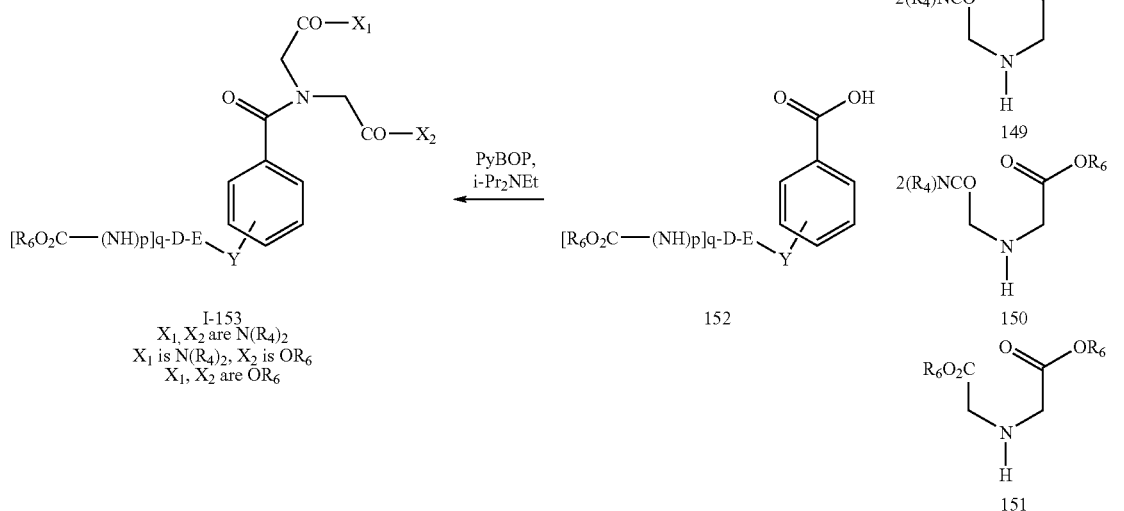

Compounds of Formula I wherein Q is taken from Q-31 or Q-32 are prepared according to the sequences illustrated in Scheme 24. Treatment of readily available sulfenamides 154 with amines 37 (Z=NH), alcohols 37 (Z=O), or alkenes 37 (Z=CH=CH$_2$), gives rise to compounds of Formula I-155. Treatment of sulfenamides I-155 with iodosobenzene in the presence of alcohols R$_6$OH gives rise to the sulfonimidates of Formula I-157 (see D. Leca et al, *Organic Letters* (2002) 4:4093). Alternatively, compounds I-155 (Z=—CH=CH) may be optionally reduced to the saturated analogs I-156 (Z=CH$_2$—CH$_2$—), which are converted to the corresponding sulfonimidates I-157.

Treatment of readily available sulfonylchlorides 154.1 with amines HN(R$_4$)$_2$ and base gives rise to compounds of Formula I-154.2.

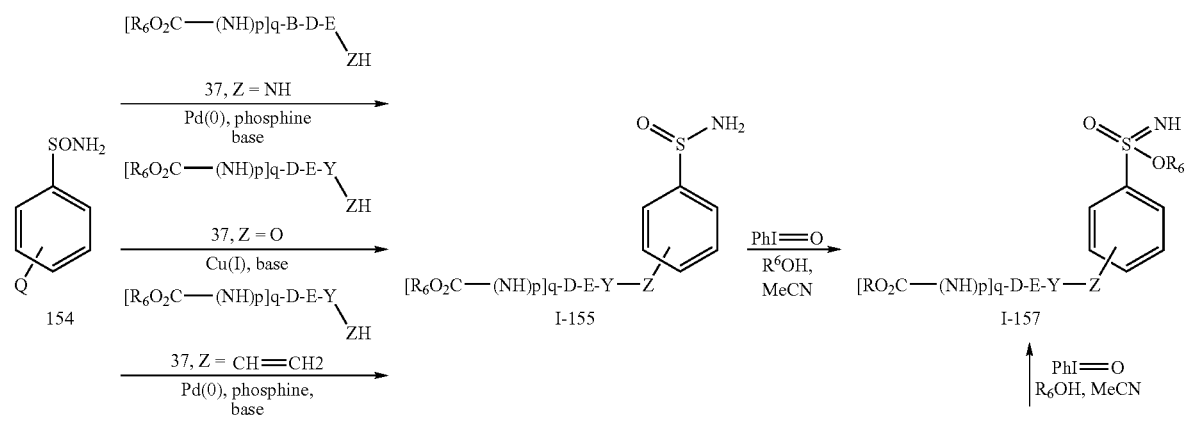

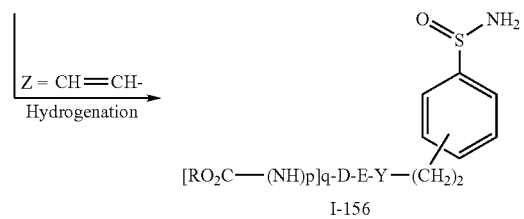

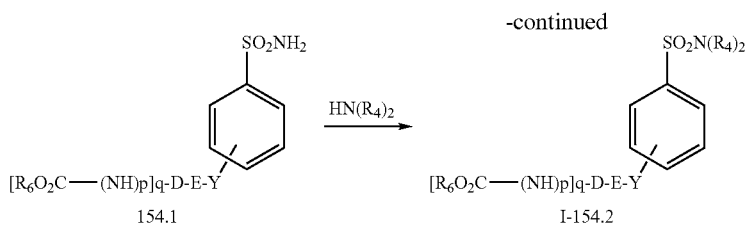

Compounds of Formula I wherein Q is taken from Q-33 are prepared as shown in Scheme 25. Readily available nitrites 158 are reacted with amines 37 (Z=NH), alcohols 37 (Z=O), or alkenes 37 (Z=—CH=CH$_2$) to afford compounds of Formula I-159. Compounds I-159 (wherein Z=CH=CH—) are optionally reduced to their saturated analogs I-160 by standard catalytic hydrogenation conditions. Treatment of compounds I-159 or I-160 with a metal azide (preferably sodium azide or zinc azide) gives rise to tetrazoles of Formula I-161.

standard hydrogenation conditions. Compounds I-163 or I-164 are converted to the desired phosphonates I-165 by an Arbuzov reaction sequence involving reduction of the esters to benzylic alcohols, conversion of the alcohols to the benzylic bromides, and treatment of the bromides with a trialkylphosphite. Optionally, phosphonates I-165 are converted to the flourinated analogs I-166 by treatment with diethylaminosulfur trifluoride (DAST).

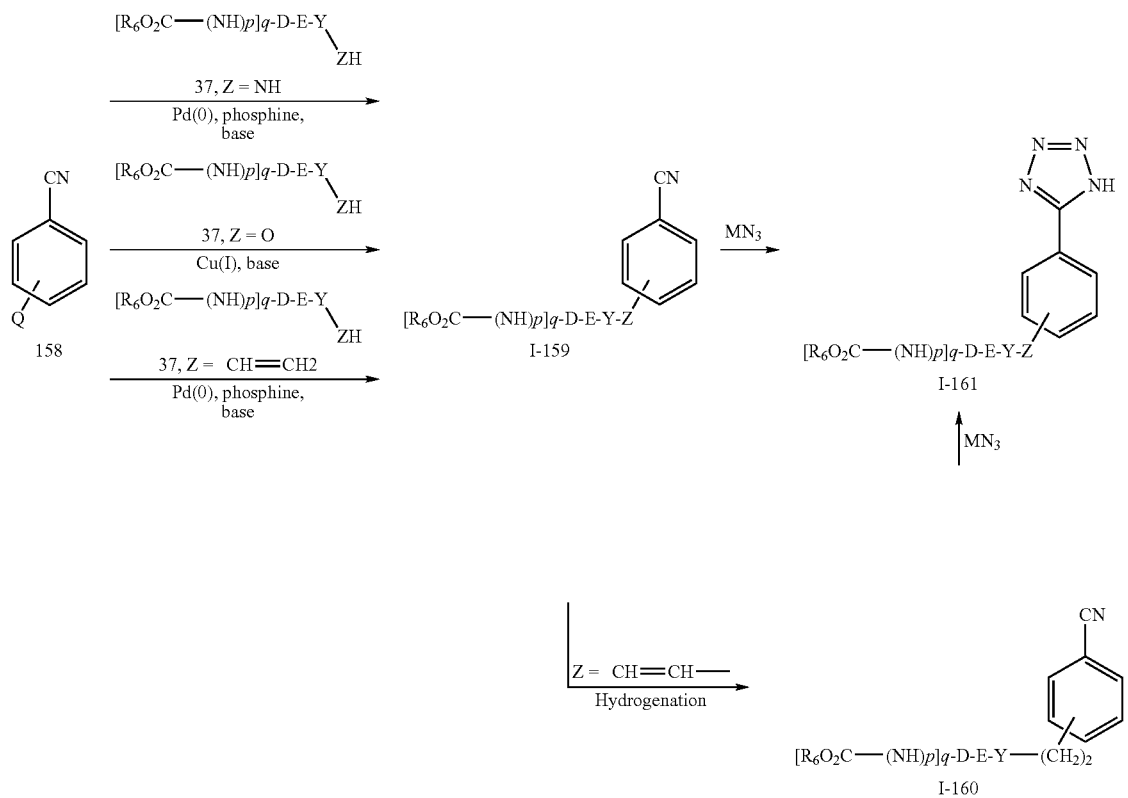

Compounds of Formula I wherein Q is taken from Q-34 are prepared as shown in Scheme 26. Readily available esters 162 are reacted with amines 37 (Z=NH), alcohols 37 (Z=0), or alkenes 37 (Z=—CH=CH$_2$) to afford compounds of Formula I-163. Compounds I-163 (wherein Z is —CH=CH—) are optionally converted to the saturated analogs I-164 by

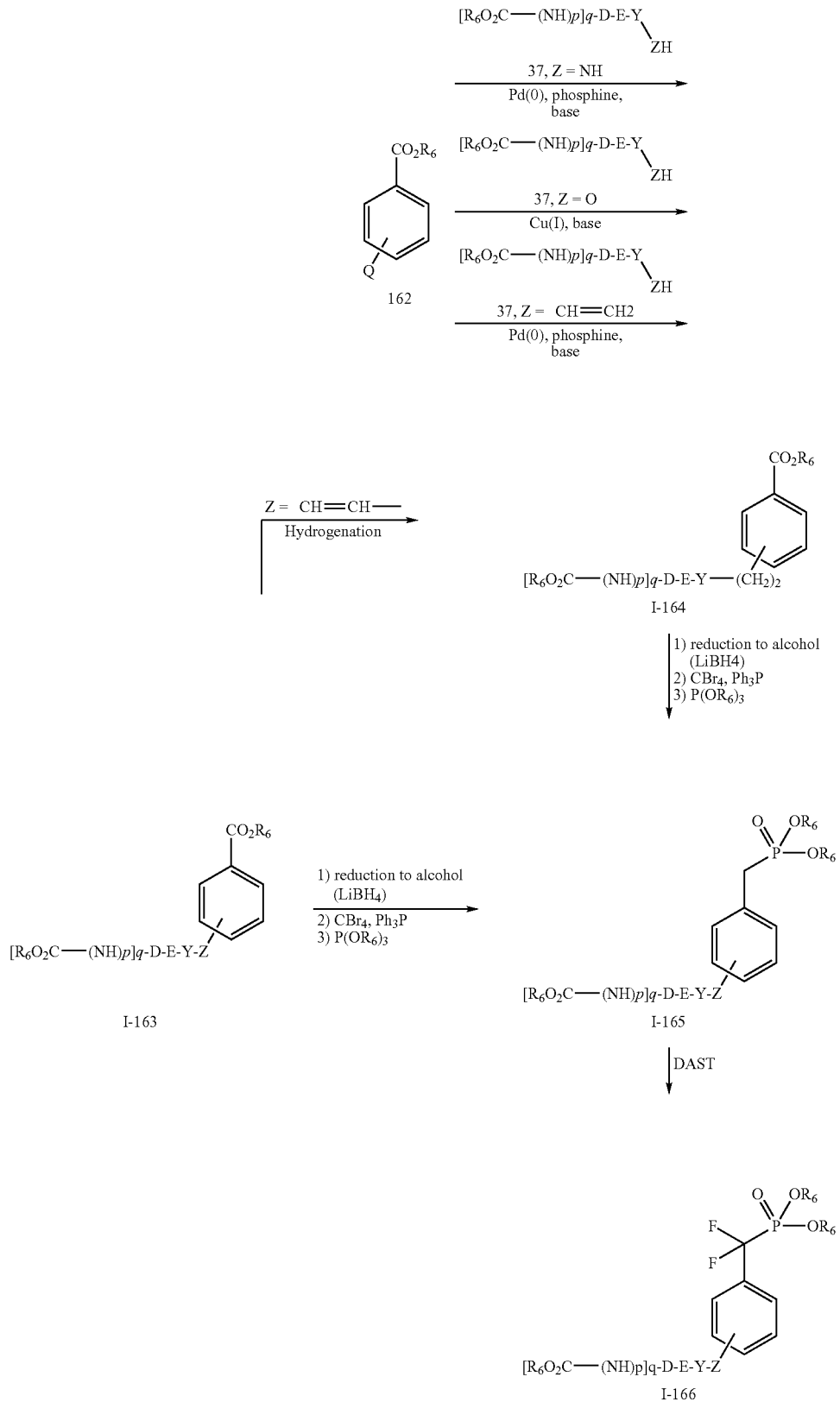

Compounds of Formula I wherein Q is taken from Q-35 are prepared according to Scheme 27. Readily available acid chlorides 167 are reacted with oxazolidones in the presence of base to afford the N-acyl oxazolidinones 168. Intermediate 168 are reacted with amines 37 (Z=NH), alcohols 37 (Z=O), or alkenes 37 (Z=—CH=CH$_2$) to afford the N-acyl oxazolidinones of Formula I-169. Compounds I-169 (wherein Z is —CH=CH—) are optionally converted to the saturated analogs I-170 under standard hydrogenation conditions.

Compounds of Formula I wherein Q is taken from Q-36 are prepared as illustrated in Schemes 28.1 and 28.2. Reductive alkylation of the t-butylsulfide substituted piperazines with the readily available aldehydes 131 gives rise to the benzylic piperazines 171. Intermediates 171 are reacted with amines 37 (Z=NH), alcohols 37 (Z=O), or alkenes 37 (Z=—CH=CH$_2$) to give compounds 172, 173, or 174, respectively. Optionally, intermediates 174 are converted to the saturated analogs 175 under standard hydrogenation conditions.

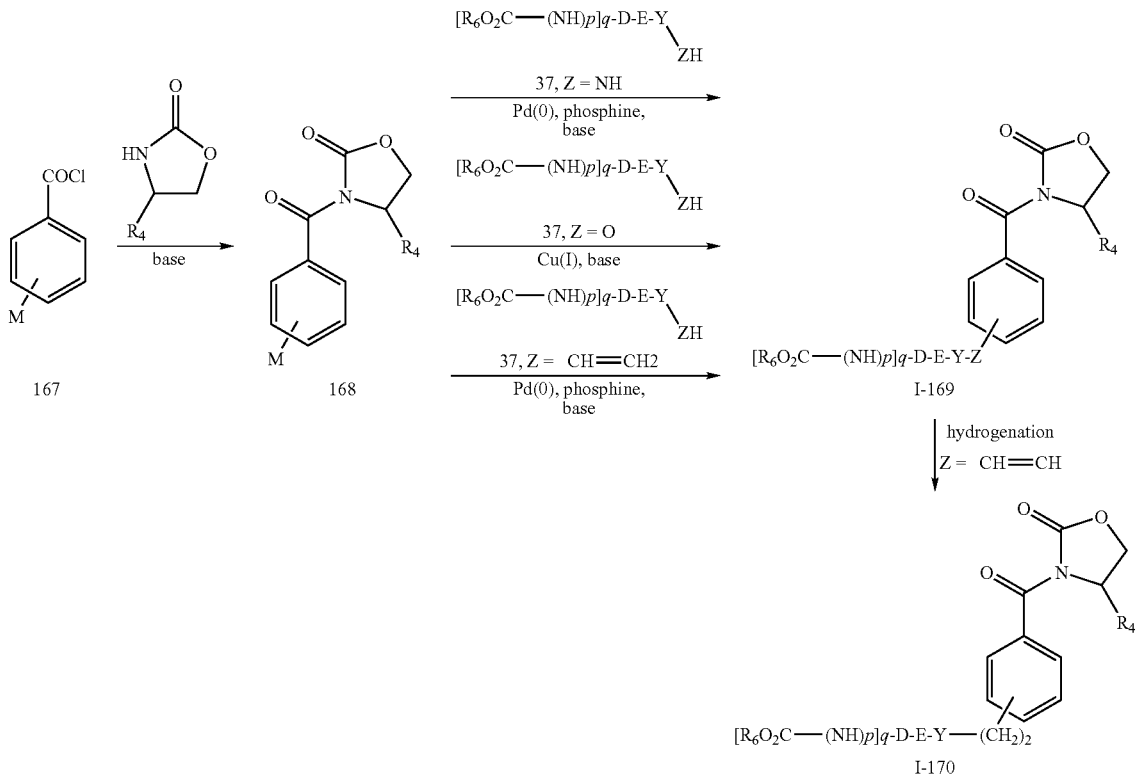

Compounds of Formula I wherein Q is taken from Q-35 are also prepared as illustrated in Scheme 27.1. Intermediate 8a, wherein M is a suitable leaving group such as chloride, bromide or iodide, is refluxed with triethyl phosphite and the resulting phosphoryl intermediate saponified under mild conditions to yield I-165.

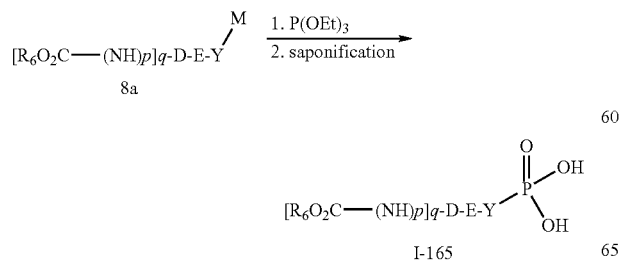

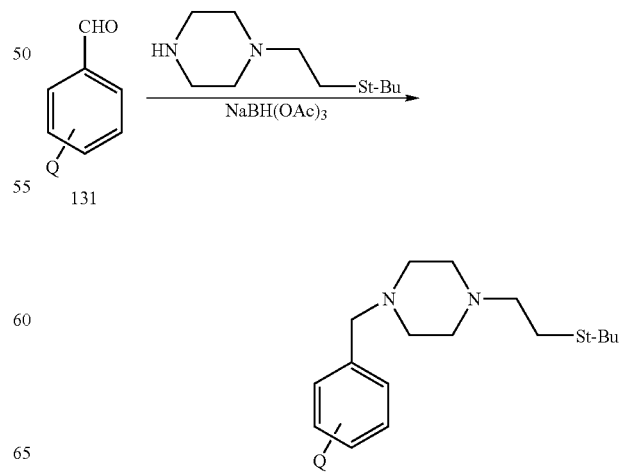

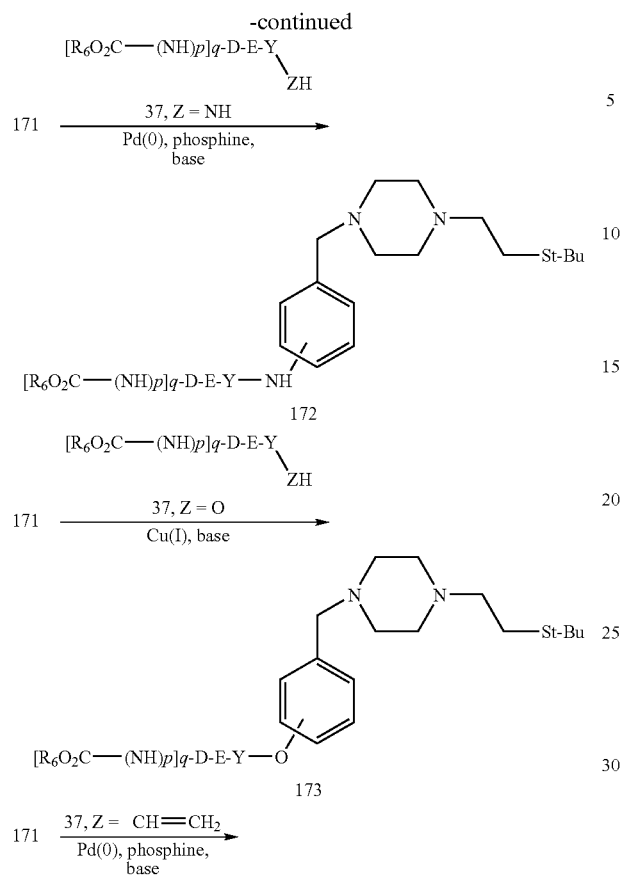

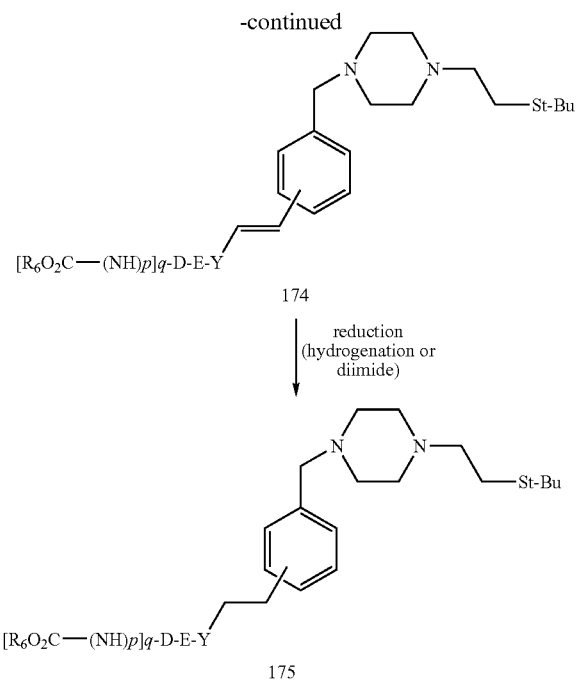

Scheme 28.2 illustrates the conversion of intermediate t-butylsulfides 172-175 to the sulfonic acids, employing a two step process involving acid-catalyzed deprotection of the t-butyl sulfide to the corresponding mercaptans, and subsequent peracid oxidation (preferably with peracetic acid or trifluoroperacetic acid) of the mercaptans to the desired sulfonic acids of Formula I-176.

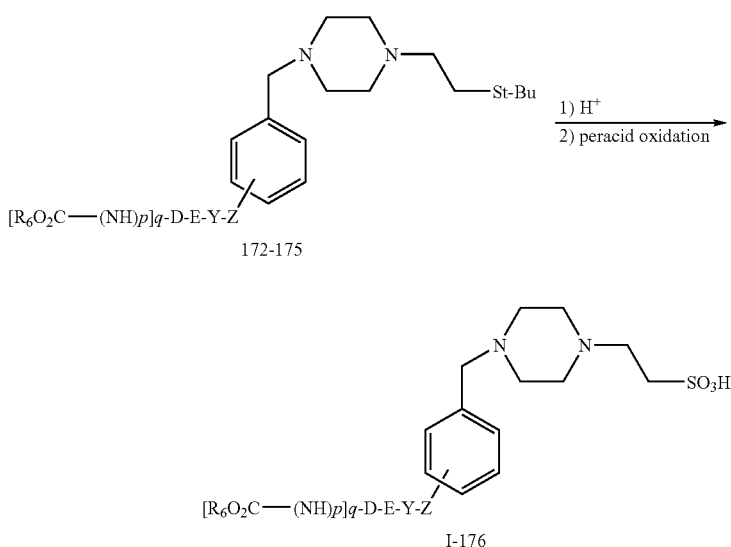

In some instances a hybrid p38-alpha kinase inhibitor is prepared which also contains an ATP-pocket binding moiety or an allosteric pocket binding moiety $R_1$-X-A. The synthesis of functionalized intermediates of formula $R_1$-X-A are accomplished as shown in Scheme 29. Readily available intermediates 177, which contain a group M capable of oxidative addition to palladium(0), are reacted with amines 178 (X=NH) under Buchwald Pd(0) amination conditions to afford 179. Alternatively amines or alcohols 178 (X=NH or O) are reacted thermally with 177 in the presence of base under nuclear aromatic substitution reaction conditions to afford 179. Alternatively, alcohols 178 (X=O) are reacted with 177 under Buchwald copper(I)-catalyzed conditions to afford 179. In cases where p=1, the carbamate of 179 is removed, preferably under acidic conditions when $R_6$ is t-butyl, to afford amines 180. In cases where p=0, the esters 179 are converted to the acids 181 preferably under acidic conditions when $R_6$ is t-butyl.

Scheme 29

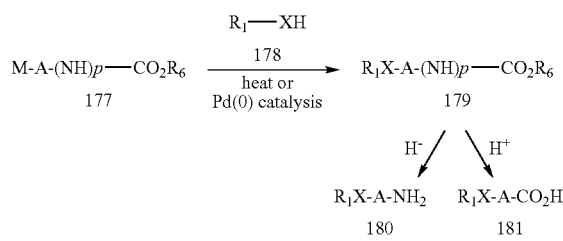

Another sequence for preparing amines 180 is illustrated in Scheme 30. Reaction of amines or alcohols 178 with nitro (hetero)arenes 182 wherein M is a leaving group, preferably M is fluoride, or M is a group capable of oxidative insertion into palladium(0), preferably M is bromo, chloro, or iodo, gives intermediates 183. Reduction of the nitro group under standard hydrogenation conditions or treatment with a reducing metal, such as stannous chloride, gives amines 180.

Scheme 30

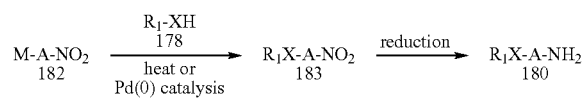

In instances when hybrid p38-alpha kinase inhibitors are prepared, compounds of Formula I-184 wherein q is 1 may be converted to amines I-185 (p=1) or acids I-186 (p=0) by analogy to the conditions described in Scheme 29. Compounds of Formula I-184 are prepared as illustrated in previous schemes 1.1, 2.1, 2.2, 3, 4, 5, 6, 7.1, 7.2, 8, 9, 10, 12, 14, 16.2, 17.2, 18, 19.1, 19.2, 19.3, 20, 21, 22, 23, 24, 25, 26, 27, or 28.2.

Scheme 31

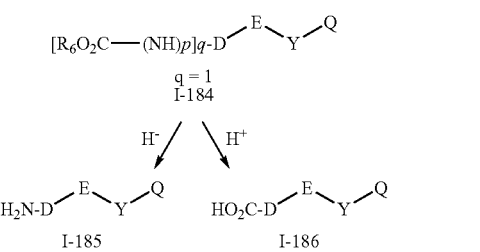

Compounds I-184 are taken from schemes 1.1, 2.1, 2.2, 3, 4, 5, 6, 7.1, 7.2, 8, 9, 10 12, 14, 16.2, 17.2, 18, 19.1, 19.2, 19.3, 20, 21, 22, 23, 24, 25, 26, 27, 28.2

The preparation of inhibitors of Formula I which contain an amide linkage -CO—NH- connecting the oxyanion pocket binding moieties and $R_1$-X-A moieties are shown in Scheme 32. Treatment of acids 181 with an activating agent, preferably PyBOP in the presence of di-iso-propylethylamine, and amines I-185 gives compounds of Formula I. Alternatively, retroamides of Formula I are formed by treatment of acids I-186 with PyBOP in the presence of di-iso-propylethylamine and amines 180.

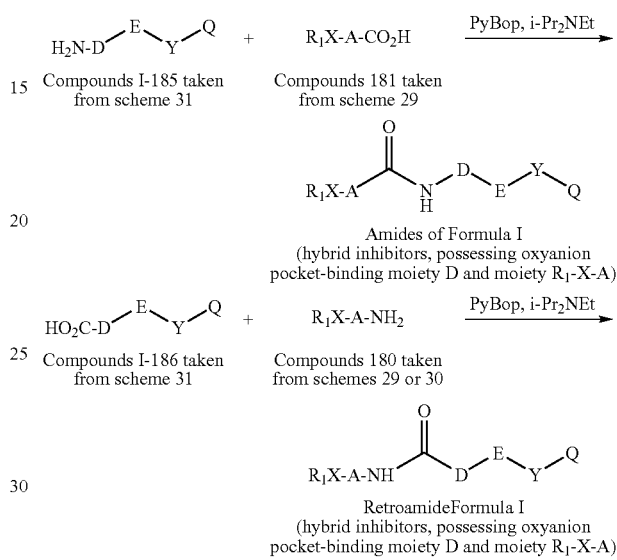

The preparation of inhibitors of Formula I which contain an urea linkage NH—CO—NH— connecting the oxyanion pocket binding moieties and the $R_1$-X-A moieties are shown in Scheme 33. Treatment of amines I-185 with p-nitrophenyl chloroformate and base affords carbamates 187. Reaction of 187 with amines 180 gives ureas of Formula I.

Scheme 33

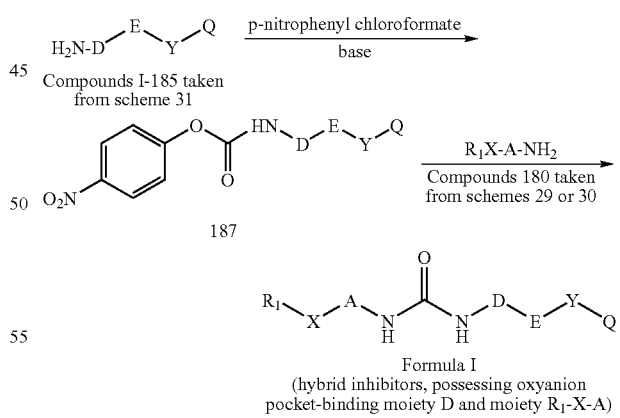

Alternatively, inhibitors of Formula I which contain an urea linkage NH—CO—NH— connecting the oxyanion pocket binding moieties and the $R_1$-X-A moieties are prepared as shown in Scheme 33. Treatment of amines 180 with p-nitrophenyl chloroformate and base affords carbamates 188. Reaction of 188 with amines I-185 gives ureas of Formula I.

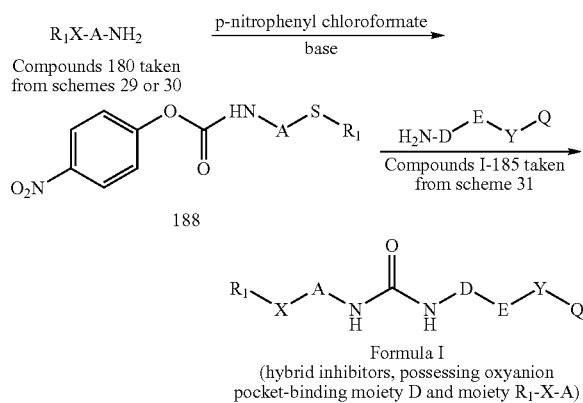

Formula I
(hybrid inhibitors, possessing oxyanion
pocket-binding moiety D and moiety $R_1$-X-A)

Affinity and Biological Assessment of P38-Alpha Kinase Inhibitors

A fluorescence binding assay is used to detect binding of inhibitors of Formula I with unphosphorylated p38-alpha kinase as previously described: see J. Regan et al, *Journal of Medicinal Chemistry* (2002) 45:2994.

1. P38 MAP Kinase Binding Assay

The binding affinities of small molecule modulators for p38 MAP kinase were determined using a competition assay with SKF 86002 as a fluorescent probe, modified based on published methods (C. Pargellis, et al Nature Structural Biology (2002) 9, 268-272. J. Regan, et al J. Med. Chem. (2002) 45, 2994-3008). Briefly, SKF 86002, a potent inhibitor of p38 kinase ($K_d$=180 nM), displays an emission fluorescence around 420 nm when excitated at 340 nm upon its binding to the kinase. Thus, the binding affinity of an inhibitor for p38 kinase can be measured by its ability to decrease the fluorescence from SKF 86002. The assay was performed in a 384 plate (Greiner uclear 384 plate) on a Polarstar Optima plate reader (BMG). Typically, the reaction mixture contained 1 µM SKF 86002, 80 nM p38 kinase and various concentrations of an inhibitor in 20 mM Bis-Tris Propane buffer, pH 7, containing 0.15% (w/v) n-octylglucoside and 2 mM EDTA in a final volume of 65 µl. The reaction was initiated by addition of the enzyme. The plate was incubated at room temperature (~25° C.) for 2 hours before reading at emission of 420 nm and excitation at 340 nm. By comparison of rfu (relative fluorescence unit) values with that of a control (in the absence of an inhibitor), the percentage of inhibition at each concentration of the inhibitor was calculated. $IC_{50}$ value for the inhibitor was calculated from the % inhibition values obtained at a range of concentrations of the inhibitor using Prism. When time-dependent inhibition was assessed, the plate was read at multiple reaction times such as 0.5, 1, 2, 3, 4 and 6 hours. The $IC_{50}$ values were calculated at the each time point. An inhibition was assigned as time-dependent if the $IC_{50}$ values decrease with the reaction time (more than two-fold in four hours).

| Example # | IC50, nM | Time-dependent |
|---|---|---|
| 1 | 292 | Yes |
| 2 | 997 | No |
| 2 | 317 | No |
| 3 | 231 | Yes |
| 4 | 57 | Yes |

-continued

| Example # | IC50, nM | Time-dependent |
|---|---|---|
| 5 | 1107 | No |
| 6 | 238 | Yes |
| 7 | 80 | Yes |
| 8 | 66 | Yes |
| 9 | 859 | No |
| 10 | 2800 | No |
| 11 | 2153 | No |
| 12 | ~10000 | No |
| 13 | 384 | Yes |
| 15 | 949 | No |
| 19 | ~10000 | No |
| 21 | 48 | Yes |
| 22 | 666 | No |
| 25 | 151 | Yes |
| 26 | 68 | Yes |
| 29 | 45 | Yes |
| 30 | 87 | Yes |
| 31 | 50 | Yes |
| 32 | 113 | Yes |
| 37 | 497 | No |
| 38 | 508 | No |
| 41 | 75 | Yes |
| 42 | 373 | No |
| 43 | 642 | No |
| 45 | 1855 | No |
| 46 | 1741 | No |
| 47 | 2458 | No |
| 48 | 3300 | No |
| 57 | 239 | Yes |

IC50 values obtained at 2 hours reaction time

Biological assessment of p38-alpha kinase inhibitors of Formula I is performed in a THP-1 cell assay, measuring inhibition of LPS-stimulated TNF-alpha production. See J. Regan et al, *Journal of Medicinal Chemistry* (2002) 45:2994.

EXAMPLES

The following examples set forth preferred methods in accordance with the invention. It is to be understood, however, that these examples are provided by way of illustration and nothing therein should be taken as a limitation upon the overall scope of the invention.

[Boc-sulfamide] aminoester (Reagent AA), 1,5,7,-trimethyl-2,4-dioxo-3-aza-bicyclo[3.3.1]nonane-7-carboxylic acid (Reagent BB), and Kemp acid anhydride (Reagent CC) was prepared according to literature procedures. See Askew et. al *J. Am. Chem. Soc.* 1989, 111, 1082 for further details.

Example A

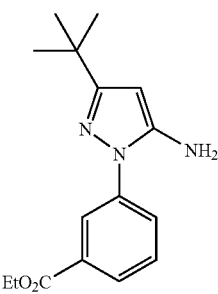

To a solution (200 mL) of m-amino benzoic acid (200 g, 1.46 mol) in concentrated HCl was added an aqueous solution (250 mL) of $NaNO_2$ (102 g, 1.46 mol) at 0° C. The reaction mixture was stirred for 1 h and a solution of $SnCl_2 \cdot 2H_2O$ (662 g, 2.92 mol) in concentrated HCl (2 L) was then added at 0° C., and the reaction stirred for an additional 2 h at RT. The precipitate was filtered and washed with ethanol and ether to yield 3-hydrazino-benzoic acid hydrochloride as a white solid.

The crude material from the previous reaction (200 g, 1.06 mol) and 4,4-dimethyl-3-oxo-pentanenitrile (146 g, 1.167 mol) in ethanol (2 L) were heated to reflux overnight. The reaction solution was evaporated in vacuo and the residue purified by column chromatography to yield ethyl 3-(3-tert-butyl-5-amino-1H-pyrazol-1-yl)benzoate (Example A, 116 g, 40%) as a white solid together with 3-(5-amino-3-tert-butyl-1H-pyrazol-1-yl)benzoic acid (93 g, 36%). $^1$H NMR (DMSO-$d_6$): 8.09 (s, 1H), 8.05 (brd, J=8.0 Hz, 1H), 7.87 (brd, J=8.0 Hz, 1H), 7.71 (t, J=8.0 Hz, 1H), 5.64 (s, 1H), 4.35 (q, J=7.2 Hz, 2H), 1.34 (t, J=7.2 Hz, 3H), 1.28 (s, 9H).

Example B

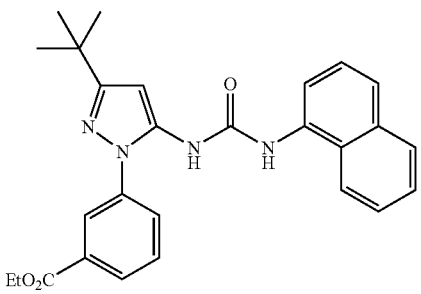

To a solution of 1-naphthyl isocyanate (9.42 g, 55.7 mmol) and pyridine (44 mL) in THF (100 mL) was added a solution of Example A (8.0 g, 27.9 mmol) in THF (200 mL) at 0° C. The mixture was stirred at RT for 1 h, heated until all solids were dissolved, stirred at RT for an additional 3 h and quenched with H$_2$O (200 mL). The precipitate was filtered, washed with dilute HCl and H$_2$O, and dried in vacuo to yield ethyl 3-[3-t-butyl-5-(3-naphthalen-1-yl)ureido)-1H-pyrazol-1-yl]benzoate (12.0 g, 95%) as a white power. $^1$H NMR (DMSO-$d_6$): 9.00 (s, 1H), 8.83 (s, 1H), 8.25 7.42 (m, 1H), 6.42 (s, 1H), 4.30 (q, J=7.2 Hz, 2H), 1.26 (s, 9H), 1.06 (t, J=7.2 Hz, 3H); MS (ESI) m/z: 457.10 (M+H$^+$).

Example C

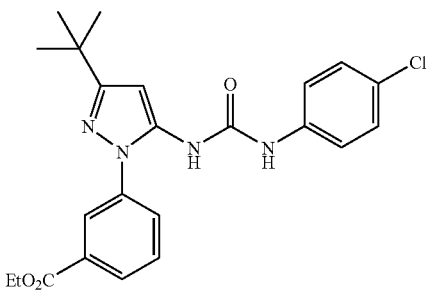

To a solution of Example A (10.7 g, 70.0 mmol) in a mixture of pyridine (56 mL) and THF (30 mL) was added a solution of 4-nitrophenyl 4-chlorophenylcarbamate (10 g, 34.8 mmol) in THF (150 mL) at 0° C. The mixture was stirred at RT for 1 h and heated until all solids were dissolved, and stirred at RT for an additional 3 h. H$_2$O (200 mL) and CH$_2$Cl$_2$ (200 μL) were added, the aqueous phase separated and extracted with CH$_2$Cl$_2$ (2×100 mL). The combined organic layers were washed with 1N NaOH, and 0.1N HCl, saturated brine and dried over anhydrous Na$_2$SO$_4$. The solvent was removed in vacuo to yield ethyl 3-{3-tert-butyl-5-[3-(4-chlorophenyl)ureido]-1H-pyrazol-1-yl}benzoate (8.0 g, 52%). $^1$H NMR (DMSO-$d_6$): δ 9.11 (s, 1H), 8.47 (s, 1H), 8.06 (m, 1H), 7.93 (d, J=7.6 Hz, 1H), 7.81 (d, J=8.0 Hz, 1H), 7.65 (dd, J=8.0, 7.6 Hz, 1H), 7.43 (d, J=8.8 Hz, 2H), 7.30 (d, J=8.8 Hz, 2H), 6.34 (s, 1H), 4.30 (q, J=6.8 Hz, 2H), 1.27 (s, 9H), 1.25 (t, J=6.8 Hz, 3H); MS (ESI) m/z: 441 (M$^+$+H).

Example D

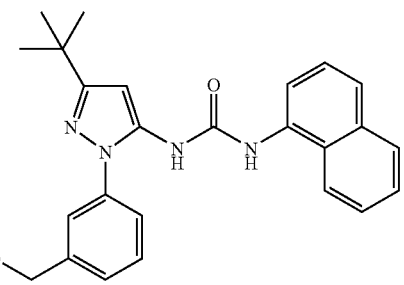

To a stirred solution of Example B (8.20 g, 18.0 mmol) in THF (500 mL) was added LiAlH$_4$ powder (2.66 g, 70.0 mmol) at −10° C. under N$_2$. The mixture was stirred for 2 h at RT and excess LiAlH$_4$ destroyed by slow addition of ice. The reaction mixture was acidified to pH=7 with dilute HCl, concentrated in vacuo and the residue extracted with EtOAc. The combined organic layers were concentrated in vacuo to yield 1-{3-tert-butyl-1-[3-(hydroxymethyl)phenyl]-1H-pyrazol-5-yl}-3-(naphthalen-1-yl)urea (7.40 g, 99%) as a white powder. $^1$H NMR (DMSO-$d_6$): 9.19 (s, 1H), 9.04 (s, 1H), 8.80 (s, 1H), 8.26-7.35 (m, 1H), 6.41 (s, 1H), 4.60 (s, 2H), 1.28 (s, 9H); MS (ESI) m/z: 415 (M+H$^+$).

Example E

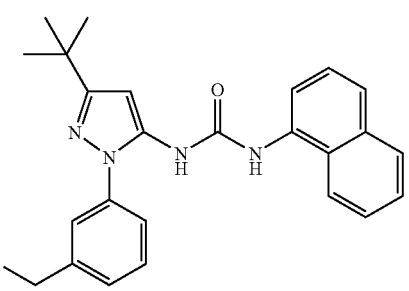

A solution of Example C (1.66 g, 4.0 mmol) and SOCl$_2$ (0.60 mL, 8.0 mmol) in CH$_3$Cl (100 mL) was refluxed for 3 h and concentrated in vacuo to yield 1-{3-tert-butyl-1-[3-chloromethyl)phenyl]-1H-pyrazol-5-yl}-3-(naphthalen-1-yl) urea (1.68 g, 97%) was obtained as white powder. $^1$H NMR (DMSO-d6): δ 9.26 (s, 1H), 9.15 (s, 1H), 8.42-7.41 (m, 11H), 6.40 (s, 1H), 4.85 (s, 2H), 1.28 (s, 9H). MS (ESI) m/z: 433 (M+H$^+$).

Example F

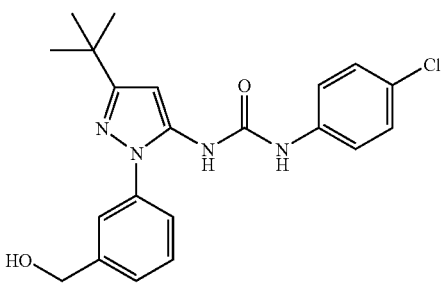

To a stirred solution of Example C (1.60 g, 3.63 mmol) in THF (200 mL) was added LiAlH$_4$ powder (413 mg, 10.9 mmol) at −10° C. under N$_2$. The mixture was stirred for 2 h and excess LiAlH$_4$ was quenched by adding ice. The solution was acidified to pH=7 with dilute HCl. Solvents were slowly removed and the solid was filtered and washed with EtOAc (200+100 mL). The filtrate was concentrated to yield 1-{3-tert-butyl-1-[3-hydroxymethyl)phenyl]-1H-pyrazol-5-yl}-3-(4-chlorophenyl)urea (1.40 g, 97%). $^1$H NMR (DMSO-d$_6$): δ 9.11 (s, 1H), 8.47 (s, 1H), 7.47-7.27 (m, 8H), 6.35 (s, 1H), 5.30 (t, J=5.6 Hz, 1H), 4.55 (d, J=5.6 Hz, 2H), 1.26 (s, 9H); MS (ESI) m/z: 399 (M+H$^+$).

Example G

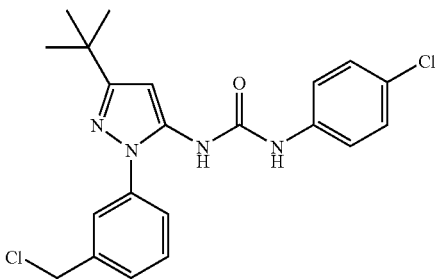

A solution of Example F (800 mg, 2.0 mmol) and SOCl$_2$ (0.30 mL, 4 mmol) in CHCl$_3$ (30 mL) was refluxed gently for 3 h. The solvent was evaporated in vacuo and the residue was taken up to in CH$_2$Cl$_2$ (2×20 mL). After removal of the solvent, 1-{3-tert-butyl-1-[3-(chloromethyl)phenyl]-1H-pyrazol-5-yl}-3-(4-chlorophenyl)urea (812 mg, 97%) was obtained as white powder. $^1$H NMR (DMSO-d$_6$): δ 9.57 (s, 1H), 8.75 (s, 1H), 7.63 (s, 1H), 7.50-7.26 (m, 7H), 6.35 (s, 1H), 4.83 (s, 2H), 1.27 (s, 9H); MS (ESI) m/z: 417 (M+H$^+$).

Example H

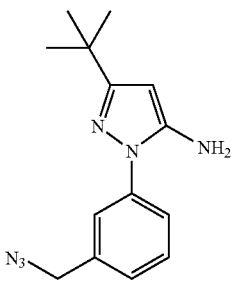

To a suspension of LiAlH$_4$ (5.28 g, 139.2 mmol) in THF (1000 mL) was added Example A (20.0 g, 69.6 mmol) in portions at 0° C. under N$_2$. The reaction mixture was stirred for 5 h, quenched with 1 N HCl at 0° C. and the precipitate was filtered, washed by EtOAc and the filtrate evaporated to yield [3-(5-amino-3-tert-butyl-1H-pyrazol-1-yl)phenyl]methanol (15.2 g, 89%). $^1$H NMR (DMSO-d$_6$): 7.49 (s, 1H), 7.37 (m, 2H), 7.19 (d, J=7.2 Hz, 1H), 5.35 (s, 1H), 5.25 (t, J=5.6 Hz, 1H), 5.14 (s, 2H), 4.53 (d, J=5.6 Hz, 2H), 1.19 (s, 9H); MS (ESI) m/z: 246.19 (M+H$^+$).

The crude material from the previous reaction (5.0 g, 20.4 mmol) was dissolved in dry THF (50 mL) and SOCl$_2$ (4.85 g, 40.8 mmol), stirred for 2 h at RT, concentrated in vacuo to yield 3-tert-butyl-1-(3-chloromethylphenyl)-1H-pyrazol-5-amine (5.4 g), which was added to N$_3$ (3.93 g, 60.5 mmol) in DMF (50 mL). The reaction mixture was heated at 30° C. for 2 h, poured into H$_2$O (50 mL), and extracted with CH$_2$Cl$_2$. The organic layers were combined, dried over MgSO$_4$, and concentrated in vacuo to yield crude 3-tert-butyl-1-[3-(azidomethyl)phenyl]-1H-pyrazol-5-amine (1.50 g, 5.55 mmol).

Example I

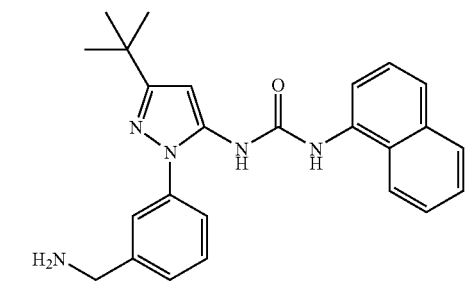

Example H was dissolved in dry THF (10 mL) and added a THF solution (10 mL) of 1-isocyano naphthalene (1.13 g, 6.66 mmol) and pyridine (5.27 g, 66.6 mmol) at RT. The reaction mixture was stirred for 3 h, quenched with H$_2$O (30 μL), the resulting precipitate filtered and washed with 1 N HCl and ether to yield 1-[2-(3-azidomethyl-phenyl)-5-t-butyl-2H-pyrazol-3-yl]-3-naphthalen-1-yl-urea (2.4 g, 98%) as a white solid.

The crude material from the previous reaction and Pd/C (0.4 g) in THF (30 mL) was hydrogenated under 1 atm at RT for 2 h. The catalyst was removed by filtration and the filtrate concentrated in vacuo to yield 1-{3-tert-butyl-1-[3-(aminomethyl)phenyl]-1H-pyrazol-5-yl)-3-(naphthalene-1-yl)urea (2.2 g, 96%) as a yellow solid. $^1$H NMR (DMSO-d$_6$): 9.02 (s, 1H), 7.91 (d, J=7.2 Hz, 1H), 7.89 (d, J=7.6 Hz, 2H), 7.67-7.33 (m, 9H), 6.40 (s, 1H), 3.81 (s, 2H), 1.27 (s, 9H); MS (ESI) m/z: 414 (M+H$^+$).

Example J

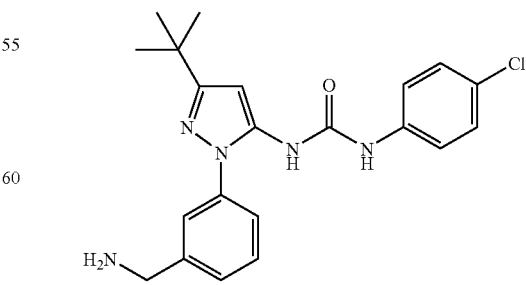

To a solution of Example H (1.50 g, 5.55 mmol) in dry THF (10 mL) was added a THF solution (10 mL) of 4-chlorophenyl isocyanate (1.02 g, 6.66 mmol) and pyridine (5.27 g, 66.6 mmol) at RT. The reaction mixture was stirred for 3 h and then H₂O (30 mL) was added. The precipitate was filtered and washed with 1N HCl and ether to give 1-{3-tert-butyl-1-[3-(aminomethyl)phenyl}-1H-pyrazol-5-yl)-3-(4-chlorophenyl)urea (2.28 g, 97%) as a white solid, which was used for next step without further purification. MS (ESI) m/z: 424 (M+H⁺).

Example K

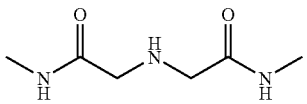

To a solution of benzyl amine (16.5 g, 154 mmol) and ethyl bromoacetate (51.5 g, 308 mmol) in ethanol (500 mL) was added K₂CO₃ (127.5 g, 924 mmol). The mixture was stirred at RT for 3 h, was filtered, washed with EtOH, concentrated in vacuo and chromatographed to yield N-(2-ethoxy-2-oxoethyl)-N-(phenylmethyl)-glycine ethyl ester (29 g, 67%). ¹H NMR (CDCl₃): δ7.39-7.23 (m, 5H), 4.16 (q, J=7.2 Hz, 4H), 3.91 (s, 2H), 3.54 (s, 4H), 1.26 (t, J=7.2 Hz, 6H); MS (ESI): m/e: 280 (M⁺+H).

A solution of N-(2-ethoxy-2-oxoethyl)-N-(phenylmethyl)-glycine ethyl ester (7.70 g, 27.6 mmol) in methylamine alcohol solution (25-30%, 50 mL) was heated to 50° C. in a sealed tube for 3 h, cooled to RT and concentrated in vacuo to yield N-(2-methylamino-2-oxoethyl)-N-(phenylmethyl)-glycine methylamide in quantitative yield (7.63 g). ¹H NMR (CDCl₃): δ 7.35-7.28 (m, 5H), 6.75 (br s, 2H), 3.71 (s, 2H), 3.20 (s, 4H), 2.81 (d, J=5.6 Hz, 6H); MS (ESI) m/e 250 (M+H⁺).

The mixture of N-(2-methylamino-2-oxoethyl)-N-(phenylmethyl)-glycine methylamide (3.09 g, 11.2 mmol) in MeOH (30 mL) was added 10% Pd/C (0.15 g). The mixture was stirred and heated to 40° C. under 40 psi H₂ for 10 h, filtered and concentrated in vacuo to yield N-(2-methylamino-2-oxoethyl)-glycine methylamide in quantitative yield (1.76 g). ¹H NMR (CDCl₃): δ 6.95 (br s, 2H), 3.23 (s, 4H), 2.79 (d, J=6.0, 4.8 Hz), 2.25 (br s 1H); MS (ESI) m/e 160 (M+H⁺)

Example 1

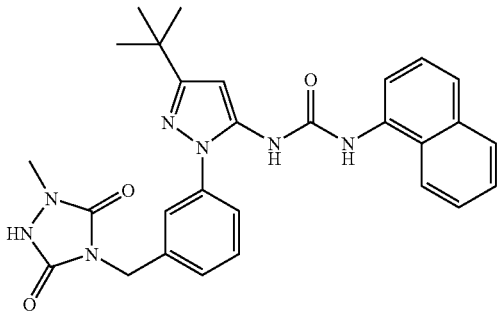

To a solution of 1-methyl-[1,2,4]triazolidine-3,5-dione (188 mg, 16.4 mmol) and sodium hydride (20 mg, 0.52 mmol) in DMSO (1 mL) was added Example E (86 mg, 0.2 mmol). The reaction was stirred at RT overnight, quenched with H₂O (10 mL), extracted with CH₂Cl₂, and the organic layer was separated, washed with brine, dried over Na₂SO₄ and concentrated in vacuo. The residue was purified by preparative HPLC to yield 1-(3-tert-butyl-1-{3-[(1-methyl-3,5-dioxo-1,2,4-triazolidin-4-yl)methyl]phenyl}-1H-pyrazol-5-yl)-3-(naphthalene-1-yl)urea (Example 1, 14 mg). ¹H NMR (CD₃OD): δ7.88-7.86 (m, 2H), 7.71-7.68 (m, 2H), 7.58 (m, 2H), 7.60-7.42 (m, 5H), 6.49 (s, 1H), 4.85 (s, 1H), 1.34 (s, 9H), 1.27 (s, 6H); MS (ESI) m/z: 525 (M+H⁺).

Example 2

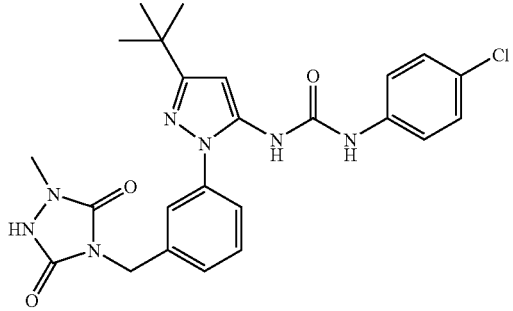

The title compound was synthesized in a manner analogous to Example 1, utilizing Example G to yield 1-(3-tert-butyl-1-{3-[(1-methyl-3,5-dioxo-1,2,4-triazolidin-4-yl)methyl]phenyl}-1H-pyrazol-5-yl)-3-(4-chlorophenyl)urea ¹H NMR (CD₃OD): δ 7.2~7.5 (m, 7H), 6.40 (s 1H), 4.70 (s, 2H), 2.60 (d, J=14 Hz, 2H), 1.90 (m, 1H), 1.50 (m, 1H), 1.45 (s, 9H), 1.30 (m, 2H), 1.21 (s, 3H), 1.18 (s, 6H); MS (ESI) m/z: 620 (M+H⁺).

Example 3

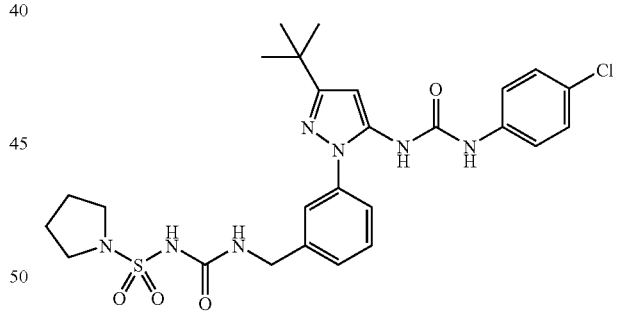

A mixture of compound 1,1-Dioxo-[1,2,5]thiadiazolidin-3-one (94 mg, 0.69 mmol) and NaH (5.5 mg, 0.23 mmol) in THF (2 mL) was stirred at −10° C. under N₂ for 1 h until all NaH was dissolved. Example E (100 mg, 0.23 mmol) was added and the reaction was allowed to stir at RT overnight, quenched with H₂O, and extracted with CH₂Cl₂. The combined organic layers were concentrated in vacuo and the residue was purified by preparative HPLC to yield 1-(3-tert-butyl-1-{[3-(1,1,3-trioxo-[1,2,5]thiadiazolidin-2-yl)methyl]phenyl}-1H-pyrazol-5-yl)-3-(naphthalen-1-yl)urea (18 mg) as a white powder. ¹H NMR (CD₃OD): δ 7.71-7.44 (m, 11H), 6.45 (s, 1H), 4.83 (s, 2H), 4.00 (s, 2H), 1.30 (s, 9H). MS (ESI) m/z: 533.40 (M+H⁺).

Example 4

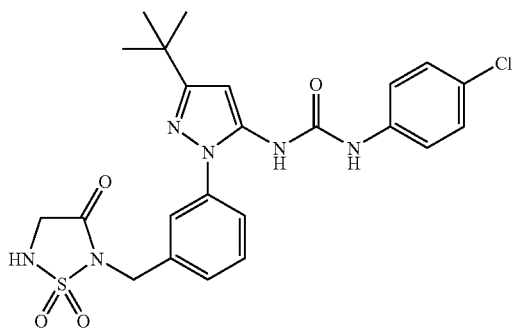

The title compound was obtained in a manner analogous to Example 3 utilizing Example G. to yield 1-(3-tert-butyl-1-{[3-(1,1,3-trioxo-[1,2,5]thiadiazolidin-2-yl)methyl]phenyl}-1H-pyrazol-5-yl)-3-(4-chlorophenyl)urea. $^1$H NMR (CD$_3$OD): δ 7.38-7.24 (m, 8H), 6.42 (s, 1H), 4.83 (s, 2H), 4.02 (s, 2H), 1.34 (s, 9H); MS (ESI) m/z: 517 (M+H$^+$).

Example 5

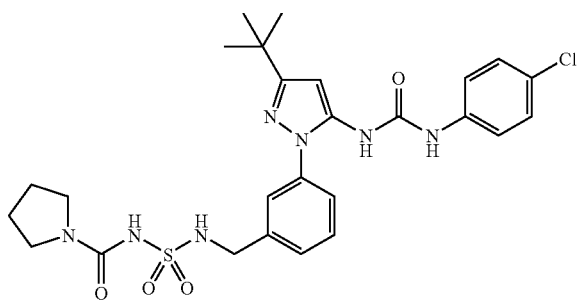

To a stirred solution of chlorosulfonyl isocyanate (19.8 μL, 0.227 mmol) in CH$_2$Cl$_2$ (0.5 mL) at 0° C. was added pyrrolidine (18.8 μL, 0.227 mmol) at such a rate that the reaction solution temperature did not rise above 5° C. After stirring for 1.5 h, a solution of Example J (97.3 mg, 0.25 mmol) and Et$_3$N (95 μL, 0.678 mmol) in CH$_2$Cl$_2$ (1.5 mL) was added at such a rate that the reaction temperature didn rise above 5° C. When the addition was completed, the reaction solution was warmed to RT and stirred overnight. The reaction mixture was poured into 10% HCl, extracted with CH$_2$Cl$_2$, the organic layer washed with saturated NaCl, dried over MgSO$_4$, and filtered. After removal of the solvents, the crude product was purified by preparative HPLC to yield 1-(3-tert-butyl-1-[[3-N-[[(1-pyrrolidinylcarbonyl)amino]sulphonyl]aminomethyl]phenyl]-H-pyrazol-5-yl)-3-(4-chlorophenyl)urea. $^1$H NMR (CD$_3$OD): δ 7.61 (s, 1H), 7.43-7.47 (m, 3H), 7.23-7.25 (dd, J=6.8 Hz, 2H), 7.44 (dd, J=6.8 Hz, 2H), 6.52 (s, 1H), 4.05 (s, 2H), 3.02 (m, 4H), 1.75 (m, 4H), 1.34 (s, 9H); MS (ESI) m/z: 574.00 (M+H$^+$).

Example 6

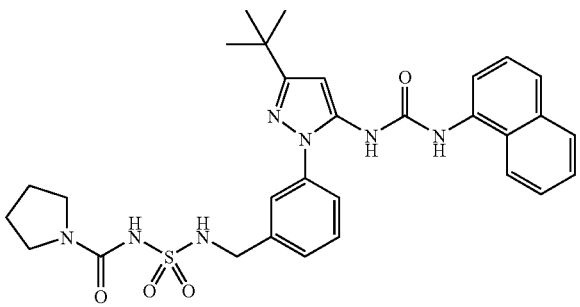

The title compound was made in a manner analogous to Example 5 utilizing Example I to yield 1-(3-tert-butyl-1-[[3-N-[[(1-pyrrolidinylcarbonyl)amino]sulphonyl]aminomethyl]-phenyl]-1H-pyrazol-5-yl)-3-(naphthalen-1-yl)urea. $^1$HNMR (CDCl$_3$): δ 7.88 (m, 2H), 7.02-7.39 (m, 2H), 7.43-7.50 (m, 7H), 6.48 (s, 1H), 4.45 (s, 1H), 3.32-3.36 (m, 4H), 1.77-1.81 (m, 4H), 1.34 (s, 9H); MS (ESI) m/z: 590.03 (M+H$^+$).

Example 7

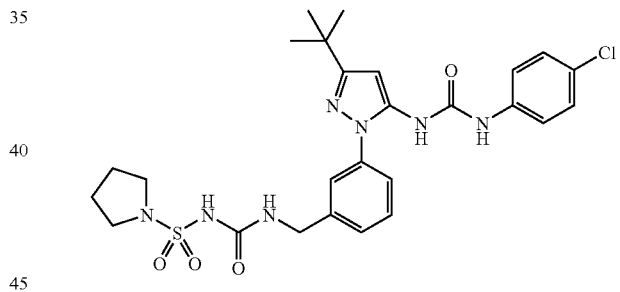

To a stirred solution of chlorosulfonyl isocyanate (19.8 μΛ, 0.227 μμολ) ιν ΧΗ$_2$Χλ$_2$ (0.5 μΛ) ατ0° C., was added Example J (97.3 mg, 0.25 mmol) at such a rate that the reaction solution temperature did not rise above 5° C. After being stirred for 1.5 h, a solution of pyrrolidine (18.8 μL, 0.227 mmol) and Et$_3$N (95 μL, 0.678 mmol) in CH$_2$Cl$_2$ (1.5 mL) was added at such a rate that the reaction temperature didn rise above 5° C. When addition was completed, the reaction solution was warmed to RT and stirred overnight. The reaction mixture was poured into 10% HCl, extracted with CH$_2$Cl$_2$, the organic layer was washed with saturated NaCl, dried over Mg$_2$SO$_4$, and filtered. After removal of the solvents, the crude product was purified by preparative HPLC to yield 1-(3-tert-butyl-1-[[3-N-[[(1-pyrrolidinylsulphonyl)amino]carbonyl]aminomethyl]phenyl]-1H-pyrazol-5-yl)-3-(4-chlorophenyl)urea. $^1$HNMR (CDCl$_3$): δ 7.38 (m, 1H), 7.36-7.42 (m, 3H), 7.23 (d, J=8.8 Hz, 2H), 7.40 (d, J=8.8 Hz, 2H), 6.43 (s, 1H), 4.59 (s, 1H), 4.43 (s, 2H), 1.81 (s, 2H), 1.33 (s, 9H); MS (ESI) m/z: 574.10 (M+H$^+$).

Example 8

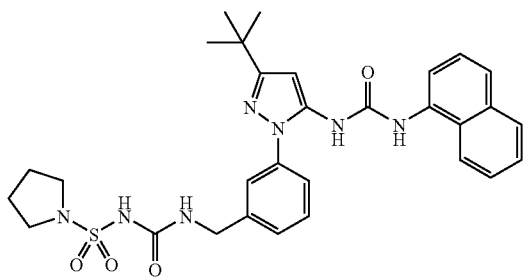

The title compound was made in a manner analogous to Example 7 utilizing Example I to yield 1-(3-tert-butyl-1-[[3-N—[[(1-pyrrolidinylsulphonyl)amino]carbonyl]aminomethyl]-phenyl]-1H-pyrazol-5-yl)-3-(naphthalen-1-yl)urea. $^1$HNMR (CDCl$_3$): δ7.88 (m, 2H), 7.02-7.39 (m, 2H), 7.43-7.50 (m, 7H), 6.48 (s, 1H), 4.45 (s, 1H), 3.32-3.36 (m, 4H), 1.77-1.81 (m, 4H), 1.34 (s, 9H); MS (ESI) m/z: 590.03 (M+H$^+$).

Example 9

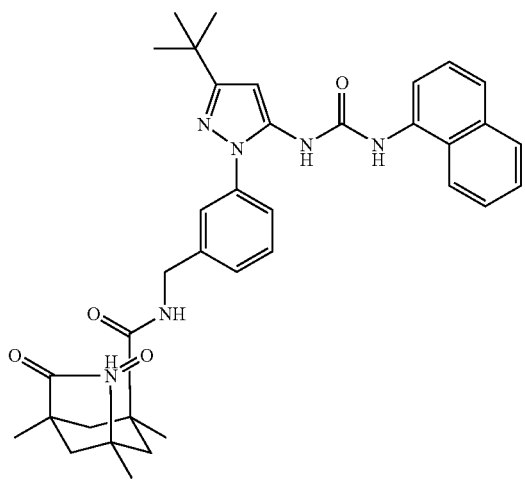

To a solution of Reagent BB (36 mg, 0.15 mmol), Example I (62 mg, 0.15 mmol), HOBt (40 mg, 0.4 mmol) and NMM (0.1 mL, 0.9 mmol) in DMF (10 mL) was added EDCI (58 mg, 0.3 mmol). After being stirred overnight, the mixture was poured into water (15 mL) and extracted with EtOAc (3 5 mL). The organic layers were combined, washed with brine, dried with Na$_2$SO$_4$, and concentrated in vacuo. The residue was purified by preparative TLC to yield 1,5,7-trimethyl-2,4-dioxo-3-azabicyclo[3.3.1]nonane-7-carboxylic acid 3-[3-t-butyl-5-(3-naphthalen-1-yl-ureido)-pyrazol-1-yl]benzylamide (22 mg). $^1$H NMR (CDCl$_3$): δ 8.40 (s, 1H), 8.14 (d, J=8.0 Hz, 2H), 7.91 (s, 1H), 7.87 (s, 1H), 7.86 (d, J=7.2 Hz, 1H), 7.78 (d, J=7.6 Hz, 1H), 7.73 (d, J=8.4 Hz, 1H), 7.69 (d, J=8.4 Hz, 1H), 7.57-7.40 (m, 4H), 7.34 (d, J=7.6 Hz, 1H), 6.69 (s, 1H), 6.32 (t, J=5.6 Hz, 1H), 5.92 (brs, 1H), 4.31 (d, J=5.6 Hz, 2H), 2.37 (d, J=14.8 Hz, 2H), 1.80 (d, J=13.2 Hz, 1H), 1.35 (s, 9H), 1.21 (d, J=13.2 Hz, 1H), 1.15 (s, 3H), 1.12 (d, J=12.8 Hz, 2H), 1.04 (s, 6H); MS (ESI) m/z: 635 (M+H$^+$).

Example 10

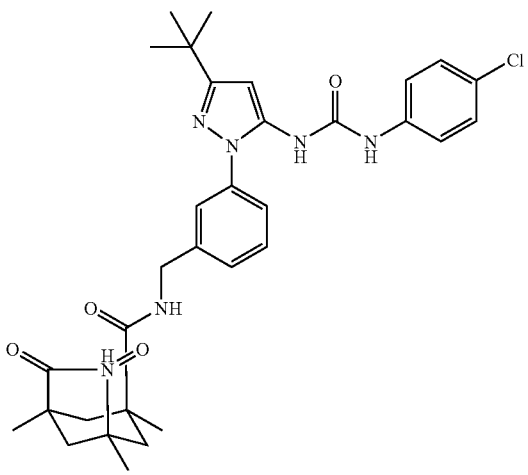

The title compound, was synthesized in a manner analogous to Example 9 utilizing Example J to yield 1,5,7-trimethyl-2,4-dioxo-3-aza-bicyclo[3.3.1]nonane-7-carboxylic acid 3-{3-t-butyl-5-[3-(4-chloro-phenyl)-ureido]-pyrazol-1-yl}benzylamide. $^1$H NMR (CDCl$_3$): δ 8.48 (s, 1H), 7.78 (s, 1H), 7.75 (d, J=8.0 Hz, 1H), 7.69 (s, 1H), 7.53 (t, J=8.0 Hz, 1H), 7.48 (d, J=8.8 Hz, 2H), 7.26 (m, 3H), 6.62 (s, 1H), 6.35 (t, J=6.0 Hz, 1H), 5.69 (brs, 1H), 4.26 (d, J=6.0 Hz, 2H), 2.48 (d, J=14.0 Hz, 2H), 1.87 (d, J=13.6 Hz, 1H), 1.35 (s, 9H), 1.25 (m, 6H), 1.15 (s, 6H); MS (ESI) m/z: 619 (M+H$^+$).

Example 11

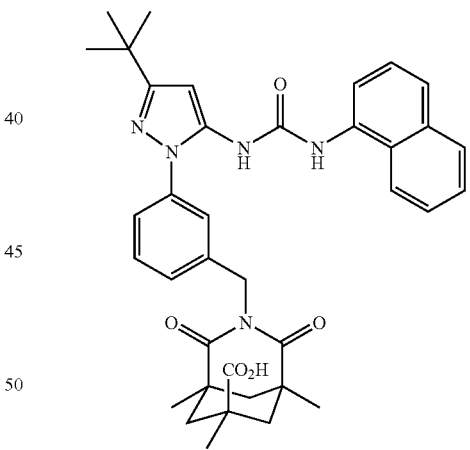

A mixture of Example I (41 mg, 0.1 mmol), Kemp acid anhydride (24 mg, 0.1 mmol) and Et$_3$N (100 mg, 1 mmol) in anhydrous CH$_2$Cl$_2$ (2 mL) were stirred overnight at RT, and concentrated in vacuo. Anhydrous benzene (20 mL) was added to the residue, the mixture was refluxed for 3 h, concentrated in vacuo and purified by preparative HPLC to yield 3-{3-[3-t-butyl-5-(3-naphthalen-1-yl-ureido)-pyrazol-1-yl]-benzyl}-1,5-di-methyl-2,4-dioxo-3-aza-bicyclo[3.3.1]nonane-7-carboxylic acid (8.8 mg, 14%). $^1$H NMR (CD$_3$OD): δ 7.3-7.4 (m, 2H), 7.20 (m, 2H), 7.4-7.6 (m, 7H), 6.50 (m, 1H), 4.80 (s, 2H), 2.60 (d, J=14 Hz, 2H), 1.90 (m, 1H), 1.40 (m, 1H), 1.30 (m, 2H), 1.20 (s, 3H), 1.15 (s, 6H); MS (ESI) m/z: 636 (M+H$^+$).

Example 12

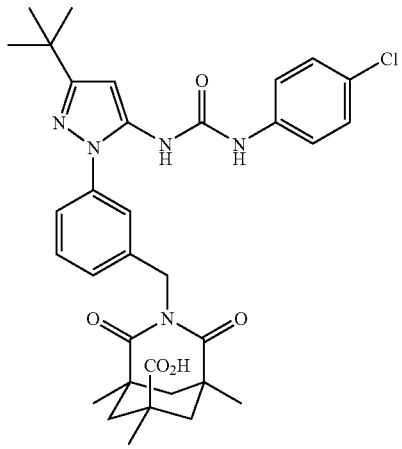

The title compound, was synthesized in a manner analogous to Example 11 utilizing Example J to yield 3-{3-[3-t-butyl-5-(3-naphthalen-1-yl-ureido)-pyrazol-1-yl]-benzyl}-1,5-dimethyl-2,4-dioxo-3-aza-bicyclo[3.3.1]nonane-7-carboxylic acid. $^1$H NMR (CD$_3$OD): δ 7.2-7.5 (m, 7H), 6.40 (s 1H), 4.70 (s, 2H), 2.60 (d, J=14 Hz, 2H), 1.90 (m, 1H), 1.50 (m, 1H), 1.45 (s, 9H), 1.30 (m, 2H), 1.21 (s, 3H), 1.18 (s, 6H); MS (ESI) m/z: 620 (M+H$^+$).

Example 13

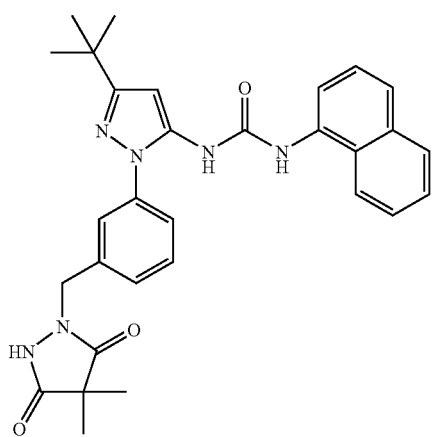

The title compound was synthesized in a manner analogous to Example 1 utilizing Example E and 4,4-dimethyl-3,5-dioxo-pyrazolidine to yield 1-(3-tert-butyl-1-{3-[(4,4-dimethyl-3,5-dioxopyrazolidin-1-yl)methyl]phenyl}-1H-pyrazol-5-yl)-3-(naphthalen-1-yl)urea. $^1$H NMR (CD$_3$OD): δ 7.88-7.86 (m, 2H), 7.71-7.68 (m, 2H), 7.58 (m, 2H), 7.60-7.42 (m, 5H), 6.49 (s, 1H), 4.85 (s, 1H), 1.34 (s, 9H), 1.27 (s, 6H); MS (ESI) m/z: 525 (M+H$^+$).

Example 14

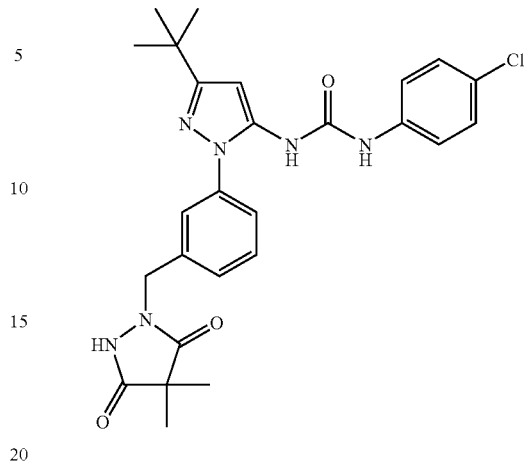

The title compound was synthesized in a manner analogous to Example 1 utilizing Example G and 4,4-dimethyl-3,5-dioxo-pyrazolidine to yield 1-(3-tert-butyl-1-{3-[(4,4-dimethyl-3,5-dioxopyrazolidin-1-yl)methyl]phenyl}-1H-pyrazol-5-yl)-3-(4-chlorophenyl)urea. $^1$H NMR (CD$_3$OD): δ 7.60-7.20 (m, 8H), 6.43 (s, 1H), 4.70 (s, 1H), 1.34 (s, 9H), 1.26 (s, 6H); MS (ESI) m/z: 509, 511 (M+H$^+$).

Example 15

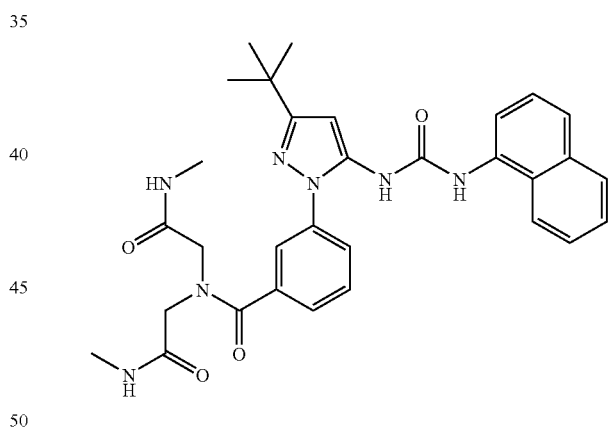

Example B was saponified with 2N LiOH in MeOH, and to the resulting acid (64.2 mg, 0.15 mmol) were added HOBt (30 mg, 0.225 mmol), Example K (24 mg, 0.15 mmol) and 4-methylmorpholine (60 mg, 0.60 mmol 4.0 equiv), and EDCI (3 mL) and EDCI (43 mg, 0.225 mmol). The reaction mixture was stirred at RT overnight and poured into H$_2$O (3 mL), and a white precipitate collected and further purified by preparative HPLC to yield 1-[1-(3-{bis[(methylcarbamoyl)methyl]carbamoyl}phenyl)-3-tert-butyl-1H-pyrazol-5-yl]-3-(naphthalen-1-yl)urea (40 mg). $^1$H NMR (CDCl$_3$): δ 8.45 (brs, 1H), 8.10 (d, J=7.6 Hz, 1H), 7.86-7.80 (m, 2H), 7.63-7.56 (m, 2H), 7.52 (s, 1H), 7.47-7.38 (m, 3H), 7.36-7.34 (m, 1H), 7.26 (s, 1H), 7.19-7.17 (m, 2H), 6.60 (s, 1H), 3.98 (s, 2H), 3.81 (s, 3H), 2.87 (s, 3H), 2.63 (s, 3H), 1.34 (s, 9H); MS (ESI) m/z: 570 (M+H$^+$).

Example 16

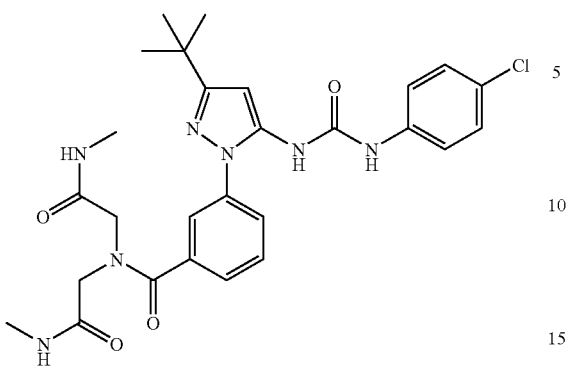

The title compound was synthesized in a manner analogous to Example 15 utilizing Example C (37 mg) and Example K to yield 1-[1-(3-{bis[(methylcarbamoyl)methyl] carbamoyl}phenyl)-3-tert-butyl-1H-pyrazol-5-yl]-3-(4-chlorophenyl)urea. $^1$H NMR (CD$_3$OD): δ 8.58 (brs, 1H), 8.39 (brs, 1H), 7.64-7.62 (m, 3H), 7.53-7.51 (m, 1H), 7.38 (d, J=9.2 Hz, 2H), 7.25 (d, J=8.8 Hz, 2H), 6.44 (s, 1H), 4.17 (s, 2H), 4.11 (s, 2H), 2.79 (s, 3H), 2.69 (s, 3H), 1.34-1.28 (m, 12H); MS (ESI) m/z: 554 (M+H$^+$).

Example 17

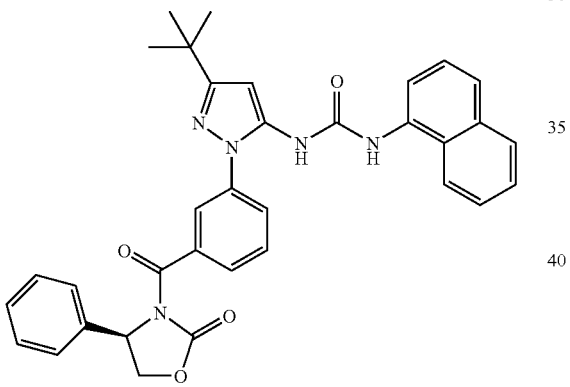

Example B was saponified with 2N LiOH in MeOH, and to the resulting acid (0.642 g, 1.5 mmol) in dry THF (25 mL) at −78° C. were added freshly distilled triethylamine (0.202 g, 2.0 mmol) and pivaloyl chloride (0.216 g, 1.80 mmol) with vigorous stirring. After stirring at −78° C. for 15 min and at 0° C. for 45 min, the mixture was again cooled to −78° C. and then transferred into the THF solution of lithium salt of D-4-phenyl-oxazolidin-2-one [*: The lithium salt of the oxazolidinone reagent was previously prepared by the slow addition of n-BuLi (2.50M in hexane, 1.20 mL, 3.0 mmol) into THF solution of D-4-phenyl-oxazoldin-2-one at −78° C.]. The reaction solution was stirred at −78° C. for 2 h and RT overnight, and then quenched with aq. ammonium chloride and extracted with dichloromethane (100 mL). The combined organic layers were dried (Na$_2$SO$_4$) and concentrated in vacuo. The residue was purified by preparative HPLC to yield D-1-{5-tert-butyl-2-[3-(2-oxo-4-phenyl-oxazolidinyl-3-carbonyl)phenyl]-2H-pyrazol-3-yl}-3-(naphthalen-1-yl)urea (207 mg, 24%). $^1$HNMR (CDCl$_3$): δ 8.14-8.09 (m, 2H), 8.06 (s, 1H), 7.86-7.81 (m, 4H), 7.79 (s, 1H), 7.68-7.61 (m, 2H), 7.51-7.40 (m, 9H), 6.75 (s, 1H), 5.80 (t, J=9.2, 7.6 Hz, 1H), 4.89 (t, J=9.2 Hz, 1H), 4.42 (dd, J=9.2, 7.6 Hz, 1H), 1.37 (s, 9H); MS (ESI) m/z: 574 (M+H$^+$).

Example 18

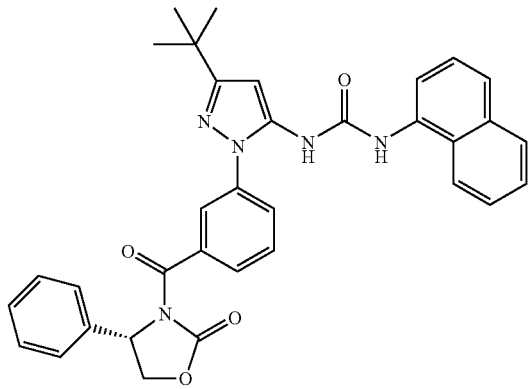

The title compound was synthesized in a manner analogous to Example 17 utilizing Example B and L-4-phenyl-oxazolidin-2-one to yield L-1-{5-tert-butyl-2-[3-(2-oxo-4-phenyl-oxazolidinyl-3-carbonyl)phenyl]-2H-pyrazol-3-yl}-3-(naphthalen-1-yl)urea $^1$H NMR (CDCl$_3$): δ 8.14-8.09 (m, 2H), 8.06 (s, 1H), 7.86-7.81 (m, 4H), 7.79 (s, 1H), 7.68-7.61 (m, 2H), 7.51-7.40 (m, 9H), 6.75 (s, 1H), 5.80 (t, J=9.2, 7.6 Hz, 1H), 4.89 (t, J=9.2 Hz, 1H), 4.42 (dd, J=9.2, 7.6 Hz, 1H), 1.37 (s, 9H); MS (ESI) m/z: 574 (M+H$^+$)

Example 19

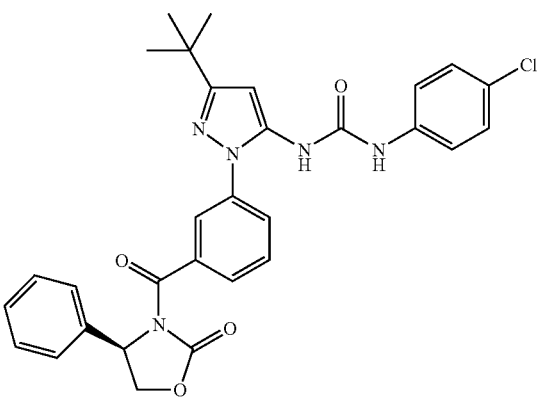

The title compound was synthesized in a manner analogous to Example 17 utilizing Example C and D-4-phenyl-oxazolidin-2-one to yield D-1-{5-tert-butyl-2-[3-(2-oxo-4-phenyl-oxazolidinyl-3-carbonyl)phenyl]-2H-pyrazol-3-yl}-3-(4-chlorophenyl)urea. $^1$H NMR (CDCl$_3$): δ 7.91 (s, 1H), 7.85 (d, J=8.0 Hz, 1H), 7.79 (d, J=7.6 Hz, 1H), 7.71 (m, 1H), 7.65 (m, 1H), 7.49-7.40 (m, 8H), 7.26-7.24 (m, 2H), 6.68 (s, 1H), 5.77 (dd, J=8.8, 8.0 Hz, 1H), 4.96 (t, 8.8 Hz, 1H), 4.44 (dd, J=8.8, 8.0 Hz, 1H), 1.36 (s, 9H); MS (ESI) m/z: 558 (M+H$^+$)

Example 20

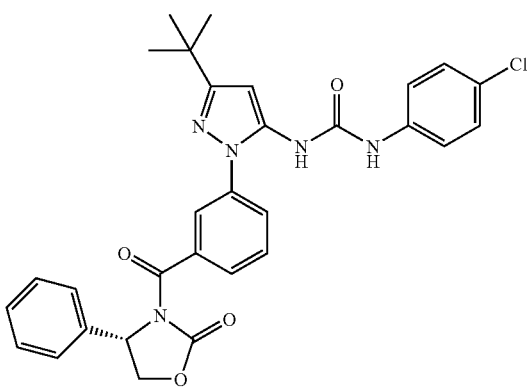

The title compound was synthesized in a manner analogous to Example 17 utilizing Example C and L-4-phenyl-oxazolidin-2-one to yield L-1-{5-tert-butyl-2-[3-(2-oxo-4-phenyl-oxazolidinyl-3-carbonyl)phenyl]-2H-pyrazol-3-yl}-3-(4-chlorophenyl)urea. $^1$H NMR (CDCl$_3$): δ 7.91 (s, 1H), 7.85 (d, J=8.0 Hz, 1H), 7.79 (d, J=7.6 Hz, 1H), 7.71 (m, 1H), 7.65 (m, 1H), 7.49-7.40 (m, 8H), 7.26-7.24 (m, 2H), 6.68 (s, 1H), 5.77 (dd, J=8.8, 8.0 Hz, 1H), 4.96 (t, 8.8 Hz, 1H), 4.44 (dd, J=8.8, 8.0 Hz, 1H), 1.36 (s, 9H); MS (ESI) m/z: 558 (M+H$^+$)

Example L

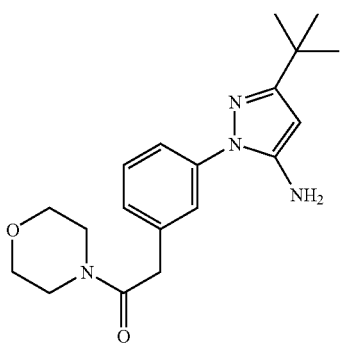

To a stirred suspension of (3-nitro-phenyl)-acetic acid (2 g) in CH$_2$Cl$_2$ (40 ml, with a catalytic amount of DMF) at 0° C. under N$_2$ was added oxalyl chloride (1.1 ml) drop wise. The reaction mixture was stirred for 40 min morpholine (2.5 g) was added. After stirring for 20 min, the reaction mixture was filtered. The filtrate was concentrated in vacuo to yield 1-morpholin-4-yl-2-(3-nitro-phenyl)-ethanone as a solid (2 g). A mixture of 1-morpholin-4-yl-2-(3-nitro-phenyl)-ethanone (2 g) and 10% Pd on activated carbon (0.2 g) in ethanol (30 ml) was hydrogenated at 30 psi for 3 h and filtered over Celite. Removal of the volatiles in vacuo provided 2-(3-amino-phenyl)-1-morpholin-4-yl-ethanone (1.7 g). A solution of 2-(3-amino-phenyl)-1-morpholin-4-yl-ethanone (1.7 g, 7.7 mmol) was dissolved in 6 N HCl (15 ml), cooled to 0° C., and vigorously stirred. Sodium nitrite (0.54 g) in water (8 ml) was added. After 30 min, tin (II) chloride dihydrate (10 g) in 6 N HCl (30 ml) was added. The reaction mixture was stirred at 0° C. for 3 h. The pH was adjusted to pH 14 with solid potassium hydroxide and extracted with EtOAc. The combined organic extracts were concentrated in vacuo provided 2-(3-hydrazin-phenyl)-1-morpholin-4-yl-ethanone (1.5 g). 2-(3-Hydrazinophenyl)-1-morpholin-4-yl-ethanone (3 g) and 4,4-dimethyl-3-oxopentanenitrile (1.9 g, 15 mmol) in ethanol (60 ml) and 6 N HCl (1 ml) were refluxed for 1 h and cooled to RT. The reaction mixture was neutralized by adding solid sodium hydrogen carbonate. The slurry was filtered and removal of the volatiles in vacuo provided a residue that was extracted with ethyl acetate. The volatiles were removed in vacuo to provide 2-[3-(3-tert-butyl-5-amino-1H-pyrazol-1-yl)phenyl]-1-morpholinoethanone (4 g), which was used without further purification.

Example 21

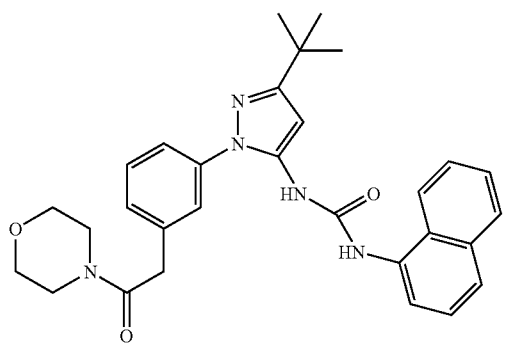

A mixture of Example L (0.2 g, 0.58 mmol) and 1-naphthylisocyanate (0.10 g, 0.6 mmol) in dry CH$_2$Cl$_2$ (4 ml) was stirred at RT under N$_2$ for 18 h. The solvent was removed in vacuo and the crude product was purified by column chromatography using ethyl acetate/hexane/CH$_2$Cl$_2$ (3/1/0.7) as the eluent (0.11 g, off-white solid) to yield 1-{3-tert-butyl-1-[3-(2-morpholino-2-oxoethyl)phenyl]-1H-pyrazol-5-yl}-3-(naphthalene-1-yl)urea. mp: 194-196; $^1$H NMR (200 MHz, DMSO-d$_6$): δ9.07 (1H, s), 8.45 (s, 1H), 8.06-7.93 (m, 3H), 7.69-7.44 (m, 7H), 7.33-7.29 (d, 6.9 Hz, 1H), 6.44 (s, 1H), 3.85 (m, 2H), 3.54-3.45 (m, 8H), 1.31 (s, 9H); MS:

Example 22

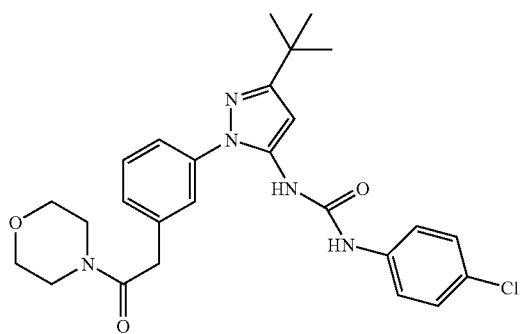

The title compound was synthesized in a manner analogous to Example 21 utilizing Example L (0.2 g, 0.58 mmol) and 4-chlorophenylisocyanate (0.09 g, 0.6 mmol) to yield 1-{3-tert-butyl-1-[3-(2-morpholino-2-oxoethyl)phenyl]-1H-pyrazol-5-yl}-3-(4-chlorophenyl)urea. mp: 100 104; $^1$H NOR (200 MHz, DMSO-d₆): δ 9.16 (s, 1H), 8.45 (s, 1H), 7.52-7.30 (m, 8H), 6.38 (s, 1H), 3.83 (m, 1H), 3.53-3.46 (m, 8H), 1.30 (s, 9H); MS:

Example 23

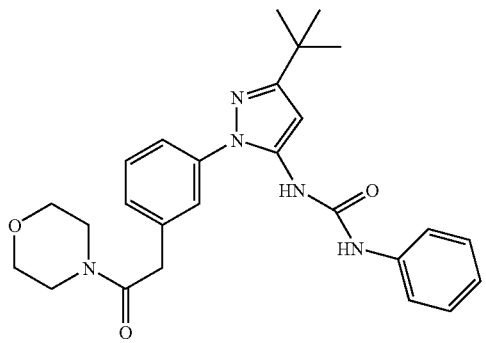

The title compound is synthesized in a manner analogous to Example 21 utilizing Example L (0.2 g, 0.58 mmol) and phenylisocyanate (0.09 g, 0.6 mmol) to yield 1-{3-tert-butyl-1-[3-(2-morpholino-2-oxoethyl)phenyl]-1H-pyrazol-5-yl}-3-phenylurea.

Example 24

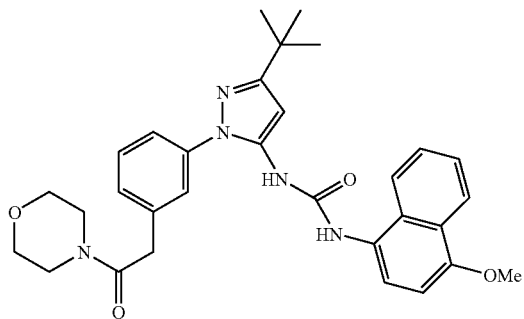

The title compound is synthesized in a manner analogous to Example 21 utilizing Example L (0.2 g, 0.58 mmol) and 1-isocyanato-4-methoxy-naphthalene to yield 1-{3-tert-butyl-1-[3-(2-morpholino-2-oxoethyl)phenyl]-1H-pyrazol-5-yl}-3-(1-methoxynaphthalen-4-yl)urea.

Example M

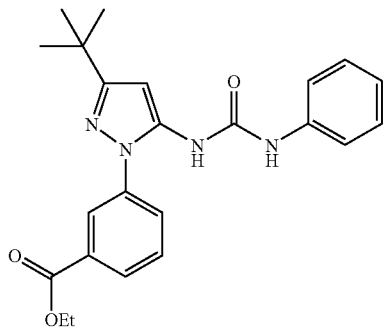

The title compound is synthesized in a manner analogous to Example C utilizing Example A and phenylisocyanate to yield ethyl 3-(3-tert-butyl-5-(3-phenylureido)-1H-pyrazol-1-yl)benzoate.

Example N

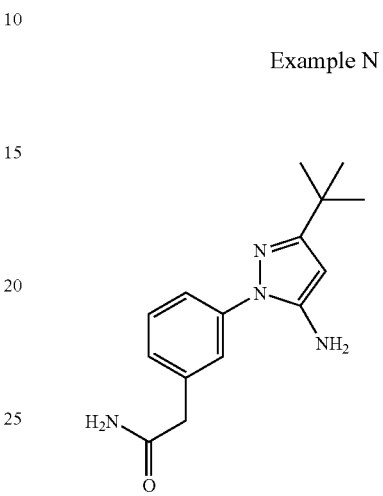

A solution of (3-nitrophenyl)acetic acid (23 g, 127 mmol) in methanol (250 ml) and a catalytic amount of concentrated in vacuo H₂SO₄ was heated to reflux for 18 h. The reaction mixture was concentrated in vacuo to a yellow oil. This was dissolved in methanol (250 ml) and stirred for 18 h in an ice bath, whereupon a slow flow of ammonia was charged into the solution. The volatiles were removed in vacuo. The residue was washed with diethyl ether and dried to afford 2-(3-nitrophenyl)acetamide (14 g, off-white solid). ¹H NMR (CDCl₃): δ 8.1 (s, 1H), 8.0 (d, 1H), 7.7 (d, 1H), 7.5 (m, 1H), 7.1 (bd s, 1H), 6.2 (brs, 1H), 3.6 (s, 2H).

The crude material from the previous reaction (8 g) and 10% Pd on activated carbon (1 g) in ethanol (100 ml) was hydrogenated at 30 psi for 18 h and filtered over Celite. Removal of the volatiles in vacuo provided 2-(3-aminophenyl)acetamide (5.7 g). A solution of this material (7 g, 46.7 mmol) was dissolved in 6 N HCl (100 ml), cooled to 0° C., and vigorously stirred. Sodium nitrite (3.22 g, 46.7 mmol) in water (50 ml) was added. After 30 min, tin (II) chloride dihydrate (26 g) in 6 N HCl (100 ml) was added. The reaction mixture was stirred at 0° C. for 3 h. The pH was adjusted to pH 14 with 50% aqueous NaOH solution and extracted with ethyl acetate. The combined organic extracts were concentrated in vacuo provided 2-(3-hydrazinophenyl)acetamide.

The crude material from the previous reaction (ca. 15 mmol) and 4,4-dimethyl-3-oxopentanenitrile (1.85 g, 15 mmol) in ethanol (60 ml) and 6 N HCl (1.5 ml) was refluxed for 1 h and cooled to RT. The reaction mixture was neutralized by adding solid sodium hydrogen carbonate. The slurry was filtered and removal of the volatiles in vacuo provided a residue, which was extracted with ethyl acetate. The solvent was removed in vacuo to provide 2-[3-(3-tert-butyl-5-amino-1H-pyrazol-1-yl)phenyl]acetamide as a white solid (3.2 g), which was used without further purification.

Example 25

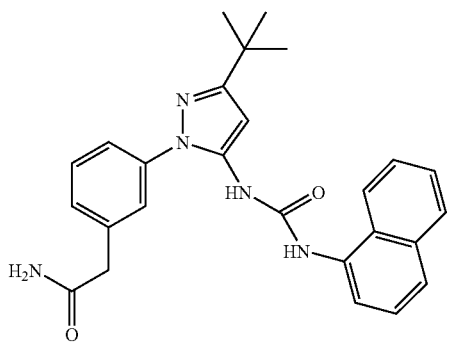

A mixture of Example N (2 g, 0.73 mmol) and 1-naphthylisocyanate (0.124 g, 0.73 mmol) in dry $CH_2Cl_2$ (4 ml) was stirred at RT under $N_2$ for 18 h. The solvent was removed in vacuo and the crude product was washed with ethyl acetate (8 ml) and dried in vacuo to yield 1-{3-tert-butyl-1-[3-(carbamoylmethyl)phenyl)-1H-pyrazol-5-yl}-3-(naphthalene-1-yl) urea as a white solid (0.22 g). mp: 230 (dec.); $^1$H NMR (200 MHz, DMSO-$d_6$): δ 9.12 (s, 1H), 8.92 (s, 1H), 8.32-8.08 (m, 3H), 7.94-7.44 (m, 8H), 6.44 (s, 1H), 3.51 (s, 2H), 1.31 (s, 9H); MS:

Example 26

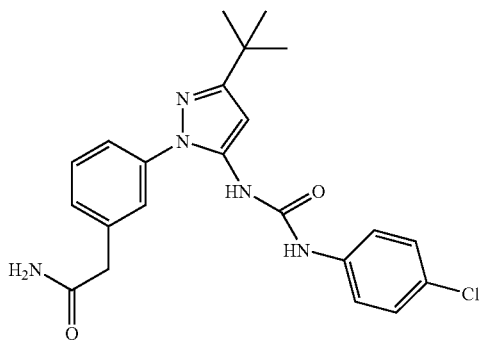

The title compound was synthesized in a manner analogous to Example 23 utilizing Example N (0.2 g, 0.73 mmol) and 4-chlorophenylisocyanate (0.112 g, 0.73 mmol) to yield 1-{3-tert-butyl-1-[3-(carbamoylmethyl)phenyl]-1H-pyrazol-5-yl}-3-(4-chlorophenyl)urea as a white solid (0.28 g). mp: 222 224. (dec.); $^1$H NMR (200 MHz, DMSO-$d_6$): δ 9.15 (s, 1H), 8.46 (s, 1H), 7.55-7.31 (m, 8H), 6.39 (s, 1H), 3.48 (s, 2H), 1.30 (s, 9H); MS:

Example O

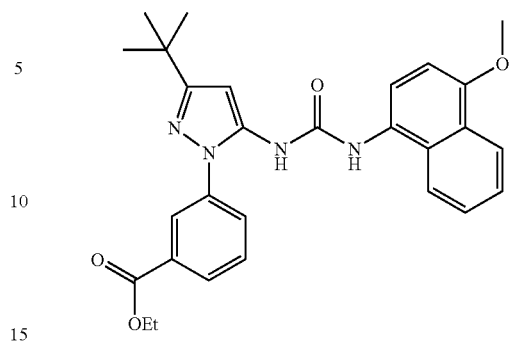

The title compound is synthesized in a manner analogous to Example C utilizing Example A and 1-isocyanato-4-methoxy-naphthaleneto yield ethyl 3-(3-tert-butyl-5-(3-(1-methoxynaphthalen-4-yl)ureido)-1H-pyrazol-1-yl)benzoate.

Example 27

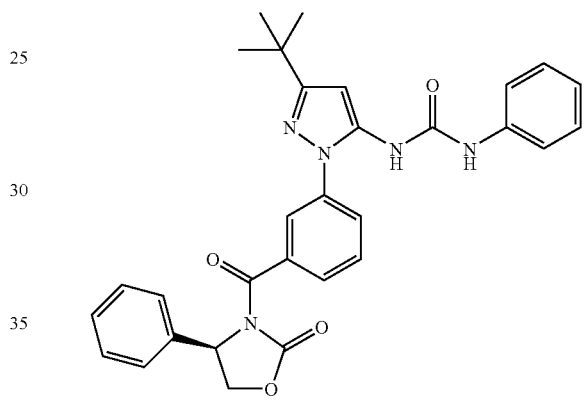

The title compound is synthesized in a manner analogous to Example 17 utilizing Example M and D-4-phenyl-oxazolidin-2-one to yield D-1-{5-tert-butyl-2-[3-(2-oxo-4-phenyl-oxazolidinyl-3-carbonyl)phenyl]-2H-pyrazol-3-yl}-3-phenylurea.

Example 28

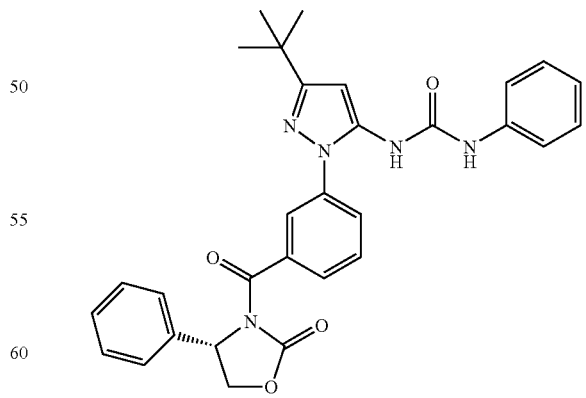

The title compound is synthesized in a manner analogous to Example 17 utilizing Example M and L-4-phenyl-oxazolidin-2-one to yield L-1-{5-tert-butyl-2-[3-(2-oxo-4-phenyl-oxazolidinyl-3-carbonyl)phenyl]-2H-pyrazol-3-yl}-3-phenylurea.

Example P

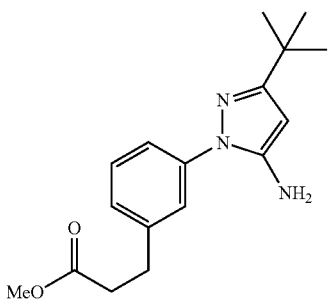

A mixture of 3-(3-amino-phenyl)-acrylic acid methyl ester (6 g) and 10% Pd on activated carbon (1 g) in ethanol (50 ml) was hydrogenated at 30 psi for 18 h and filtered over Celite. Removal of the volatiles in vacuo provided 3-(3-amino-phenyl)propionic acid methyl ester (6 g).

A vigorously stirred solution of the crude material from the previous reaction (5.7 g, 31.8 mmol) dissolved in 6 N HCl (35 ml) was cooled to 0° C., and sodium nitrite (2.2 g) in water (20 ml) was added. After 1 h, tin (11) chloride dihydrate (18 g) in 6 N HCl (35 ml) was added. And the mixture was stirred at 0° C. for 3 h. The pH was adjusted to pH 14 with solid KOH and extracted with EtOAc. The combined organic extracts were concentrated in vacuo provided methyl 3-(3-hydrazino-phenyl)propionate (1.7 g).

A stirred solution of the crude material from the previous reaction (1.7 g, 8.8 mmol) and 4,4-dimethyl-3-oxopentanenitrile (1.2 g, 9.7 mmol) in ethanol (30 ml) and 6 N HCl (2 ml) was refluxed for 18 h and cooled to RT. The volatiles were removed in vacuo and the residue dissolved in EtOAc and washed with 1 N aqueous NaOH. The organic layer was dried (Na$_2$SO$_4$) and concentrated in vacuo and the residue was purified by column chromatography using 30% ethyl acetate in hexane as the eluent to provide methyl 3-[3-(3-tert-butyl-5-amino-1H-pyrazol-1-yl)phenyl]propionate (3.2 g), which was used without further purification

Example 29

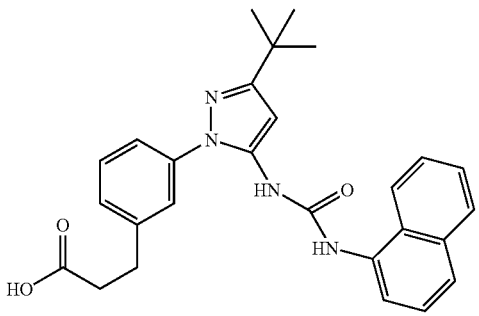

A mixture of Example P (0.35 g, 1.1 mmol) and 1-naphthylisocyanate (0.19 g, 1.05 mmol) in dry CH$_2$Cl$_2$ (5 ml) was stirred at RT under N$_2$ for 20 h. The solvent was removed in vacuo and the residue was stirred in a solution of THF (3 ml)/MeOH (2 ml)/water (1.5 ml) containing lithium hydroxide (0.1 g) for 3 h at RT, and subsequently diluted with EtOAc and dilute citric acid solution. The organic layer was dried (Na$_2$SO$_4$), and the volatiles removed in vacuo. The residue was purified by column chromatography using 3% methanol in CH$_2$Cl$_2$ as the eluent to yield 3-(3-{3-tert-butyl-5-[3-(naphthalen-1-yl)ureido]-1H-pyrazol-1-yl)phenylpropionic acid (0.22 g, brownish solid). mp: 105-107; $^1$H NMR (200 MHz, CDCl$_3$): δ 7.87-7.36 (m, 10H), 7.18-7.16 (m, 1H), 6.52 (s, 1H), 2.93 (t, J=6.9 Hz, 2H), 2.65 (t, J=7.1 Hz, 2H), 1.37 (s, 9H); MS

Example 30

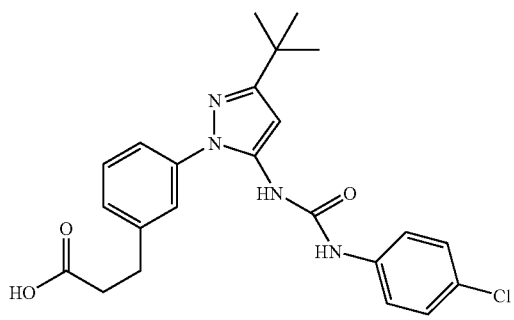

The title compound was synthesized in a manner analogous to Example 29 utilizing Example P (0.30 g, 0.95 mmol) and 4-chlorophenylisocyanate (0.146 g, 0.95 mmol) to yield 3-(3-{3-tert-butyl-5-[3-(4-chloropnehyl)ureido]-1H-pyrazol-1-yl)phenyl)propionic acid (0.05 g, white solid). mp: 85 87; $^1$H NMR (200 MHz, CDCl$_3$): δ8.21 (s, 1H), 7.44-7.14 (m, 7H), 6.98 (s, 1H), 6.55 (s, 1H), 2.98 (t, J=5.2 Hz, 2H), 2.66 (t, J=5.6 Hz, 2H), 1.40 (s, 9H); MS

Example Q

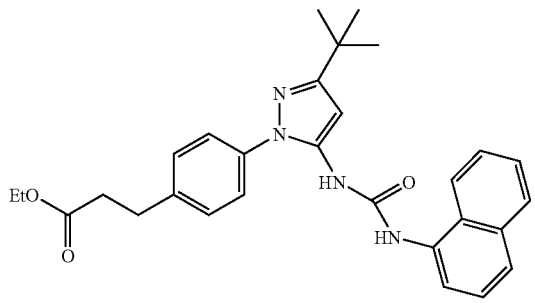

A mixture of ethyl 3-(4-aminophenyl)acrylate (1.5 g) and 10% Pd on activated carbon (0.3 g) in ethanol (20 ml) was hydrogenated at 30 psi for 18 h and filtered over Celite. Removal of the volatiles in vacuo provided ethyl 3-(4-aminophenyl)propionate (1.5 g).

A solution of the crude material from the previous reaction (1.5 g, 8.4 mmol) was dissolved in 6 N HCl (9 ml), cooled to 0° C., and vigorously stirred. Sodium nitrite (0.58 g) in water (7 ml) was added. After 1 h, tin (II) chloride dihydrate (5 g) in 6 N HCl (10 ml) was added. The reaction mixture was stirred at 0° C. for 3 h. The pH was adjusted to pH 14 with solid KOH and extracted with EtOAc. The combined organic extracts were concentrated in vacuo provided ethyl 3-(4-hydrazinophenyl)-propionate(1 g).

The crude material from the previous reaction (1 g, 8.8 mmol) and 4,4-dimethyl-3-oxopentanenitrile (0.7 g) in ethanol (8 ml) and 6 N HCl (1 ml) was refluxed for 18 h and cooled to RT. The volatiles were removed in vacuo. The residue was dissolved in ethyl acetate and washed with 1 N aqueous sodium hydroxide solution. The organic layer was dried (Na$_2$SO$_4$) and concentrated in vacuo. The residue was purified by column chromatography using 0.7% methanol in CH$_2$Cl$_2$ as the eluent to provide ethyl 3-{4-[3-tert-butyl-5-(3-(naphthalene-1-yl)ureido]-1H-pyrazol-1-yl}phenyl)propanoate (0.57 g).

Example 31

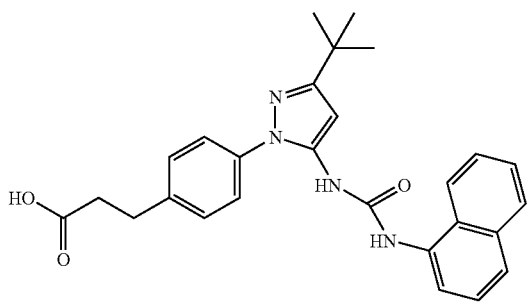

A mixture of Example Q (0.25 g, 0.8 mmol) and 1-naphthylisocyanate (0.13 g, 0.8 mmol) in dry CH$_2$Cl$_2$ (5 ml) was stirred at RT under N$_2$ for 20 h. The solvent was removed in vacuo and the residue was stirred in a solution of THF (3 ml)/MeOH (2 ml)/water (1.5 ml) containing lithium hydroxide (0.1 g) for 3 h at RT and diluted with EtOAc and diluted citric acid solution. The organic layer was dried (Na$_2$SO$_4$), and the volatiles removed in vacuo. The residue was purified by column chromatography using 4% methanol in CH$_2$Cl$_2$ as the eluent to yield 3-{4-[3-tert-butyl-5-(3-(naphthalene-1-yl)ureido]-1H-pyrazol-1-yl}phenyl)propanonic acid (0.18 g, off-white solid). mp: 120 122; $^1$H NMR (200 MHz, CDCl$_3$): δ 7.89-7.06 (m, 11H), 6.5 (s, 1H), 2.89 (m, 2H), 2.61 (m, 2H), 1.37 (s, 9H); MS Example 32

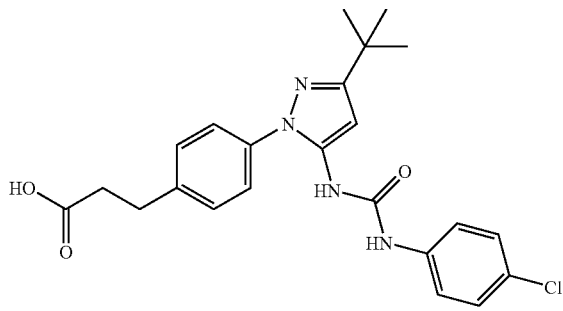

The title compound was synthesized in a manner analogous to Example 31 utilizing Example Q (0.16 g, 0.5 mmol) and 4-chlorophenylisocyanate (0.077 g, 0.5 mmol) to yield 3-{4-[3-tert-butyl-5-(3-(4-chlorphenyl)ureido]-1H-pyrazol-1-yl}phenyl)propanonic acid acid (0.16 g, off-white solid). mp: 112-114; $^1$H NMR (200 MHz, CDCl$_3$): δ 8.16 (s, 1H), 7.56 (s, 1H), 7.21 (s, 2H), 7.09 (s, 2H), 6.42 (s, 1H), 2.80 (m, 2H), 2.56 (m, 2H), 1.32 (s, 9H); MS Example R

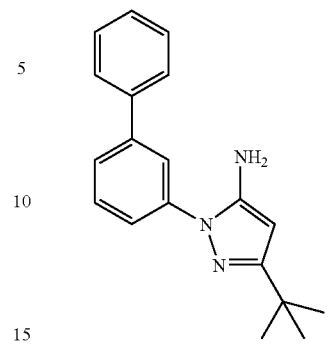

A 250 mL pressure vessel (ACE Glass Teflon screw cap) was charged with 3-nitrobiphenyl (20 g, 0.10 mol) dissolved in THF (~100 mL) and 10% Pd/C (3 g). The reaction vessel was charged with H$_2$ (g) and purged three times. The reaction was charged with 40 psi H$_2$ (g) and placed on a Parr shaker hydrogenation apparatus and allowed to shake overnight at RT. HPLC showed that the reaction was complete thus the reaction mixture was filtered through a bed of Celite and evaporated to yield the amine: 16.7 g (98% yield)

In a 250 mL Erlenmeyer flask with a magnetic stir bar, the crude material from the previous reaction (4.40 g, 0.026 mol) was added to 6 N HCl (40 mL) and cooled with an ice bath to ~0° C. A solution of NaNO$_2$ (2.11 g, 0.0306 mol, 1.18 eq.) in water (5 mL) was added drop wise. After 30 min, SnCl$_2$2H$_2$O (52.0 g, 0.23 mol, 8.86 eq.) in 6N HCl (100 mL) was added and the reaction mixture was allowed to stir for 3 h, then subsequently transferred to a 500 mL round bottom flask. To this, 4,4-dimethyl-3-oxopentanenitrile (3.25 g, 0.026 mol) and EtOH (100 ml) were added and the mixture refluxed for 4 h, concentrated in vacuo and the residue extracted with EtOAc (2×100 mL). The residue was purified by column chromatograph using hexane/EtOAc/Et$_3$N (8:2:0.2) to yield 0.53 g of Example R. $^1$H NMR (CDCl$_3$): δ 7.5 (m, 18H), 5.8 (s, 1H), 1.3 (s, 9H).

Example 33

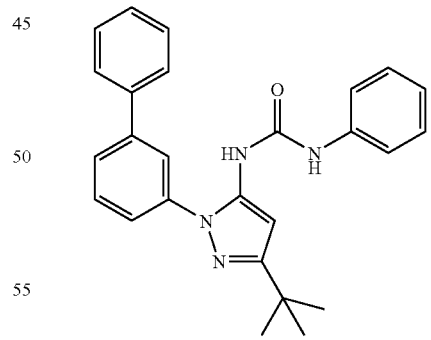

In a dry vial with a magnetic stir bar, Example R (0.145 g; 0.50 mmol) was dissolved in 2 mL CH$_2$Cl$_2$ (anhydrous) followed by the addition of phenylisocyanate (0.0544 mL; 0.50 mmol; 1 eq.). The reaction was kept under argon and stirred for 17 h. Evaporation of solvent gave a crystalline mass that was triturated with hexane/EtOAc (4:1) and filtered to yield 1-(3-tert-butyl-1-(3-phenylphenyl)-1H-pyrazol-5-yl)-3-phenylurea (0.185 g, 90%). HPLC purity: 96%; mp: 80 84; $^1$H NMR (CDCl$_3$): δ 7.3 (m, 16H), 6.3 (s, 1H), 1.4 (s, 9H).

Example 34

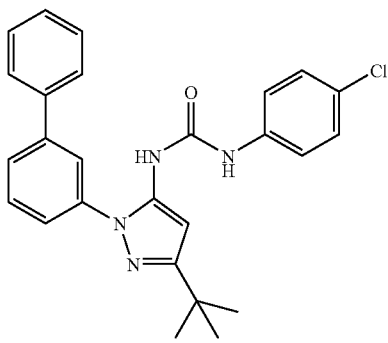

The title compound was synthesized in a manner analogous to Example 33 utilizing Example R (0.145 g; 0.50 mmol) and p-chlorophenylisocyanate (0.0768 g, 0.50 mmol, 1 eq.) to yield 1-(3-tert-butyl-1-(3-phenylphenyl)-1H-pyrazol-5-yl)-3-(4-chlorophenyl)urea (0.205 g, 92%). HPLC purity: 96.5%; mp: 134 136; $^1$H NMR (CDCl$_3$): δ 7.5 (m, 14H), 7.0 (s, 1H), 6.6 (s, 1H), 6.4 (s, 1H), 1.4 (s, 9H).

Example S

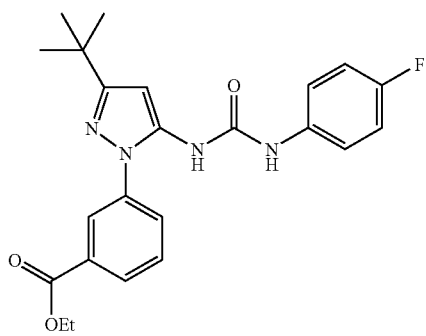

The title compound is synthesized in a manner analogous to Example C utilizing Example A and 4-fluorophenyl isocyanate yield ethyl 3-(3-tert-butyl-5-(3-(4-fluorophenyl)ureido)-1H-pyrazol-1-yl)benzoate.

Example 35

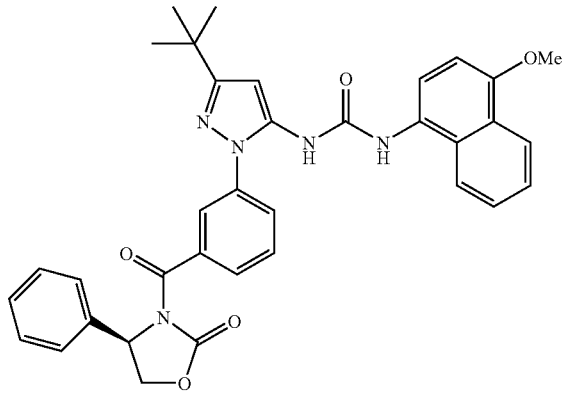

The title compound is synthesized in a manner analogous to Example 17 utilizing Example M and D-4-phenyl-oxazolidin-2-one to yield D-1-{5-tert-butyl-2-[3-(2-oxo-4-phenyl-oxazolidinyl-3-carbonyl)phenyl]-2H-pyrazol-3-yl}-3-(naphthalen-1-yl)urea.

Example 36

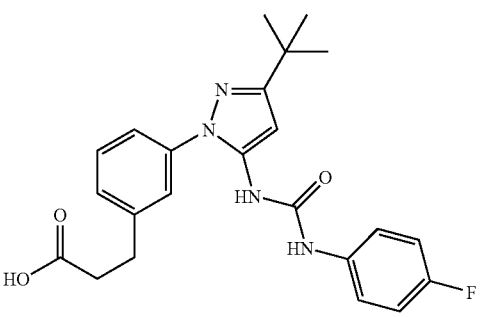

The title compound is synthesized in a manner analogous to Example 29 utilizing Example P (0.30 g, 0.95 mmol) and 4-fluOrophenylisocyanate (0.146 g, 0.95 mmol) to yield 3-(3-(3-tert-butyl-5-(3-(4-fluorophenyl)ureido)-1H-pyrazol-1-yl)phenyl)propanoic acid.

Example T

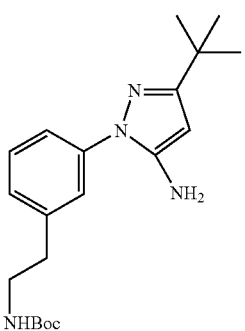

To a stirred solution of Example N (2 g, 7.35 mmol) in THF (6 ml) was added borane-methylsulfide (18 mmol). The mixture was heated to reflux for 90 min and cooled to RT, after which 6 N HCl was added and heated to reflux for 10 min. The mixture was basified with NaOH and extracted with EtOAc. The organic layer was dried (Na$_2$SO$_4$) filtered and concentrated in vacuo to yield 3-tert-butyl-1-[3-(2-aminoethyl)phenyl]-1H-pyrazol-5 amine (0.9 g).

A mixture of the crude material from the previous reaction (0.8 g, 3.1 mmol) and di-tert-butylcarbonate (0.7 g, 3.5 mmol) and catalytically amount of DMAP in dry CH$_2$Cl$_2$ (5 ml) was stirred at RT under N$_2$ for 18 h. The reaction mixture was concentrated in vacuo and the residue was purified by column chromatography using 1% methanol in CH$_2$Cl$_2$ as the eluent to yield tert-butyl 3-(3-tert-butyl-5-amino-1H-pyrazol-1-yl)phenylcarbamate (0.5 g).

Example 37

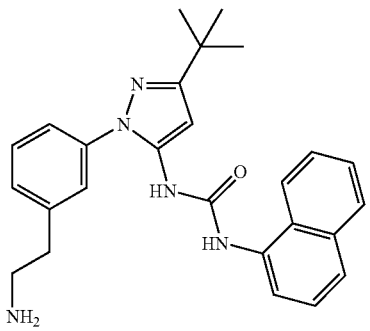

A mixture of Example T (0.26 g, 0.73 mmol) and 1-naphthylisocyanate (0.123 g, 0.73 mmol) in dry CH$_2$Cl$_2$ (5 ml) was stirred at RT under N$_2$ for 48 h. The solvent was removed in vacuo and the residue was purified by column chromatography using 1% methanol in CH$_2$Cl$_2$ as the eluent (0.15 g, off-white solid). The solid was then treated with TFA (0.2 ml) for 5 min and diluted with EtOAc. The organic layer was washed with saturated NaHCO$_3$ solution and brine, dried (Na$_2$SO$_4$), filtered and concentrated in vacuo to yield 1-{3-tert-butyl-1-[3-(2-Aminoethyl)phenyl]-1H-pyrazol-5-yl}-3-(naphthalen-1-yl)urea as a solid (80 mg). mp: 110-112; $^1$HNMR (200 MHz, DMSO-d$_6$): δ 9.09 (s, 1H), 8.90 (s, 1H), 8.01-7.34 (m, 11H), 6.43 (s, 1H), 3.11 (m, 2H), 2.96 (m, 2H), 1.29 (s, 9H); MS

Example 38

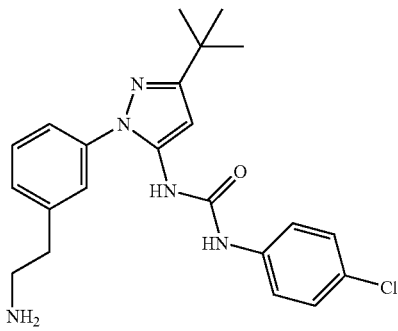

The title compound was synthesized in a manner analogous to Example 37 utilizing Example T (0.15 g, 0.42 mmol) and 4-chlorophenylisocyanate (0.065 g, 0.42 mmol) to yield 1-{3-tert-butyl-1-[3-(2-Aminoethyl)phenyl]-1H-pyrazol-5-yl}-3-(4-chlorophenyl)urea as an off-white solid (20 mg). mp: 125-127; $^1$H NMR (200 MHz, CDCl$_3$): δ 8.81 (s, 1H), 8.66 (s, 1H), 7.36-7.13 (m, 8H), 6.54 (s, 1H), 3.15 (brs, 2H), 2.97 (brs, 2H), 1.32 (s, 9H); MS

Example U

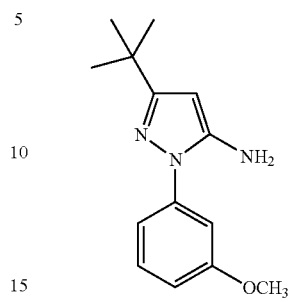

In a 250 mL Erlenmeyer flask with a magnetic stir bar, m-anisidine (9.84 g, 0.052 mol) was added to 6 N HCl (80 mL) and cooled with an ice bath to 0° C. A solution of NaNO$_2$ (4.22 g, 0.0612 mol, 1.18 eq.) in water (10 mL) was added drop wise. After 30 min, SnCl$_2$2H$_2$O (104.0 g, 0.46 mol, 8.86 eq.) in 6 N HCl (200 mL) was added and the reaction mixture was allowed to stir for 3 h., and then subsequently transferred to a 1000 mL round bottom flask. To this, 4,4-dimethyl-3-oxopentanenitrile (8.00 g, 0.064 mol) and EtOH (200 mL) were added and the mixture refluxed for 4 h, concentrated in vacuo and the residue recrystallized from CH$_2$Cl$_2$ to yield 3-tert-butyl-1-(3-methoxyphenyl)-1H-pyrazol-5-amine as the HCl salt (13.9 g).

The crude material from the previous reaction (4.65 g, 0.165 mol) was dissolved in 30 mL of CH$_2$Cl$_2$ with Et$_3$N (2.30 mL, 0.0165 mol, 1 eq.) and stirred for 30 min Extraction with water followed by drying of the organic phase with Na$_2$SO$_4$ and concentration in vacuo yielded a brown syrup that was the free base, 3-tert-butyl-1-(3-methoxyphenyl)-1H-pyrazol-5-amine (3.82 g, 94.5%), which was used without further purification.

Example 39

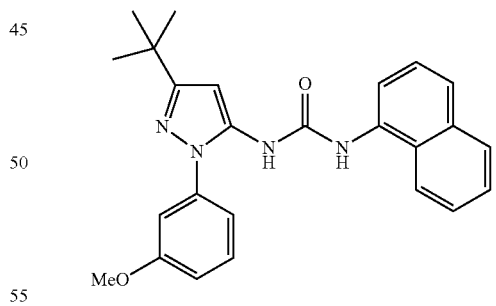

In a dry vial with a magnetic stir bar, Example U (2.62 g, 0.0107 mol) was dissolved in CH$_2$Cl$_2$ (5 mL, anhydrous) followed by the addition of 1-naphthylisocyanate (1.53 mL, 0.0107 mol, 1 eq.). The reaction was kept under Ar and stirred for 18 h. Evaporation of solvent followed by column chromatography with EtOAc/hexane/Et$_3$N (7:2:0.5) as the eluent yielded 1-[3-tert-butyl-1-(3-methoxyphenyl)-1H-pyrazol-5-yl]-3-(naphthalen-1-yl)urea (3.4 g, 77%). HPLC: 97%; mp: 78-80; $^1$H NMR (CDCl$_3$): δ 7.9-6.8 (m, 15H), 6.4 (s, 15H), 3.7 (s, 3H), 1.4 (s, 9H).

Example 40

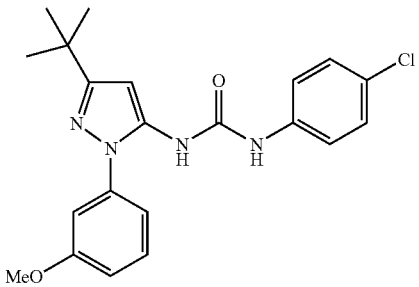

The title compound was synthesized in a manner analogous to Example 39 utilizing Example U (3.82 g; 0.0156 mol) and p-chlorophenylisocyanate (2.39 g, 0.0156 mol, 1 eq.), purified by trituration with hexane/EtOAc (4:1) and filtered to yield 1-[3-tert-butyl-1-(3-methoxyphenyl)-1H-pyrazol-5-yl]-3-(4-chlorophenyl)urea (6.1 g, 98%). HPLC purity: 95%; mp: 158-160; $^1$H NMR (CDCl$_3$): δ 7.7 (s, 1H); δ 7.2 6.8 (m, 8H), 6.4 (s, 1H), 3.7 (s, 3H), 1.3 (s, 9H).

Example 41

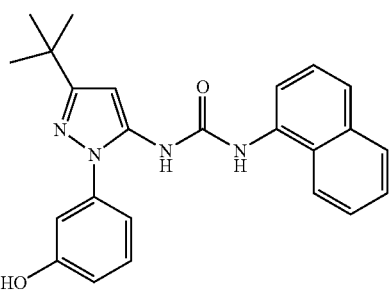

In a 100 ml round bottom flask equipped with a magnetic stir bar, Example 39 (2.07 g) was dissolved in CH$_2$Cl$_2$ (20 mL) and cooled to 0° C. with an ice bath. BBr$_3$ (1 M in CH$_2$Cl$_2$; 7.5 mL) was added slowly. The reaction mixture was allowed to warm to RT overnight. Additional BBr$_3$ (1 M in CH$_2$Cl$_2$, 2×1 mL, 9.5 mmol total added) was added and the reaction was quenched by the addition of MeOH. Evaporation of solvent led to a crystalline material that was chromatographed on silica gel (30 g) using CH$_2$Cl$_2$/MeOH (9.6:0.4) as the eluent to yield 1-[3-tert-butyl-1-(3-hydroxyphenyl)-1H-pyrazol-5-yl]-3-(naphthalene-1-yl)urea (0.40 g, 20%). $^1$H NMR (DMSO-d$_6$): δ 9.0 (s, 1H), 8.8 (s, 1H), 8.1-6.8 (m, 11H), 6.4 (s, 1H), 1.3 (s, 9H). MS (ESI) m/z: 401 (M+H$^+$).

Example 42

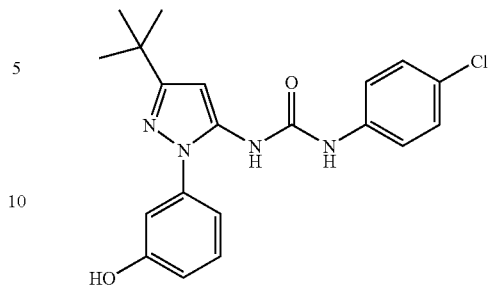

The title compound was synthesized in a manner analogous to Example 41 utilizing Example 40 (2.00 g, 5 mmol) that resulted in a crystalline material that was filtered and washed with MeOH to yield 1-[3-tert-butyl-1-(3-hydroxyphenyl)-1H-pyrazol-5-yl]-3-(4-chlorophenyl)urea (1.14 g, 60%). HPLC purity: 96%; mp: 214-216; $^1$HNMR (CDCl$_3$): δ8.4 (s, 1H), 7.7 (s, 1H), 7.4-6.6 (m, 9H), 1.3 (s, 9H).

Example V

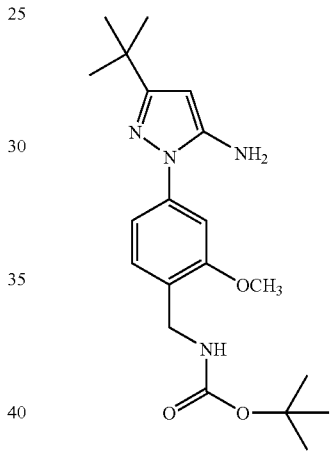

The starting material, 1-[4-(aminomethyl)phenyl]-3-tert-butyl-N-nitroso-1H-pyrazol-5-amine, was synthesized in a manner analogous to Example A utilizing 4-aminobenzamide and 4,4-dimethyl-3-oxopentanenitrile.

A 1 L four-necked round bottom flask was equipped with a stir bar, a source of dry-Ar, a heating mantle, and a reflux condenser. The flask was flushed with Ar and charged with the crude material from the previous reaction (12 g, 46.5 mmol; 258.1 g/mol) and anhydrous THF (500 ml). This solution was treated cautiously with LiAlH$_4$ (2.65 g, 69.8 mmol) and the reaction was stirred overnight. The reaction was heated to reflux and additional LiAlH$_4$ was added complete (a total of 8.35 g added). The reaction was cooled to 0 and H$_2$O (8.4 ml), 15% NaOH (8.4 ml) and H$_2$O (24 ml) were added sequentially; The mixture was stirred for 2 h, the solids filtered through Celite, and washed extensively with THF, the solution was concentrated in vacuo to yield 1-(4-(aminomethyl-3-methoxy)phenyl)-3-tert-butyl-1H-pyrazol-5-amine (6.8 g) as an oil.

A 40 mL vial was equipped with a stir bar, a septum, and a source of Ar. The vial was charged with the crude material from the previous reaction (2 g, 8.2 mmol, 244.17 g/mol) and CHCl$_3$ (15 mL) were cooled to 0 under Ar and di-tert-butyl-carbonate (1.9 g, 9.0 mmol) dissolved in CHCl$_3$ (51 mL) was added drop wise over a 2 min period. The mixture was treated with 1N KOH (2 mL), added over a 2 h period. The resulting emulsion was broken with the addition of saturated NaCl solution, the layers were separated and the aqueous phase extracted with CH$_2$Cl$_2$ (2×1.5 ml). The combined organic phases were dried over Na$_2$SO$_4$, filtered, concentrated in vacuo to yield tert-butyl [4-(3-tert-butyl-5-amino-1H-pyrazol-1-yl)-2-methoxybenzylcarbamate (2.23 g, 79%) as a light yellow solid. $^1$H NMR (CDCl$_3$): δ 7.4 (m, 5H), 5.6 (s, 1H), 4.4 (d, 2H), 1.5 (s, 9H), 1.3 (s, 9H).

Example 43

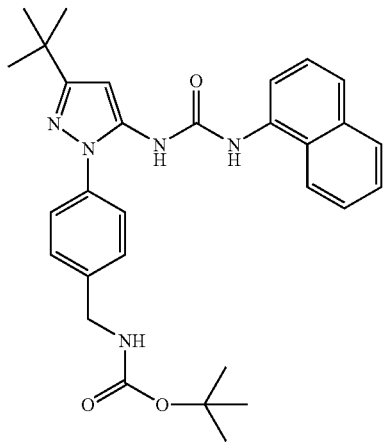

A 40 mL vial was equipped with a septum, a stir bar and a source of Ar, and charged with Example V (2 g, 5.81 mmol), flushed with Ar and dissolved in CHCl$_3$ (20 mL). The solution was treated with 2-naphthylisocyanate (984 mg, 5.81 mmol) in CHCl$_3$ (5 mL) and added over 1 min The reaction was stirred for 8 h, and additional 1-naphthylisocyanate (81 mg) was added and the reaction stirred overnight. The solid was filtered and washed with CH$_2$Cl$_2$ to yield tert-butyl 4-[3-tert-butyl-5-(3-naphthalen-1-yl)ureido)-1H-pyrazol-1-yl]benzylcarbamate (1.2 g). HPLC purity: 94.4%; $^1$H NMR (DMSO-d$_6$): δ 9.1 (s, 1H), 8.8 (s, 1H), 8.0 (m, 3H), 7.6 (m, 9H), 6.4 (s, 1H), 4.2 (d, 2H), 1.4 (s, 9H), 1.3 (s, 9H).

Example 44

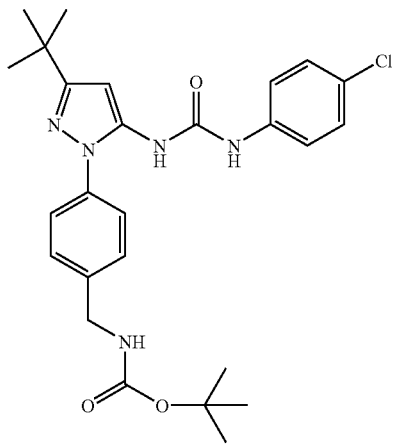

The title compound was synthesized in a manner analogous to Example 43 utilizing Example V (2.0 g, 5.81 mmol) and p-chlorophenylisocyanate (892 mg) to yield tert-butyl 4-[3-tert-butyl-5-(3-(4-chloropnehyl)ureido)-1H-pyrazol-1-yl]benzylcarbamate (1.5 g). HPLC purity: 97%; $^1$H NMR (DMSO-d$_6$): δ 9.2 (s, 1H), 8.4 (s, 1H), 7.4 (m, 8H), 6.4 (s, 1H), 4.2 (d, 2H), 1.4 (s, 9H), 1.3 (s, 9H).

Example 45

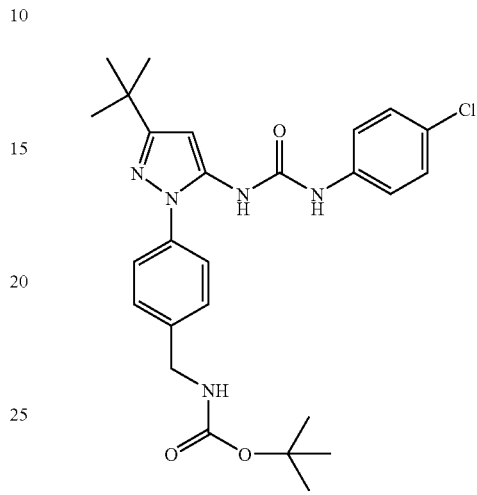

A 10 mL flask equipped with a stir bar was flushed with Ar and charged with Example 43 (770 mg, 1.5 mmol) and CH$_2$Cl$_2$ (1 ml) and 1:1 CH$_2$Cl$_2$: TFA (2.5 mL). After 1.5 h, reaction mixture was concentrated in vacuo, the residue was dissolved in EtOAc (15 mL), washed with saturated NaHCO$_3$ (10 mL) and saturated NaCl (10 mL). The organic layers was dried, filtered and concentrated in vacuo to yield 1-{3-tert-butyl-1-[4-(aminomethyl)phenyl]-1H-pyrazol-5-yl}-3-(naphthalen-1-yl)urea (710 mg). $^1$H NMR (DMSO-d$_6$): δ 7.4 (m, 1H), 6.4 (s, 1H), 3.7 (s, 2H), 1.3 (s, 9H).

Example 46

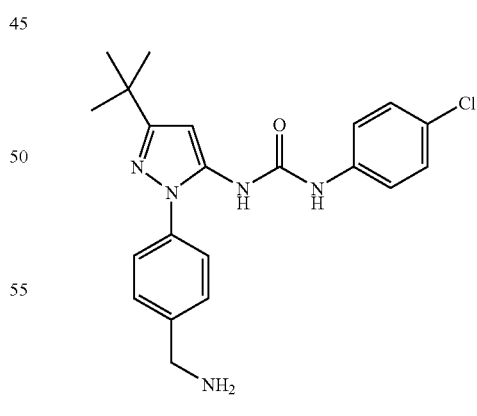

The title compound was synthesized in a manner analogous to Example 45 utilizing Example 44 (1.5 g, 1.5 mmol) to yield 1-{3-tert-butyl-1-[4-(aminomethyl)phenyl]-1H-pyrazol-5-yl}-3-(4-chlorophenyl)urea (1.0 g). HPLC purity: 93.6%; mp: 100-102; $^1$H NMR (CDCl$_3$): δ 8.6 (s, 1H), 7.3 (m, 8H), 6.3 (s, 1H), 3.7 (brs, 2H), 1.3 (s, 9H).

Example 47

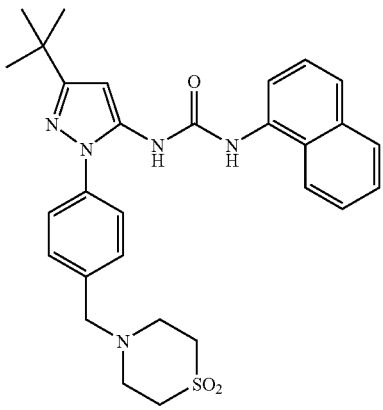

A 10 ml vial was charged with Example 45 (260 mg, 63 mmol) and absolute EtOH (3 mL) under Ar. Divinylsulfone (63 uL, 74 mg, 0.63 mmol) was added drop wise over 3 min and the reaction was stirred at RT for 1.5 h. and concentrated in vacuo to yield a yellow solid, which was purified via preparative TLC, developed in 5% MeOHCH$_2$Cl$_2$. The predominant band was cut and eluted off the silica with 1:1 EtOAc:MeOH, filtered and concentrated in vacuo to yield 1-{3-tert-butyl-1-[4-(1,1-dioxothiomorpholin-4-yl)methylphenyl]-1H-pyrazol-5-yl}-3-(naphthalen-1-yl)urea (150 mg). HPLC purity: 96%; $^1$H NMR (DMSO-d$_6$): δ 9.1 (s, 1H), 9.0 (s, 1H), 7.9 (m, 3H), 7.5 (m, 8H), 6.4 (s, 1H), 3.1 (brs, 4H), 2.9 (brs, 4H), 1.3 (s, 9H).

Example 48

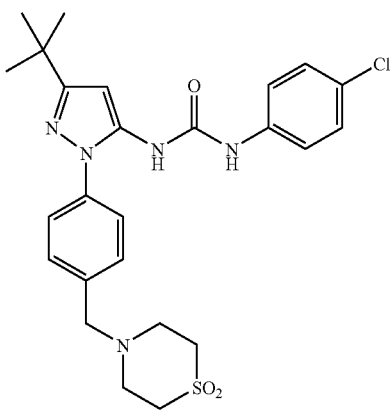

The title compound was synthesized in a manner analogous to Example 47 utilizing Example 46 (260 mg, 0.66 mmol) to yield 1-{3-tert-butyl-1-[4-(1,1-dioxothiomorpholin-4-yl)methylphenyl]-1H-pyrazol-5-yl}-3-(4-chlorophenyl)urea (180 mg). HPLC purity: 93%; mp: 136-138; $^1$H NMR (DMSO-d$_6$): δ 9.2 (s, 1H), 8.5 (s, 1H), 7.4 (m, 9H), 6.4 (s, 1H), 3.1 (brs, 4H), 3.0 (brs, 4H), 1.3 (s, 9H).

Example 49

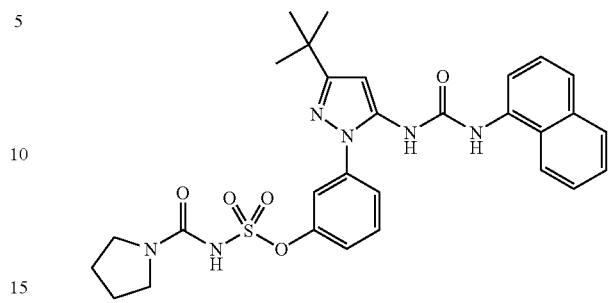

To a stirring solution of chlorosulfonyl isocyanate (0.35 g, 5 mmol) in CH$_2$Cl$_2$ (20 mL) at 0° C. was added pyrrolidine (0.18 g, 5 mmol) at such a rate that the reaction temperature did not rise above 5° C. After stirring for 2 h, a solution of Example 41 (1.10 g, 6.5 mmol) and triethylmine (0.46 g, 9 mmol) in CH$_2$Cl$_2$ (20 mL) was added. When the addition was complete, the mixture was allowed to warm to RT and stirred overnight. The reaction mixture was poured into 10% HCl (10 mL) saturated with NaCl, the organic layer was separated and the aqueous layer extracted with ether (20 mL). The combined organic layers were dried (Na$_2$SO$_4$) and concentrated in vacuo, purified by preparative HPLC to yield (pyrrolidine-1-carbonyl)sulfamic acid 3-[3-tert-butyl-5-(3-naphthalen-1-yl-ureido)-pyrazol-1-yl]phenyl ester (40 mg). $^1$H NMR (CDCl$_3$): δ 9.12 (brs, 1H), 8.61 (brs, 1H), 7.85-7.80 (m, 3H), 7.65 (d, J=8.0 Hz, 2H), 7.53-7.51 (m, 1H), 7.45-7.25 (m, 5H), 6.89 (s, 4H), 3.36-3.34 (brs, 1H), 3.14-3.13 (brs, 2H), 1.69 (brs, 2H), 1.62 (brs, 2H), 1.39 (s, 9H); MS (ESI) m/z: 577 (M+H$^+$).

Example 50

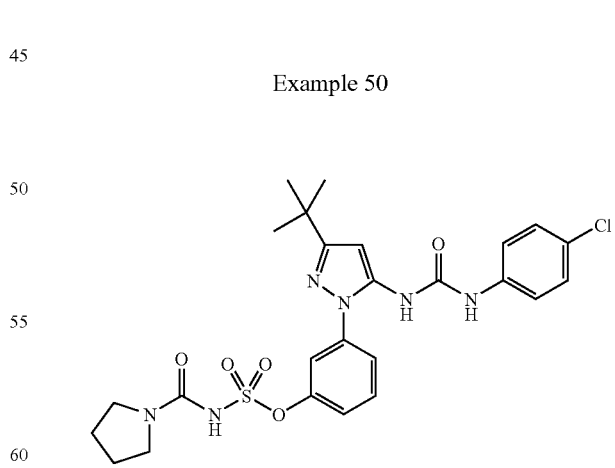

The title compound was synthesized in a manner analogous to Example 49 utilizing Example 42 to yield (pyrrolidine-1-carbonyl)sulfamic acid 3-[3-tert-butyl-5-(4-chlorophenyl-1-yl-ureido)pyrazol-1-yl]phenyl ester. MS (ESI) m/z: 561 (M+H$^+$).

Example W

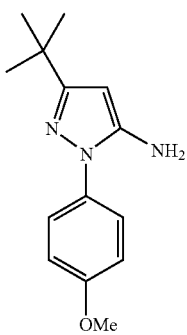

Solid 4-methoxyphenylhydrazine hydrochloride (25.3 g) was suspended in toluene (100 mL) and treated with triethylamine (20.2 g). The mixture was stirred at RT for 30 min and treated with pivaloylacetonitrile (18 g). The reaction was heated to reflux and stirred overnight. The hot mixture was filtered, the solids washed with hexane and dried in vacuo to afford 3-tert-butyl-1-(4-methoxyphenyl)-1H-pyrazol-5-amine (25 g, 70%). $^1$H NMR (DMSO-d$_6$): δ 7.5 (d, 2H), 7.0 (d, 1H), 6.4 (s, 1H), 6.1 (s, 2H), 3.9 (s, 3H), 1.3 (s, 9H).

Example 51

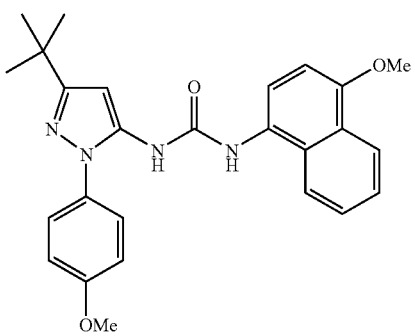

To a solution of 1-isocyanato-4-methoxy-naphthalene (996 mg) in anhydrous CH$_2$Cl$_2$ (20 mL) of was added Example W (1.23 g). The reaction solution was stirred for 3 h, the resulting white precipitate filtered, treated with 10% HCl and recrystallized from MeOH, and dried in vacuo to yield 1-[3-tert-butyl-1-(4-methoxyphenyl)-H-pyrazol-5-yl]-3-(1-methoxynaphthalen-4-yl-urea as white crystals (900 mg, 40%). HPLC purity: 96%; mp: 143-144; $^1$H NMR (DMSO-d$_6$): δ 8.8 (s, 1H), 8.5 (s, 1H), 8.2 (d, 1H), 8.0 (d, 1H), 7.6 (m, 5H), 7.1 (d, 2H), 7.0 (d, 1H), 6.3 (s, 1H), 4.0 (s, 3H), 3.9 (s, 3H); 1.3 (s, 9H).

Example 52

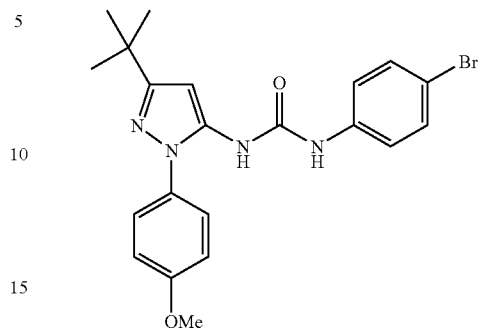

The title compound was synthesized in a manner analogous to Example 51 utilizing Example W and p-bromophenylisocyanate (990 mg) to yield 1-{3-tert-butyl-1-(4-methoxyphenyl)-1H-pyrazol-5-yl}-3-(4-bromophenyl)urea as off-white crystals (1.5 g, 68%). HPLC purity: 98%; mp: 200-201; $^1$H NMR (DMSO-d$_6$): δ 9.3 (s, 1H), 8.3 (s, 1H), 7.4 (m, 6H), 7.0 (d, 2H), 6.3 (s, 1H), 3.8 (s, 3H), 1.3 (s, 9H).

Example 53

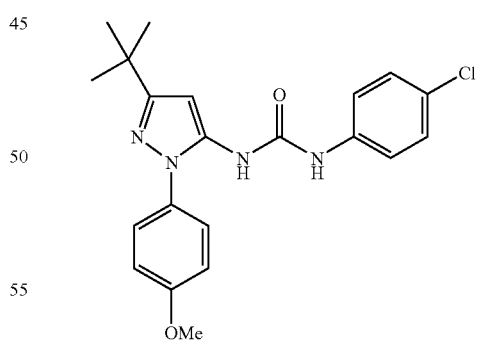

The title compound was synthesized in a manner analogous to Example 51 utilizing Example W and p-chlorophenylisocyanate (768 mg) into yield 1-{3-tert-butyl-1-(4-methoxyphenyl)-1H-pyrazol-5-yl}-3-(4-chlorophenyl)urea as white crystals (1.3 g, 65%). HPLC purity: 98%; mp: 209-210; $^1$H NMR (DMSO-d$_6$): δ 9.1 (s, 1H), 8.3 (s, 1H), 7.4 (m, 4H), 7.3 (d, 2H), 7.1 (d, 2H), 6.3 (s, 1H), 3.8 (s, 3H), 1.3 (s, 9H).

Example 54

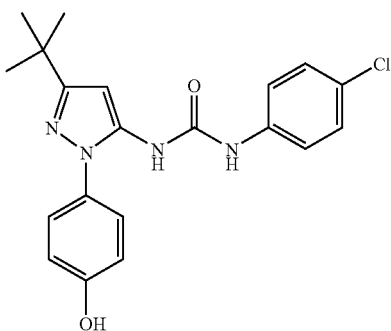

The title compound was synthesized in a manner analogous to Example 41 utilizing Example 53 (500 mg) to yield 1-{3-tert-butyl-1-(4-hydroxyphenyl)-1H-pyrazol-5-yl}-3-(4-chlorophenyl)urea as white crystals (300 mg, 62%). HPLC purity: 94%; mp: 144-145; $^1$H NMR (DMSO-d$_6$): δ 9.7 (s, 1H), 9.1 (s, 1H), 8.3 (s, 1H), 7.4 (d, 2H), 7.3 (m, 4H); 6.9 (d, 2H), 6.3 (s, 1H), 1.3 (s, 9H)

Example 55

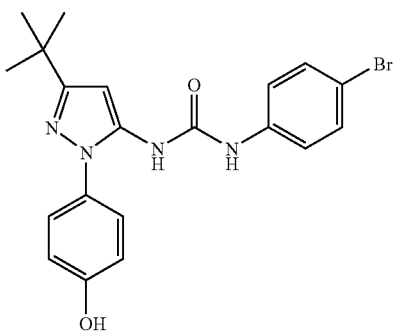

The title compound was synthesized in a manner analogous to Example 41 utilizing Example 52 (550 mg) to yield 1-{3-tert-butyl-1-(4-hydroxyphenyl)-1H-pyrazol-5-yl}-3-(4-bromophenyl)urea as a white crystalline solid (400 mg, 70%). HPLC purity: 93%; mp: 198 200; $^1$H NMR (DMSO-d$_6$): δ 9.7 (s, 1H), 9.2 (s, 1H), 8.3 (s, 1H), 7.4 (d, 4H), 7.2 (m, 2H), 6.9 (d, 2H), 6.3 (s, 1H), 1.3 (s, 9H).

Example X

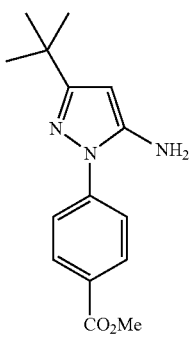

Methyl 4-(3-tert-butyl-5-amino-1H-pyrazol-1-yl)benzoate (3.67 mmol) was prepared from methyl 4-hydrazinobenzoate and pivaloylacetonitrile by the procedure of Regan, et al., *J. Med. Chem.*, 45, 2994 (2002).

Example 56

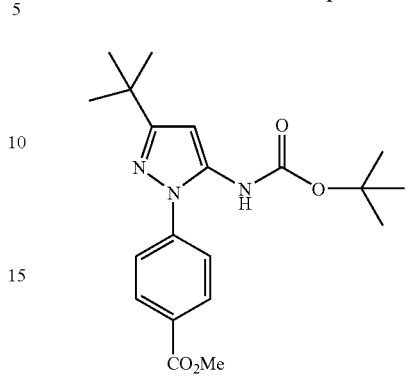

A 500 mL round bottom flask was equipped with a magnetic stir bar and an ice bath. The flask was charged with Example X (1 g) and this was dissolved in CH$_2$Cl$_2$ (100 mL). Saturated sodium bicarbonate (100 mL) was added and the mixture rapidly stirred, cooled in an ice bath and treated with diphosgene (1.45 g) and the heterogeneous mixture stirred for 1 h. The layers were separated and the CH$_2$Cl$_2$ layer treated with tert-butanol (1.07 g) and the solution stirred overnight at RT. The solution was washed with H$_2$O (2×150 mL), dried (Na$_2$SO$_4$), filtered, concentrated in vacuo, and purified by flash chromatography using 1:2 ethyl acetate:hexane as the eluent to yield tert-buthyl 1-(4-(methoxycarbonyl)phenyl)-3-tert-butyl-1H-pyrazol-5-ylcarbamate (100 mg) as an off-white solid. $^1$H NMR (DMSO-d$_6$): δ 9.2 (s, 1H), 8.1 (d, 2H), 7.7 (d, 2H), 6.3 (s, 1H), 3.3 (s, 3H), 1.3 (s, 18H).

Example 57

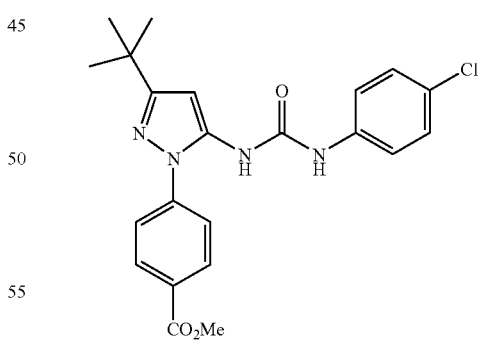

The title compound was synthesized in a manner analogous to Example 41 utilizing Example X (1.37 g) and p-chlorophenylisocyanate (768 mg) to yield methyl 4-{3-tert-butyl-5-[3-(4-chlorophenyl)ureido]-1H-pyrazol-1-yl}benzoate as white crystals (1.4 g 66%). HPLC purity: 98%; mp: 160-161; $^1$H NMR (DMSO-d$_6$): δ 9.2 (s, 1H), 8.6 (s, 1H), 8.1 (d, 2H), 7.8 (d, 2H), 7.5 (d, 2H), 7.3 (d, 2H), 6.4 (s, 1H), 3.9 (s, 3H), 1.3 (s, 9H).

Example 58

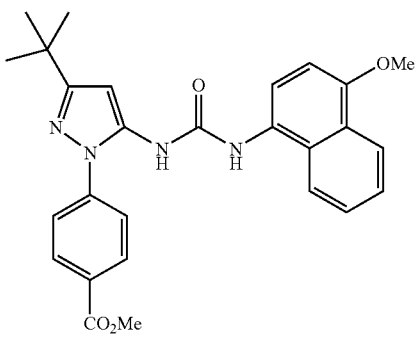

The title compound was synthesized in a manner analogous to Example 41 utilizing Example X (1.27 g) and 1-isocyanato-4-methoxy-naphthalene (996 mg) to yield methyl 4-{3-tert-butyl-5-[3-(1-methoxynaphthalen-4-yl)ureido]-1H-pyrazol-1-yl}benzoate as white crystals (845 mg, 36%). HPLC purity: 98%; mp: 278 280; $^1$H NMR (DMSO-$d_6$): δ 8.76 (s, 1H), 8.73 (s, 1H), 8.1 (m, 3H), 7.9 (d, 1H), 7.7 (d, 2H), 7.6 (m, 3H), 7.0 (d, 1H), 7.0 (d, 1H), 6.3 (s, 1H), 4.0 (s, 3H), 3.9 (s, 3H), 1.3 (s, 9H).

Example 59

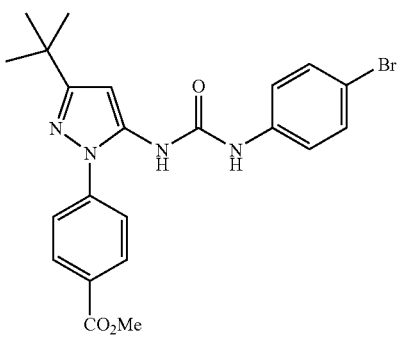

The title compound was synthesized in a manner analogous to Example 41 utilizing Example X (1.37 g) and p-bromophenylisocyanate (990 mg) to yield methyl 4-{3-tert-butyl-5-[3-(4-bromophenyl)ureido]-1H-pyrazol-1-yl}benzoate as white crystals (1.4 g, 59%). HPLC purity: 94%; mp: 270 272; $^1$H NMR (DMSO-$d_6$): δ 9.2 (s, 1H), 8.6 (s, 1H), 8.1 (d, 2H), 7.7 (d, 2H), 7.4 (d, 4H), 6.4 (s, 1H), 3.9 (s, 3H), 1.3 (s, 9H).

Example 60

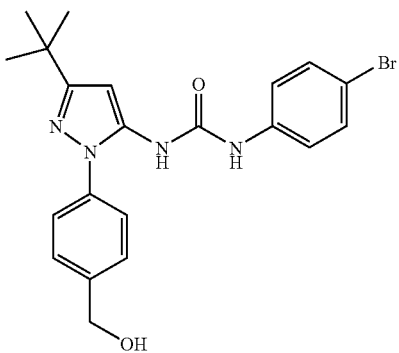

To a solution of Example 59 (700 mg) in 30 mL of toluene at −78° C., was added dropwise a solution of diisobutylaluminum hydride in toluene (1M in toluene, 7.5 mL) over 10 min. The reaction mixture was stirred for 30 min at −78° C., and then 30 min at 0° C. The reaction mixture was concentrated in vacuo to dryness and treated with $H_2O$. The solid was filtered and treated with acetonitrile. The solution was evaporated to dryness and the residue was dissolved in ethyl acetate, and precipitated by hexanes to afford yellow solid which was dried under vacuum to give 1-[3-tert-butyl-1-(4-hydroxymethyl)phenyl)-1H-pyrazol-5-yl]urea (400 mg, 61%). HPLC purity: 95%; $^1$H NMR (DMSO-$d_6$): δ 9.2 (s, 1H), 8.4 (s, 1H), 7.5 (m, 8H), 6.4 (s, 1H), 5.3 (t, 1H), 4.6 (d, 2H), 1.3 (s, 9H).

Example 1

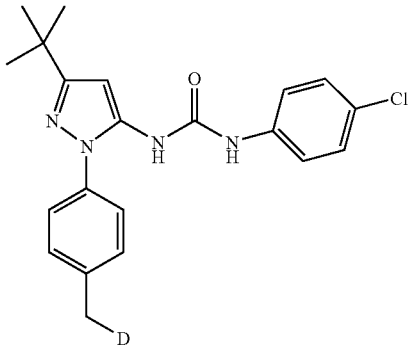

Example 2

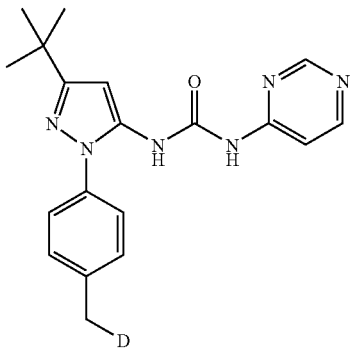

Example 3

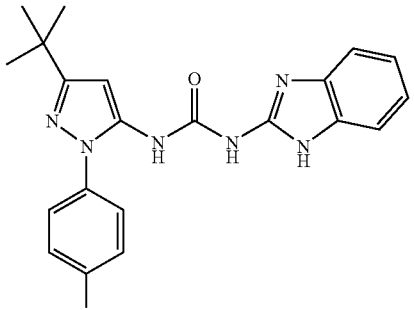

Example 4

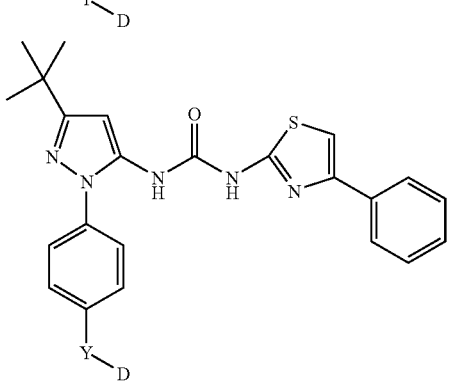

-continued
Example 5
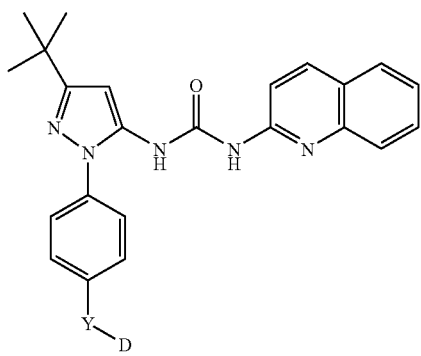
Example 6
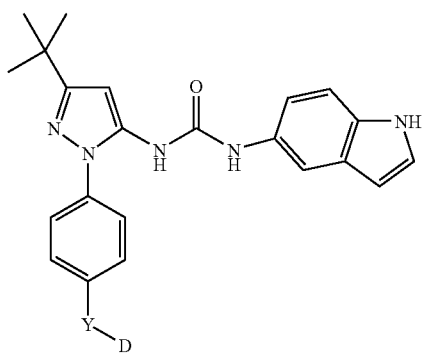
Wherein Y is O, S, NR6, —NR6SO2-, NR6CO—, alkylene, O—(CH2)n-, NR6-(CH2)n-, wherein one of the methylene units may be substituted with an oxo group, or Y is a direct bond; D is taken from the groups identified in Chart I:
Chart 1
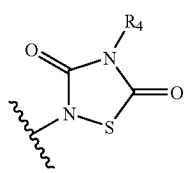
Q-1
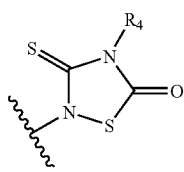
Q-2
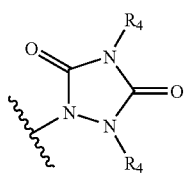
Q-3
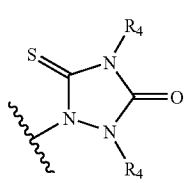
Q-4
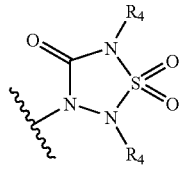
Q-4
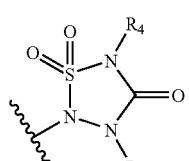
Q-6
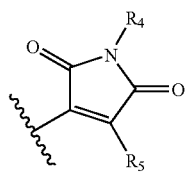
Q-7
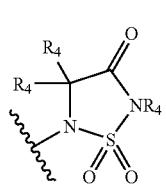
Q-8
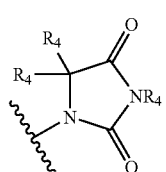
Q-9
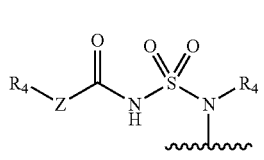
Q-10
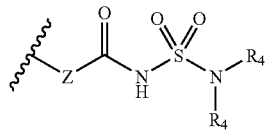
Q-11
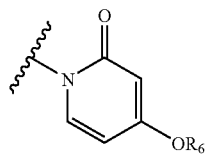
Q-12
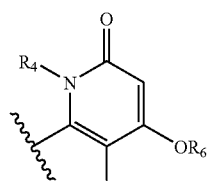
Q-13

-continued
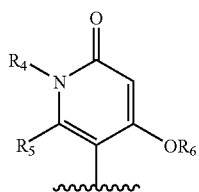
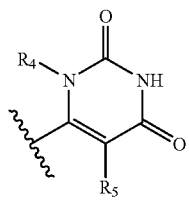
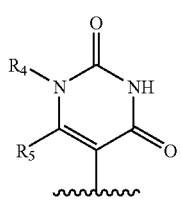
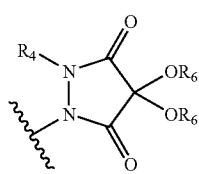
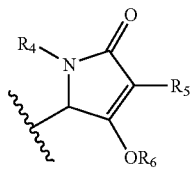
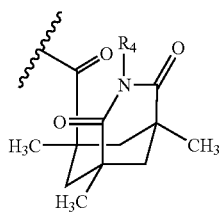
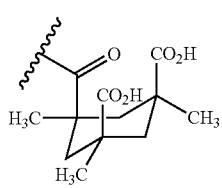
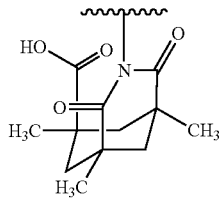
-continued
Q-14
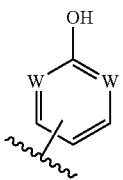
Q-15
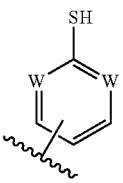
Q-16
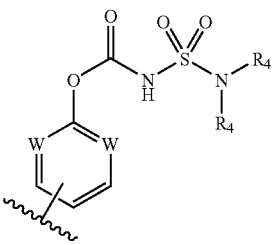
Q-17
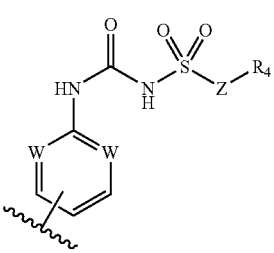
Q-18
Q-19
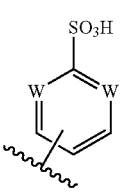
Q-20
Q-21
Q-22
Q-23
Q-24
Q-25
Q-26
Q-27
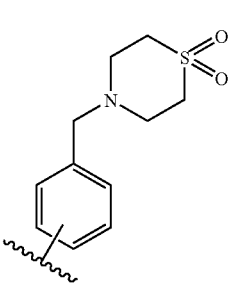
Q-28
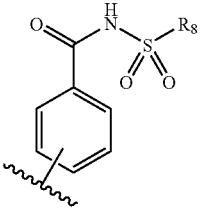

-continued
Q-29 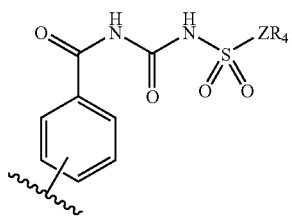
Q-30 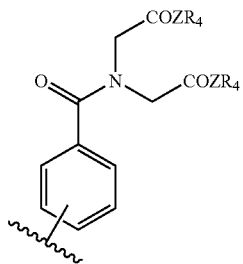
Q-31 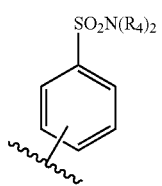
Q-32 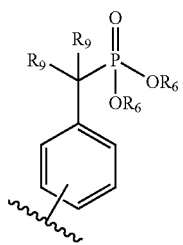
Q-33 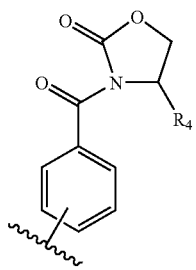
Q-34 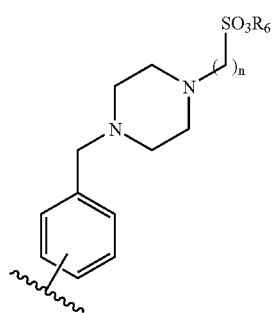
-continued
Q-35 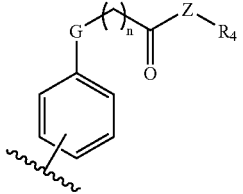
Example 7 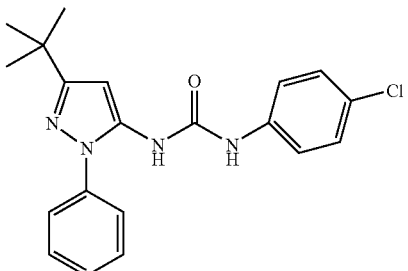
Example 8 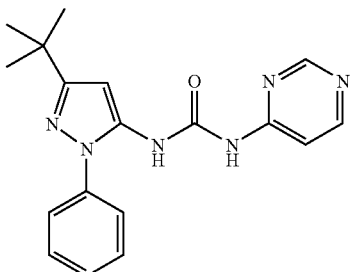
Example 9 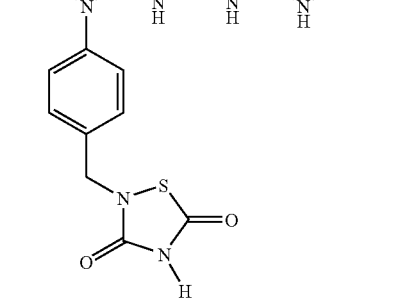

-continued
Example 10
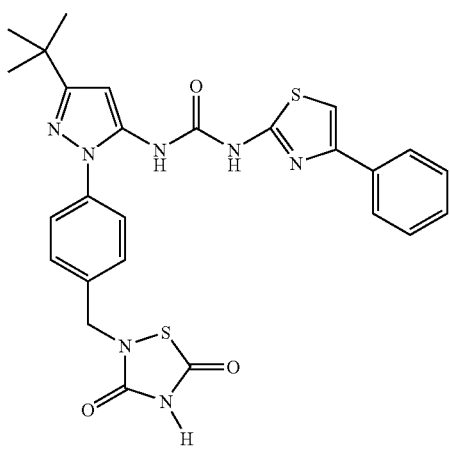
Example 11
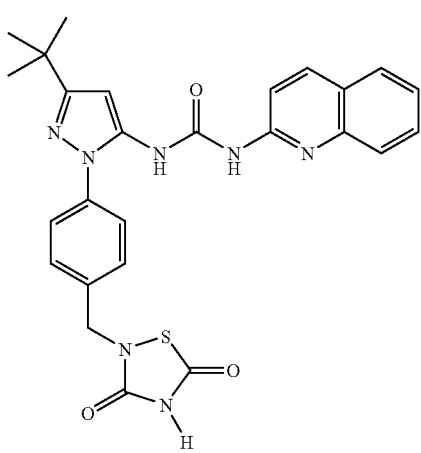
Example 12
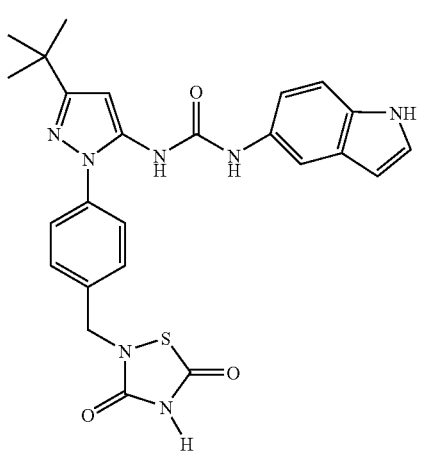
-continued
Example 13
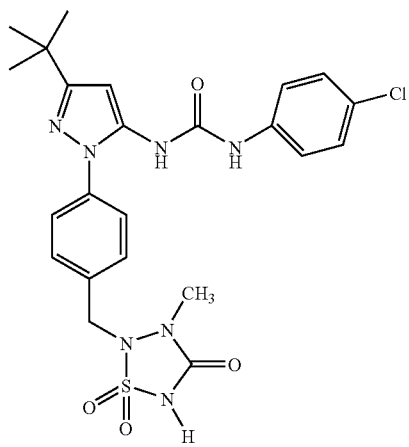
Example 14
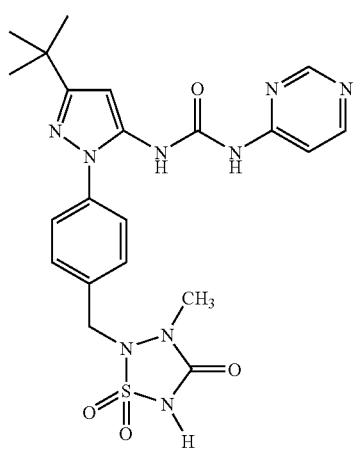
Example 15
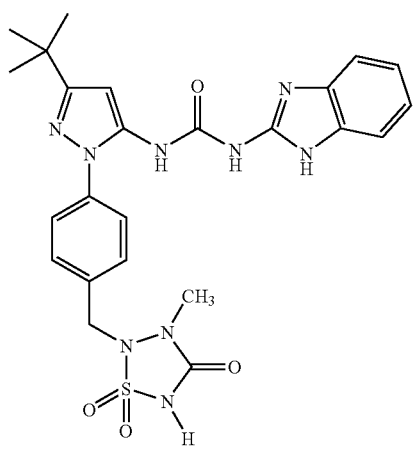

-continued
Example 16
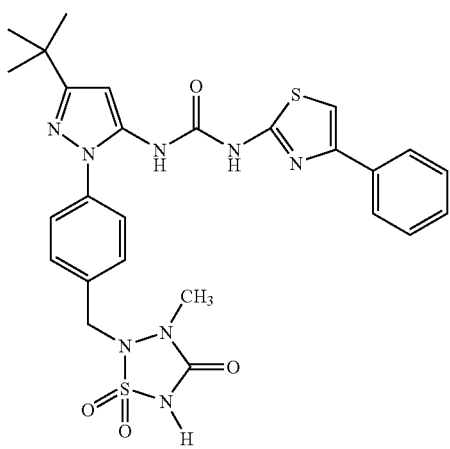
Example 17
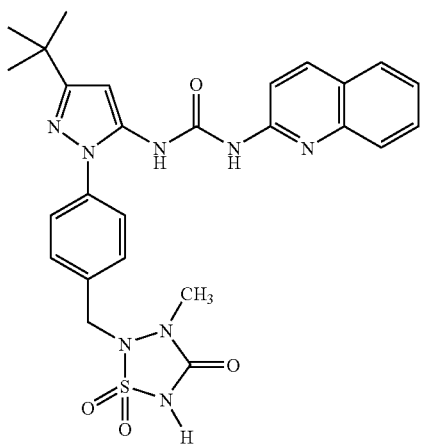
Example 18
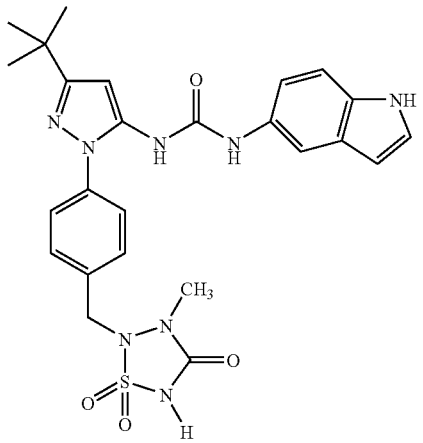
-continued
Example 19
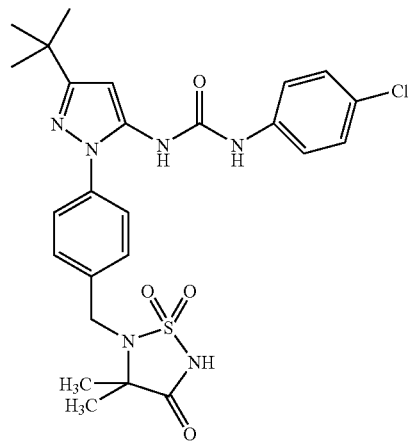
Example 20
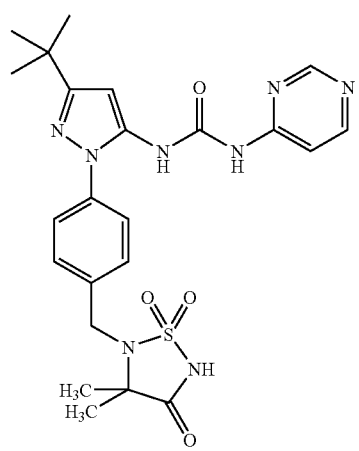
Example 21
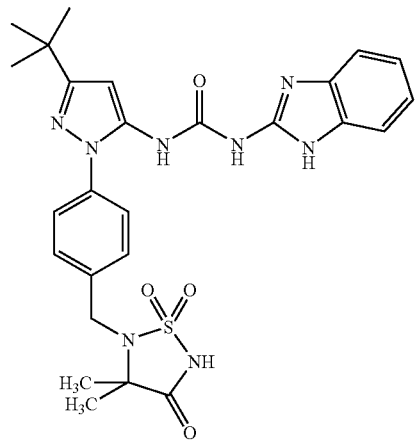

-continued
Example 22
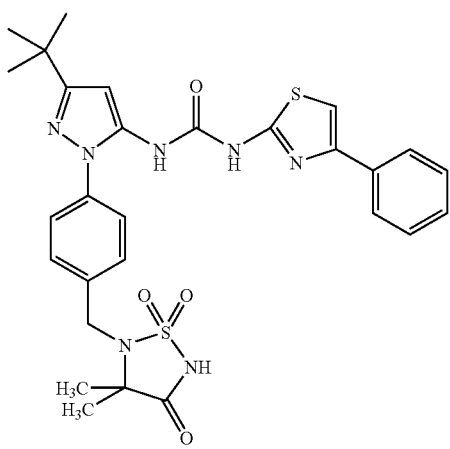
Example 23
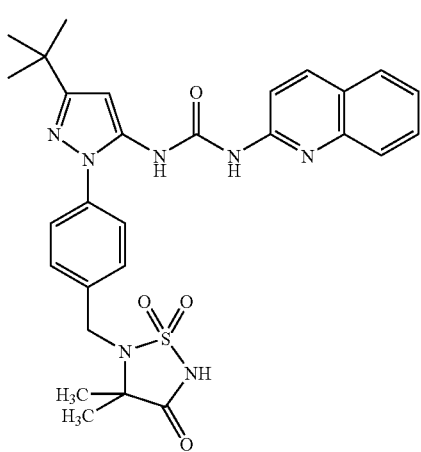
Example 24
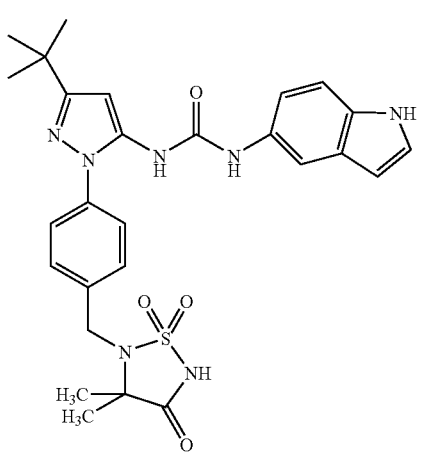
-continued
Example 25
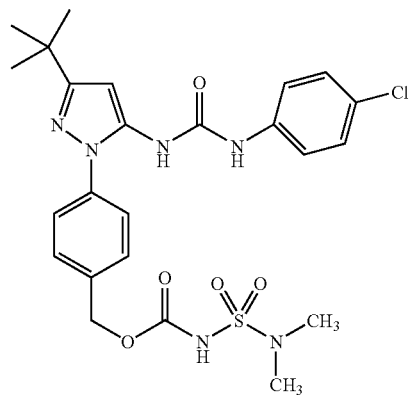
Example 26
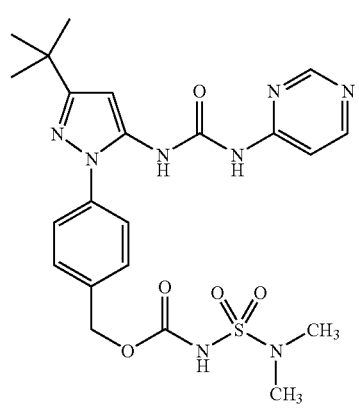
Example 27
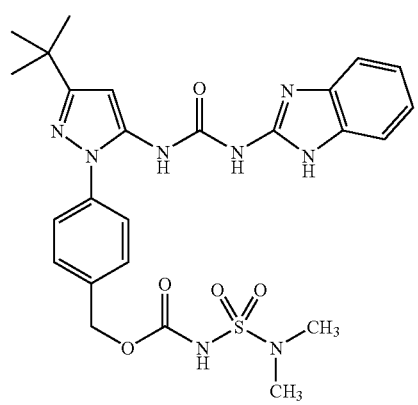
Example 28
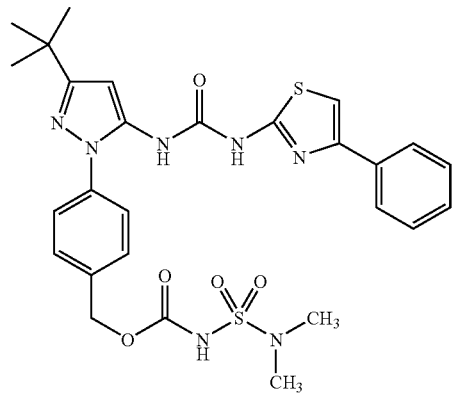

Example 29
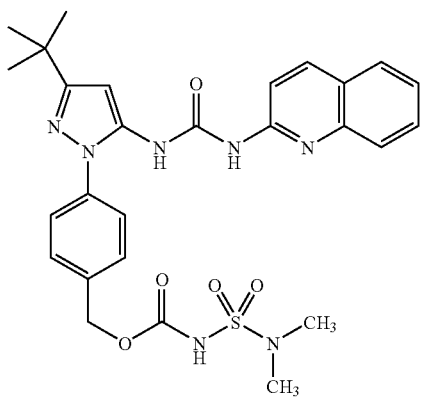
Example 30
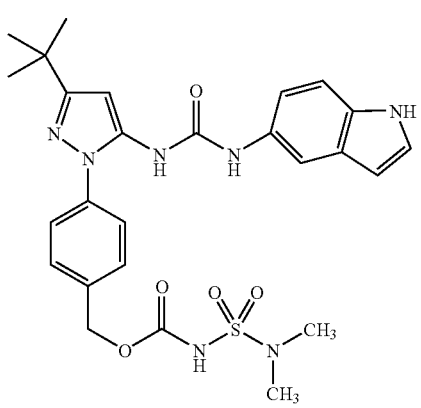
Example 31
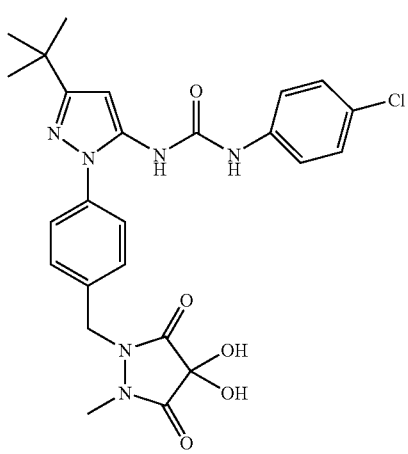
Example 32
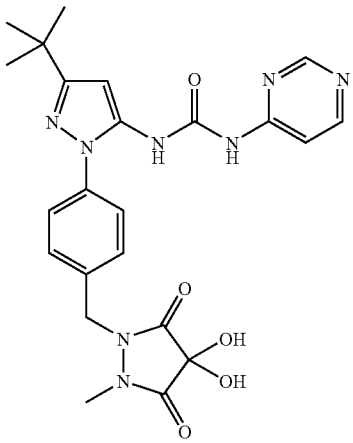
Example 33
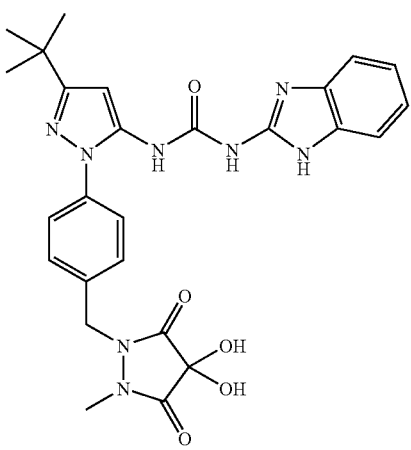
Example 34
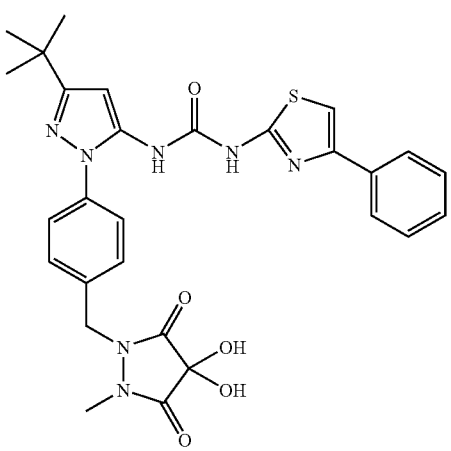

Example 35
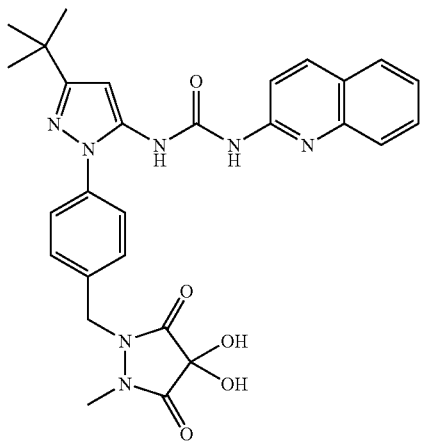
Example 36
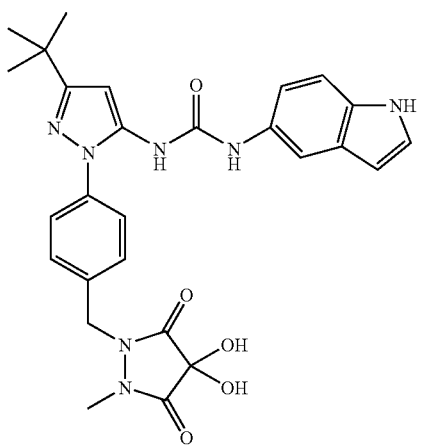
Example 37
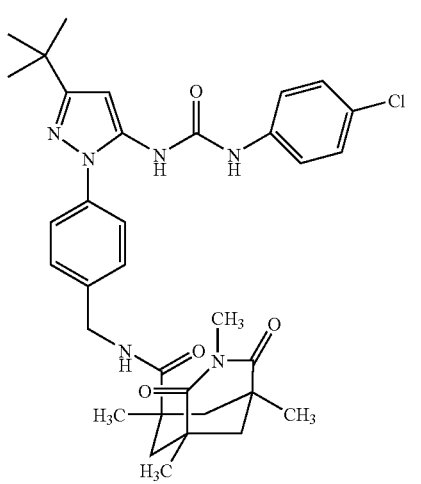
Example 38
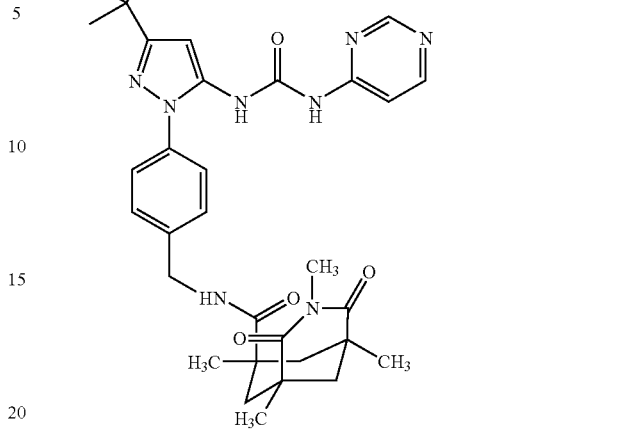
Example 39
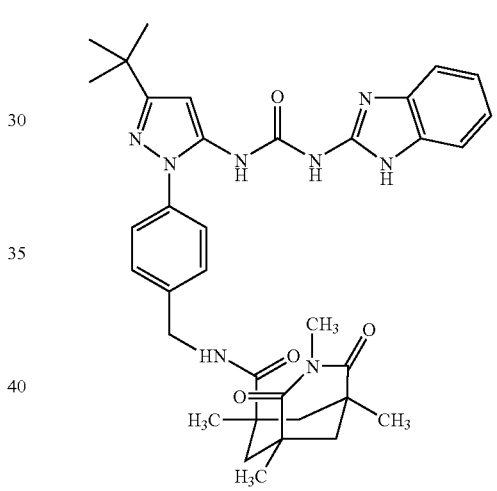
Example 40
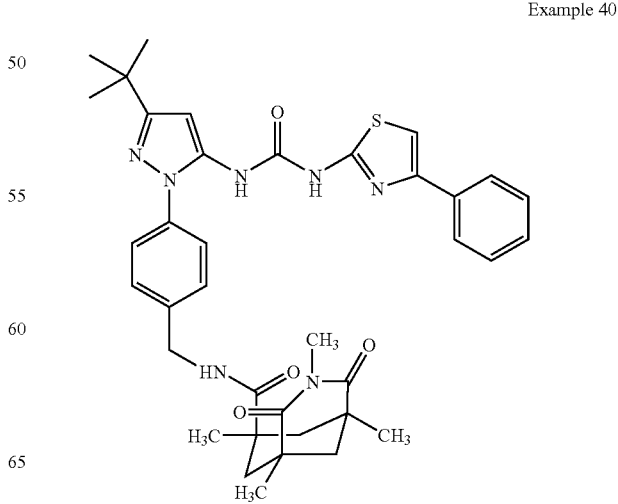

Example 41
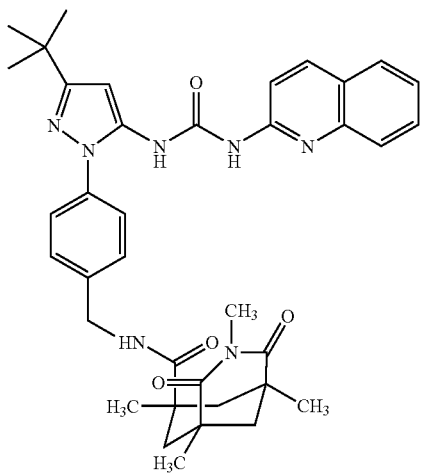
Example 42
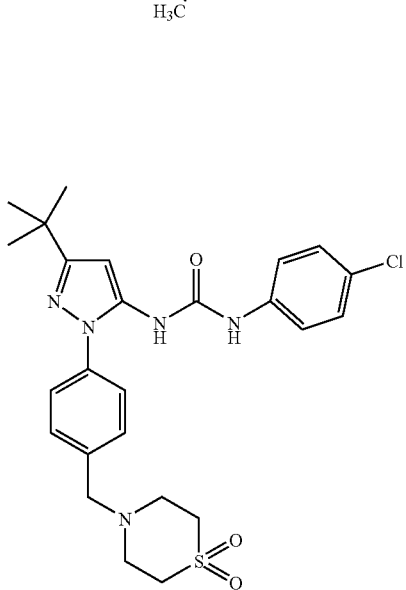
Example 43
Example 44
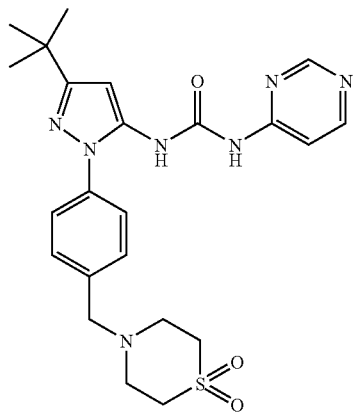
Example 45
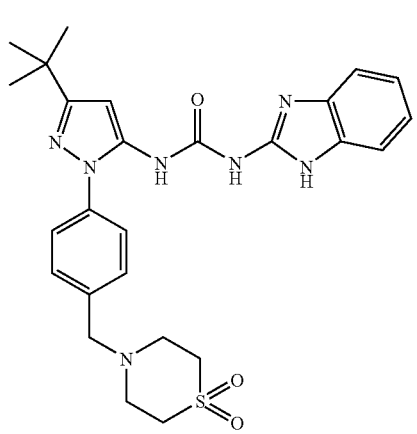
Example 46
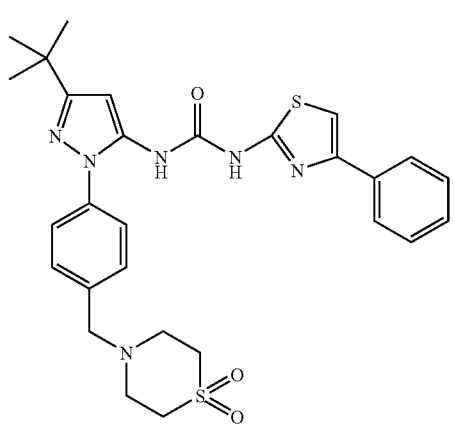

Example 47
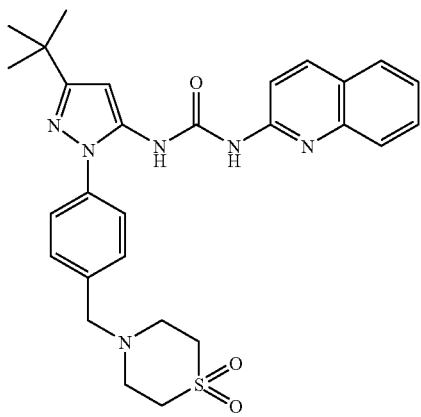
Example 48
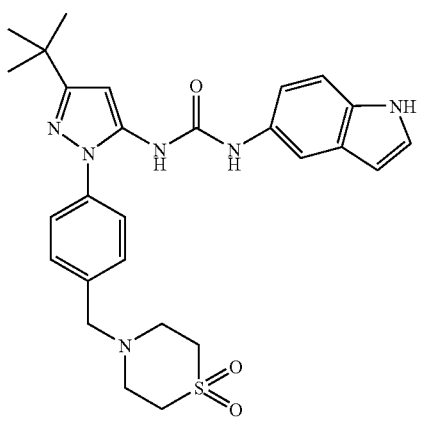
Example 49
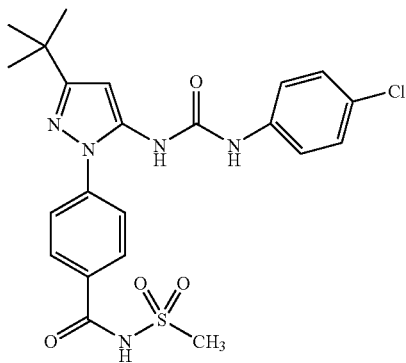
Example 50
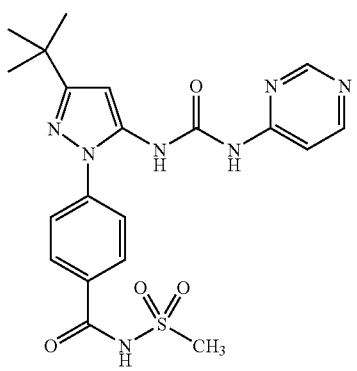
Example 51
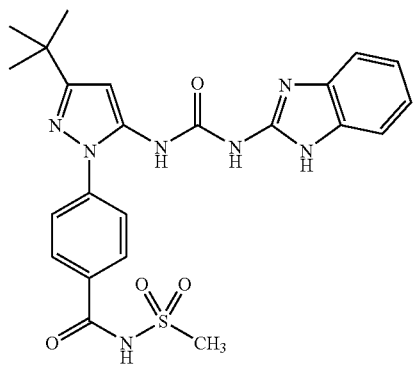
Example 52
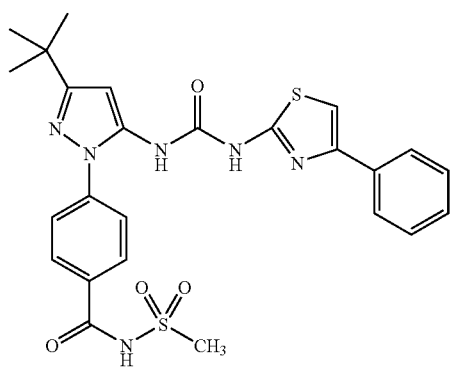
Example 53
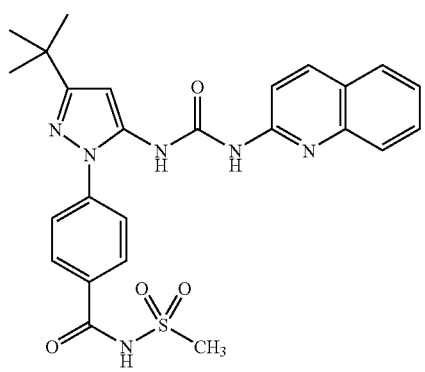
Example 54
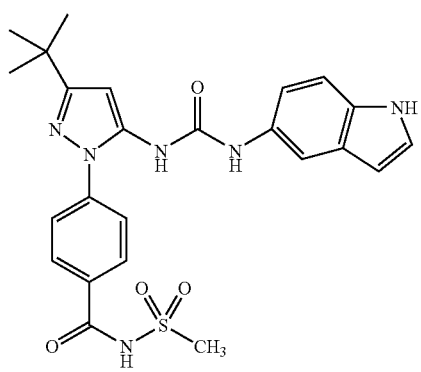

-continued
Example 55
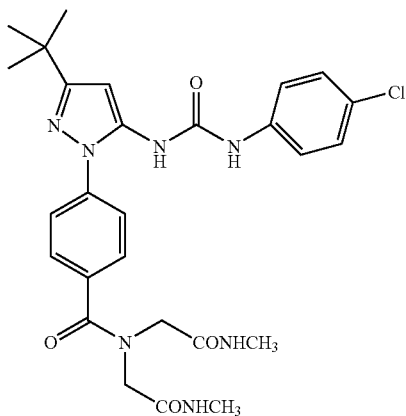
Example 56
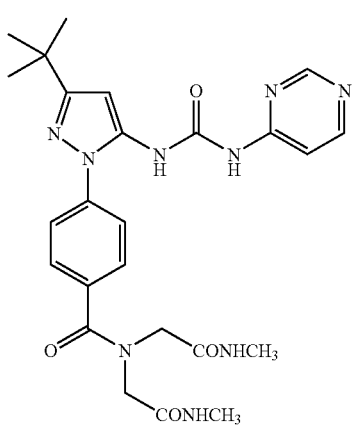
Example 57
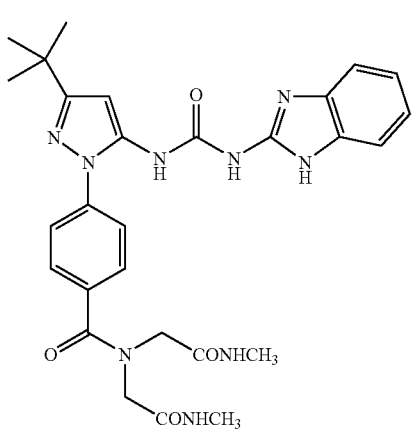
-continued
Example 58
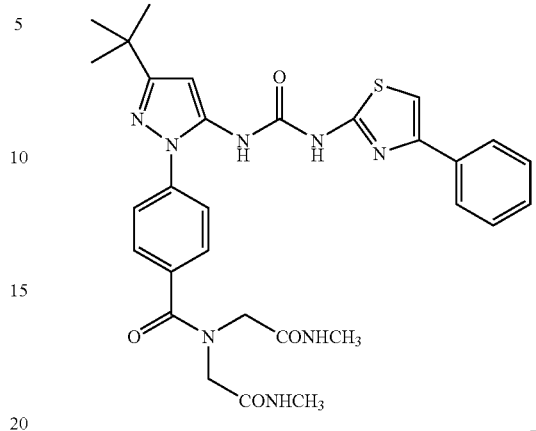
Example 59
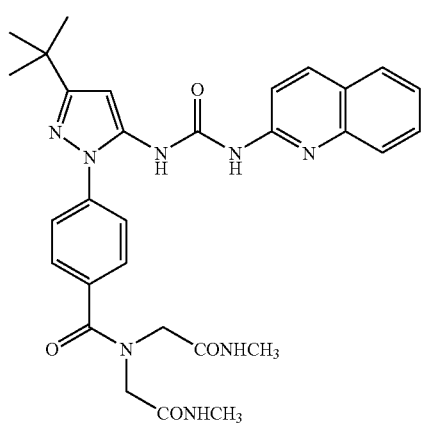
Example 60
Example 61
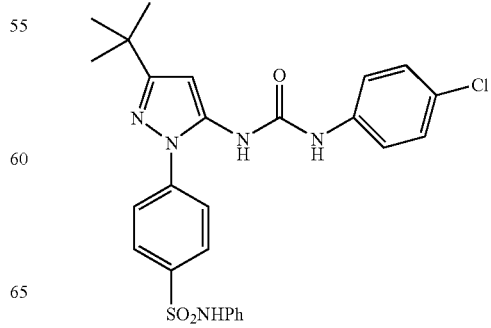

-continued
Example 62
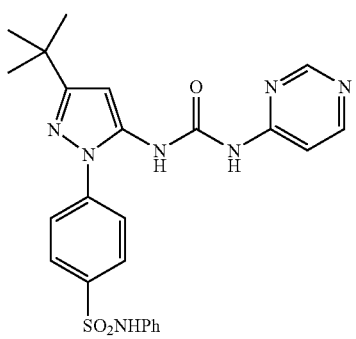
Example 63
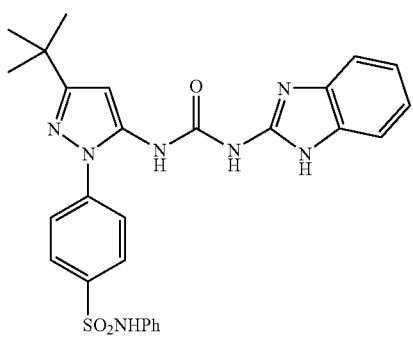
Example 64
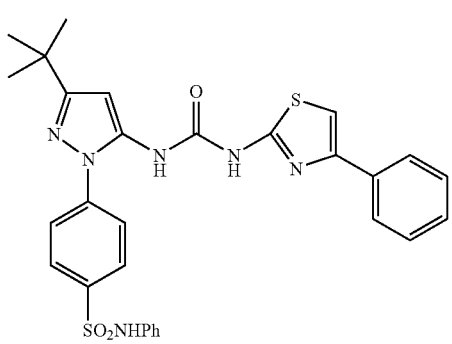
Example 65
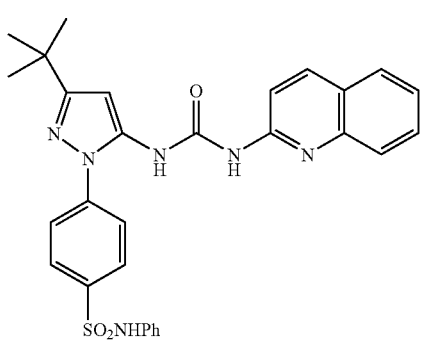
-continued
Example 66
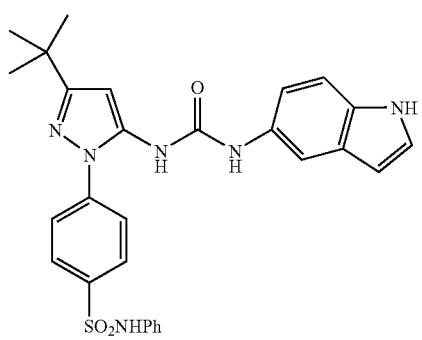
Example 67
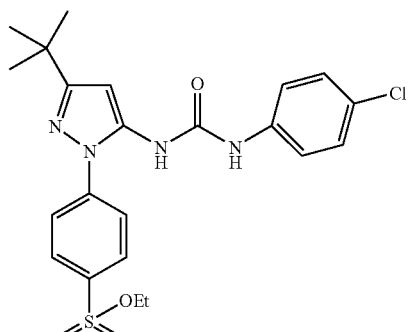
Example 68
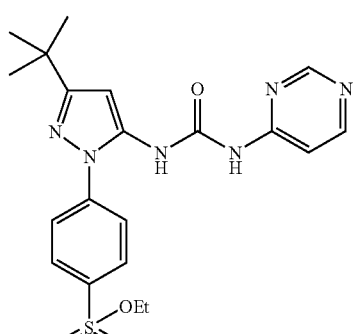
Example 69
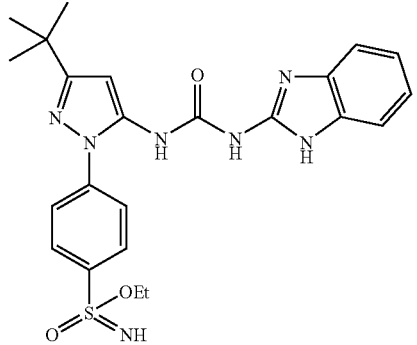

Example 70
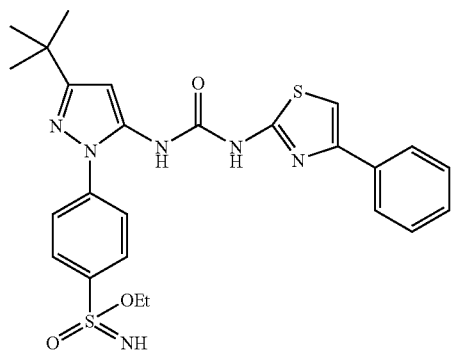
Example 74
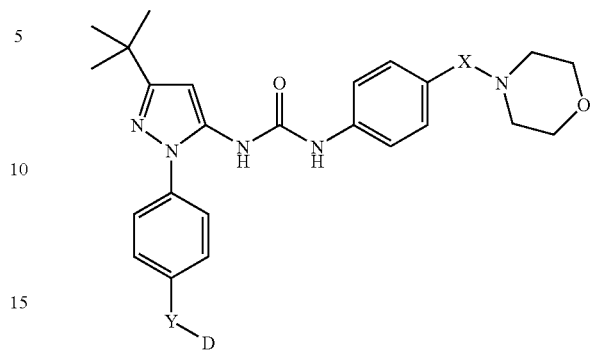
Example 71
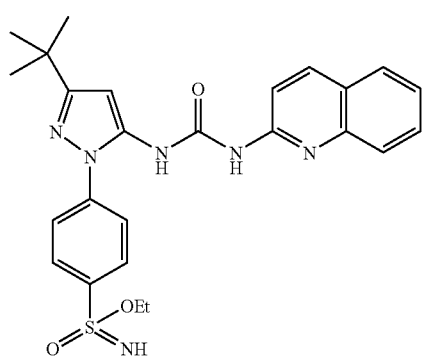
Example 75
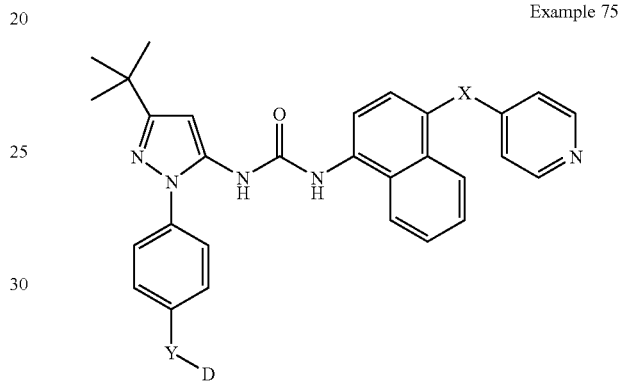
Example 72
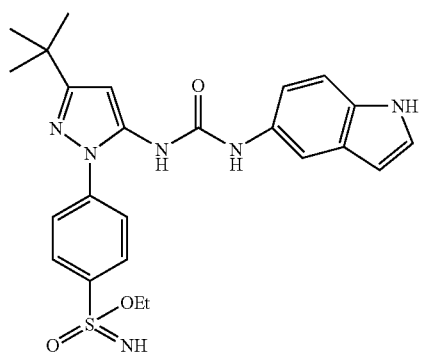
Example 76
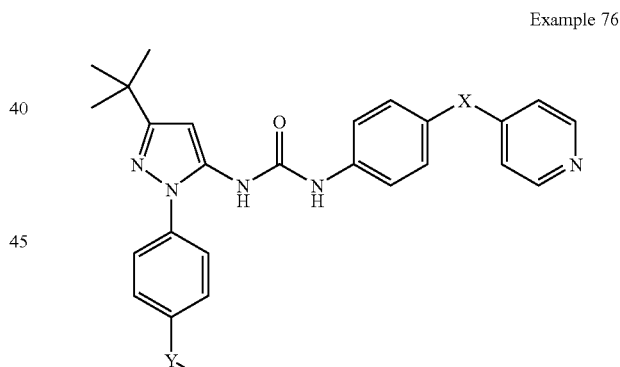
Example 73
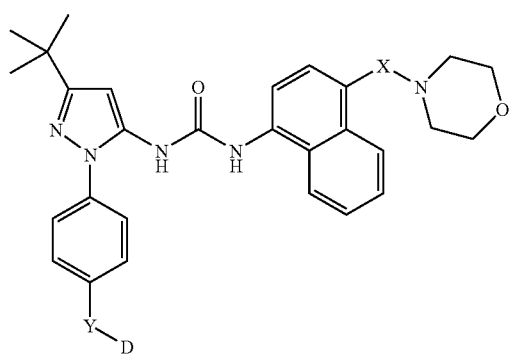
Example 77
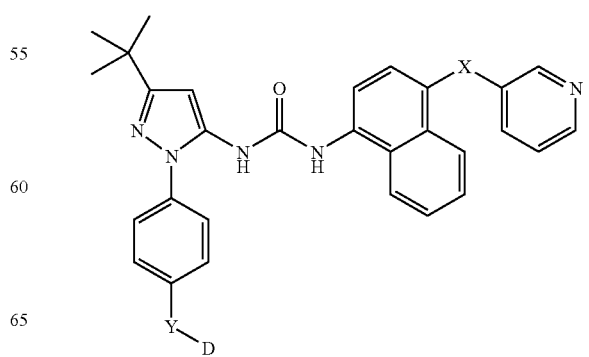

Example 78
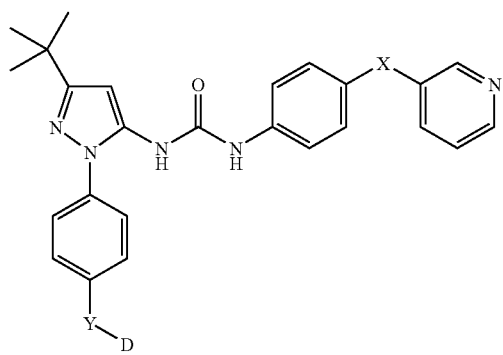
wherein X or Y is O, S, NR6, —NR6SO2-, NR6CO—, alkylene, O—(CH2)n-, NR6-(CH2)n-, wherein one of the methylene units may be substituted with an oxo group, or X or Y is a direct bond; D is taken from the groups identified in Chart I:
D-1
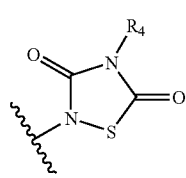
D-2
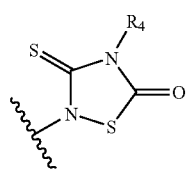
D-3
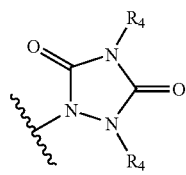
D-4
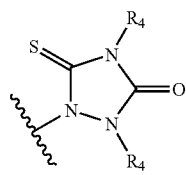
D-5
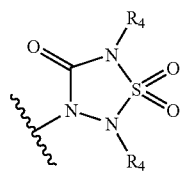
D-6
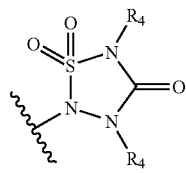
D-7
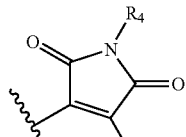
D-8
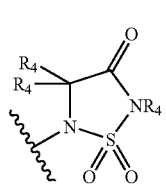
D-9
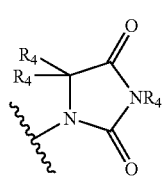
D-10
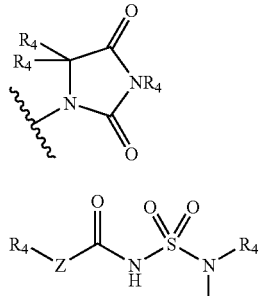
D-11
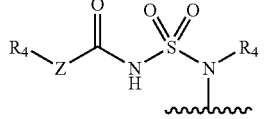
D-12
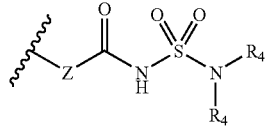
D-13
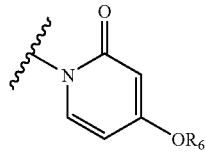
D-14
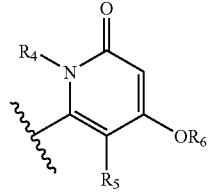
D-15
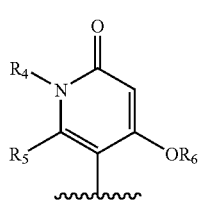

-continued
D-16 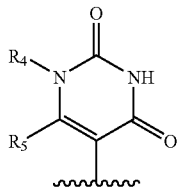
D-17 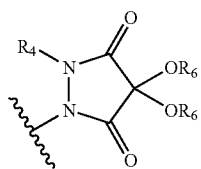
D-18 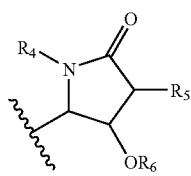
D-19 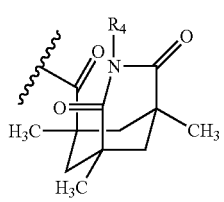
D-20 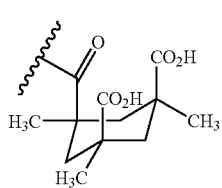
D-21 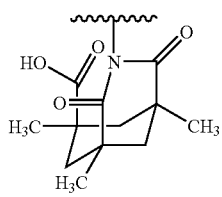
D-22 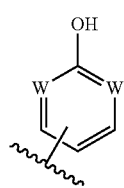
D-23 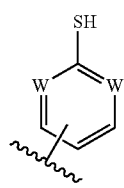
-continued
D-24 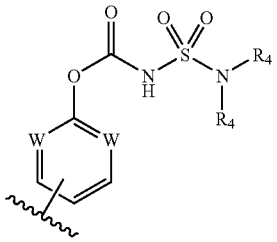
D-25
D-26
D-27
D-28
D-29 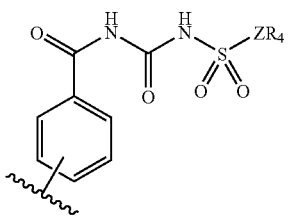

-continued
D-30
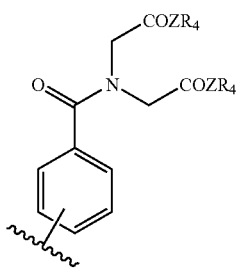
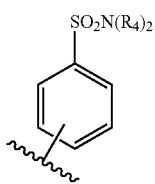
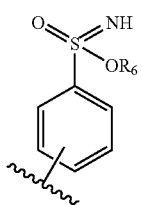
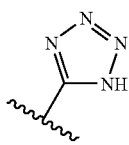
D-32
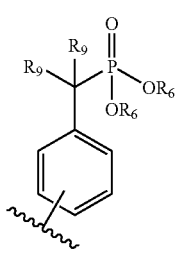
D-35
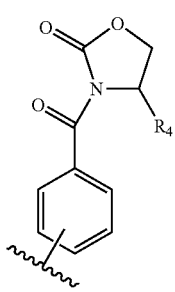
-continued
D-36
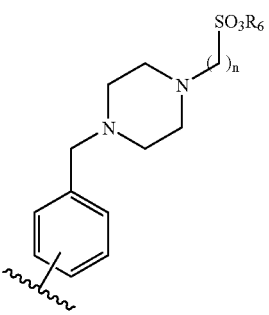
D-31
Specific examples of the present invention are illustrated by their structural formulae below:
Example 79
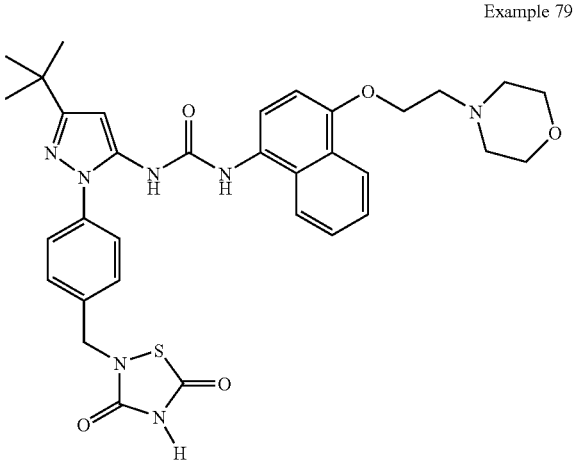
D-33
D-34
Example 80
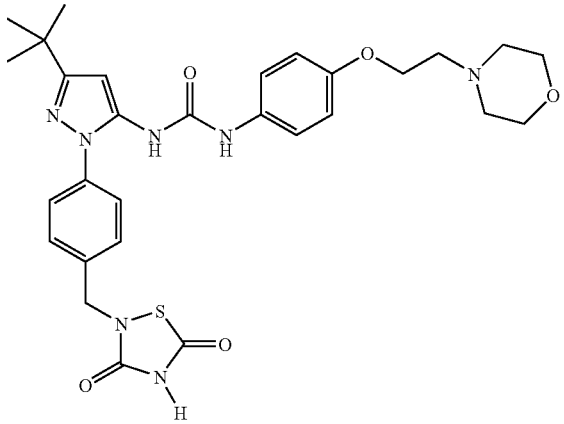

Example 81
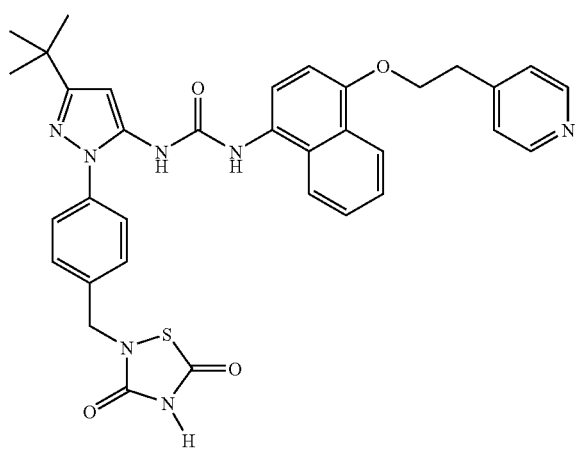
Example 84
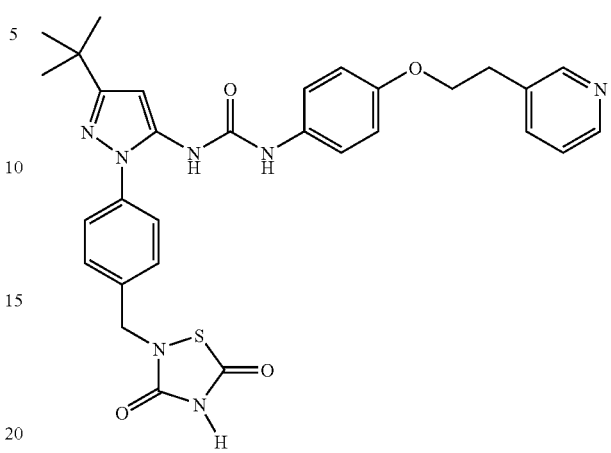
Example 82
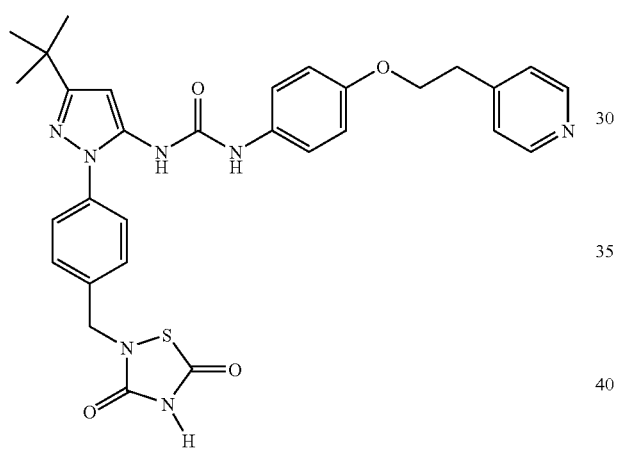
Example 85
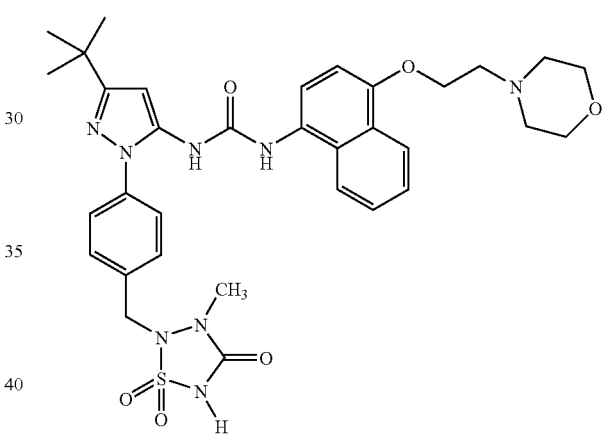
Example 83
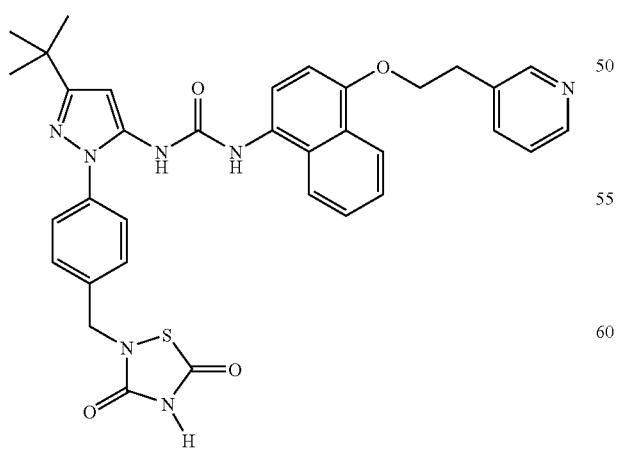
Example 86
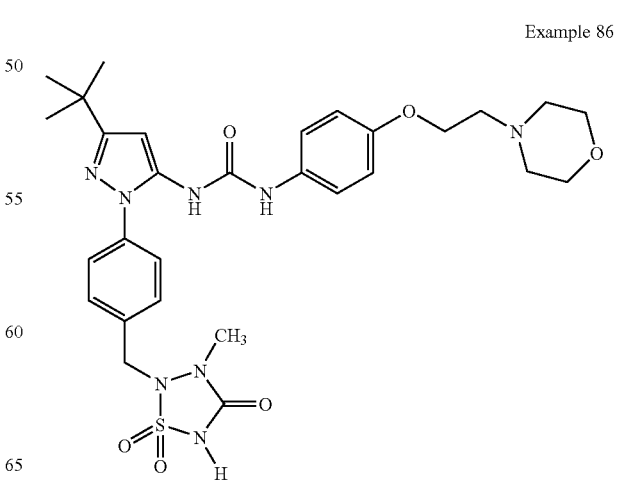

-continued
Example 87
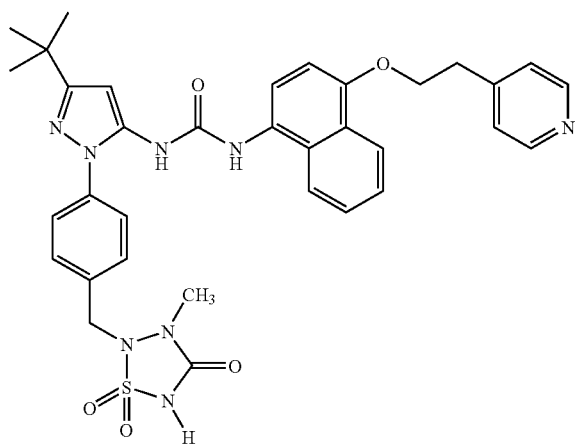
Example 88
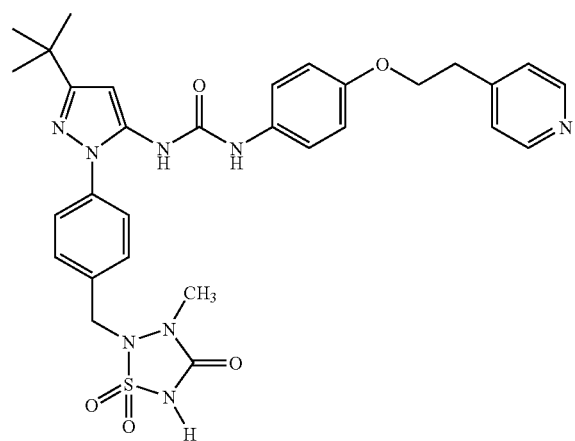
Example 89
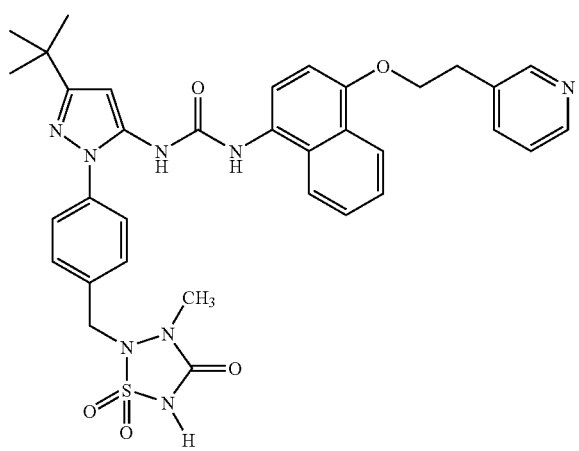
-continued
Example 90
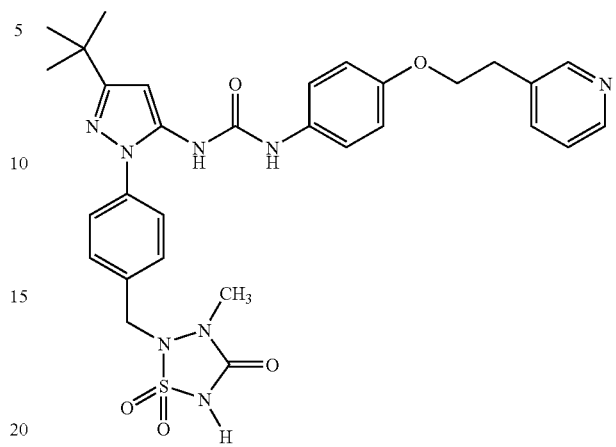
Example 91
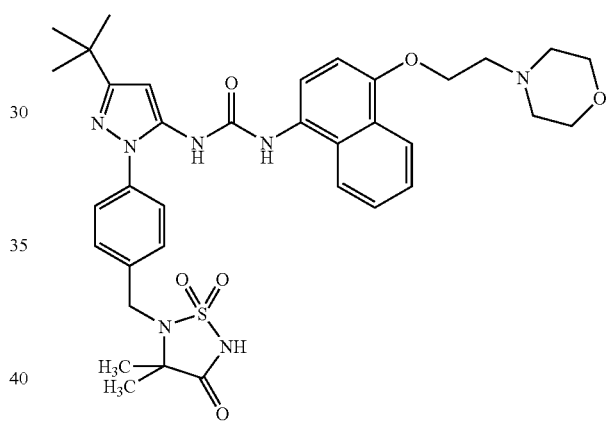
Example 92
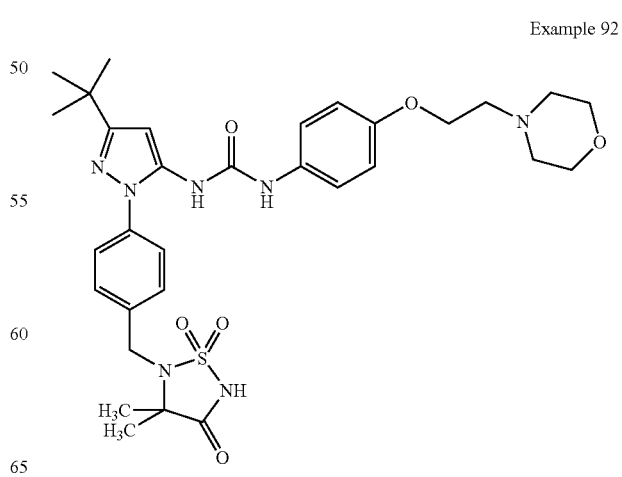

171
-continued
Example 93
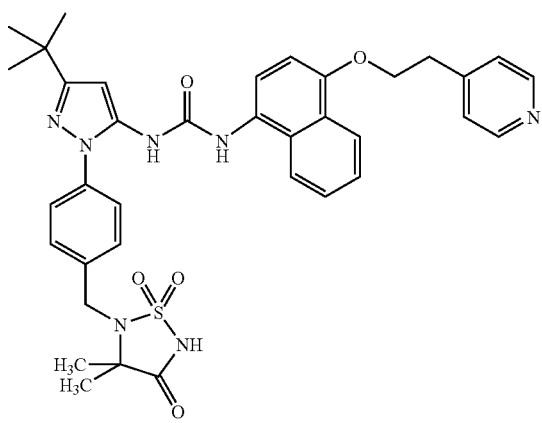
Example 94
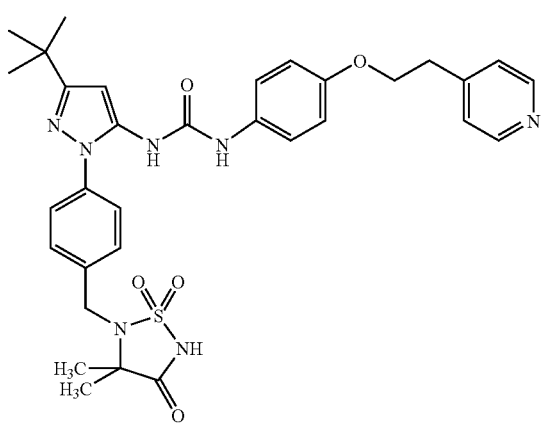
Example 95
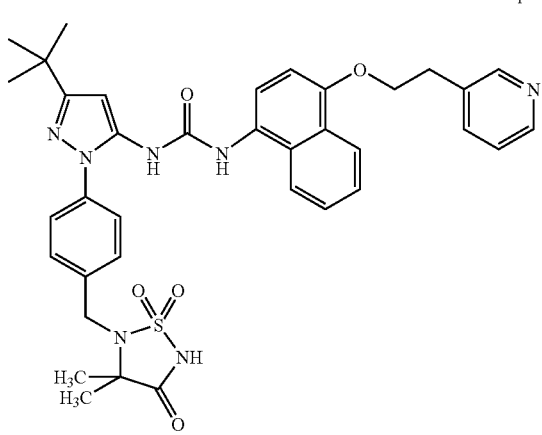
172
-continued
Example 96
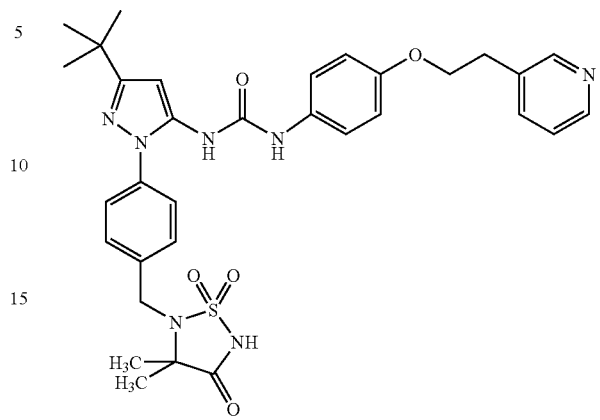
Example 97
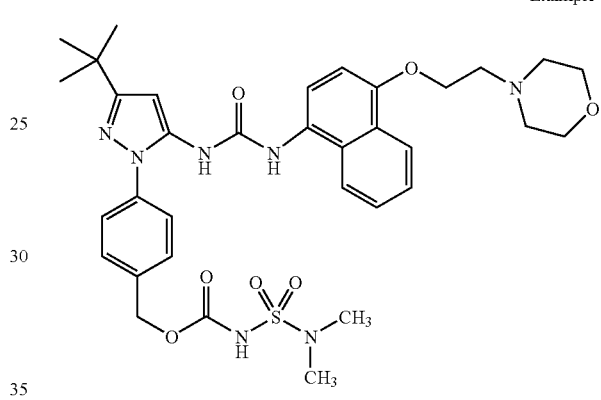
Example 98
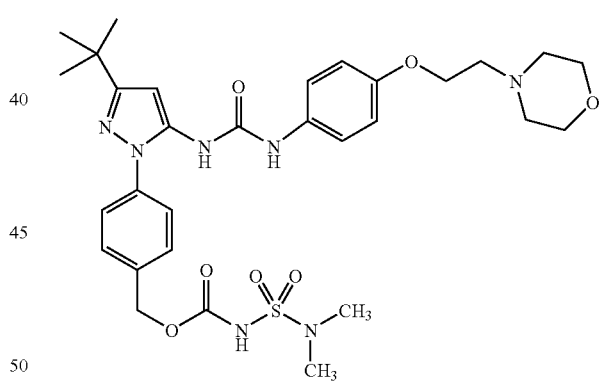
Example 99
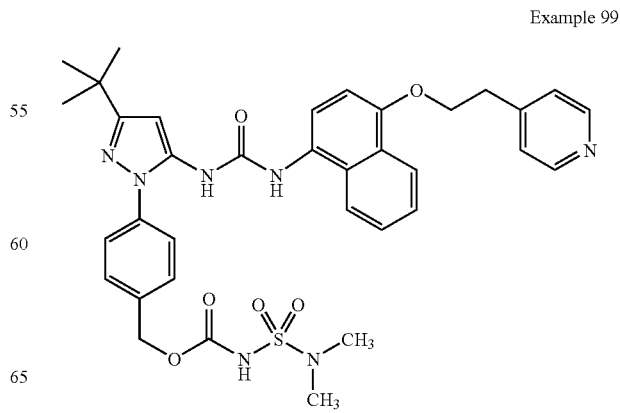

Example 100
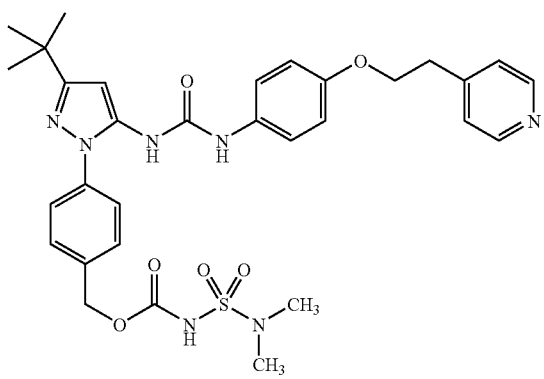
Example 101
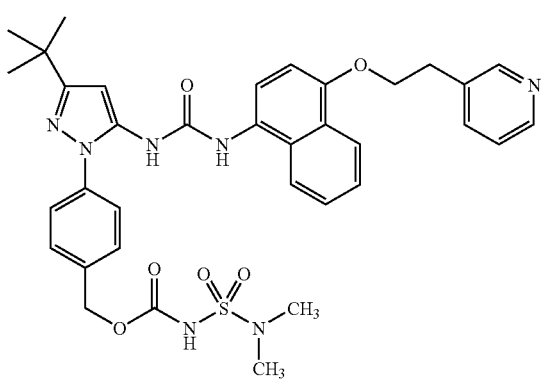
Example 102
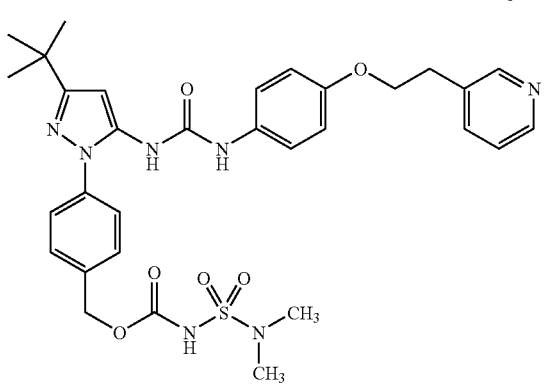
Example 103
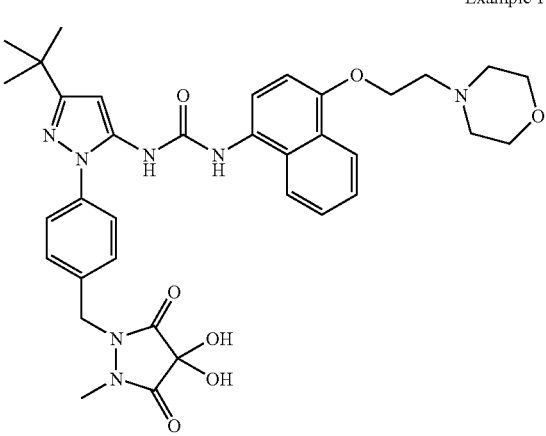
Example 104
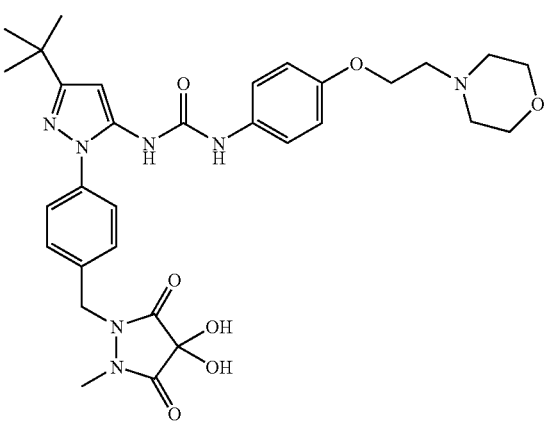
Example 105
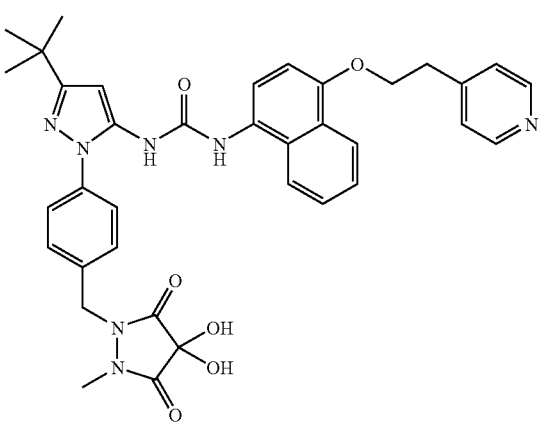
Example 106
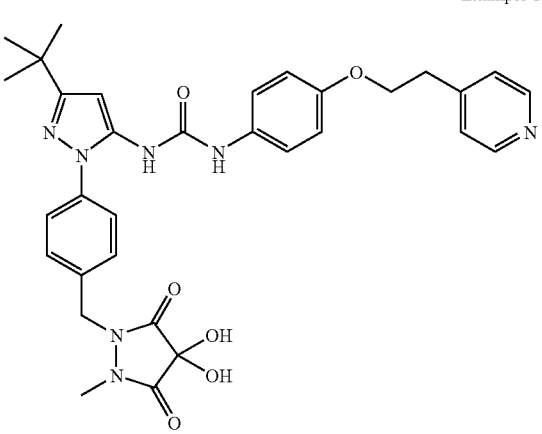

Example 107
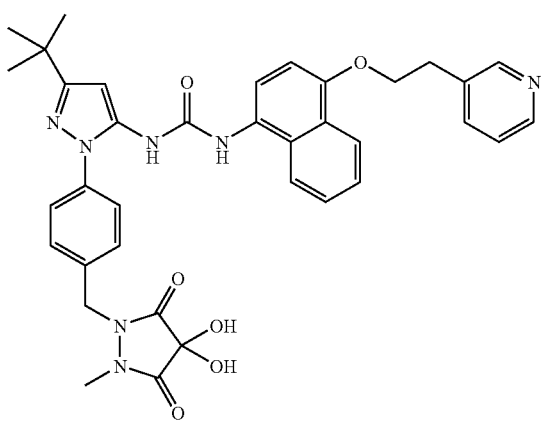
Example 108
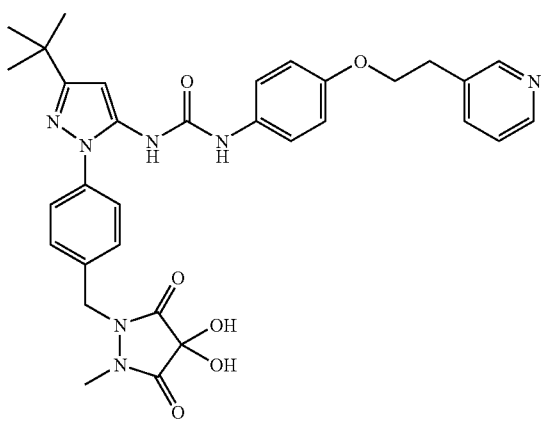
Example 109
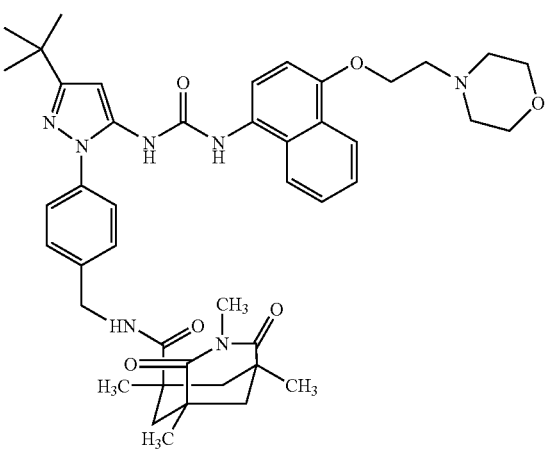
Example 110
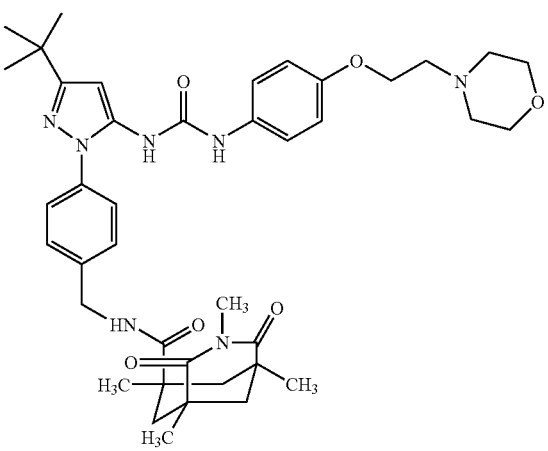
Example 111
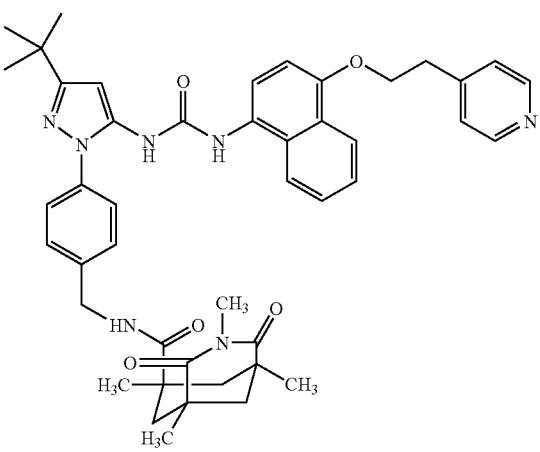
Example 112
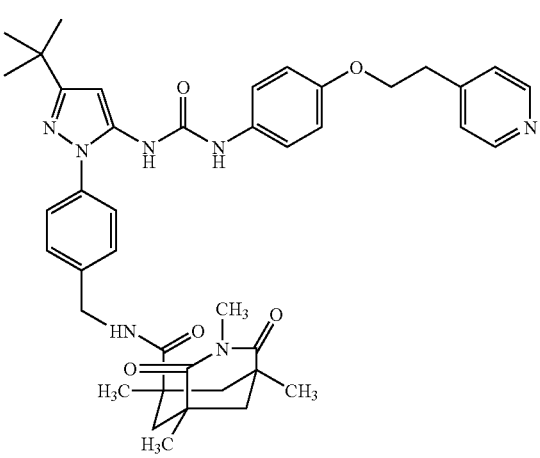

-continued

Example 113

Example 114

Example 115

-continued

Example 116

Example 117

Example 118

Example 119

-continued
Example 120
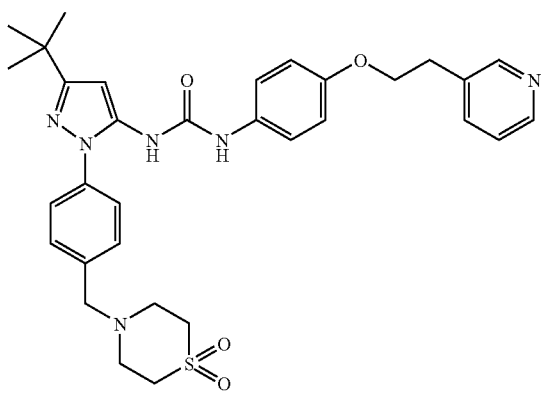
Example 124
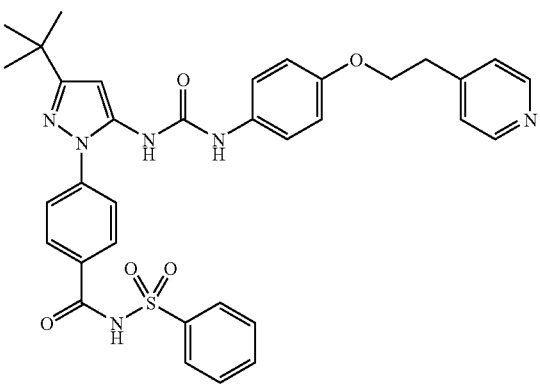
Example 121
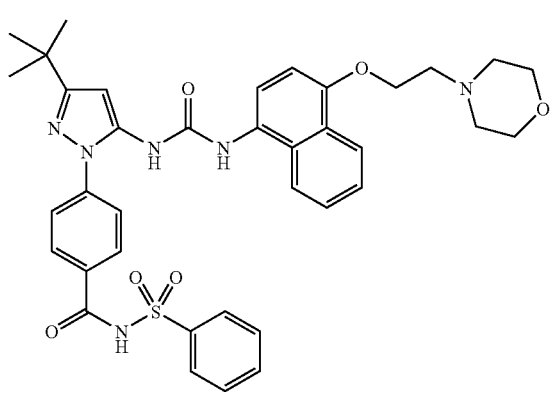
Example 125
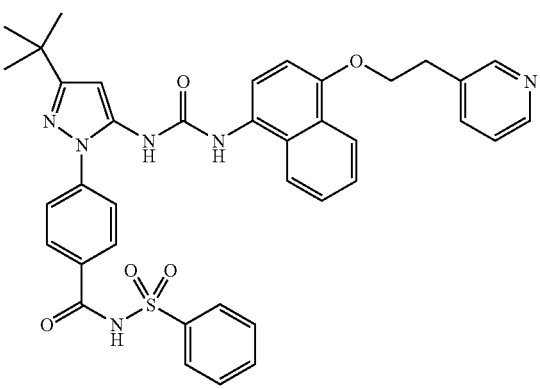
Example 122
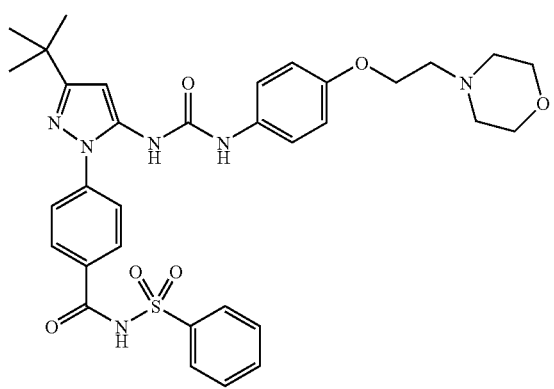
Example 126
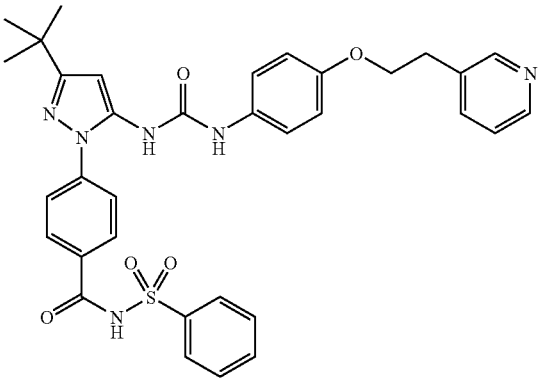
Example 123
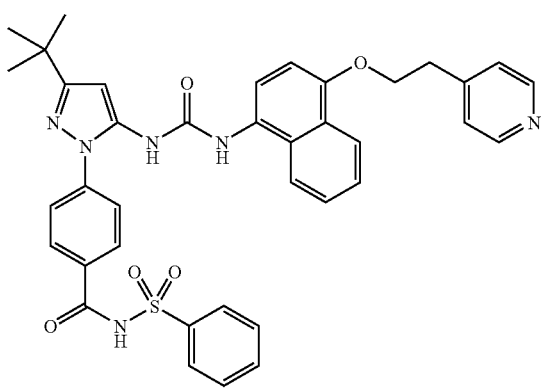
Example 127
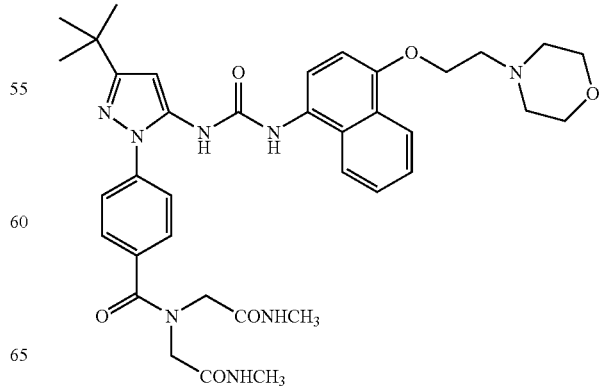

Example 128
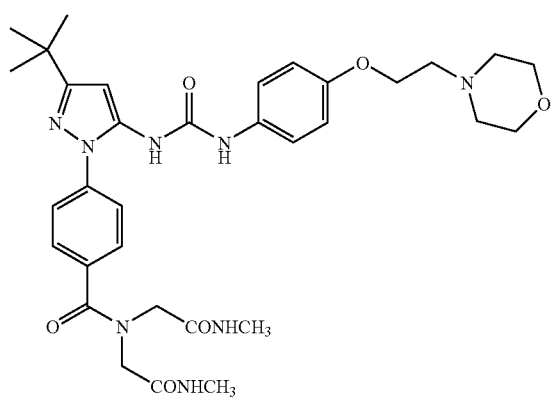
Example 129
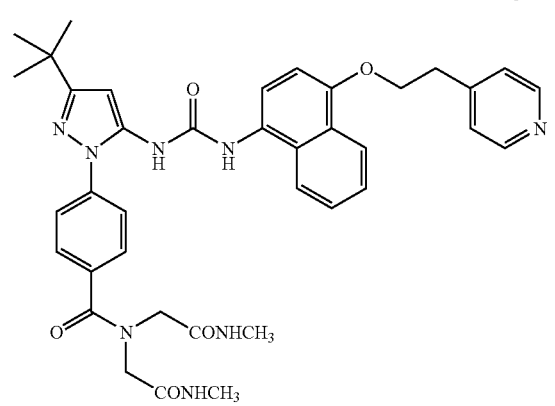
Example 130
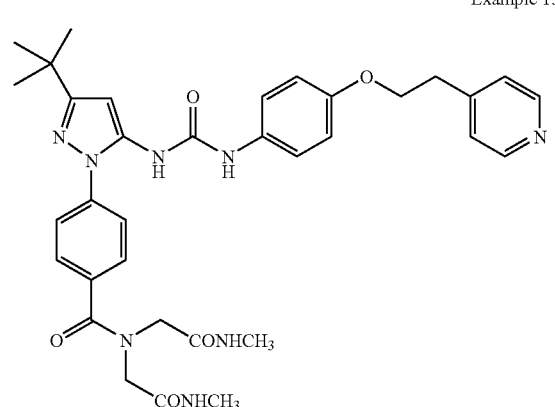
Example 131
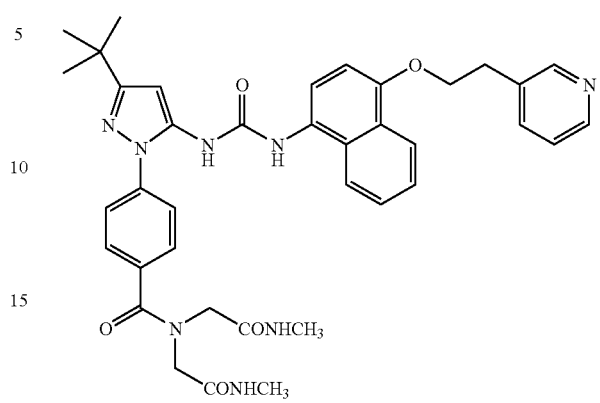
Example 132
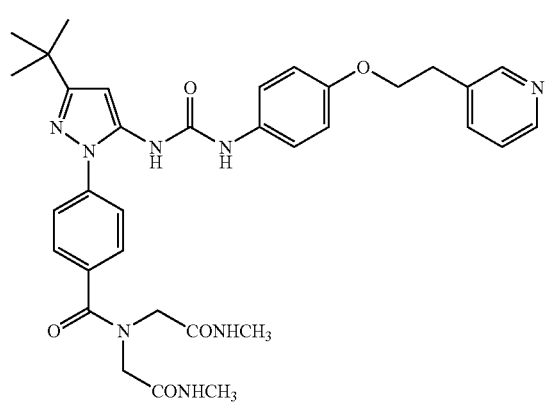
Example 133
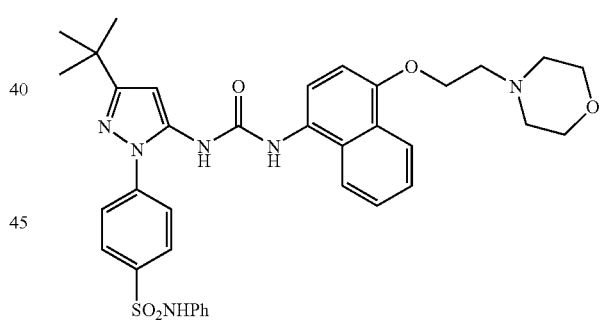
Example 134
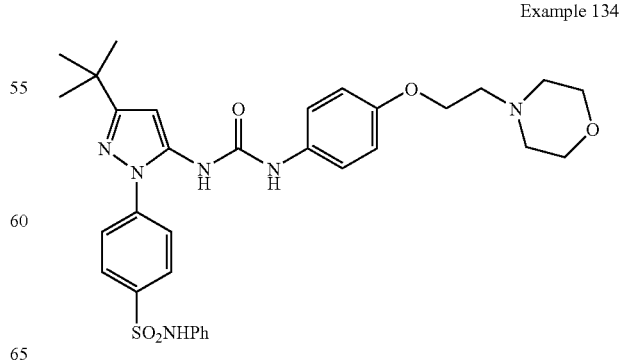

Example 135

Example 136

Example 137

Example 138

Example 139

Example 140

Example 141

Example 142

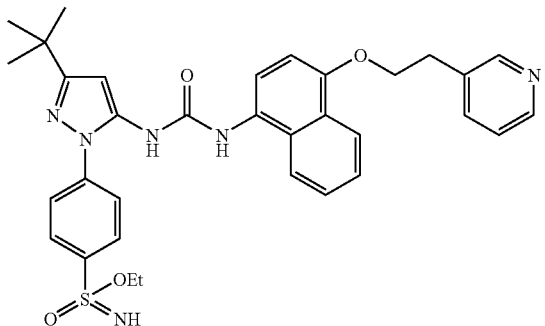

Example 143

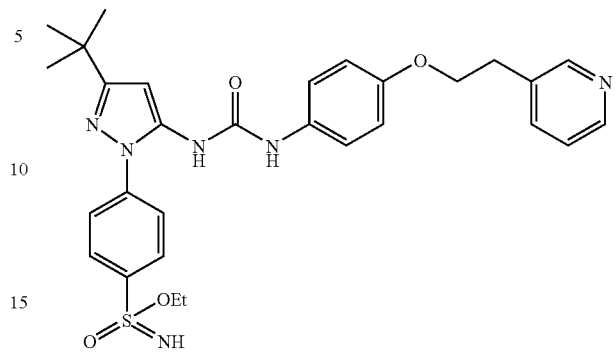

Example 144

All of the references above identified are incorporated by reference herein. In addition, two simultaneously applications are also incorporated by reference, namely Modulation of Protein Functionalities, Ser. No. 10/746,545, filed Dec. 24, 2003, and Anti-Cancer Medicaments, Ser. No. 10/746,607 filed Dec. 24, 2003.

---

We claim:

1. An adduct comprising a molecule binding with a kinase, said molecule having the formula

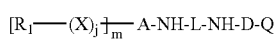

(I)

wherein:

R₁ is selected from the group consisting of

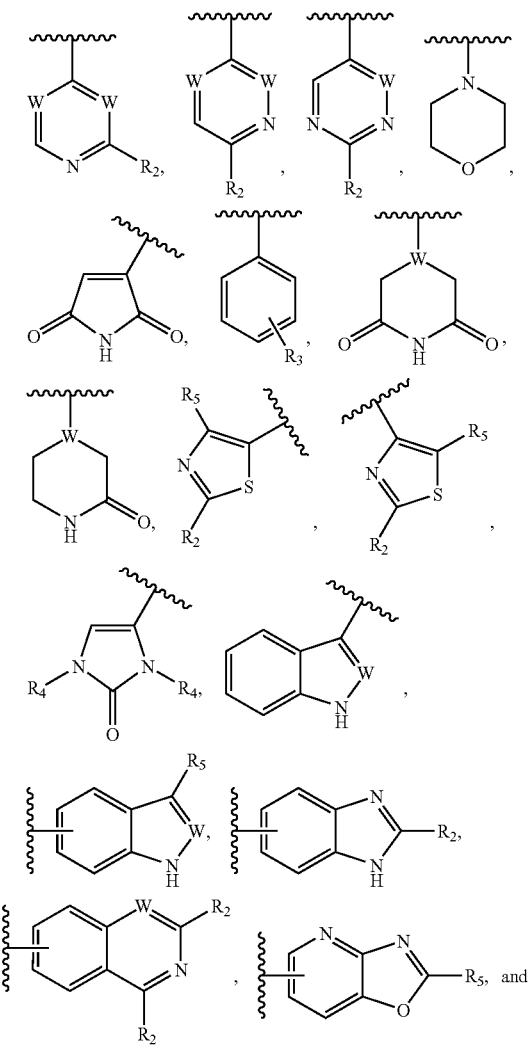

each R₂ is individually selected from the group consisting of —H, alkyls, aminos, alkylaminos, arylaminos, cycloalkylaminos, heterocyclylaminos, halogens, alkoxys, and hydroxys;

wherein each W is individually selected from the group consisting of —CH— and —N—;

each R₃ is individually selected from the group consisting of —H, alkyls, alkylaminos, arylaminos, cycloalkylaminos, heterocyclylaminos, alkoxys, hydroxys, cyanos, halogens, perfluoroalkyls, alkylsulfinyls, alkylsulfonyls, R₄NHSO₂—, and —NHSO₂R₄;

each R₅ is individually selected from the group consisting of —H, alkyls, aryls, heterocyclyls, alkylaminos, arylaminos, cycloalkylaminos, heterocyclylaminos, hydroxys, alkoxys, aryloxys, alkylthios, arylthios, cyanos, halogens, perfluoroalkyls, alkylcarbonyls, and nitros; and each W is individually selected from the group consisting of CH and N;

each X is individually selected from the group consisting of —O—, —S—, —NR₆—, —NR₆SO₂—, —NR₆CO—, alkynyls, alkenyls, alkylenes, —O(CH₂)ₕ—, and —NR₆(CH₂)ₕ—, where each h is individually selected from the group consisting of 1, 2, 3, and 4, and where for each of alkylenes, —O(CH₂)ₕ—, and —NR₆(CH₂)ₕ—, one of the methylene groups present therein may be optionally double-bonded to a side-chain oxo group except that where —O(CH₂)ₕ— the introduction of the side-chain oxo group does not form an ester moiety;

A is selected from the group consisting of phenyl, naphthyl, pyridyl, pyrimidyl, thienyl, furyl, pyrrolyl, thiazolyl, oxazolyl, imidazolyl, indolyl, indazolyl, benzimidazolyl, benzotriazolyl, isoquinolyl, quinolyl, benzothiazolyl, benzofuranyl, benzothienyl, pyrazolylpyrimidinyl, imidazopyrimidinyl, purinyl, and

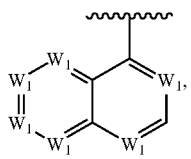

where each $W_1$ is individually selected from the group consisting of —CH— and —N—;

D is phenyl or a five-membered heterocyclic ring selected from the group consisting of pyrazolyl, pyrrolyl, imidazolyl, oxazolyl, thiazolyl;

G is —CH$_2$—;

L is —C(O)—;

j is 0 or 1;

m is 0 or 1;

n is 0 or 1;

Q is

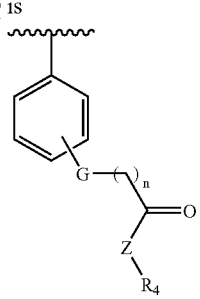

each $R_4$ group is individually selected from the group consisting of —H, alkyls, aminoalkyls, alkoxyalkyls, aryls, aralkyls, heterocyclyls, and heterocyclylalkyls except when the $R_4$ substituent places a heteroatom on an alpha-carbon directly attached to a ring nitrogen on Q;

when two $R_4$ groups are bonded with the same atom, the two $R_4$ groups optionally form an alicyclic or heterocyclic 4-7 membered ring;

each $R_6$ is individually selected from the group consisting of —H, alkyls, allyls, and β-trimethylsilylethyl;

each Z is individually selected from the group consisting of —O— and —N($R_4$)—;

each ring of formula (I) optionally includes one or more of $R_7$, where $R_7$ is a noninterfering substituent individually selected from the group consisting of —H, alkyls, aryls, heterocyclyls, alkylaminos, arylaminos, cycloalkylaminos, heterocyclylaminos, hydroxys, alkoxys, aryloxys, alkylthios, arthylthios, cyanos, halogens, nitrilos, nitros, alkylsulfinyls, alkylsulfonyls, aminosulfonyls, and perfluoroalkyls.

2. The adduct of claim 1, wherein m is 0; wherein D is substituted by a first $R_7$ substituent.

3. The adduct of claim 2, wherein A is phenyl substituted by one or more second $R_7$ substituents, said second $R_7$ substituents being halogens.

4. The adduct of claim 2, wherein A is an $R_7$-substituted naphthyl.

5. The adduct of claim 1, wherein m is 1; $R_1$ is taken from the group consisting of

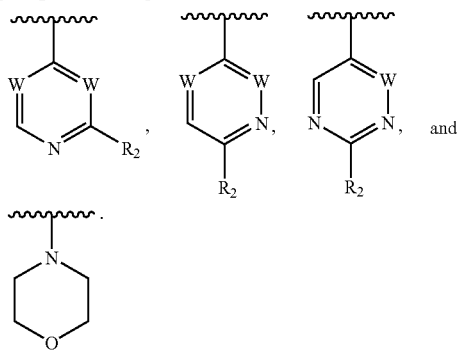

6. The adduct of claim 5, wherein A is taken from phenyl or naphthyl.

7. The adduct of claim 1 having the formula IB (IB)

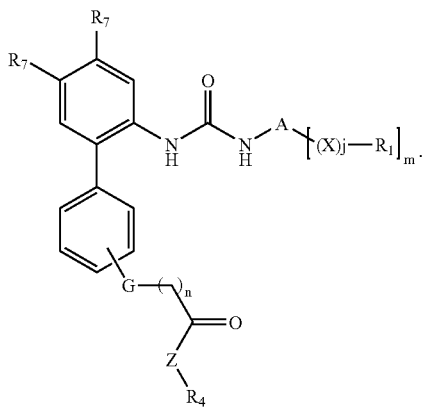

8. A adduct of claim 1 having the formula IC (IC)

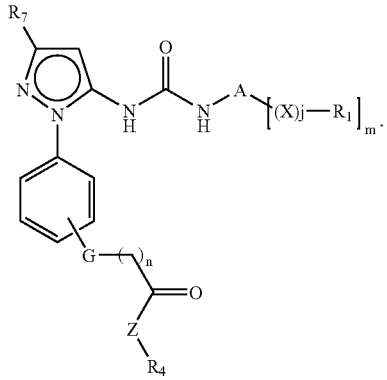

* * * * *